US010954564B2

(12) United States Patent
Dong et al.

(10) Patent No.: US 10,954,564 B2
(45) Date of Patent: Mar. 23, 2021

(54) COMBINATIONS OF CELL FREE NUCLEIC ACIDS

(71) Applicants: Yafeng Dong, Overland Park, KS (US); Carl Weiner, Mission Hills, KS (US)

(72) Inventors: Yafeng Dong, Overland Park, KS (US); Carl Weiner, Mission Hills, KS (US)

( * ) Notice: Subject to any disclaimer, the term of this patent is extended or adjusted under 35 U.S.C. 154(b) by 198 days.

(21) Appl. No.: 15/991,725

(22) Filed: May 29, 2018

(65) Prior Publication Data

US 2018/0265929 A1 Sep. 20, 2018

Related U.S. Application Data

(60) Continuation-in-part of application No. 14/851,809, filed on Sep. 11, 2015, now abandoned, which is a division of application No. 13/990,495, filed as application No. PCT/US2011/062661 on Nov. 30, 2011, now abandoned.

(60) Provisional application No. 61/418,368, filed on Nov. 30, 2010, provisional application No. 61/418,375, filed on Nov. 30, 2010.

(51) Int. Cl.
*C12Q 1/6883* (2018.01)
*C12Q 1/6876* (2018.01)

(52) U.S. Cl.
CPC ......... *C12Q 1/6883* (2013.01); *C12Q 1/6876* (2013.01); *C12Q 2600/158* (2013.01); *C12Q 2600/178* (2013.01); *G01N 2800/368* (2013.01)

(58) Field of Classification Search
None
See application file for complete search history.

(56) References Cited

U.S. PATENT DOCUMENTS

| 7,807,366 | B2 | 10/2010 | Strauss et al. |
| 2007/0037165 | A1 | 2/2007 | Venter et al. |
| 2007/0083334 | A1 | 4/2007 | Mintz et al. |
| 2008/0090759 | A1 | 4/2008 | Kokenyesi et al. |
| 2008/0254454 | A1 | 10/2008 | Strauss et al. |
| 2009/0117107 | A1 | 5/2009 | Xavier Brys et al. |
| 2010/0112581 | A1 | 5/2010 | Lao et al. |
| 2011/0098192 | A1 | 4/2011 | Lo et al. |

FOREIGN PATENT DOCUMENTS

WO 2009093254 A2 7/2009

OTHER PUBLICATIONS

Kabakchiev (Gastroenterology vol. 136, Issue 5 A-172 May 2009).*
Maron (The Journal of Clinical Investigation Oct. 2007 vol. 117 No. 10 pp. 3007-3019).*
Pradervand (BioTechniques vol. 44 No. 6 2008 pp. 759-762).*
Tani et al., "Circulating Cell-free mRNA in Plasma as a Tumor Marker for Patients with Primary and Recurrent Gastric Cancer", Anticancer Reasearch, 2007, vol. 27, pp. 1207-1212.
ABS (Applied Biosystems Application Note—TaqMan Gene Expression Assays), "Using TaqMan Endogenous Control Assays to select an endogenous control for experimental studies", Pub Jan. 2006, accessed online at https://assets.thermofisher.com/TFS-Assets/LSG/Application-Notes/cms_042279.pdf on Jun. 12, 2018.
Purwosunu et al., "Cell-free mRNA concentrations of CRH, PLAC1, and selectin-p. are increased in the plasma of pregnant women with preeclampsia", Prenatal Diagnosis, 2007, vol. 27, pp. 772-777, DOI: 10.1002/pd.1780.
Final Office Action dated Jun. 18, 2018 in U.S. Appl. No. 14/851,809.
Tanaka et al. "Down-Regulation of miR-92 in Human Plasma Is a Novel Marker for Acute Leukemia Patients" (PloS ONE May 2009 vol. 4 Issue 5 e5532 pp. 1-5).
Mehurg et al. "Abstract 3472: Relationship Between the Temporal Profile of Plasma microRNA and Left Ventricular Remodeling in Patients Following Myocardial Infarction" (circulation Nov. 3, 2009 vol. 120 Suppl Issue 18 S806).
GenBank Accession NR_029660 Oct. 29, 2009).
GenBank (Accession NR_004394.1 Nov. 27, 2007).
Weiner et al. "Human effector/initiator gene sets that regulate myometrial contractility during term and preterm labor", American journal of obstetrics and gynecology 202.5 (2010): 474-e1-e20.
International Search Report and Written Opinion dated Jun. 21, 2012 in International Application No. PCT/US2011/062661.
European Search Report and Written Opinion mailed in European Application No. 11845889.
Mayor-Lynn K et al. "Expression Profile of MicroRNAs and mRNAs in Human Placentas From Pregnancies Complicated by Preeclampsia and Preterm Labor", Reproductive Sciences 2011 Sage Publications Inc. USA, vol. 18, No. 1, Nov. 15, 2010, pp. 46-56, XP002729181, ISSN: 1933-7191.
Yogev Y et al."110: Spontaneous preterm labor—a possible role for micro-RNA", American Journal of Obstetrics & Gynecology, Mosby, St Louis, MO, US, vol. 197, No. 6, Dec. 1, 2007, p. S44, XP022591296, ISSN: 0002-9378, DOI: 10.1016/J.AJOG.2007.10.121.
Yogev Y et al."459: Mircro RNA: A central new player in post-transcriptional regulation pathway in preeclampsia", American Journal of Obstetrics & Gynecology, Mosby, St Louis, MO, US, vol. 197, No. 6, Dec. 1, 2007, p. S135, XP022591645, ISSN: 0002-9378; DOI: 10.1016/J.AJOG.2007.10.478.

(Continued)

*Primary Examiner* — Amanda Haney
(74) *Attorney, Agent, or Firm* — Maschoff Brennan; Jonathan M. Benns

(57) ABSTRACT

A method of detecting a combination of nucleic acid biomarkers in a human subject can include: obtaining a nucleic acid sample from the human subject; selecting the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard.

17 Claims, 6 Drawing Sheets

Specification includes a Sequence Listing.

(56) References Cited

OTHER PUBLICATIONS

Chim Stepehn S C et al. "Detection and characterization of placental microRNAs in maternal plasma", Clinical Chemistry, American Association for Clinical Chemistry, Washington, DC, vol. 54, No. 3, Mar. 1, 2008, pp. 482-490, XP002518104, ISSN: 0009-0147, DOI: 10.1373/CLINCHEM.2007.097972.

Farina et al. "High levels of fetal cell-free DNA in maternal serum: A risk factor for spontaneous preterm delivery", American Journal of Obstetrics & Gynecology, Mosby, St Louis, MO, US, vol. 193, No. 2, Aug. 1, 2005, pp. 421-425, XP005079561, ISSN: 0002.9378, DOI: 10.1016/J.AJOG.2004.12.023.

Litton C et al. "Noninvasive prenatal diagnosis: Past, present, and future", Mount Sinai Journal of Medicine 2009 John Wiley and Sons Inc. USA, vol. 76, No. 6, Dec. 2009, pp. 521-528, XP002729182, ISSN: 0027.2507.

Wright C F et al. "The use of cell-free fetal nucleic acids in maternal blood for non-invasive prenatal diagnosis", Human Reproduction Update, Oxford University Press, Oxford, GB, vol. 15, No. 1, Jan. 1, 2009, pp. 139-151, XP002613058, ISSN: 1355-4786, DOI: 10.1093/HUMUPS/DMN047.

\* cited by examiner

COMBINATIONS OF CELL FREE NUCLEIC ACIDS

CROSS-REFERENCE TO RELATED APPLICATIONS

This patent application is a continuation-in-part of U.S. patent application Ser. No. 14/851,809 filed Sep. 11, 2015, which is a divisional of U.S. patent application Ser. No. 13/990,495 filed Jul. 9, 2013, which is a section 371 nationalization of PCT/US2011/062661 filed Nov. 30, 2011, which claims the benefit of U.S. Provisional Patent Applications 61/418,368 and 61/418,375, which were both filed on Nov. 30, 2010, and which applications are incorporated herein by specific reference in their entirety.

SEQUENCE LISTING

The instant application contains a Sequence Listing which has been submitted in ASCII format via EFS-Web and is hereby incorporated by reference in its entirety. Said ASCII copy, created on May 22, 2018, is named W2460-10001US05_CIP_Sequence_Listing.txt and is 248 kilobytes in size.

BACKGROUND

Preterm birth remains a major societal problem due to the short and long term health complications of the preterm infants. Many preterm infants live the initial parts of their lives in intensive and critical care units, and often have excess health problems through adulthood compared to infants delivered at term. Approximately 12% of infants delivered are a product of a preterm birth (PTB), which can be characterized as a spontaneous birth before 37 weeks of pregnancy. PTB is also associated with >70% of neonatal deaths and nearly half of long-term neurologic disabilities. Despite great effort among all health sectors, the PTB rate has continued to increases. Accordingly, there remains a great need to identify women at risk of having a PTB and to better understand the mechanisms culminating in PTB.

SUMMARY

In some embodiments, a method of detecting a combination of nucleic acid biomarkers in a human subject can include: obtaining a nucleic acid sample from the human subject; selecting the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard, wherein the combination of nucleic acid biomarkers includes at least two of: miRNA-let-7g having a nucleotide sequence of or complementary to SEQ ID NO: 13 with a variation less than the transcription standard; PSME2 having a nucleotide sequence of or complementary to SEQ ID NO: 68 with a variation less than the transcription standard; APOA1 having a nucleotide sequence of or complementary to SEQ ID NO: 53 with a variation less than the transcription standard; and NAMPT having a nucleotide sequence of or complementary to SEQ ID NO: 71 with a variation less than the transcription standard. In some aspects: the variation for miRNA-let-7g is about −1.8 fold change; the variation for PSME2 is about −5.6 fold change; the variation for APOA1 is about −1.9 fold change; and/or the variation for NAMPT is −2.3 fold change. In some aspects, the analyzing includes hybridizing each nucleic acid biomarker in the nucleic acid sample with a complementary nucleic acid configured as a primer or a probe, the method comprising detecting the hybridizing.

In some embodiments, the combination of nucleic acid biomarkers includes one of: PSME2 and APOA1; PSME2 and miRNA-let-7g; NAMPT and APOA1; or miRNA-let-7g, PSME2, APOA1, and NAMPT. In some aspects, the combination of nucleic acid biomarkers includes all of miRNA-let-7g, PSME2, APOA1, and NAMPT, and further includes: APOA4 having a nucleotide sequence of or complementary to SEQ ID NO: 71, wherein the variation for APOA4 is less than the transcription standard. In some aspects, the variation for APOA4 is about −1.5 fold change.

In some embodiments, the combination of nucleic acid biomarkers includes at least one of: miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548L having a nucleotide sequence of or complementary to SEQ ID NO: 5 with a variation greater than the transcription standard.

In some embodiments, the combination of nucleic acid biomarkers includes at least one of: miRNA-99b having a nucleotide sequence of or complementary to SEQ ID NO: 7 with about a 1.7 fold change variation greater than the transcription standard; miRNA-99a having a nucleotide sequence of or complementary to SEQ ID NO: 6 with about a 1.6 fold change variation greater than the transcription standard; and miRNA-548L having a nucleotide sequence of or complementary to SEQ ID NO: 5 with about a 1.5 variation greater than the transcription standard.

In some embodiments, the combination of nucleic acid biomarkers includes at least one of: miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In some embodiments, the combination of nucleic acid biomarkers includes at least one of: miRNA-490 having a nucleotide sequence of or complementary to SEQ ID NO: 304 with about a −4.7 fold change variation less than the transcription standard; miRNA-491 having a nucleotide sequence of or complementary to SEQ ID NO: 9 with about a −2.2 fold change variation less than the transcription standard; miRNA-31 having a nucleotide sequence of or complementary to SEQ ID NO: 11 with about a −1.9 fold change variation less than the transcription standard; miRNA-382 having a nucleotide sequence of or complementary to SEQ ID NO: 8 with about a −1.8 fold change variation less than the transcription standard; miRNA-342 having a nucleotide sequence of or complementary to SEQ ID NO: 12 with about a −1.5 fold change variation less than the transcription standard; miRNA-194 having a nucleotide sequence of or complementary to SEQ ID NO: 305 with about a −1.5 fold change variation less than the transcription standard; miRNA-214 having a nucleotide sequence of or complementary to SEQ ID NO: 10 with about a −1.5 fold change variation less than the transcription standard; miRNA-371 having a nucleotide sequence of or complementary to SEQ ID NO: 306 with about a −1.4 fold change variation less than the transcription standard; and/or miRNA-519c having a nucleotide sequence of or complementary to SEQ ID NO: 307 with about a −1.3 fold change variation less than the transcription standard.

In some embodiments, the combination of nucleic acid biomarkers includes at least one of: SF3A3 having a nucleotide sequence of or complementary to SEQ ID NO: 25 with a variation greater than the transcription standard; FLJ16171 having a nucleotide sequence of or complementary to SEQ ID NO: 21 with a variation greater than the transcription standard; REG3G having a nucleotide sequence of or complementary to SEQ ID NO: 22 with a variation greater than the transcription standard; NDUFA2 having a nucleotide sequence of or complementary to SEQ ID NO: 24 with a variation greater than the transcription standard; LCE2A having a nucleotide sequence of or complementary to SEQ ID NO: 26 with a variation greater than the transcription standard KRTAP6-2 having a nucleotide sequence of or complementary to SEQ ID NO: 42 with a variation less than the transcription standard; CHCHD10 having a nucleotide sequence of or complementary to SEQ ID NO: 50 with a variation less than the transcription standard; OR4D1 having a nucleotide sequence of or complementary to SEQ ID NO: 62 with a variation less than the transcription standard; BLOC1S1 having a nucleotide sequence of or complementary to SEQ ID NO: 52 with a variation less than the transcription standard; PDZK1 having a nucleotide sequence of or complementary to SEQ ID NO: 56 with a variation less than the transcription standard; KRT17 having a nucleotide sequence of or complementary to SEQ ID NO: 58 with a variation less than the transcription standard; CSRP2 having a nucleotide sequence of or complementary to SEQ ID NO: 61 with a variation less than the transcription standard; PSG9 having a nucleotide sequence of or complementary to SEQ ID NO: 46 with a variation less than the transcription standard; ARMC10 having a nucleotide sequence of or complementary to SEQ ID NO: 48 with a variation less than the transcription standard; CD3E having a nucleotide sequence of or complementary to SEQ ID NO: 54 with a variation less than the transcription standard; GUCA2B having a nucleotide sequence of or complementary to SEQ ID NO: 47 with a variation less than the transcription standard; TNFRSF13C having a nucleotide sequence of or complementary to SEQ ID NO: 64 with a variation less than the transcription standard; LOC643008 having a nucleotide sequence of or complementary to SEQ ID NO: 41 with a variation less than the transcription standard; MRPS21 having a nucleotide sequence of or complementary to SEQ ID NO: 65 with a variation less than the transcription standard; NAT14 having a nucleotide sequence of or complementary to SEQ ID NO: 57 with a variation less than the transcription standard; PRTN3 having a nucleotide sequence of or complementary to SEQ ID NO: 45 with a variation less than the transcription standard; OR2A2 having a nucleotide sequence of or complementary to SEQ ID NO: 44 with a variation less than the transcription standard; RPL8 having a nucleotide sequence of or complementary to SEQ ID NO: 63 with a variation less than the transcription standard; TMEM188 having a nucleotide sequence of or complementary to SEQ ID NO: 60 with a variation less than the transcription standard; RPS19BP1 having a nucleotide sequence of or complementary to SEQ ID NO: 59 with a variation less than the transcription standard; and/or JSRP1 having a nucleotide sequence of or complementary to SEQ ID NO: 67 with a variation less than the transcription standard.

In some embodiments, the combination of nucleic acid biomarkers includes at least one of: SF3A3 having a nucleotide sequence of or complementary to SEQ ID NO: 25 with about a 2.7 fold change variation greater than the transcription standard; FLJ16171 having a nucleotide sequence of or complementary to SEQ ID NO: 21 with about a 2.6 fold change variation greater than the transcription standard; REG3G having a nucleotide sequence of or complementary to SEQ ID NO: 22 with about a 1.9 fold change variation greater than the transcription standard; NDUFA2 having a nucleotide sequence of or complementary to SEQ ID NO: 24 with about a 1.6 fold change variation greater than the transcription standard; LCE2A having a nucleotide sequence of or complementary to SEQ ID NO: 26 with about a 2.3 fold change variation greater than the transcription standard KRTAP6-2 having a nucleotide sequence of or complementary to SEQ ID NO: 42 with about a −2.1 fold change variation less than the transcription standard; CHCHD10 having a nucleotide sequence of or complementary to SEQ ID NO: 50 with about a −2.6 fold change variation less than the transcription standard; OR4D1 having a nucleotide sequence of or complementary to SEQ ID NO: 62 with about a −2.3 fold change variation less than the transcription standard; BLOC1S1 having a nucleotide sequence of or complementary to SEQ ID NO: 52 with about a −2.2 fold change variation less than the transcription standard; PDZK1 having a nucleotide sequence of or complementary to SEQ ID NO: 56 with about a −2.0 fold change variation less than the transcription standard; KRT17 having a nucleotide sequence of or complementary to SEQ ID NO: 58 with about a −2.0 fold change variation less than the transcription standard; CSRP2 having a nucleotide sequence of or complementary to SEQ ID NO: 61 with about a −1.8 fold change variation less than the transcription standard; PSG9 having a nucleotide sequence of or complementary to SEQ ID NO: 46 with about a −1.8 fold change variation less than the transcription standard; ARMC10 having a nucleotide sequence of or complementary to SEQ ID NO: 48 with about a −1.7 fold change variation less than the transcription standard; CD3E having a nucleotide sequence of or complementary to SEQ ID NO: 54 with about a −1.7 fold change variation less than the transcription standard; GUCA2B having a nucleotide sequence of or complementary to SEQ ID NO: 47 with about a −1.7 fold change variation less than the transcription standard; TNFRSF13C having a nucleotide sequence of or complementary to SEQ ID NO: 64 with about a −1.6 fold change variation less than the transcription standard; LOC643008 having a nucleotide sequence of or complementary to SEQ ID NO: 41 with about a −1.6 fold change variation less than the transcription standard; MRPS21 having a nucleotide sequence of or complementary to SEQ ID NO: 65 with about a −1.6 fold change variation less than the transcription standard; NAT14 having a nucleotide sequence of or complementary to SEQ ID NO: 57 with about a −1.6 fold change variation less than the transcription standard; PRTN3 having a nucleotide sequence of or complementary to SEQ ID NO: 45 with about a −1.6 fold change variation less than the transcription standard; OR2A2 having a nucleotide sequence of or complementary to SEQ ID NO: 44 with about a −1.6 fold change variation less than the transcription standard; RPL8 having a nucleotide sequence of or complementary to SEQ ID NO: 63 with about a −1.5 fold change variation less than the transcription standard; TMEM188 having a nucleotide sequence of or complementary to SEQ ID NO: 60 with about a −1.5 fold change variation less than the transcription standard; RPS19BP1 having a nucleotide sequence of or complementary to SEQ ID NO: 59 with about a −1.5 fold change variation less than the transcription standard; and/or JSRP1 having a nucleotide sequence of or complementary to SEQ ID NO: 67 with about a −1.5 fold change variation less than the transcription standard.

In some embodiments, the method includes providing the transcription standard for each nucleic acid biomarker for the combination of nucleic acid biomarkers.

In some embodiments, the method includes providing the combination of nucleic acid biomarkers as a set of primers and/or probes.

In some embodiments, the method includes obtaining cell free plasma RNA as the nucleic acid sample. In some embodiments, the nucleic acid biomarkers are RNA.

In some embodiments, the method can include: selecting a normalization nucleic acid; analyzing the transcriptome of the human subject for the normalization nucleic acid in the nucleic acid sample from the human subject; and detecting in the nucleic acid sample the presence of the normalization nucleic acid, wherein normalization nucleic acid has a variation from a transcription standard, wherein the normalization nucleic acid has a nucleotide sequence of or complementary to one of SEQ ID NOs: 1-4 and 301-303.

In some embodiments, the method can include generating a report, the report reciting the presence of the combination of nucleic acid biomarkers being present in the nucleic acid sample of the human subject being present in a biomarker amount that is varied from the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7g having a nucleotide sequence of or complementary to SEQ ID NO: 13 with a variation less than the transcription standard; miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548L having a nucleotide sequence of or complementary to SEQ ID NO: 5 with a variation greater than the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7g having a nucleotide sequence of or complementary to SEQ ID NO: 13 with a variation less than the transcription standard; miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In one embodiment, a kit includes purified or isolated nucleic acids, wherein the nucleic acids have the sequences of each of the nucleic acid biomarkers in the combination of biomarkers. As such, each recited combination can be uniquely included in a kit.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1A:
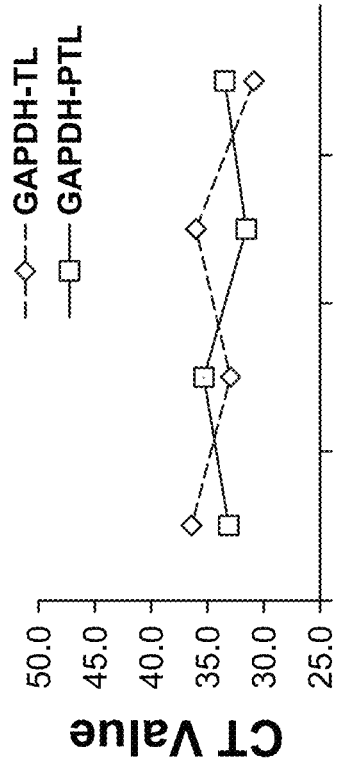
FIGS. 1A-1D illustrate that our new discovered messenger RNA (mRNA) normalization sequences of PPIA are more stabilized (FIG. 1D) compared to published normalization sequences (FIGS. 1A, 1B, and 1C)
Figure 1C:
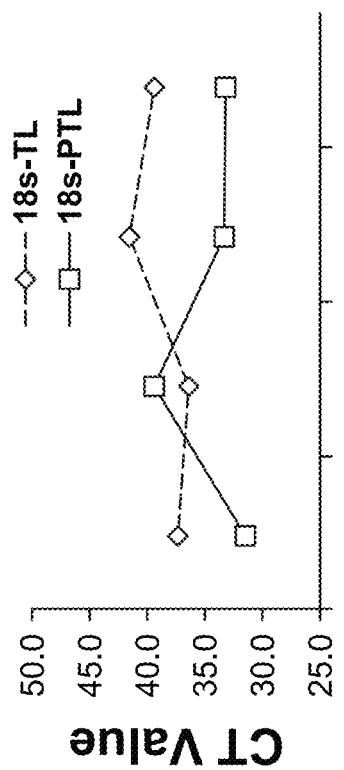
Figure 1B:
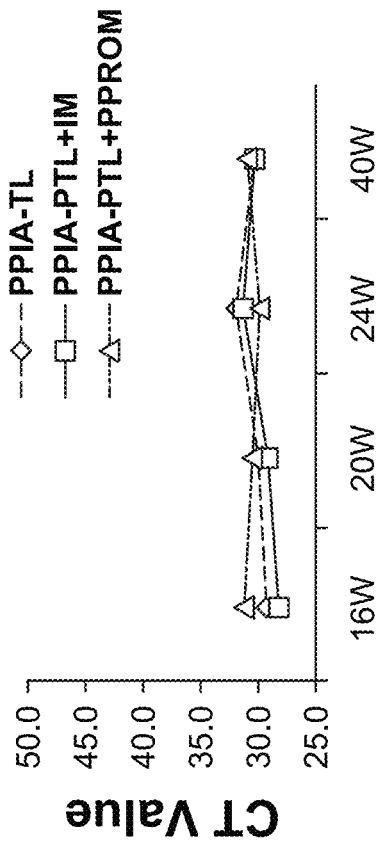

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to the use of nucleic acids to predict preterm birth (PTB) or determine the probability or susceptibility of PTB in a woman. The nucleic acids useful for PTB diagnostics can include nucleic acid primers and/or probes that bind with specific nucleic acid sequences as well as the nucleic acids that are increased or decreased in a woman that may be susceptible to PTB. The nucleic acids can include specific nucleic acid sequences relevant to PTB, which sequences function as biomarkers for PTB. Diagnostic kits can be provided with specific nucleic acid primers and/or probes, labeled or unlabeled, that can selectively bind with nucleic acids associated with PTB. The diagnostic kits can also include nucleic acid primers that can be used for amplifying nucleic acids associated with PTB. The diagnostic kits can include probes that can identify the presence of certain nucleic acid sequences. In one aspect, all PTB specific nucleic acids can be included on customized PCR cards. By utilizing high throughput PCR technique, the PCR cards can be used for diagnostics and determination of nucleic acid presence and/or amount. The methods of the present invention can include diagnosing whether or not a pregnant woman is susceptible to PTB.

The present invention can also include normalization nucleic acids (e.g., mRNA and miRNA) that have normalization sequences that can be used to normalize the relative levels of nucleic acid data from one sample to the next. We illustrate that our new discovered mRNA and miRNA normalization sequence are stabilized and not impacted by gestational age compared to previously published reports. These normalization nucleic acids can be also be included in diagnostic kits. The methods of the present invention can use the normalization nucleic acids in sample normalization protocols. These protocols can be useful for normalizing nucleic acid amounts between samples. While these normalization nucleic acids are useful for PTB diagnostic protocols, they can also be used to normalize nucleic acid amounts for any purpose.

While RNA is a preferred nucleic acid for the compositions and methods described herein, it is possible that DNA or RNA/DNA hybrids could also be used as nucleic acid probes and/or primers for diagnostics or normalization protocols. However, the nucleic acids that are identified to be present, up-regulated, or down-regulated in diagnostic protocols will generally be RNA as it is transcribed from DNA (e.g., complementary RNA) or as processed into mRNA. The RNA may also be regulatory RNA, such as non-coding small RNA (miRNA, siRNA, snRNA, or snoRNA) that are involved in gene silencing or transcription or translation regulation. Also, normalization protocols will generally be performed with RNA.

The nucleic acids can be cell free plasma (CFP) RNA, which refers to RNA derived from a variety of cells within differing organs, and circulates systemically. CFP RNA may include several types including coding RNA (e.g., mRNA) and non-coding RNAs (e.g., siRNA, miRNA, snoRNA, snRNA). Using microarray techniques, we screen all gene mRNA and non-coding RNAs including siRNA, miRNA, snoRNA, and snRNA. We found only some mRNA and miRNA can be altered by preterm labor. In one aspect, the CFP RNAs can include maternal CFP mRNA and CFP miRNA. The CFP RNAs can be detectable in plasma from the mother's peripheral circulation long before any symptoms or signs of preterm labor. The nucleic acids can be characterized as CFP RNA PTB biomarkers as they can individually or in combination provide a biomarker for PTB and prediction of PTB or PTB susceptibility. The CFP RNA PTB biomarkers can be used to provide a pattern of PTB biomarkers that may reflect the underlying mechanisms that result in PTB or susceptibility thereto.

In one embodiment, the CFP RNA can be specific RNA nucleic acid sequences. That is, the sequences can be a whole or portion of an mRNA or miRNA. The sequences themselves can be used for preparing primers and/or probes for the methods described herein, and may be used at targets for detection as well as for further studies in developing targeted therapies. The CFP RNA nucleic acid sequences are provided in the Sequence Listing and have SEQ ID NOs: 1-307. These sequences in the Sequence Listing are provided in DNA format; however, these sequences can be employed with the RNA format with uracil (U) replacing thymine (T). Accordingly, references to the SEQ ID NOs 1-307 of the Sequence Listing can be in RNA format, DNA format, or DNA/RNA hybrid. In a preferred embodiment, the SEQ ID NOs 1-307 of the Sequence Listing are specifically RNA, such as for the miRNA and mRNA described herein, and thereby any "T" is replaced with a "U" as understood by one of ordinary skill in the art. Thus, a recitation of SEQ ID NOs 1-307 of the Sequence Listing can specifically refer to the corresponding RNA nucleic acids, and thereby reference to a SEQ ID NO references the RNA nucleic acid with all of the "T" is replaced with a "U" as understood by one of ordinary skill in the art.

Accordingly, CFP RNA PTB biomarkers can be used for the development of targeted pharmacotherapy that could be initiated before myometrial activation occurs, as opposed to after the onset of symptoms such as cervical shortening or contractions. The CFP RNA PTB biomarkers can be used in order to design a therapy that can modulate the production of certain biological substances, such as proteins associated with myometrial activation or the inhibition of myometrial activation. The PTB biomarkers may also be used in diagnostic protocols for other pregnancy disorders, such as abnormal placentation (e.g., preeclampsia, IUGR, etc.), dysfunctional cervical ripening, short cervix, or others where the pathologic mechanisms overlap or intersect. The PTB biomarkers can be used to identify maternal CFP transcriptome patterns indicative of certain fetal malformations, such as for diagnosis of common triploidies.

In one embodiment, the present invention can use a combination of CFP RNA PTB biomarkers for diagnosing a pregnancy disorder or susceptibility thereof, and providing a therapy in order to treat and/or prevent the pregnancy disorder. For example, a diagnostic protocol can be used to diagnose or predict the ultimate development of a sonographically short cervix, and then a medical professional can treat the condition with progesterone supplementation from information obtained from the PTB biomarkers, which diagnosis and treatment could be as early as 12, 16, 18, or 22 weeks gestation before the cervix has actually shortened.

In one embodiment, a diagnostic kit can be provided with one or more CFP RNA PTB biomarkers and instructions of use that can be used to identify susceptibility of PTB in women as early as possible (e.g., 12, 16, 18, 20, 22, 24, 26, 28, 30, or up to 32 weeks) to allow for intervention before a PTB indicator such as either myometrial activation or cervical ripening or both is irrevocably activated. The diagnostic kit can include one or multiple PTB biomarkers in a single composition or PCR card or PCR card spot, where each PTB biomarker can be used for targeting different causes of PTB. Alternatively, two or more of such PTB biomarkers may be used together to maximize the predictive values of the test. The diagnostic kit can include nucleic acids that are the complement of CFP RNA PTB biomarker sequences that are used to perform the diagnostic. These nucleic acids can be the primers and/or probes for such a diagnostic protocol. The nucleic acids can also be included in plasmids for expression of the PTB biomarker sequences. The diagnostic kit can also identify the CFP RNA PTB biomarker sequences that are to be identified as up-regulated or down-regulated, and may specify the mRNA, miRNA, general sequence thereof, or the exact sequences in such CFP RNA PTB biomarkers that are specific to which the primers and/or probes hybridize. The CFP RNA PTB biomarkers have sequences that are included in the Sequence Listing having SEQ ID NOs: 5-300 and 304-307. In some instances, such as shorter sequences, the entire recited sequence can be used, and in other instances unique portions of the sequences that are unique and specific for that mRNA or miRNA can be used in the invention described herein.

Normalization Sequences

Quantification of nucleic acids (e.g., RNA) extracted from a biological sample can be important data. The actual quantification of RNA in a sample and its comparison to other RNA sequences in a single sample or in multiple samples usually requires a nucleic acid normalization sequence. The normalization sequence can be RNA that has an amount or expression level is generally stable under the conditions studied. That is, the normalization sequence can have an amount or level that is substantially unaffected by any physiological circumstances present in a subject, and thereby the normalization sequence can be used to normalize the amount of nucleic acid in separate samples for comparison. The separate samples can be from different subjects or the same subject at different time points, such as different time points in pregnancy. For example, the normalization sequence can be used to normalize the amount of RNA in Q-rtPCR studies, such as by normalizing the amount of the RNA sequence of interest. The normalization sequences described herein can be used alone or in combination, and may be used to normalize samples to be assayed for PTB biomarkers. However, the normalization sequences can be used to normalize the amount of RNA in different samples for other purposes than for PTB biomarkers. Thereby, the normalization sequences can be used as general normalization sequences to normalize the amount of RNA in different samples for any purpose. Thus, the normalization sequences provided herein can be for quantification of free RNA isolated from biological samples.

Figure 1D:
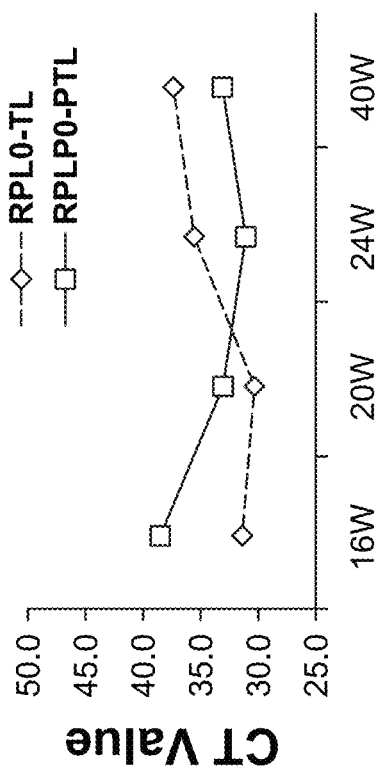
Figure 2B:
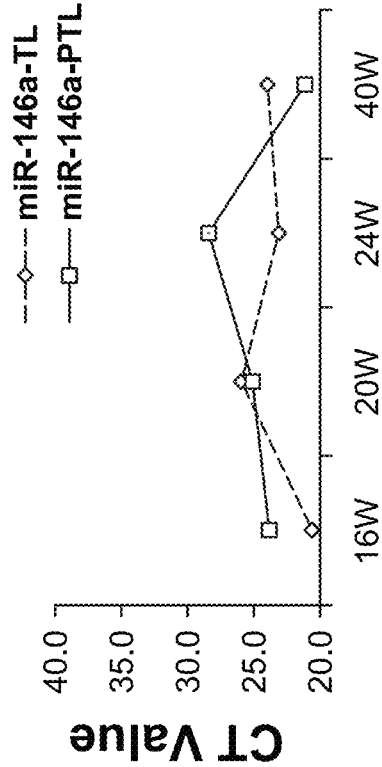
FIGS. 2A-2D illustrate that our new discovered snRNA: U6 is not impacted by different gestational age; snRNA:U6 plays a better role as micro RNA (miRNA) normalization sequences compared to reported sequences.
Figure 2D:
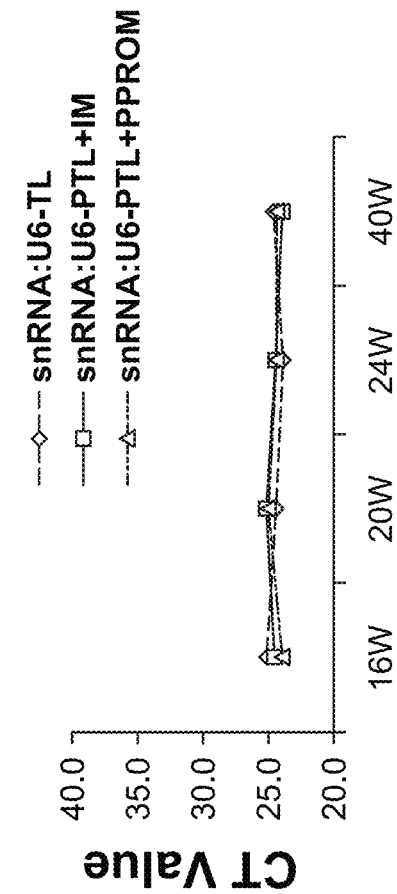
Figure 2A:
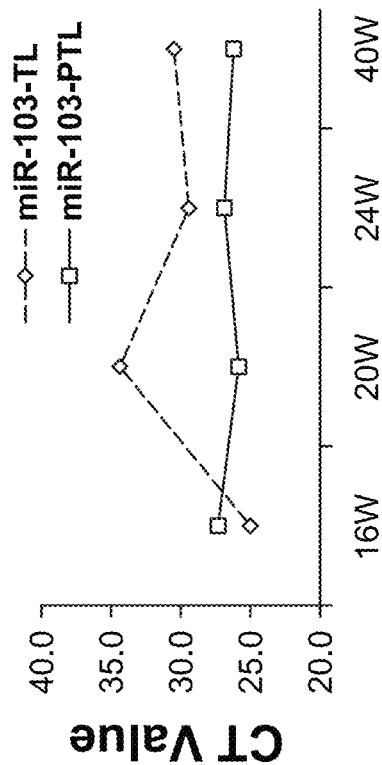
Figure 2C:
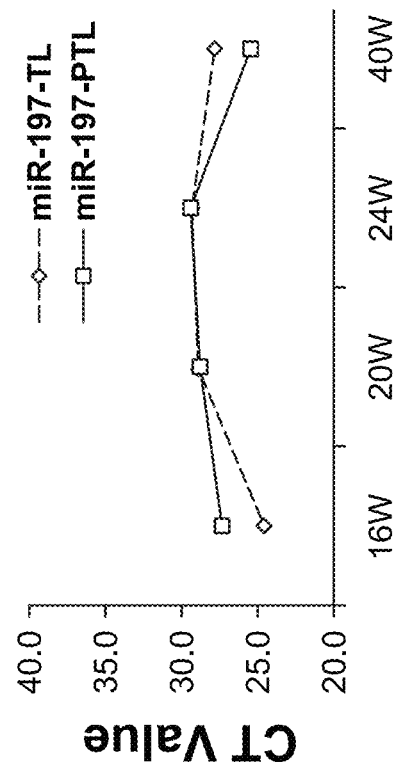

It has been determined that previously reported normalization sequences utilized in other tissues for quantification of isolated RNA (e.g., mRNA: 18s RNA, RPLPO, GAPDH; miRNA: miR-103, miR-146a, and miR-197) were either expressed inconsistently in control plasma samples or were altered by either pregnancy, gestational age or disease (see FIGS. 1A-1C and 2A-2C). Thus, new normalization sequences were sought and identified (see FIGS. 1D, and 2D). These new normalization sequences can include CFP mRNA and CFP miRNA sequences that are substantially unchanged by any condition, such as by pregnancy. However, the CFP RNA normalization sequences and related process can be equally applicable to almost any disease state ranging from pregnancy and PTB to malignancy to cardiovascular disease to bone disease or joint disease or the like.

In one embodiment, the normalization sequence includes a circulating RNA. Such a normalization sequence can be described as human (i.e., *homo sapiens*) peptidylprolyl isomerase A (i.e., cyclophilin A, rotmase A), which is encoded by the PPIA gene. The normalization sequence can be the mRNA for peptidylprolyl isomerase. The peptidylprolyl isomerase normalization sequence can be found at accession number: NM_021130 and/or NM_001008741, which is incorporated herein by specific reference. The peptidylprolyl isomerase normalization sequence is defined herein as SEQ ID NO: 1), and can be useful for normalization of mRNA.

In one embodiment, the normalization sequence can include miRNA. Such a normalization sequence can be a *Drosophila melanogaster* small nuclear RNA, such as snRNA:U6. The snRNA:U6 normalization sequence can be snRNA:U6 at 96Aa, 96:Ab, and/or 96Ac. These normalization sequences can be described as snRNA:U6:96Aa (SEQ ID NO: 2 for miRNA), snRNA:U6:96Ab (SEQ ID NO: 3 for miRNA), and/or snRNA:U6:96Ac (SEQ ID NO: 4 for miRNA), and can be found at the following accession numbers, respectively: NR_002081 (snRNA:U6:96Aa); NR_002082 (snRNA:U6:96Ab); and NR_002083 (snRNA: U6:96Ac), which accession numbers and information associated therewith are incorporated herein by specific reference. FIGS. 1A-1D and 2A-2D illustrate the impact of gestational age, preterm premature rupture of membranes (PPROM) and ultimate spontaneous preterm birth on some of the sequences rejected and the one mRNA and miRNA selected for normalization (see FIGS. 1D and 2D). Accordingly, SEQ ID NOs: 2-4 for miRNA, and SEQ ID No 1 for mRNA can be used for normalization sequences generally, and particularly for normalization of PTB biomarkers. Primers and probes for these sequences can be readily obtained by one of ordinary skill in the art with this application. For example, sequences for the forward primer, reverse primer, and probe for SEQ ID NO: 1 (e.g., for mRNA normalization sequence of PPIA) will be: Forward primer: GCTTTGGGTCCAGGAATGG—SEQ ID NO: 301; Reverse primer: GTTGTCCACAGTCAGCAATGGT—SEQ ID NO: 302; and Probe: AGACCAGCAAGAAGAT—SEQ ID NO: 303, which can also be considered normalization sequences for the invention recited herein.

In one embodiment, a normalization kit can be provided that includes one or more of these normalization sequences in nucleic acid format, such as RNA, DNA, or RNA/DNA hybrid. Preferably, the sequences of the normalization kit will include the complement of the sequences recited in the SEQ ID NO: 1-4. Also preferably, the sequences of the normalization kit will include the sequences recited in SEQ ID NO: 301-303 as these sequences are complementary to SEQ ID NO 1. Also, the normalization kit may also be included in a PTB diagnostic kit as described herein. The normalization kit can include individual compositions that have a single normalization sequence, or a single composition can include one, two, three, or all four of the normalization sequences and/or primers and/or probes thereof. Each sequence may be on a separate nucleic acid, or multiple sequences can be on a single nucleic acid. The normalization sequences can be provided with or without a label, such as a visual label or radiolabel. The normalization sequences can be provided on a customized PCR card or similar device configured for use in nucleic acid detection and/or quantification and/or qualification, which card or similar device can be configured as a high-throughput Real-time Q-PCR system. One or more sample spots on a customized PCR card can have one, two, three, or all four of the normalization sequences and/or the primers and/or probes thereof. For example, the PCR card can have one spot with one normalization sequence or a spot with up to all four normalization sequences and/or primers and/or probes thereof. Such a PCR card can have one or more normalization sequences spots, which spots can be reaction wells or the like. The PCR card may also have assay spots having nucleic acids to be assayed. For example, the customized PCR card can be configured as an ABI high-through put Real-time PCR system. The incorporation of these normalization sequences in the various PCR card products allows them to be more readily used for plasma-derived samples, and in repeated measures of CFP mRNA and CFP miRNA or other nucleic acid normalization.

In one embodiment, a normalization sequence can be a nucleic acid that contains or consists of the sequence. The normalization sequence can be identical to one of SEQ ID NOs: 2-4 for miRNA, and SEQ ID NO 1 for mRNA as well as SEQ ID NOs: 301-303, or can be a complement thereof, sense or antisense, as well as a sequence that hybridizes therewith under suitable conditions. The normalization sequence can have perfect complementarity or greater than or about 95% complementarity, greater than or about 90% complementarity, greater than or about 85% complementarity, or greater than or about 80% complementarity. Complementarity can be considered with respect to a nucleic acid in a biological sample or natural nucleic acid obtained therefrom. The normalization sequence can be a continuous or it can have one or more bulges or mismatches upon hybridization. The normalization sequence can also include one or more chemical modifications, such as a 2' carbon modification. The normalization sequence may or may not form an overhang upon hybridization. The normalization sequence can include a sequence from about 15 nucleotides to the full sequence, from about 16 nucleotides to about 100 nucleotides, from about 17 nucleotides to about 50 nucleotides, from about 18 nucleotides to about 30 nucleotides, from about 19 nucleotides to about 25 nucleotides, or from about 20 to about 22 nucleotides in sequence of one of SEQ ID NOs: 2-3 for miRNA, and SEQ ID 1 for mRNA. The normalization sequence can include a unique sequence segment or complement thereof of the full sequence having a length as described.

In one embodiment, the present invention can include a method of identifying a normalization sequence, such as a pregnancy normalization sequence. The method can include obtaining a plurality of plasma free (e.g., CFP) RNA, CFP mRNA, and/or CFP miRNA sequences from a plurality of subjects (e.g., men or women) prior to a particular disease state (e.g. spontaneous preterm birth in women or prostate cancer in men, without limitation thereto). When pregnant women, the sequences can be obtained prior to or at 32 weeks, 30 weeks, 28 weeks, 26 weeks, 24 weeks, 22 weeks, 20 weeks, 18 weeks, 16, or 12 weeks of pregnancy, and possibly even earlier in pregnancy. Once obtained, one or more CFP mRNA and/or CFP miRNA sequences that are unchanged between disease states (e.g. between two or more women destined for a spontaneous preterm birth of less than 32 weeks) can be identified, and these unchanged sequences can be determined to be normalization sequences. Different disease states can be prior to onset of a disease and then after onset of disease. The identified sequences can be assayed and confirmed to be CFP mRNA and/or CFP miRNA or other CFP RNA that are substantially unchanged between two or more of the samples. The unchanged sequences can be further confirmed to be unchanged between additional sequences. The unchanged sequences can be normalization sequences as described herein.

Another embodiment of a method of identifying a CFP normalization nucleic acid can include obtaining a plurality of plasma free (e.g., CFP) mRNA or miRNA sequences from a plurality of nonpregnant women or pregnant women prior to 32 weeks, such as between about 12-32 weeks of pregnancy. The sequences can be from one woman that is or becomes pregnant or from a plurality of women that are or become pregnant, where one or more sequences can be from a woman that becomes pregnant and that is susceptible to PTB. One or more sequences can even be after birth or after a PTB. After obtained, the sequences can be assayed in order to identify one or more plasma cell free mRNA or miRNA sequences unchanged between different pregnancy states. The different pregnancy states can be between two or more women, or between nonpregnant and pregnant, or between early pregnancy (e.g., before about 16 weeks), or late pregnancy (e.g., after about 16 weeks), or between prior to onset of a PTB-indicating symptom or after a PTB-indicating symptom, or between pregnancy and having or had preterm birth of less than 32 weeks, or combination thereof. The sequences can then be analyzed in order to confirm (e.g., by Qrt-PCR) that the CFP mRNA or miRNA are unchanged between two or more samples having the sequences. The analysis can be between different women or different pregnancy states. Unchanged sequence presence or amount of sequence is indicative that the sequence can be a normalization sequence as described herein.

In another embodiment, a method of identifying CFP normalization nucleic acids or sequences thereof can include: obtaining a plurality of CFP mRNA or CFP miRNA sequences from a plurality of women between 16-28 weeks of pregnancy or prior to birth or PTB; identifying one or more CFP mRNA or miRNA sequences unchanged between two or more women having, had, or that will have PTB of less than 32 weeks; and confirming, by Qrt-PCR, that the CFP mRNA or miRNA is unchanged between two or more samples of CFP RNA and/or CFP miRNA from one or more other women that are un-pregnant, pregnant or two or more women having, had, or that will have PTB of less than 32 weeks. Also, a plurality of CFP RNA can be obtained from women after having a term birth or a PTB.

In one embodiment, the unchanged sequences or possible normalization sequences can be assayed by confirming the sequences to be unchanged or normalization sequences between randomly selected samples.

In one embodiment, the present invention includes a method of quantification of CFP RNA. Such a method can include providing a CFP normalization nucleic acid, and comparing a sample of purified plasma RNA (CFP RNA) from a subject with the CFP normalization sequence, such as a nucleic acid having the normalization sequence. Such a comparison can then be used to determine the amount of CFP RNA in the sample and across two or more samples. Accordingly, different samples from different sources can be normalized using the CFP normalization sequence. One, two, three, or four of the different normalization sequences and/or primers and/or probes thereof can be used for quantification of CFP RNA. The method of quantification of CFP RNA can be performed substantially as known or later developed by using the normalizations sequences described herein.

In another embodiment, a method of normalizing CFP normalization nucleic acids or sequences thereof can include: obtaining a plurality of CFP mRNA or CFP miRNA sequences from a plurality of women between 12 and 32 weeks or 16-28 weeks of pregnancy or prior to birth or PTB; providing one or more CFP mRNA or miRNA sequences unchanged between two or more women having, had, or that will have PTB of less than 32 weeks; and normalizing the CFP mRNA or miRNA sequences with the known unchanged CFP mRNA or miRNA sequences.

In one embodiment, a method of normalizing CFP mRNA or miRNA sequences can include normalizing with one or more of SEQ ID NOs: 1-4 or primer and/or probe thereof or SEQ ID NOs: 301-303 via standard normalization protocols.

The methods described can also include obtaining samples that have RNA from a subject and processing the sample in order to obtain CFP RNA.

PTB Biomarker Sequences

Quantification of PTB biomarker nucleic acids (e.g., RNA) extracted from a biological sample can be used in order to determine whether or not a pregnant woman is susceptible to PTB. Accordingly, identification of PTB biomarkers can be important in order to diagnose PTB susceptibility or predict PTB. The present invention generally includes new RNA biomarkers and processes to identify plasma RNA biomarkers, and use of the RNA biomarkers to identify pre-disease states related to PTB. The present invention can use RNA biomarkers associated with pregnancy disease states in order to predict whether a pregnant women may develop or become susceptible to developing a particular disease state that may cause PTB. Generally, the PTB biomarkers include nucleic acids that are CFP RNA as described herein.

CFP RNA biomarkers can include maternal and fetal derived RNA sequences. Since myometrial activation can result in spontaneous birth, and since myometrial quiescence is a genomically rich period, changes in the CFP transcriptome (e.g., RNA transcriptome) can be used to predict spontaneous PTB. Such a change in the CFP transcriptome can be indicative of PTB regardless of whether the stimulus originated in either the maternal or fetal compartments. The CFP RNA PTB biomarkers have now been identified and are provided in the Sequence Listing as SEQ ID NOs: 5-300. These CFP RNA PTB biomarker sequences are involved in the biological and regulatory process of pregnancy, and modulation of these CFP RNA PTB biomarkers can be an indication of disease. Also, modulation of these CFP RNA PTB biomarker may be used to inhibit, prevent, or treat a disease associated with the particular mRNA or miRNA of the CFP RNA PTB biomarker.

Briefly, CFP mRNA was obtained at 26-28 weeks from 5 randomly selected women destined for PTB (e.g., birth <32 weeks) absent PPROM (i.e., preterm, premature rupture of membranes), and from 5 control women destined for delivery at term. In a 'Discovery Phase' of CFP mRNA identification, the extracted RNA were run on the Affymetrix Human Whole-Transcript Expression Array, and the mRNA sequences altered in women destined for PTB were identified based on fold change (e.g., ≥1.5×, a standard cutoff used across science) and p value from control (p<0.01). The CFP mRNA were ordered by narrowness of distribution (e.g., Ingenuity Systems Pathway Analysis) since a narrow distribution is a highly desirable test characteristic for any selected marker, where the narrower the distribution of disease and normal, the smaller the overlap in population distributions. Of the 25,934 RNA sequences identified to comprise the CFP transcriptome at 26 weeks, 88 CFP mRNA PTB biomarkers were altered in women destined for PTB; 22 CFP mRNA PTB biomarkers (SEQ ID NOs: 19-41) were up-regulated and 66 CFP mRNA (SEQ ID NOs: 42-106) were down-regulated. Genomic mapping revealed the CFP mRNA PTB marker sequences were associated with expression, cell growth and proliferation, cell cycle, cell death, and cellular assembly and organization.

CFP RNA PTB biomarkers can include but are not limited to non-coding RNA, such as miRNA and snRNA and snoRNA, and others are mRNA. In one embodiment, the CFP RNA PTB biomarkers can include a biomarker that indicates susceptibility to PTB. These CFP RNA PTB biomarkers can include: (SEQ ID NO: 19) Homo sapiens taspase, threonine aspartase, 1 (TASP1), mRNA, accession number NM_017714; (SEQ ID NO: 20) Homo sapiens zinc finger protein 99 (ZNF99), mRNA, accession numbers NM_001080409 and XM 001132267; (SEQ ID NO: 21) Homo sapiens cDNA FI116171 fis, clone BRHIP2003272, accession number AK131247; (SEQ ID NO: 22) Homo sapiens regenerating islet-derived 3 gamma (REG3G), transcript variant 1, mRNA, accession number NM_001008387; (SEQ ID NO: 23) Homo sapiens olfactory receptor, family 51, subfamily A, member 2 (OR51A2), mRNA, accession numbers NM_001004748 and XM_377159; (SEQ ID NO: 24) Homo sapiens NADH dehydrogenase (ubiquinone) 1 alpha subcomplex, 2, 8 kDa (NDUFA2), nuclear gene encoding mitochondrial protein, transcript variant 1, mRNA, accession number NM_002488; (SEQ ID NO: 25) Homo sapiens splicing factor 3a, subunit 3, 60 kDa (SF3A3), mRNA, accession number NM_006802; (SEQ ID NO: 26) Homo sapiens late cornified envelope 2A (LCE2A), mRNA, accession number NM_178428; (SEQ ID NO: 27) Homo sapiens S100 calcium binding protein A14 (S100A14), mRNA, accession number NM_020672; (SEQ ID NO: 28) Homo sapiens six transmembrane epithelial antigen of the prostate 1 (STEAP1), mRNA, accession numbers NM_012449 and XM_940149; (SEQ ID NO: 29) Homo sapiens cDNA FLJ11733 fis, clone HEMBA1005426, accession number AK021795; (SEQ ID NO: 30) Homo sapiens speedy homolog E1 (Xenopus laevis) (SPDYE1), mRNA, accession numbers NM_175064, XM_938448, XM_943679, XM_943682, XM_943684, XM_943688, and XM_943692; (SEQ ID NO: 31) Homo sapiens tripartite motif-containing 48 (TRIM48), mRNA, accession number NM_024114; (SEQ ID NO: 32) Homo sapiens non-protein coding RNA 152 (NCRNA00152), transcript variant 1, non-coding RNA, accession numbers NR_024204, XR_042051, and XR_042052; (SEQ ID NO: 33) Homo sapiens cDNA FLJ39739 fis, clone SMINT2016440, accession number AK097058; (SEQ ID NO: 34) Homo sapiens FXYD domain containing ion transport regulator 2 (FXYD2), transcript variant c, mRNA, accession number NM_001127489; (SEQ ID NO: 35) Homo sapiens chromosome 1 open reading frame 104, mRNA (cDNA clone MGC:70363 IMAGE:5183308), complete cds, accession number BC062571; (SEQ ID NO: 36) *Homo sapiens* phosphoserine aminotransferase 1 (PSAT1), transcript variant 1, mRNA, accession number NM_058179; (SEQ ID NO: 37) *Homo sapiens* KIAA1274 (KIAA1274), mRNA, accession numbers NM_014431 and XM_166125; (SEQ ID NO: 38) *Homo sapiens* taste receptor, type 2, member 10 (TAS2R10), mRNA, accession number NM_023921; (SEQ ID NO: 39) *Homo sapiens* ribosomal protein S20 (RPS20), transcript variant 2, mRNA, accession number NM_001023; (SEQ ID NO: 40) *Homo sapiens* glycerol-3-phosphate acyltransferase 2, mitochondrial (GPAT2), nuclear gene encoding mitochondrial protein, mRNA, accession number NM_207328; (SEQ ID NO: 41) *Homo sapiens* hypothetical protein LOC643008 (LOC643008), transcript variant 1, mRNA, accession numbers NM_001162995 and NR_024379; (SEQ ID NO: 42) *Homo sapiens* keratin associated protein 6-2 (KRTAP6-2), mRNA, accession number NM_181604; (SEQ ID NO: 43) *Homo sapiens* saitohin (STH), mRNA, accession number NM_001007532; (SEQ ID NO: 44) *Homo sapiens* olfactory receptor, family 2, subfamily A, member 2 (OR2A2), mRNA, accession number NM_001005480 and XM_498253; (SEQ ID NO: 45) *Homo sapiens* proteinase 3 (PRTN3), mRNA, accession number NM_002777; (SEQ ID NO: 46) *Homo sapiens* pregnancy specific beta-1-glycoprotein 9 (PSG9), mRNA, accession number NM_002784; (SEQ ID NO: 47) *Homo sapiens* guanylate cyclase activator 2B (uroguanylin) (GUCA2B), mRNA, accession number NM_007102; (SEQ ID NO: 48) *Homo sapiens* armadillo repeat containing 10 (ARMC10), transcript variant A, mRNA, accession number NM_031905; (SEQ ID NO: 49) *Homo sapiens* chromosome 11 open reading frame 59 (C11orf59), mRNA, accession number NM_017907; (SEQ ID NO: 50) *Homo sapiens* coiled-coil-helix-coiled-coil-helix domain containing 10, (CHCHD10), mRNA, accession number NM_213720; (SEQ ID NO: 51) *Homo sapiens* 2-oxoglutarate and iron-dependent oxygenase domain containing 2 (OGFOD2), mRNA, accession number NM_024623; (SEQ ID NO: 52) *Homo sapiens* biogenesis of lysosomal organelles complex-1, subunit 1 (BLOC1S1), mRNA, accession number NM_001487; (SEQ ID NO: 53) *Homo sapiens* apolipoprotein A-I (APOA1), mRNA, accession number NM_000039; (SEQ ID NO: 54) *Homo sapiens* CD3e molecule, epsilon (CD3-TCR complex) (CD3E), mRNA, accession number NM_000733; (SEQ ID NO: 55) *Homo sapiens* keratinocyte differentiation-associated protein (KRTDAP), mRNA, accession number NM_207392; (SEQ ID NO: 56) *Homo sapiens* PDZ domain containing 1 (PDZK1), mRNA, accession numbers NM_002614, XM_936907, XM_943050, XM_943061, and XM_943068; (SEQ ID NO: 57) *Homo sapiens* N-acetyltransferase 14 (GCN5-related, putative) (NAT14), mRNA, accession number NM_020378; (SEQ ID NO: 58) *Homo sapiens* keratin 17 (KRT17), mRNA, accession number NM_000422; (SEQ ID NO: 59) *Homo sapiens* ribosomal protein S19 binding protein 1 (RPS19BP1), mRNA, accession numbers NM_194326 and XM_039373; (SEQ ID NO: 60) *Homo sapiens* transmembrane protein 188 (TMEM188), mRNA, accession number NM_153261; (SEQ ID NO: 61) *Homo sapiens* cysteine and glycine-rich protein 2 (CSRP2), mRNA, accession number NM_001321; (SEQ ID NO: 62) *Homo sapiens* olfactory receptor, family 4, subfamily D, member 1 (OR4D1), mRNA, accession numbers NM_012374 and XM_292627; (SEQ ID NO: 63) *Homo sapiens* ribosomal protein L8 (RPL8), transcript variant 1, mRNA, accession number NM_000973; (SEQ ID NO: 64) *Homo sapiens* tumor necrosis factor receptor superfamily, member 13C (TNFRSF13C), mRNA, accession number NM_052945; (SEQ ID NO: 65) *Homo sapiens* mitochondrial ribosomal protein S21 (MRPS21), nuclear gene encoding mitochondrial protein, transcript variant 2, mRNA, accession number NM_018997; (SEQ ID NO: 66) *Homo sapiens* apolipoprotein A-IV (APOA4), mRNA, accession number NM_000482; (SEQ ID NO: 67) *Homo sapiens* junctional sarcoplasmic reticulum protein 1 (JSRP1), mRNA, accession number NM_144616; (SEQ ID NO: 68) *Homo sapiens* proteasome (prosome, macropain) activator subunit 2 (PA28 beta) (PSME2), mRNA, accession number NM_002818; (SEQ ID NO: 69) *Homo sapiens* zinc finger and BTB domain containing 5 (ZBTB5), mRNA, accession number NM_014872 and XM_376832; (SEQ ID NO: 70) *Homo sapiens* chromosome 10 open reading frame 95, mRNA (cDNA clone MGC:161737 IMAGE:8992175), complete cds, accession number, BC126459; (SEQ ID NO: 71) *Homo sapiens* nicotinamide phosphoribosyltransferase (NAMPT), mRNA, accession number NM_005746; (SEQ ID NO: 72) *Homo sapiens* trace amine associated receptor 6 (TAAR6), mRNA, accession number, NM_175067; (SEQ ID NO: 73) *Homo sapiens* myosin, light chain 6, alkali, smooth muscle and non-muscle (MYL6), transcript variant 1, mRNA, accession numbers NM_021019 and NM_079424; (SEQ ID NO: 74) *Homo sapiens* ATP synthase, H+ transporting, mitochondrial Fo complex, subunit C2 (subunit 9) (ATP5G2), nuclear gene encoding mitochondrial protein, transcript variant 2, mRNA, accession number NM_005176; (SEQ ID NO: 75) *Homo sapiens* family with sequence similarity 18, member B2 (FAM18B2), transcript variant 1, mRNA, accession numbers NM_145301 and XM_936923; (SEQ ID NO: 76) *Homo sapiens* Sp6 transcription factor (SP6), mRNA, accession numbers NM_199262 and XM_292621; (SEQ ID NO: 77) *Homo sapiens* inverted formin, FH2 and WH2 domain containing (INF2), transcript variant 1, mRNA, accession number NM_022489; (SEQ ID NO: 78) *Homo sapiens* Rho GDP dissociation inhibitor (GDI) alpha (ARHGDIA), transcript variant 2, mRNA, accession number NM_004309; (SEQ ID NO: 79) *Homo sapiens* OTU domain containing 6A (OTUD6A), mRNA, accession number NM_207320; (SEQ ID NO: 80) *Homo sapiens* zinc finger and BTB domain containing 12 (ZBTB12), mRNA, accession number NM_181842; (SEQ ID NO: 81) *Homo sapiens* mitotic spindle organizing protein 2B (MZT2B), mRNA, accession number NM_025029; (SEQ ID NO: 82) *Homo sapiens* olfactory receptor, family 52, subfamily E, member 2 (OR52E2), mRNA, accession number NM_001005164 and XM_061610; (SEQ ID NO: 83) *Homo sapiens* hypothetical LOC150622 (LOC150622), non-coding RNA, accession number NR_026832, XR_041760, XR_041761, and XR_041762; (SEQ ID NO: 84) *Homo sapiens* selenophosphate synthetase 1 (SEPHS1), transcript variant 1, mRNA, accession number NM_012247; (SEQ ID NO: 85) *Homo sapiens* barrier to autointegration factor 1 (BANF1), transcript variant 1, mRNA, accession number NM_003860; (SEQ ID NO: 86) *Homo sapiens* general transcription factor IIB (GTF2B), mRNA, accession number NM_001514; (SEQ ID NO: 87) *Homo sapiens* RGM domain family, member A (RGMA), transcript variant 4, mRNA, accession number NM_020211; (SEQ ID NO: 88) *Homo sapiens* prolactin releasing hormone receptor (PRLHR), mRNA, accession number NM_004248 and NM_005287; (SEQ ID NO: 89) *Homo sapiens* dpy-19-like 2 pseudogene 2 (*C. elegans*) (DPY19L2P2), transcript variant 2, non-coding RNA, accession number NR_003561; (SEQ ID NO: 90) *Homo sapiens* meteorin, glial cell differentiation regulator (METRN), mRNA, accession number NM_024042; (SEQ ID NO: 91) *Homo sapiens* free fatty acid receptor 1 (FFAR1), mRNA, accession number NM_005303; (SEQ ID NO: 92) *Homo sapiens* natriuretic peptide B (NPPB), mRNA, accession number NM_002521; (SEQ ID NO: 93) *Homo sapiens* BCL2/adenovirus E1B 19 kDa interacting protein 3 (BNIP3), nuclear gene encoding mitochondrial protein, mRNA, accession number NM_004052; (SEQ ID NO: 94) *Homo sapiens* basic helix-loop-helix family, member a15 (BHLHA15), mRNA, accession number NM_177455; (SEQ ID NO: 95) *Homo sapiens* Finkel-Biskis-Reilly murine sarcoma virus (FBR-MuSV) ubiquitously expressed (FAU), mRNA, accession number NM_001997; (SEQ ID NO: 96) *Homo sapiens* chromosome 9 open reading frame 70 (C9orf70), non-coding RNA, accession number NR_026663 and XM_001721481 XM_001723928 XM_001724353; (SEQ ID NO: 97) *Homo sapiens* ribosomal protein L30 (RPL30), mRNA, accession number NM_000989; (SEQ ID NO: 98) *Homo sapiens* meteorin, glial cell differentiation regulator-like (METRNL), mRNA, accession number NM_001004431 and XM_209073; (SEQ ID NO: 99) *Homo sapiens* ubiquitin-like 5 (UBL5), transcript variant 1, mRNA, accession number NM_024292; (SEQ ID NO: 100) *Homo sapiens* potassium inwardly-rectifying channel, subfamily J, member 4, (KCNJ4), transcript variant 1, mRNA, accession number NM_152868; (SEQ ID NO: 101) *Homo sapiens* nascent polypeptide-associated complex alpha subunit (NACA), transcript variant 1, mRNA, accession number NM_001113203; (SEQ ID NO: 102) *Homo sapiens* small EDRK-rich factor 2 (SERF2), mRNA, accession number NM_001018108; (SEQ ID NO: 103) *Homo sapiens* sulfotransferase family, cytosolic, 1A, phenol-preferring, member 2 (SULT1A2), transcript variant 2, mRNA, accession number NM_177528; (SEQ ID NO: 104) *Homo sapiens* olfactory receptor, family 51, subfamily G, member 2 (OR51G2), mRNA, accession number NM_001005238; (SEQ ID NO: 105) *Homo sapiens* basic transcription factor 3 (BTF3), transcript variant 1, mRNA, accession number NM_001037637; and (SEQ ID NO: 106) *Homo sapiens* LSM10, U7 small nuclear RNA associated (LSM10), mRNA, accession number NM_032881, which accession numbers and information associated therewith are incorporated herein by specific reference.

In one embodiment, the CFP RNA PTB biomarkers can include a biomarker that is up-regulated in order to indicate susceptibility to PTB having SEQ ID NOs: 107-142, wherein the Probset ID, accession numbers, Gene Symbols, and start and stop of the sequences thereof are incorporated herein by specific reference:

| SEQ ID NO: | # | Probeset ID | Gene Symbol | RefSeq (Accession) | Seqname | Start | Stop |
| --- | --- | --- | --- | --- | --- | --- | --- |
| SEQ ID NO: | 107 | 2391026 | C1orf159 | BC008788 | chr1 | 1020631 | 1020674 |
| SEQ ID NO: | 108 | 2465373 | AHCTF1 | NM_015446 | chr1 | 247063497 | 247063521 |
| SEQ ID NO: | 109 | 2321026 | C1orf158 | NM_152290 | chr1 | 12821062 | 12821086 |
| SEQ ID NO: | 110 | 2370564 | CACNA1E | NM_000721 | chr1 | 181705411 | 181705435 |
| SEQ ID NO: | 111 | 2445415 | ASTN1 | NM_004319 | chr1 | 176927594 | 176927618 |
| SEQ ID NO: | 112 | 2383404 | ADCK3 | NM_020247 | chr1 | 227165195 | 227165219 |
| SEQ ID NO: | 113 | 3314648 | C10orf92 | BC034223 | chr10 | 134628211 | 134628236 |
| SEQ ID NO: | 114 | 3332991 | C11orf66 | NM_145017 | chr11 | 61257978 | 61258037 |
| SEQ ID NO: | 115 | 3377201 | CDC42BPG | NM_017525 | chr11 | 64601758 | 64601797 |
| SEQ ID NO: | 116 | 3381279 | ARAP1 | BC056401 | chr11 | 72411090 | 72411124 |
| SEQ ID NO: | 117 | 3403055 | ATN1 | NM_001007026 | chr12 | 7045236 | 7045261 |
| SEQ ID NO: | 118 | 3655114 | CD19 | NM_001178098 | chr16 | 28943903 | 28943933 |
| SEQ ID NO: | 119 | 3739970 | ABR | NM_021962 | chr17 | 913969 | 913994 |
| SEQ ID NO: | 120 | 3774020 | C17orf70 | NR_033338 | chr17 | 79518798 | 79518881 |
| SEQ ID NO: | 121 | 3774725 | CCDC57 | ENST00000324808 | chr17 | 80109446 | 80109470 |
| SEQ ID NO: | 122 | 3741735 | CAMKK1 | AF370377 | chr17 | 3773035 | 3773059 |
| SEQ ID NO: | 123 | 3830886 | ARHGAP33 | NM_052948 | chr19 | 36273687 | 36273769 |
| SEQ ID NO: | 124 | 3835887 | APOE | NM_000041 | chr19 | 45412388 | 45412412 |
| SEQ ID NO: | 125 | 3866306 | AP2S1 | NM_004069 | chr19 | 47342008 | 47342032 |
| SEQ ID NO: | 126 | 2546857 | CAPN13 | NM_144575 | chr2 | 30993219 | 30993282 |
| SEQ ID NO: | 127 | 2576644 | C2orf27B | BC043584 | chr2 | 132552867 | 132552917 |
| SEQ ID NO: | 128 | 2546826 | CAPN13 | NM_144575 | chr2 | 30961299 | 30961323 |
| SEQ ID NO: | 129 | 2708707 | C3orf70 | NM_001025266 | chr3 | 184870647 | 184870677 |
| SEQ ID NO: | 130 | 2622179 | BSN | NM_003458 | chr3 | 49699843 | 49699867 |
| SEQ ID NO: | 131 | 2870730 | BCLAF1 | NM_014739 | chr5 | 110285528 | 110285604 |
| SEQ ID NO: | 132 | 2902959 | C4A | ENST00000428956 | chr6 | 31949811 | 31949835 |
| SEQ ID NO: | 133 | 2953468 | C6orf130 | ENST00000488238 | chr6 | 41043021 | 41043070 |
| SEQ ID NO: | 134 | 3031798 | ABCB8 | NM_007188 | chr7 | 150744493 | 150744517 |
| SEQ ID NO: | 135 | 3039763 | ANKMY2 | NM_020319 | chr7 | 16666684 | 16666799 |
| SEQ ID NO: | 136 | 3023426 | AHCYL2 | NM_001130723 | chr7 | 129008311 | 129008335 |
| SEQ ID NO: | 137 | 3031951 | AGAP3 | NM_031946 | chr7 | 150841064 | 150841088 |
| SEQ ID NO: | 138 | 3031944 | AGAP3 | AL442089 | chr7 | 150838958 | 150838982 |
| SEQ ID NO: | 139 | 3206269 | ATP5A1 | NM_001001937 | chr9 | 41799773 | 41799797 |
| SEQ ID NO: | 140 | 4001353 | BEND2 | NM_153346 | chrX | 18221855 | 18222031 |
| SEQ ID NO: | 141 | 3969900 | CA5B | ENST00000479740 | chrX | 15768063 | 15768093 |
| SEQ ID NO: | 142 | 3966810 | CD99P1 | NR_033380 | chrX | 2541426 | 12541450 |

In one embodiment, the CFP RNA PTB biomarkers can include a biomarker that is down-regulated in order to indicate susceptibility to PTB, wherein the Probset ID, accession numbers, Gene Symbols, and start and stop of the sequences thereof are incorporated herein by specific reference:

| SEQ ID NO: | # | Probeset ID | Gene Symbol | RefSeq (Accession) | Seqname | start | stop |
|---|---|---|---|---|---|---|---|
| SEQ ID NO: | 143 | 2434348 | APH1A | AK125685 | chr1 | 150239436 | 150239470 |
| SEQ ID NO: | 144 | 2347527 | ABCD3 | NM_001122674 | chr1 | 94944215 | 94944239 |
| SEQ ID NO: | 145 | 2347504 | ABCD3 | NM_002858 | chr1 | 94884035 | 94884129 |
| SEQ ID NO: | 146 | 2347024 | CCDC18 | NM_206886 | chr1 | 93645587 | 93645967 |
| SEQ ID NO: | 147 | 2383766 | ARF1 | NM_001024227 | chr1 | 228286406 | 228286440 |
| SEQ ID NO: | 148 | 2411671 | AGBL4 | ENST00000411952 | chr1 | 49052585 | 49052609 |
| SEQ ID NO: | 149 | 2316059 | ATAD3A | NM_018188 | chr1 | 1469347 | 1469376 |
| SEQ ID NO: | 150 | 2391349 | ACAP3 | AB051503 | chr1 | 1240376 | 1240469 |
| SEQ ID NO: | 151 | 2385702 | C1orf57 | NM_032324 | chr1 | 233086457 | 233086481 |
| SEQ ID NO: | 152 | 2393833 | C1orf174 | NM_207356 | chr1 | 3816811 | 3816835 |
| SEQ ID NO: | 153 | 2440696 | B4GALT3 | NM_003779 | chr1 | 161147290 | 161147314 |
| SEQ ID NO: | 154 | 2383363 | ADCK3 | ENST00000366779 | chr1 | 227096295 | 227096344 |
| SEQ ID NO: | 155 | 2318458 | CAMTA1 | NM_015215 | chr1 | 6845541 | 6845635 |
| SEQ ID NO: | 156 | 2392132 | C1orf86 | ENST00000378545 | chr1 | 2130199 | 2130245 |
| SEQ ID NO: | 157 | 2399312 | ALDH4A1 | NM_003748 | chr1 | 19199312 | 19199336 |
| SEQ ID NO: | 158 | 3286039 | CCNYL2 | ENST00000345581 | chr10 | 42965620 | 42965646 |
| SEQ ID NO: | 159 | 3282296 | ACBD5 | ENST00000375888 | chr10 | 27529434 | 27529579 |
| SEQ ID NO: | 160 | 3261217 | BTRC | NM_033637 | chr10 | 103285926 | 103285955 |
| SEQ ID NO: | 161 | 3284165 | C1D | NM_173177 | chr10 | 32800666 | 32800698 |
| SEQ ID NO: | 162 | 3245187 | ANXA8L2 | NM_001630 | chr10 | 47747028 | 47747107 |
| SEQ ID NO: | 163 | 3251356 | ANAPC16 | NM_173473 | chr10 | 73975872 | 73975896 |
| SEQ ID NO: | 164 | 3380994 | C11orf59 | NM_017907 | chr11 | 71814234 | 71814263 |
| SEQ ID NO: | 165 | 3353451 | C11orf63 | NM_024806 | chr11 | 122774660 | 122774979 |
| SEQ ID NO: | 166 | 3370889 | ALX4 | NM_021926 | chr11 | 44296901 | 44297069 |
| SEQ ID NO: | 167 | 3364964 | ABCC8 | NM_000352 | chr11 | 17453766 | 17453791 |
| SEQ ID NO: | 168 | 3377365 | BATF2 | NM_138456 | chr11 | 64757241 | 64757266 |
| SEQ ID NO: | 169 | 3351287 | CD3E | NM_000733 | chr11 | 118175668 | 118175692 |
| SEQ ID NO: | 170 | 3323765 | ANO5 | NM_213599 | chr11 | 22215039 | 22215069 |
| SEQ ID NO: | 171 | 3352074 | CBL | NM_005188 | chr11 | 119077128 | 119077154 |
| SEQ ID NO: | 172 | 3332702 | CD6 | NM_006725 | chr11 | 60785827 | 60785851 |
| SEQ ID NO: | 173 | 3378518 | C1QBP | NM_001212 | chr11 | 66529422 | 66529450 |
| SEQ ID NO: | 174 | 3334998 | CAPN1 | NM_005186 | chr11 | 64978760 | 64978949 |
| SEQ ID NO: | 175 | 3316546 | AP2A2 | NM_012305 | chr11 | 1010548 | 1010572 |
| SEQ ID NO: | 176 | 3358122 | C11orf35 | NM_173573 | chr11 | 556268 | 556374 |
| SEQ ID NO: | 177 | 3457551 | ANKRD52 | NM_173595 | chr12 | 56631722 | 56631752 |
| SEQ ID NO: | 178 | 3440081 | CACNA2D4 | NM_172364 | chr12 | 1909167 | 1909199 |
| SEQ ID NO: | 179 | 3431564 | C12orf24 | AK297684 | chr12 | 110924538 | 110924563 |
| SEQ ID NO: | 180 | 3434501 | CABP1 | NM_031205 | chr12 | 121088358 | 121088431 |
| SEQ ID NO: | 181 | 3435685 | ARL6IP4 | NM_018694 | chr12 | 123466154 | 123466179 |
| SEQ ID NO: | 182 | 3413611 | CACNB3 | NM_000725 | chr12 | 49212713 | 49212756 |
| SEQ ID NO: | 183 | 3523859 | C13orf27 | NM_138779 | chr13 | 103418821 | 103418856 |
| SEQ ID NO: | 184 | 3573232 | ALKBH1 | NM_006020 | chr14 | 78140155 | 78140183 |
| SEQ ID NO: | 185 | 3563711 | C14orf138 | NM_024558 | chr14 | 50583243 | 50583268 |
| SEQ ID NO: | 186 | 3543628 | C14orf169 | NM_024644 | chr14 | 73957998 | 73958031 |
| SEQ ID NO: | 187 | 3576909 | ATXN3 | NR_028453 | chr14 | 92547321 | 92547345 |
| SEQ ID NO: | 188 | 3557166 | ACIN1 | NM_014977 | chr14 | 23564322 | 23564348 |
| SEQ ID NO: | 189 | 3604597 | ADAMTS7 | NM_014272 | chr15 | 82611989 | 82612090 |
| SEQ ID NO: | 190 | 3601544 | CCDC33 | NM_025055 | chr15 | 74536429 | 74536486 |
| SEQ ID NO: | 191 | 3605931 | ALPK3 | NM_020778 | chr15 | 85411431 | 85411647 |
| SEQ ID NO: | 192 | 3619410 | C15orf52 | NM_207380 | chr15 | 40627985 | 40628027 |
| SEQ ID NO: | 193 | 3605398 | ADAMTSL3 | NM_207517 | chr15 | 84324481 | 84324513 |
| SEQ ID NO: | 194 | 3636496 | BTBD1 | NM_025238 | chr15 | 83735879 | 83735903 |
| SEQ ID NO: | 195 | 3628544 | CA12 | NM_001218 | chr15 | 63637686 | 63637806 |
| SEQ ID NO: | 196 | 3601237 | CD276 | NM_001024736 | chr15 | 73992032 | 73992056 |
| SEQ ID NO: | 197 | 3607736 | C15orf42 | NM_152259 | chr15 | 90167064 | 90167094 |
| SEQ ID NO: | 198 | 3620776 | CDAN1 | NM_138477 | chr15 | 43026443 | 43026535 |
| SEQ ID NO: | 199 | 3619407 | C15orf52 | NM_207380 | chr15 | 40627389 | 40627585 |
| SEQ ID NO: | 200 | 3617732 | ACTC1 | NM_005159 | chr15 | 35084610 | 35084634 |
| SEQ ID NO: | 201 | 3619427 | C15orf52 | AK126485 | chr15 | 40631674 | 40631701 |
| SEQ ID NO: | 202 | 3655082 | ATP2A1 | NM_173201 | chr16 | 28909568 | 28909754 |
| SEQ ID NO: | 203 | 3656848 | BCKDK | NM_001122957 | chr16 | 31123381 | 31123415 |
| SEQ ID NO: | 204 | 3695322 | CDH16 | NM_004062 | chr16 | 66944302 | 66944327 |
| SEQ ID NO: | 205 | 3704743 | ANKRD11 | NM_013275 | chr16 | 89351849 | 89352020 |
| SEQ ID NO: | 206 | 3662891 | CCDC135 | NM_032269 | chr16 | 57738788 | 57738820 |
| SEQ ID NO: | 207 | 3687096 | BOLA2 | NM_001031827 | chr16 | 30204743 | 30204770 |
| SEQ ID NO: | 208 | 3686627 | APOB48R | NM_018690 | chr16 | 28507548 | 28507572 |
| SEQ ID NO: | 209 | 3770812 | CASKIN2 | NM_020753 | chr17 | 73499499 | 73499557 |
| SEQ ID NO: | 210 | 3767486 | AXIN2 | NM_004655 | chr17 | 63533032 | 63533167 |
| SEQ ID NO: | 211 | 3742217 | ALOX15 | NM_001140 | chr17 | 4535481 | 4535558 |
| SEQ ID NO: | 212 | 3742483 | CAMTA2 | NM_015099 | chr17 | 4876890 | 4877042 |
| SEQ ID NO: | 213 | 3764300 | BZRAP1 | BX648763 | chr17 | 56382268 | 56382298 |
| SEQ ID NO: | 214 | 3722682 | C17orf88 | NR_026770 | chr17 | 41994608 | 41994632 |
| SEQ ID NO: | 215 | 3766544 | CD79B | NM_000626 | chr17 | 62008702 | 62008726 |
| SEQ ID NO: | 216 | 3748962 | ALDH3A1 | NM_001135168 | chr17 | 19641470 | 19641494 |

-continued

| SEQ ID NO: | # | Probeset ID | Gene Symbol | RefSeq (Accession) | Seqname | start | stop |
|---|---|---|---|---|---|---|---|
| SEQ ID NO: | 217 | 3774985 | C17orf101 | NR_033265 | chr17 | 80350291 | 80350395 |
| SEQ ID NO: | 218 | 3764359 | BZRAP1 | NM_004758 | chr17 | 56404109 | 56404137 |
| SEQ ID NO: | 219 | 3774706 | CCDC57 | NM_198082 | chr17 | 80059693 | 80059731 |
| SEQ ID NO: | 220 | 3773685 | AZI1 | NM_014984 | chr17 | 79172707 | 79172736 |
| SEQ ID NO: | 221 | 3773633 | AATK | ENST00000417379 | chr17 | 79105718 | 79105746 |
| SEQ ID NO: | 222 | 3848059 | C3 | NM_000064 | chr19 | 6684786 | 6684810 |
| SEQ ID NO: | 223 | 3866980 | CARD8 | NM_001184900 | chr19 | 48715191 | 48715220 |
| SEQ ID NO: | 224 | 3850462 | AP1M2 | NM_005498 | chr19 | 10685580 | 10685611 |
| SEQ ID NO: | 225 | 3854387 | ANO8 | NM_020959 | chr19 | 17439225 | 17439281 |
| SEQ ID NO: | 226 | 3837683 | C19orf68 | BC043386 | chr19 | 48700487 | 48700516 |
| SEQ ID NO: | 227 | 3867278 | CA11 | NM_001217 | chr19 | 49143358 | 49143452 |
| SEQ ID NO: | 228 | 3865986 | CCDC8 | NM_032040 | chr19 | 46916087 | 46916262 |
| SEQ ID NO: | 229 | 3846260 | C19orf28 | NM_021731 | chr19 | 3557104 | 3557128 |
| SEQ ID NO: | 230 | 3868520 | ASPDH | NM_001114598 | chr19 | 51014987 | 51015030 |
| SEQ ID NO: | 231 | 3860221 | ALKBH6 | NM_198867 | chr19 | 36502307 | 36502333 |
| SEQ ID NO: | 232 | 3815214 | AZU1 | NM_001700 | chr19 | 828320 | 828371 |
| SEQ ID NO: | 233 | 3817205 | ATCAY | NM_033064 | chr19 | 3917745 | 3917775 |
| SEQ ID NO: | 234 | 3846377 | APBA3 | NM_004886 | chr19 | 3754199 | 3754228 |
| SEQ ID NO: | 235 | 3830369 | CD22 | NM_001771 | chr19 | 35823497 | 35823523 |
| SEQ ID NO: | 236 | 3842076 | BRSK1 | NM_032430 | chr19 | 55805471 | 55805501 |
| SEQ ID NO: | 237 | 3852137 | CACNA1A | NM_000068 | chr19 | 13318294 | 13318431 |
| SEQ ID NO: | 238 | 3824734 | ARRDC2 | NM_015683 | chr19 | 18121452 | 18121479 |
| SEQ ID NO: | 239 | 3834055 | AXL | NM_021913 | chr19 | 41737096 | 41737140 |
| SEQ ID NO: | 240 | 3846299 | C19orf29 | NM_001080543 | chr19 | 3613163 | 3613278 |
| SEQ ID NO: | 241 | 3836141 | BLOC1S3 | NM_212550 | chr19 | 45683121 | 45683155 |
| SEQ ID NO: | 242 | 3832352 | CATSPERG | NM_021185 | chr19 | 38852853 | 38852886 |
| SEQ ID NO: | 243 | 3843980 | A1BG-AS | BC040926 | chr19 | 58864701 | 58864725 |
| SEQ ID NO: | 244 | 3846310 | C19orf29 | NM_001080543 | chr19 | 3620730 | 3620754 |
| SEQ ID NO: | 245 | 3839117 | ATF5 | NM_012068 | chr19 | 50436321 | 50436349 |
| SEQ ID NO: | 246 | 2521240 | CCDC150 | NM_001080539 | chr2 | 197504344 | 197504405 |
| SEQ ID NO: | 247 | 2474325 | C2orf28 | NM_016085 | chr2 | 27435237 | 27435334 |
| SEQ ID NO: | 248 | 2574650 | BIN1 | NM_139343 | chr2 | 127808094 | 127808098 |
| SEQ ID NO: | 249 | 2473975 | C2orf18 | NM_017877 | chr2 | 27001867 | 27001894 |
| SEQ ID NO: | 250 | 2500292 | BCL2L11 | AB071199 | chr2 | 111887709 | 111887791 |
| SEQ ID NO: | 251 | 2505925 | ARHGEF4 | NM_015320 | chr2 | 131804327 | 131804358 |
| SEQ ID NO: | 252 | 2532302 | ALPPL2 | NM_031313 | chr2 | 233272604 | 233272635 |
| SEQ ID NO: | 253 | 2536644 | BOK | NM_032515 | chr2 | 242512472 | 242512497 |
| SEQ ID NO: | 254 | 2566556 | C2orf55 | NM_207362 | chr2 | 99454585 | 99454610 |
| SEQ ID NO: | 255 | 2532289 | ALPP | NM_001632 | chr2 | 233246242 | 233246266 |
| SEQ ID NO: | 256 | 2604401 | ARL4C | NM_005737 | chr2 | 235404210 | 235404234 |
| SEQ ID NO: | 257 | 3874441 | CDC25B | NM_021873 | chr20 | 3776523 | 3776523 |
| SEQ ID NO: | 258 | 3882227 | BPIL3 | NM_174897 | chr20 | 31625440 | 31625473 |
| SEQ ID NO: | 259 | 3894422 | ANGPT4 | NM_015985 | chr20 | 865725 | 865751 |
| SEQ ID NO: | 260 | 3874383 | ATRN | NM_139321 | chr20 | 3614963 | 3615036 |
| SEQ ID NO: | 261 | 3892803 | C20orf200 | NR_033263 | chr20 | 61142540 | 61142567 |
| SEQ ID NO: | 262 | 3914081 | ARFRP1 | NM_001134758 | chr20 | 62331883 | 62331908 |
| SEQ ID NO: | 263 | 3882563 | CBFA2T2 | NM_005093 | chr20 | 32194762 | 32194787 |
| SEQ ID NO: | 264 | 3907034 | ADA | NM_000022 | chr20 | 43280223 | 43280248 |
| SEQ ID NO: | 265 | 3926166 | C21orf91 | ENST00000405964 | chr21 | 19191195 | 19191284 |
| SEQ ID NO: | 266 | 3932407 | C21orf88 | NR_026542 | chr21 | 40984265 | 40984292 |
| SEQ ID NO: | 267 | 3922457 | ABCG1 | NM_016818 | chr21 | 43639267 | 43639291 |
| SEQ ID NO: | 268 | 3918143 | C21orf63 | AK126660 | chr21 | 33829548 | 33829572 |
| SEQ ID NO: | 269 | 3951118 | ACR | ENST00000216139 | chr22 | 51176638 | 51176663 |
| SEQ ID NO: | 270 | 3946042 | CACNA1I | NM_021096 | chr22 | 40081973 | 40082331 |
| SEQ ID NO: | 271 | 3955347 | C22orf13 | ENST00000407973 | chr22 | 24951587 | 24951829 |
| SEQ ID NO: | 272 | 2644874 | BPESC1 | NR_026783 | chr3 | 138824138 | 138824168 |
| SEQ ID NO: | 273 | 2641457 | CCDC48 | NM_024768 | chr3 | 128751742 | 128751767 |
| SEQ ID NO: | 274 | 2627379 | C3orf49 | NR_026866 | chr3 | 63830699 | 63830723 |
| SEQ ID NO: | 275 | 2624738 | CACNA2D3 | NM_018398 | chr3 | 54913057 | 54913081 |
| SEQ ID NO: | 276 | 2681152 | C3orf64 | AK304102 | chr3 | 69062765 | 69062816 |
| SEQ ID NO: | 277 | 2687780 | CD47 | NM_001777 | chr3 | 107769425 | 107769449 |
| SEQ ID NO: | 278 | 2719502 | CC2D2A | NM_001080522 | chr4 | 15504114 | 15504140 |
| SEQ ID NO: | 279 | 2852783 | C1QTNF3 | NM_030945 | chr5 | 34033484 | 34033517 |
| SEQ ID NO: | 280 | 2881766 | ANXA6 | NM_001155 | chr5 | 150496698 | 150496722 |
| SEQ ID NO: | 281 | 2842463 | C5orf25 | AK126204 | chr5 | 175721931 | 175722032 |
| SEQ ID NO: | 282 | 2878396 | APBB3 | AK125244 | chr5 | 139943693 | 139943736 |
| SEQ ID NO: | 283 | 4047621 | BTNL8 | NM_024850 | chr5 | 180375920 | 180375946 |
| SEQ ID NO: | 284 | 2901692 | ABCF1 | NM_001025091 | chr6 | 30545599 | 30545665 |
| SEQ ID NO: | 285 | 2973284 | C6orf174 | NM_001012279 | chr6 | 127837554 | 127837578 |
| SEQ ID NO: | 286 | 2937603 | C6orf70 | NM_018341 | chr6 | 170175406 | 170175442 |
| SEQ ID NO: | 287 | 2999777 | AEBP1 | NM_001129 | chr7 | 44148940 | 44148940 |
| SEQ ID NO: | 288 | 3001005 | ABCA13 | NM_152701 | chr7 | 48285460 | 48285484 |
| SEQ ID NO: | 289 | 3017084 | ARMC10 | NM_031905 | chr7 | 102716226 | 102716250 |
| SEQ ID NO: | 290 | 3006668 | AUTS2 | NM_015570 | chr7 | 69599533 | 69599557 |
| SEQ ID NO: | 291 | 3158462 | C8ORFK29 | NR_015428 | chr8 | 145577092 | 145577180 |
| SEQ ID NO: | 292 | 3121027 | C8orf33 | NM_023080 | chr8 | 146278059 | 146278089 |
| SEQ ID NO: | 293 | 3105606 | CA2 | ENST00000285379 | chr8 | 86376123 | 86376148 |

-continued

| SEQ ID NO: | # | Probeset ID | Gene Symbol | RefSeq (Accession) | Seqname | start | stop |
|---|---|---|---|---|---|---|---|
| SEQ ID NO: | 294 | 3204670 | CD72 | ENST00000396759 | chr9 | 35618756 | 35618861 |
| SEQ ID NO: | 295 | 3221925 | AKNA | NM_030767 | chr9 | 117103978 | 117104002 |
| SEQ ID NO: | 296 | 3223849 | C5 | NM_001735 | chr9 | 123812463 | 123812487 |
| SEQ ID NO: | 297 | 3190991 | C9orf106 | NM_001012715 | chr9 | 132083295 | 132083325 |
| SEQ ID NO: | 298 | 3222599 | ASTN2 | NM_198186 | chr9 | 119449350 | 119449382 |
| SEQ ID NO: | 299 | 3229062 | BRD3 | NM_007371 | chr9 | 136905156 | 136905186 |
| SEQ ID NO: | 300 | 3986675 | ATG4A | ENST00000457035 | chrX | 107335082 | 107335109 |

An investigation was conducted to determine whether or not specific miRNA could be PTB biomarkers. The same total RNA extracted from the 26-28 week samples, described above, were run on the Affymetrix GeneChip non-coding small RNA array (e.g., 847 human non-coding small RNAs including miRNA, siRNA, snRNA, snoRNA, etc), and only miRNA altered in women destined for PTB were identified by fold change (e.g., ≥1.5×) and p value from control (p<0.01). The miRNA were ordered by narrowness of distribution (e.g., Affymetrix miRNA QC Tool and Ingenuity Systems Pathway Analysis). Of the 847 non-coding small RNA, only 14 were altered at 26 weeks in women destined for PTB; 3 CFP miRNA increased or were up-regulated (e.g., miRNA-548L (SEQ ID NO: 5), miRNA-99a (SEQ ID NO: 6), and miRNA-99b (SEQ ID NO: 7)); and 10 CFP miRNA decreased or were down-regulated (e.g., miRNA-382 (SEQ ID NO:8), miRNA-491 (SEQ ID NO: 9), miNRA-214 (SEQ ID NO: 10), miRNA-31 (SEQ ID NO: 11), miRNA-342 (SEQ ID NO: 12), miRNA-let-7g (SEQ ID NO: 13), miRNA-194-1 (SEQ ID NO: 14), miRNA-194-2 (SEQ ID NO: 15), miRNA 92b (SEQ ID NO: 16), miRNA 320b-1 (SEQ ID NO: 17), and miRNA 320b-2 (SEQ ID NO: 18). Genomic mapping revealed the PTB marker miRNAs were associated with cell regulation, muscle dysfunction, contractility and inflammation.

None are previously described in pregnancy and only a few previously associated with reproductive tissues. As miRNA reduce transcription and/or translation and 11 of 14 affected miRNAs are reduced, the findings may explain the activation process of myometrial activation which must precede PTB. That the pattern of miRNA change varied among PTB women suggests the patterns may reflect the underlying mechanism that causes PTB.

In one embodiment, the CFP miRNA PTB biomarkers can include a biomarker that increases in order to indicate susceptibility to PTB. These increasing CFP miRNA PTB biomarkers can include: miRNA-548L (SEQ ID NO: 5), see accession number NR_031630; miRNA-99a (SEQ ID NO: 6), see accession number NR_029514; and miRNA-99b (SEQ ID NO: 7), see accession number NR_029843, which accession numbers and information associated therewith are incorporated herein by specific reference.

In one embodiment, the CFP miRNA PTB biomarkers can include biomarker that decrease in order to indicate susceptibility to PTB. These decreasing CFP miRNA PTB biomarkers can include: miRNA-382 (SEQ ID NO:8), accession number NR_029874; miRNA-491 (SEQ ID NO: 9), accession number NR_030166; miNRA-214 (SEQ ID NO: 10), accession number NR_029627; miRNA-31 (SEQ ID NO: 11), accession number NR_029505; miRNA-342 (SEQ ID NO: 12), accession number NR_029888; miRNA-let-7g (SEQ ID NO: 13), accession number NR_029660; miRNA-194-1 (SEQ ID NO: 14), accession number NR_029711; miRNA-194-2 (SEQ ID NO: 15), accession number NR_029829; miRNA 92b (SEQ ID NO: 16), accession number NR_030281; miRNA 320b-1 (SEQ ID NO: 17), accession number NR_031564; and miRNA 320b-2 (SEQ ID NO: 18), accession number NR_031574, which accession numbers and information associated therewith are incorporated herein by specific reference.

Figure 3:
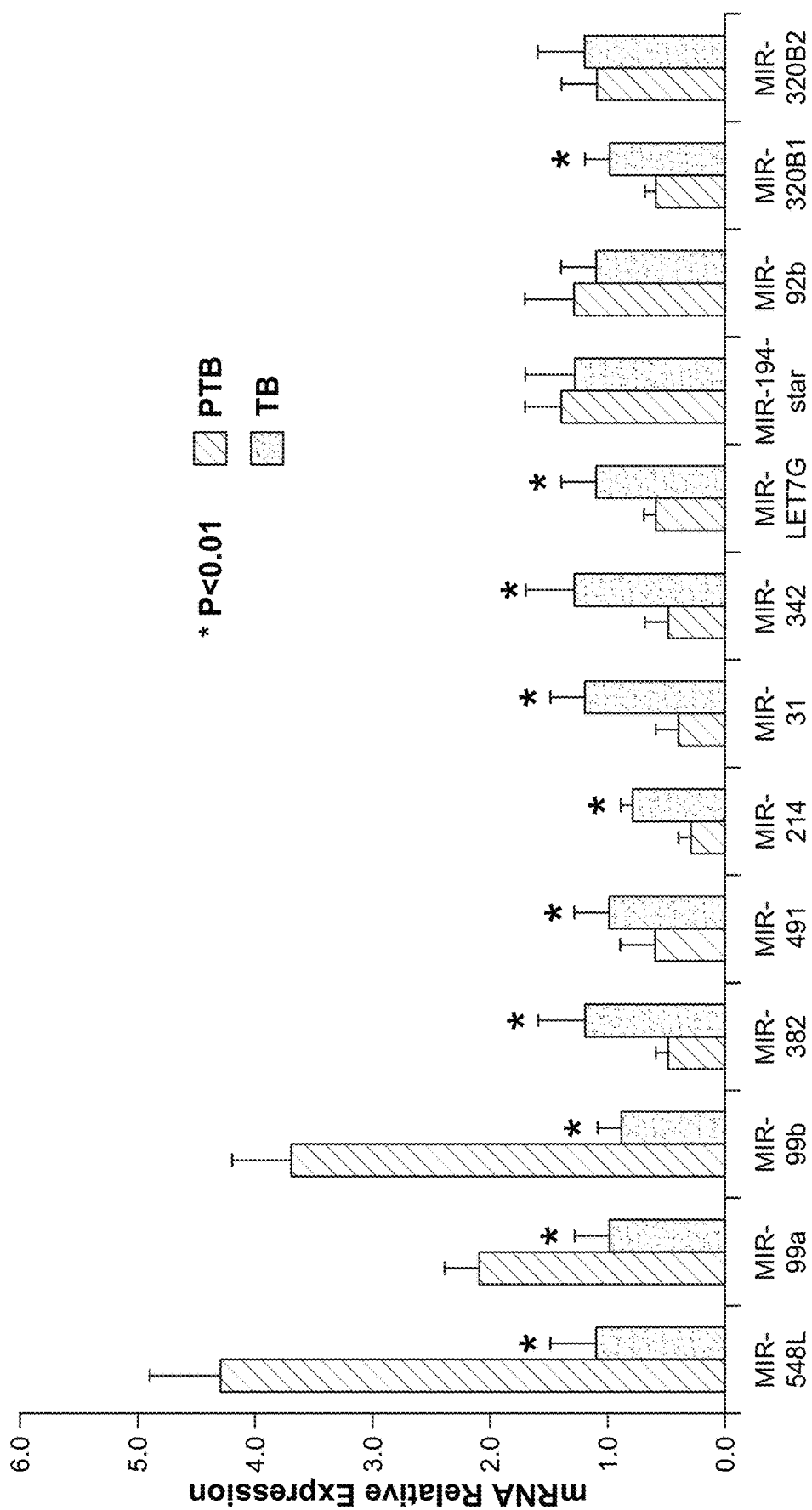
FIG. 3 illustrates results of a high through-put gene Real-time PCR platform validated microarray selected CFP miRNA as PTB biomarkers.
Figure 4A:
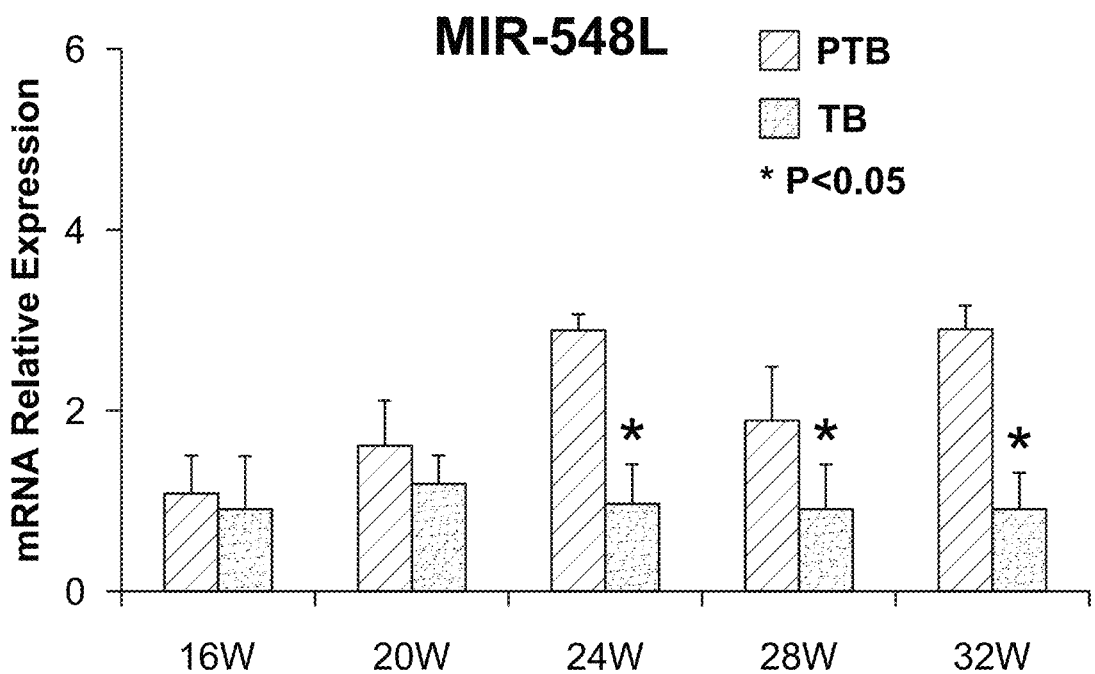
FIGS. 4A-4B illustrates that CFP miRNA PTB biomarkers can be altered by gestation, MIR-99a can be triggered as early as 16 weeks.
Figure 4B:
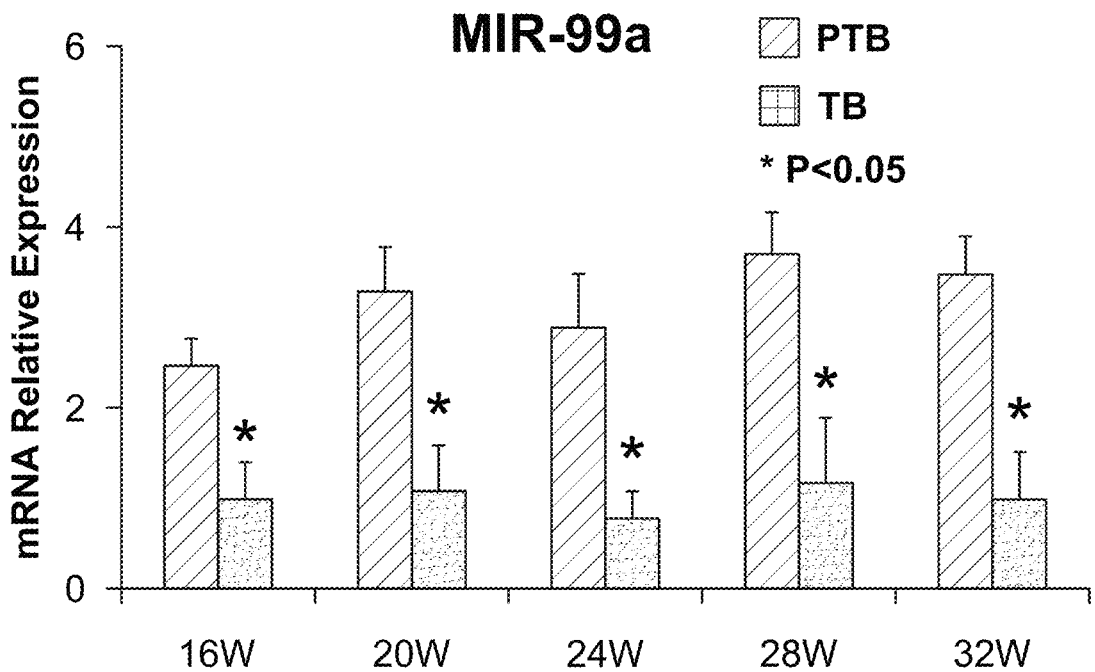

An investigation was also conducted to determine the pattern of miRNA that are altered as early as at 16 weeks in women destined for PTB. Validation of the array results was conducted by high-through put Real-time PCR. Briefly, 3 miRNA that were increased, 7 miRNA that were decreased, respectively at 26 weeks in women destined for spontaneous PTB, and Q-rtPCR was conducted and the miRNA were normalized with the normalization sequences described herein. FIG. 3 confirms the 10/14 of miRNA array findings were significant altered in the miRNA PTB biomarker cell free plasma levels at 26 weeks in women destined for PTB. We also found that gestational age impact on CFP miRNA level. PCR studies were expanded to all biweekly samples available for these same pregnancies, and the PCR were normalized result with the normalization sequences (e.g., miRNA normalization sequence). FIG. 4A indicates that the levels of miRNA-548L is altered only in early $2^{nd}$ trimester, and FIG. 4B illustrates that miRNA-99a are actually significantly increased by 16 weeks gestation raising the possibility of a late $1^{st}$ testing window. This indicates that testing can be as early as 12 weeks, 10 weeks, and possibly even earlier. That is, the diagnostic testing can be implemented as early as the CFP RNA PTB biomarkers are modulated within the pregnant woman.

To simultaneously complete the validation of the about 296 CFP RNA PTB biomarkers and quantitate their levels across gestation, a PCR card was designed with custom designed primers to amplify the CFP miRNA PTB biomarkers and miRNA normalization sequences (e.g., an Applied Biosciences Taqman card preloaded with custom designed primers for the identified CFP miRNA PTB biomarkers and normalization miRNA sequences, wherein the primers can be readily determined from the sequences of the sequence listing by convention techniques, and may encompass low stringency, medium stringency and high stringency primers, and thereby the primer sequences that are useful can be changed within the sequences provided in the Sequence Listing). This PCR card utilizes high throughput microfluidic technology and allows for up to 384 Q-rtPCR wells with custom designed nested primers such as the CFP miRNA PTB biomarkers and normalization sequences. It is assumed commercialization will lead to the manufacture of large cards and the present invention is not limited to the existing dimensions. Each card requires only 50 ng of total miRNA. The cards were designed to accommodate multiple samples. Isolated CFP RNA was then applied to the custom PTB miRNA card in order to validate the miRNA array. That result is shown in FIG. 3. With a sample size of 6 per group, the microarray results were validated for 10 of the 14 miRNA PTB markers. The miRNA symbols are shown as in FIG. 3.

In one embodiment, the present invention includes a method of determining a primer or a probe for a CFP RNA PTB biomarker. Such a method can include analyzing one or more of the sequences of the Sequence Listing having SEQ ID NO: 5-300 and 304-307 and determining a unique or sufficiently unique specific target sequence that is useful as a primer or a probe therefore. The primers can be readily determined from the sequences of the sequence listing by convention techniques, and may encompass low stringency, medium stringency and high stringency primers, and thereby the primer sequences that are useful can be changed within the sequences provided in the Sequence Listing While all of these CFP RNA PTB biomarkers are from humans, other biomarkers from other animals may also be found and used in veterinary practices.

In one embodiment, the CFP RNA PTB biomarkers can be used to predict whether or not a woman is destined for or susceptible to PTB. This determination can be performed by a blood test at least as early as 12 or 16 weeks gestation. Also, this same process can be applied to women with a multiple gestation with same markers. However, a newly derived set of unique markers applicable only to twins may be identified. Accordingly, the CFP RNA biomarkers identified herein can be combined in a mathematical algorithm that can predict likelihood of preterm birth. As there appears to be multiple pathways that lead to preterm birth. The algorithm may also be used to determine the mechanism causing the PTB in a given woman. The mathematics to create the algorithm is well known and not proprietary. Such an algorithm for predicting PTB can be run on a computing system, and may be configured as software and/or or hardware. Data can be input into the computing system in order to operate and optimize the PTB prediction algorithm.

In one embodiment, the present invention can include a method for predicting PTB in a woman pregnant with one fetus. Such a method can include determining a change in the CFP RNA transcriptome of a pregnant mother, wherein the change is predictive of preterm birth by the pregnant mother. Such a prediction of PTB can include extracting and isolating RNA from a body fluid of the pregnant mother at less than 32 weeks (e.g., 26-28 weeks, or as low as 12 weeks) of pregnancy. The isolated RNA can be used for determining a change in the RNA amount (e.g., at least a fold change, such as ≥1.5×) in the CFP RNA transcriptome of the pregnant mother, wherein the change is predictive of preterm birth by the pregnant mother.

In one embodiment, the present invention provides a method for predicting preterm birth in a woman pregnant with twins. Such a method of predicting PTB of twins can include determining a change in the pregnant woman's CFP RNA transcriptome, where the change is predictive of preterm birth by the pregnant mother. This method can include extracting and isolating RNA from a body fluid of the pregnant mother at less than 32 weeks (e.g., 26-28 weeks, or as low as 12 weeks) of pregnancy. The isolated RNA can be used for determining a change (e.g., at least a fold change, such as ≥1.5×) in the CFP RNA transcriptome of the pregnant mother, wherein the change is predictive of preterm birth by the pregnant mother.

In one embodiment, the present invention can include a method for predicting a pregnancy disease state. Such a method can include determining a change in the CFP RNA transcriptome of a pregnant mother, wherein the change is predictive of a pregnancy disease state. The method can include extracting and isolating RNA from a body fluid of the pregnant mother at less than 32 weeks (e.g., 26-28 weeks, or as low as 12 weeks) of pregnancy. The isolated RNA can then be used for determining a change (e.g., at least a fold change, such as ≥1.5×) in the CFP RNA transcriptome of the pregnant mother, wherein the change is predictive of a pregnancy disease state. For example, the pregnancy disease state can be poor placentation, fetal growth restriction, preeclampsia, or fetal anomalies.

In one embodiment, a method for predicting preterm birth can be performed by using the CFP RNA PTB biomarkers. Such a method can include determining a change in a CFP RNA transcriptome of a pregnant mother, wherein the change is predictive of preterm birth by the pregnant mother. Also, the method can include extracting and isolating CFP RNA from a body fluid of a pregnant mother at less than 32 weeks (e.g., 26-28 weeks, or as low as 12 weeks) of pregnancy. The method can also include determining a change, such as at least a fold change (e.g., ≥1.5×), in the CFP RNA transcriptome of the pregnant mother. The change in the CFP RNA transcriptome is predictive of preterm birth by the pregnant mother. In one aspect, the pregnant mother can be selected to be pregnant at less than 32 weeks of pregnancy and lacking preterm, premature rupture of membranes.

In one aspect, the extracted RNA from the pregnant mother can be processed through a whole-transcript expression array. In another aspect, the method can include identifying one or more RNA sequences that are predictive of preterm birth. For example, the pregnant mother can have one or more altered levels of RNA sequences selected from CFP RNA PTB biomarker sequences that are associated with expression, cell growth, cell proliferation, cell cycle, cell death, and cellular assembly and organization. The CFP RNA can be any type of CFP RNA, such as miRNA or mRNA. The RNA can be associated with cell regulation, muscle dysfunction, contractility and inflammation, and/or can be associated with myometrial quiescence and/or activation, and/or associated with expression, cell growth, cell proliferation, cell cycle, cell death, and cellular assembly and organization.

In one embodiment, the present invention can include a method of predicting preterm birth before 32 weeks of pregnancy. Such a method can include obtaining data regarding levels of biomarkers and gestation age and optionally other health factors. The data can then be input into a machine, which can process the data by computing the data in a mathematic model having parameters of levels of markers and gestation age and optionally other health factors. Such computing can be used for determining patient specific risk to preterm birth. In this method, the mathematical model can include parameters related to change in a preterm birth RNA biomarker amount, whether becoming present, increasing, or decreasing. The preterm birth RNA biomarker can be any of the RNA PTB biomarkers as described herein.

In one embodiment, the present invention can include a method of inhibiting, preventing, or treating PTB. Such a method would reflect identification of the mechanism causing the PTB in the individual woman based on the profile of the predictive PTB markers. The method can include various drug screening protocols that can impact or regulate a particular PTB biomarker, where such regulation can result in a reduced onset of PTB. The method can include obtaining a substance that blocks a message from one of the PTB RNA described herein. This can include blocking a biological signal of a PTB small RNA, mRNA, non-coding RNA, and/or miRNA. Once obtained, the substance can be administering to a pregnant woman prior to 32 weeks of pregnancy in order to block the effect of the PTB marker on the uterus and its contents. For example, the blocked RNA can be one or more of the CFP RNA PTB biomarker described herein, where blocking the RNA can interrupt one or more myometrial preterm birth initiator genes. Also, the CFP RNA PTB biomarker being blocked can be one or more PTB biomarker miRNA, where blocking the miRNA blocks a preterm birth initiator gene.

In one embodiment, the CFP RNA PTB biomarker isolated from the pregnant mother can be normalized against a normalization sequence. If a CFP mRNA PTB biomarker, the isolated RNA can be normalized against the peptidyl-prolyl isomerase normalization sequence (SEQ ID NO: 1). If a CFP miRNA PTB biomarker, the isolated RNA can be normalized against one or more of normalization sequences snRNA:U6:96Aa (SEQ ID NO: 2), snRNA:U6:96Ab (SEQ ID NO: 3), and/or snRNA:U6:96Ac (SEQ ID NO: 4).

The methods described herein can also include any method of isolating RNA from blood components. This can include isolation from whole blood or blood plasma.

In one embodiment, a diagnostic kit can be provided that includes sequences to identify one or more of these CFP miRNA PTB biomarkers and/or one or more of these CFP mRNA PTB biomarkers. These sequences can be the sequences of the Sequence Listing having SEQ ID NOs: 5-300 and 304-307 and/or primers and/or probes thereof. The primers and probes can be at least substantially unique for these CFP RNA PTB biomarker sequences with adequate hybridization thereto for the methods and protocols described herein. The primers and/or probes of the CFP RNA PTB biomarkers recited in the Sequence Listing can also be considered to be CFP RNA PTB biomarkers for the purpose of the invention as these primers and/or probes target to and hybridize with select specific sequences within the CFP RNA PTB biomarkers of the Sequence Listing. The RNA biomarkers can be configured to be in nucleic acid format, such as RNA, DNA, or RNA/DNA hybrid. The diagnostic kit can include individual compositions that each have a single CFP RNA PTB biomarker, or a single composition can include one or more of these CFP miRNA PTB biomarkers and/or one or more of these CFP mRNA PTB biomarkers. The CFP RNA PTB biomarkers can be provided with or without a label, such as a visual label or radiolabel. The CFP RNA PTB biomarker can be provided on a chip or a card configured for use in nucleic acid detection and/or quantification and/or qualification, which chip or card can be configured as a microarray. One or more sample spots on a microarray can one or more of these CFP miRNA PTB biomarkers and/or one or more of these CFP mRNA PTB biomarkers and/or the primers and/or probes thereof. For example, the microarray can have one spot with one of the primer and/or probe CFP miRNA PTB biomarkers and/or one of the primer and/or probe CFP mRNA PTB biomarkers. Such a microarray can have one or more CFP RNA PTB biomarker spots, which spots can be reaction wells or the like. For example, the microarray can be configured as an Affymetrix microarray card or any advancement in technology reasonably related thereto. The incorporation of these CFP RNA PTB biomarkers in the various microarray products allows them to be more readily used for plasma-derived samples, and in repeated measures of CFP RNA PTB biomarkers.

In one embodiment, a CFP RNA PTB biomarker can be a nucleic acid that contains or consists of the sequence which defines the CFP RNA PTB biomarker target or complement thereof. The CFP RNA PTB biomarker can be identical to one of SEQ ID NOs: 5-18 and/or 5-106 and/or 19-106 and/or 5-300 and/or 107-300 and/or 107-142 and/or 143-300 and/or 304-307, or can be a complement thereof, sense or antisense, as well as a sequence that hybridizes therewith under suitable conditions as well as primers and/or probes therefore. For the purposes of this invention, the primers and/or probes of the recited sequences can be considered to be CFP RNA PTB biomarkers as they are used to target the particular RNA produced within a subject. The primers and probes will be complementary to the sequences of SEQ ID NOs: 5-300 and 304-307, as these sequences are the targets. The CFP RNA PTB biomarker can have perfect complementarity or greater than or about 95% complementarity, greater than or about 90% complementarity, greater than or about 85% complementarity, or greater than or about 80% complementarity with the sequences recited or the probes and/or primers thereof. The CFP RNA PTB biomarker can be continuous or it can have one or more bulges or mismatches upon hybridization. The CFP RNA PTB biomarker can also include one or more chemical modifications, such as a 2' carbon modification. The CFP RNA PTB biomarker may or may not form an overhang upon hybridization. The CFP RNA PTB biomarker can include a sequence from about 15 nucleotides to the full sequence, from about 16 nucleotides to about 100 nucleotides, from about 17 nucleotides to about 50 nucleotides, from about 18 nucleotides to about 30 nucleotides, from about 19 nucleotides to about 25 nucleotides, or from about 20 to about 22 nucleotides in sequence of or complement to one of SEQ ID NOs: 5-18 and/or 5-106 and/or 19-106 and/or 5-300 and/or 107-300 and/or 107-142 and/or 143-300 and/or 304-307. The CFP RNA PTB biomarker can include a unique sequence segment of the full sequence having a length as described.

In one embodiment, the methods described herein can be performed with exon and miRNA microarrays, and can quantitate their levels using high throughput PCR. The RNA can be obtained from one or more pregnant women at least by 12 weeks of pregnancy until delivery. The RNA biomarkers can be validated using a high throughput, customized PCR card having the PTB biomarkers as described herein. The PTB biomarkers from one group of women can be validated against a second group of randomly selected women with PTB and or control women that do not have PTB or that have a term birth.

In one embodiment, the CFP mRNA/miRNA PTB biomarkers can be manipulated in presence or amount in order to modify myometrial $Ca^{2+}$ flux that is mediated by myometrial PTB genes. It has now been found that CFP RNA PTB biomarkers that were significantly increased or decreased in women destined for PTB may be manipulated to modify myometrial $Ca^{2+}$ flux which in turn regulates myometrial contractility. For example, the expression of the CFP mRNA APOA-4 ((SEQ ID NO: 66) *Homo sapiens* apolipoprotein A-IV (APOA4), mRNA, accession number NM_000482) increased myometrial intracellular $Ca^{2+}$ flux. Other CFP RNA PTB biomarkers may be similarly used for manipulation of myometrial function.

RNA Purification

Existing RNA isolation techniques can yield enough CFP RNA for an array, but not for the needed PCR validation of the hundreds of genes identified by the array unless the plasma volume is high. This explains the common practice of using solid tissues (e.g. placenta, myometrium, cervix) to identify candidates and then hope to individually quantitate them in plasma using Q-rtPCR.

Accordingly, the present invention provides a method that in one process separates intact RNA, including mRNA and miRNA, DNA and protein. The process is based on a phenol/guanidium isothiocyanate/glycerol phase separation and results in large quantities of high quality CFP nucleic acid with total RNA yields of 1.5-30 ug or more from only 2 mL of plasma. This amount is more than enough for array technology and the performance of numerous PCR reactions using a clinically practical, single patient sample.

The RNA isolation method described herein allows for the isolation of 1.5 micrograms to 70 micrograms of CFP RNA from a 2 mL sample, which is more than enough for both array use and PCR validation. The method can include obtaining: 2 mL or more of sample from a subject, such as plasma; DEPC-treated Water (Ambion); Ethanol (Sigma); Chloroform (Sigma); 3M, pH: 5.5 Sodium Acetate (Ambion); Phonel (Sigma); Guanidium isothiocyanate (Sigma); Glycerol (Sigma); Aliquot 2 mL of sample (e.g., plasma) from one patient sample into 8 tubes, 250 uL plasma in each tube. The RNA purification is conducted as follows: spin plasma at 200×g for 5 minutes at 4 C; add 750 uL phenol/guanidium isothiocyanate/glycerol lysis buffer per 2 mL sample, and vortex samples vigorously for 15 seconds and incubate them for 5 min; add 200 uL chloroform per sample and vortex sample vigorously and incubate at room temperature for 10 min; centrifuge the samples at 10,000×g for 15 minutes at 4 C, and obtain upper aqueous phase for RNA isolation, and lower red/phenol/chloroform phase can be used for DNA and Protein isolation; transfer 300 uL upper aqueous phase carefully without disturbing the interphase into a fresh tube, and add 1/10 volume of 3M Sodium acetate (pH: 5.5) (30 ul) plus 3 volumes of 100% iced cold ethanol at 900 uL to each tube (note: 2 mL plasma from one patient sample can result in 13-14 tubes); incubate the tubes overnight at −20° C.; centrifuge at 12,000×g for 75 minute (e.g., 4° C.), and remove all liquid; add 50 uL ice cold 80% ethanol to each tube, and then wash the pellet, then transfer all of the sample tubes into one tube, add then add 300-350 mL ice cold ethanol to make the ethanol an amount of about 1 mL; centrifuge at 12,000×g for 60 minutes at 4° C.; remove all liquid, and set at 37° C. to dry for 40 minutes; re-suspend the pellet in about 20-40 uL DEPC water, and incubate at 56° C. for 10 minutes to dissolve RNA, and then put the RNA sample in ice for 30 minutes; and using 2 uL RNA, take OD at 260 nm and 280 nm to determine sample concentration and purity.

Modulating PTB Genes

Figure 5A:
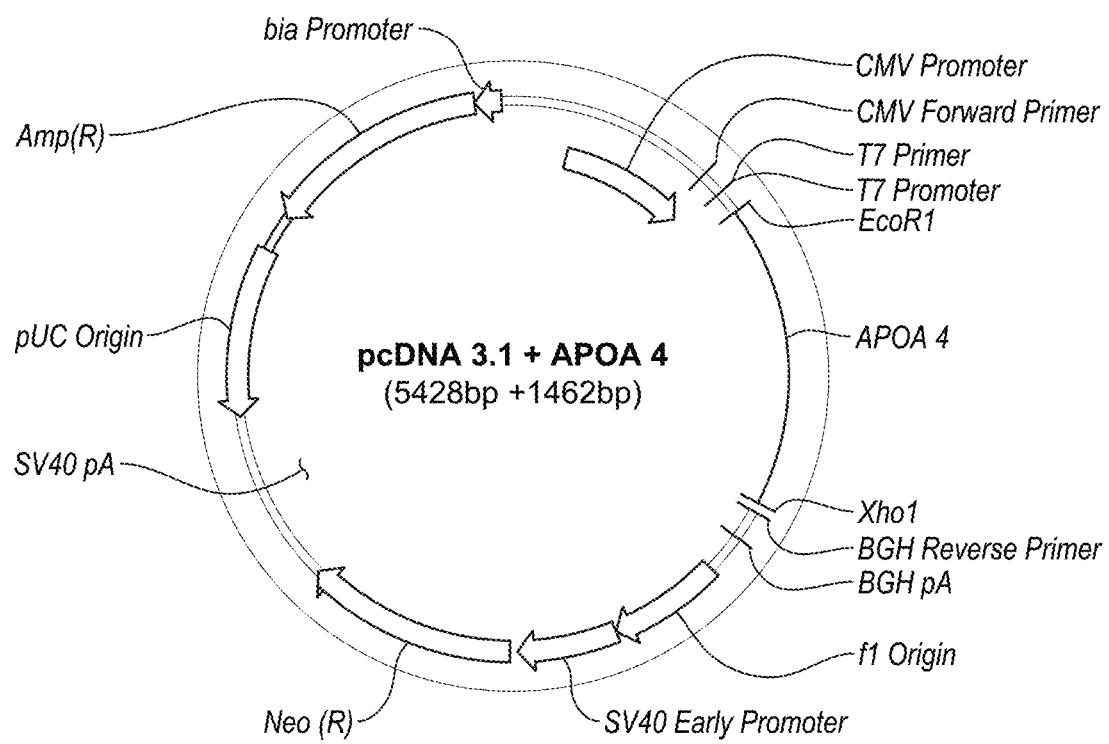
FIG. 5A includes a plasmid DNA reconstruction containing one of the CFP mRNA-APOA4.
Figure 5B:
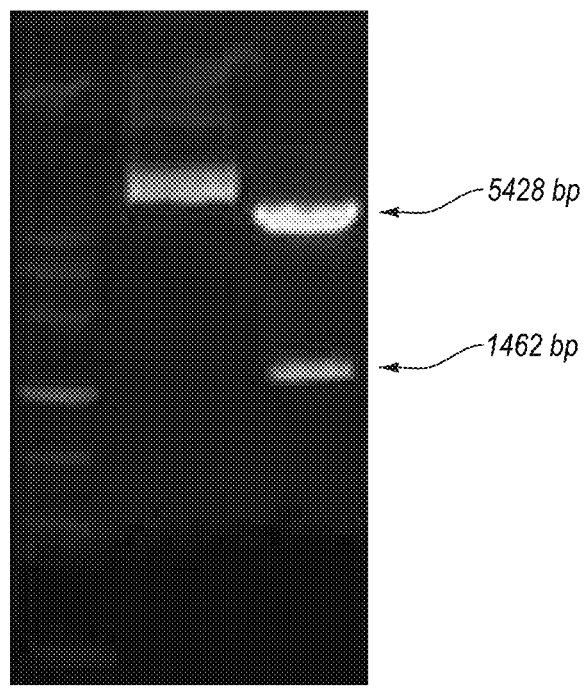
FIG. 5B includes an image of a gel electrophoresis illustrates that the APOA4 Vector reconstruction is successful.
Figure 5C:
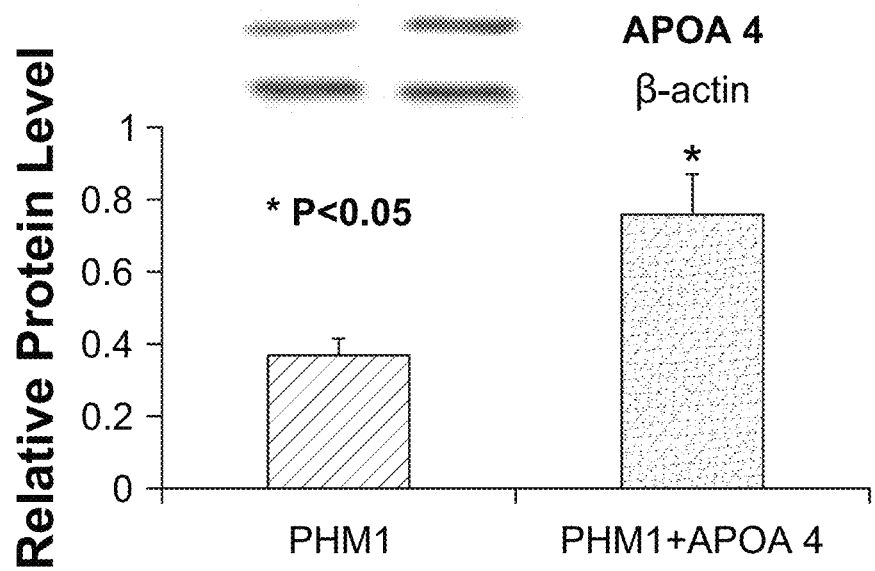
FIG. 5C illustrates that myometrium cell APOA4 protein can be up-regulated by APOA4 plasmid DNA.
Figure 5D:
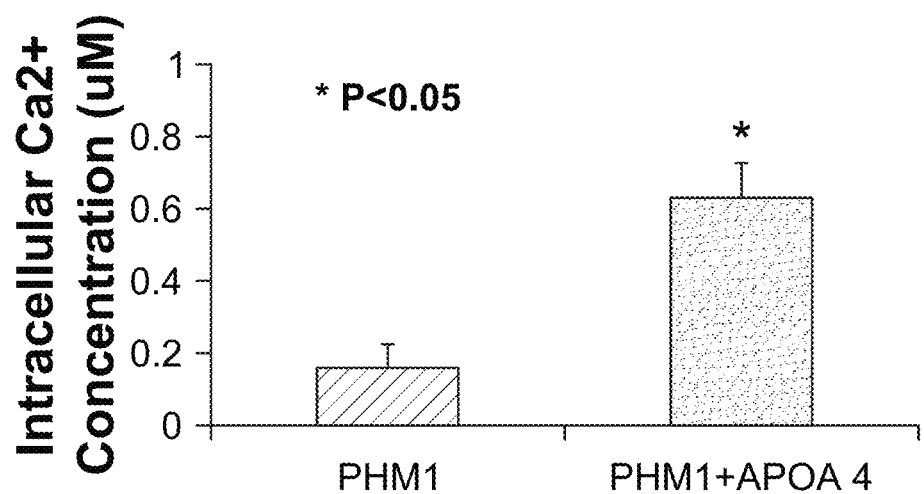
FIG. 5D illustrates that CFP mRNA biomarker-APOA4 can trigger intracellular $Ca^{2+}$ concentration in myometrium cell consistent with enhanced contractility.

In one embodiment, the present invention can modulate CFP RNA in order to regulate intracellular $Ca^{2+}$ flux via their effect on myometrial preterm initiator genes. For example, the CFP RNA can be used to regulate myometrial contractility. It was determined that there was an interaction between 4 CFP mRNA PTB biomarkers (e.g., PSME2, NAMPT, APOA1 and APOA 4) and 6 myometrial PTB initiator genes (e.g., IFNG, CD3E, HLA-DOA, NDRG4, VPS33A and ABCA7), and between 1 PTB marker CFP miRNA (miRLET7 G) and 1 PTB Initiator gene (SORCS). This finding supports the possibility CFP mRNA and/or miRNA PTB biomarkers could be used to alter the transcription and/or translation of myometrial preterm initiator genes. It was found that 7 PTB initiator genes that were identified to be associated with these markers could all directly or indirectly be linked to $Ca^{2+}$ flux. A pcDNA 3.1 vector was constructed with the full length of the APOA4 mRNA (FIG. 5A). Successful gene vector cloning was confirmed by EcoR1 and Xhol restriction enzyme digests (FIG. 5B). The vector was transferred into immortalized pregnant human myometrial cells PHM1, and the APOA4 was overexpressed in the PHM1 cells (FIG. 5C). Over expression of the APOA4 protein dramatically increased intracellular $Ca^{2+}$ as shown in FIG. 5D. Since APOA4 is not normally expressed in cultured myometrial cells, it is conceived that the APOA4 effect on intracellular $Ca^{2+}$ is mediated by local myometrium initiator genes. Accordingly, it is conceived that $Ca^{2+}$ flux can be modulated with the other CFP mRNA PTB biomarkers (e.g., PSME2, NAMPT, APOA1), and the CFP miRNA PTB biomarker (e.g., miR-LET7 G). This approach could be used to identify drugs that target and modulate the CFP RNA PTB biomarkers described herein or later developed. This approach can therefore be used in methods of treating women in need of labor induction, but resistant to existing methods. Also, a similar approach can be used in methods of treating women in need of labor inhibition or prevention, but resistant to existing methods.

Methods

Maternal Plasma: isolated in EDTA as previously described; aliquoted and stored at −80° C.

Plasma RNA Isolation: Plasma RNA is isolated by a proprietary method developed this past year. The plasma sample is lysed by phenol/guanidium isothiocyanate/glycerol buffer, and RNA, DNA and protein isolated from different aqueous phases, then precipitated using a series of proprietary chemical solutions, the pellets cleaned and resuspended in 20-40 uL DEPC water, incubated at 56° C. for 10 min to dissolve RNA, and stored at −80° C. RNA yield, purity and integrity are identified by Nanospectrometer and Aligent Bio-analyzer.

Affymetrix Microarray: Affymetrix whole genome transcript and miRNA microarrays are run. Microarray QC evaluation can be performed. Each protocol is as instructed by the manufacturer.

High-throughput miRNA/mRNA Gene Validation: The ABI VIIA™ 7 is used for high-throughput mRNA/miRNA gene quantification using an ABI customized array card system. The system allows for 384 Real-time PCR reactions in 2 hours using one PCR array card (picture insert). In general, the TagMan microRNA/RNA reverse transcription kit is used to create the cDNA pool. A megaplex RT primers pool is generated based on each validated gene, and cDNA synthesized under the following thermal cycling conditions: 16° C. for 2 minutes, 42° C. for 1 minute, 50° C. for 1 second for 40 cycles, then hold 85° C. for 5 minutes. A preamplification reaction is used to enlarge gene signals. PreAmp primer pools are prepared for each validated gene. TaqMan PreAmp Master Mix will be used. PreAmplification reactions are performed under the following conditions: 95° C. or 10 minutes, 55° C. for 2 minutes, 72° C. for 2 minutes, then 12 cycle of 95° C. for 15 seconds and 60° C. for 4 minutes, then 99.9° C. for final denaturing step. PreAmplified cDNAs are used as the template. Validation parameters are designed and selected based on customized gene sequences.

Myometrial Cell Culture: Primary myometrial cell culture and immortalized pregnant myometrial cell are cultured using standard procedures. All primary cell lines can be derived from a large fundal myometrial biopsy from a single patient at term prior to labor.

Construction of recombinant plasmid pcDNA-CFP genes: Vector construction is used for CFP marker gene over expression. The target genes are selected from the array and IPA analyses (Preliminary Results). The purified CFP gene products and plasmid eukaryotic expression vector (pcDNA 3.1) are digested with EcoR1 and Xhol. The ligation reaction is conducted according to the manufacturer's protocol (Invitrogen). The final plasmid pcDNA-CFP genes are then transformed into *E. coli* JM 2163. The ligation products are cultured with LB medium containing ampicillin (100 ug/ml) overnight. Afterward, the recombinant plasmid is extracted from colony transformants prior to being identified by digesting with EcoR1 and Xhol, and confirmed by agarose gel electrophoresis. Lipofectamine will be used for transfection. Over expression of CFP marker genes will be proven by Western blot and Real-time PCR. The technique is established in our laboratory (FIG. 6A).

$Ca^{2+}$ Flux Measurement: myometrial cells are suspended in 2 mL of DMEM media consisting of 10% fetal bovine serum, 30 μg fungizone, 1% penicillin-streptomycin, 0.5% L-glutamine in DMEM (all ingredients from GIBCO Life Technologies), warmed to 37° C., and then plated on 25-mm glass coverslips. Cells are incubated in fura 2-AM ($2 \times 10^6$ mol/L) for 40 minutes at room temperature in the dark. Coverslips are inserted into an open microincubator (PDMI-2, Medical Systems) and attached to the stage of an inverted microscope (Nikon EclipseTE2000, Nikon; Melville, N.Y.). The microincubator is maintained at 37° C. with a bipolar temperature controller (TC-202, Medical Systems). Images are collected using Nikon EZ-C1 software and processed with Volocity imaging software (Improvision Inc., Lexington, Mass.). Data are expressed as a ratio of emitted fluorescence at 510 nm in cells excited at 340 and 380 nm. Responses to genes or their respective vehicles (DMSO, ethanol) are analyzed by directly transfected siRNA or gene expression vector. Changes in the 340/380 nm emission ratios are recorded. $Ca^{2+}$ influx rate is calculated based on previous reports. Data are expressed as a ratio of emitted fluorescence at 510 nm in cells excited at 340 and 380 nm. Responses to genes or their respective vehicles (DMSO, ethanol) are analyzed by directly transfected siRNA or gene expression vector. Changes in the 340/380 nm emission ratios are recorded and $Ca^{2+}$ influx rate is calculated.

Combinations of Nucleic Acid Biomarkers

In some embodiments, a method of detecting a combination of nucleic acid biomarkers in a human subject can include: obtaining a nucleic acid sample from the human subject; selecting the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard, wherein the combination of nucleic acid biomarkers includes at least two of: miRNA-let-7g having a nucleotide sequence of or complementary to SEQ ID NO: 13 with a variation less than the transcription standard; PSME2 having a nucleotide sequence of or complementary to SEQ ID NO: 68 with a variation less than the transcription standard; APOA1 having a nucleotide sequence of or complementary to SEQ ID NO: 53 with a variation less than the transcription standard; and NAMPT having a nucleotide sequence of or complementary to SEQ ID NO: 71 with a variation less than the transcription standard. In some aspects: the variation for miRNA-let-7g is about −1.8 fold change; the variation for PSME2 is about −5.6 fold change; the variation for APOA1 is about −1.9 fold change; and/or the variation for NAMPT is −2.3 fold change. In some aspects, the analyzing includes hybridizing each nucleic acid biomarker in the nucleic acid sample with a complementary nucleic acid configured as a primer or a probe, the method comprising detecting the hybridizing.

In some embodiments, the combination of nucleic acid biomarkers includes one of: PSME2 and APOA1; PSME2 and miRNA-let-7g; NAMPT and APOA1; or miRNA-let-7g, PSME2, APOA1, and NAMPT. In some aspects, the combination of nucleic acid biomarkers includes all of miRNA-let-7g, PSME2, APOA1, and NAMPT, and further includes: APOA4 having a nucleotide sequence of or complementary to SEQ ID NO: 71, wherein the variation for APOA4 is less than the transcription standard. In some aspects, the variation for APA4 is about −1.5 fold change.

In some embodiments, the combination of nucleic acid biomarkers includes at least one of: miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548L having a nucleotide sequence of or complementary to SEQ ID NO: 5 with a variation greater than the transcription standard.

In some embodiments, the combination of nucleic acid biomarkers includes at least one of: miRNA-99b having a nucleotide sequence of or complementary to SEQ ID NO: 7 with about a 1.7 fold change variation greater than the transcription standard; miRNA-99a having a nucleotide sequence of or complementary to SEQ ID NO: 6 with about a 1.6 fold change variation greater than the transcription standard; and miRNA-548L having a nucleotide sequence of or complementary to SEQ ID NO: 5 with about a 1.5 variation greater than the transcription standard.

In some embodiments, the combination of nucleic acid biomarkers includes at least one of: miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In some embodiments, the combination of nucleic acid biomarkers includes at least one of: miRNA-490 having a nucleotide sequence of or complementary to SEQ ID NO: 304 with about a −4.7 fold change variation less than the transcription standard; miRNA-491 having a nucleotide sequence of or complementary to SEQ ID NO: 9 with about a −2.2 fold change variation less than the transcription standard; miRNA-31 having a nucleotide sequence of or complementary to SEQ ID NO: 11 with about a −1.9 fold change variation less than the transcription standard; miRNA-382 having a nucleotide sequence of or complementary to SEQ ID NO: 8 with about a −1.8 fold change variation less than the transcription standard; miRNA-342 having a nucleotide sequence of or complementary to SEQ ID NO: 12 with about a −1.5 fold change variation less than the transcription standard; miRNA-194 having a nucleotide sequence of or complementary to SEQ ID NO: 305 with about a −1.5 fold change variation less than the transcription standard; miRNA-214 having a nucleotide sequence of or complementary to SEQ ID NO: 10 with about a −1.5 fold change variation less than the transcription standard; miRNA-371 having a nucleotide sequence of or complementary to SEQ ID NO: 306 with about a −1.4 fold change variation less than the transcription standard; and/or miRNA-519c having a nucleotide sequence of or complementary to SEQ ID NO: 307 with about a −1.3 fold change variation less than the transcription standard.

In some embodiments, the combination of nucleic acid biomarkers includes at least one of: SF3A3 having a nucleotide sequence of or complementary to SEQ ID NO: 25 with a variation greater than the transcription standard; FLJ16171 having a nucleotide sequence of or complementary to SEQ ID NO: 21 with a variation greater than the transcription standard; REG3G having a nucleotide sequence of or complementary to SEQ ID NO: 22 with a variation greater than the transcription standard; NDUFA2 having a nucleotide sequence of or complementary to SEQ ID NO: 24 with a variation greater than the transcription standard; LCE2A having a nucleotide sequence of or complementary to SEQ ID NO: 26 with a variation greater than the transcription standard KRTAP6-2 having a nucleotide sequence of or complementary to SEQ ID NO: 42 with a variation less than the transcription standard; CHCHD10 having a nucleotide sequence of or complementary to SEQ ID NO: 50 with a variation less than the transcription standard; OR4D1 having a nucleotide sequence of or complementary to SEQ ID NO: 62 with a variation less than the transcription standard; BLOC1S1 having a nucleotide sequence of or complementary to SEQ ID NO: 52 with a variation less than the transcription standard; PDZK1 having a nucleotide sequence of or complementary to SEQ ID NO: 56 with a variation less than the transcription standard; KRT17 having a nucleotide sequence of or complementary to SEQ ID NO: 58 with a variation less than the transcription standard; CSRP2 having a nucleotide sequence of or complementary to SEQ ID NO: 61 with a variation less than the transcription standard; PSG9 having a nucleotide sequence of or complementary to SEQ ID NO: 46 with a variation less than the transcription standard; ARMC10 having a nucleotide sequence of or complementary to SEQ ID NO: 48 with a variation less than the transcription standard; CD3E having a nucleotide sequence of or complementary to SEQ ID NO: 54 with a variation less than the transcription standard; GUCA2B having a nucleotide sequence of or complementary to SEQ ID NO: 47 with a variation less than the transcription standard; TNFRSF13C having a nucleotide sequence of or complementary to SEQ ID NO: 64 with a variation less than the transcription standard; LOC643008 having a nucleotide sequence of or complementary to SEQ ID NO: 41 with a variation less than the transcription standard; MRPS21 having a nucleotide sequence of or complementary to SEQ ID NO: 65 with a variation less than the transcription standard; NAT14 having a nucleotide sequence of or complementary to SEQ ID NO: 57 with a variation less than the transcription standard; PRTN3 having a nucleotide sequence of or complementary to SEQ ID NO: 45 with a variation less than the transcription standard; OR2A2 having a nucleotide sequence of or complementary to SEQ ID NO: 44 with a variation less than the transcription standard; RPL8 having a nucleotide sequence of or complementary to SEQ ID NO: 63 with a variation less than the transcription standard; TMEM188 having a nucleotide sequence of or complementary to SEQ ID NO: 60 with a variation less than the transcription standard; RPS19BP1 having a nucleotide sequence of or complementary to SEQ ID NO: 59 with a variation less than the transcription standard; and/or JSRP1 having a nucleotide sequence of or complementary to SEQ ID NO: 67 with a variation less than the transcription standard.

In some embodiments, the combination of nucleic acid biomarkers includes at least one of: SF3A3 having a nucleotide sequence of or complementary to SEQ ID NO: 25 with about a 2.7 fold change variation greater than the transcription standard; FLJ16171 having a nucleotide sequence of or complementary to SEQ ID NO: 21 with about a 2.6 fold change variation greater than the transcription standard; REG3G having a nucleotide sequence of or complementary to SEQ ID NO: 22 with about a 1.9 fold change variation greater than the transcription standard; NDUFA2 having a nucleotide sequence of or complementary to SEQ ID NO: 24 with about a 1.6 fold change variation greater than the transcription standard; LCE2A having a nucleotide sequence of or complementary to SEQ ID NO: 26 with about a 2.3 fold change variation greater than the transcription standard KRTAP6-2 having a nucleotide sequence of or complementary to SEQ ID NO: 42 with about a −2.1 fold change variation less than the transcription standard; CHCHD10 having a nucleotide sequence of or complementary to SEQ ID NO: 50 with about a −2.6 fold change variation less than the transcription standard; OR4D1 having a nucleotide sequence of or complementary to SEQ ID NO: 62 with about a −2.3 fold change variation less than the transcription standard; BLOC1S1 having a nucleotide sequence of or complementary to SEQ ID NO: 52 with about a −2.2 fold change variation less than the transcription standard; PDZK1 having a nucleotide sequence of or complementary to SEQ ID NO: 56 with about a −2.0 fold change variation less than the transcription standard; KRT17 having a nucleotide sequence of or complementary to SEQ ID NO: 58 with about a −2.0 fold change variation less than the transcription standard; CSRP2 having a nucleotide sequence of or complementary to SEQ ID NO: 61 with about a −1.8 fold change variation less than the transcription standard; PSG9 having a nucleotide sequence of or complementary to SEQ ID NO: 46 with about a −1.8 fold change variation less than the transcription standard; ARMC10 having a nucleotide sequence of or complementary to SEQ ID NO: 48 with about a −1.7 fold change variation less than the transcription standard; CD3E having a nucleotide sequence of or complementary to SEQ ID NO: 54 with about a −1.7 fold change variation less than the transcription standard; GUCA2B having a nucleotide sequence of or complementary to SEQ ID NO: 47 with about a −1.7 fold change variation less than the transcription standard; TNFRSF13C having a nucleotide sequence of or complementary to SEQ ID NO: 64 with about a −1.6 fold change variation less than the transcription standard; LOC643008 having a nucleotide sequence of or complementary to SEQ ID NO: 41 with about a −1.6 fold change variation less than the transcription standard; MRPS21 having a nucleotide sequence of or complementary to SEQ ID NO: 65 with about a −1.6 fold change variation less than the transcription standard; NAT14 having a nucleotide sequence of or complementary to SEQ ID NO: 57 with about a −1.6 fold change variation less than the transcription standard; PRTN3 having a nucleotide sequence of or complementary to SEQ ID NO: 45 with about a −1.6 fold change variation less than the transcription standard; OR2A2 having a nucleotide sequence of or complementary to SEQ ID NO: 44 with about a −1.6 fold change variation less than the transcription standard; RPL8 having a nucleotide sequence of or complementary to SEQ ID NO: 63 with about a −1.5 fold change variation less than the transcription standard; TMEM188 having a nucleotide sequence of or complementary to SEQ ID NO: 60 with about a −1.5 fold change variation less than the transcription standard; RPS19BP1 having a nucleotide sequence of or complementary to SEQ ID NO: 59 with about a −1.5 fold change variation less than the transcription standard; and/or JSRP1 having a nucleotide sequence of or complementary to SEQ ID NO: 67 with about a −1.5 fold change variation less than the transcription standard.

In some embodiments, the method includes providing the transcription standard for each nucleic acid biomarker for the combination of nucleic acid biomarkers.

In some embodiments, the method includes providing the combination of nucleic acid biomarkers as a set of primers and/or probes.

In some embodiments, the method includes obtaining cell free plasma RNA as the nucleic acid sample. In some embodiments, the nucleic acid biomarkers are RNA.

In some embodiments, the method can include: selecting a normalization nucleic acid; analyzing the transcriptome of the human subject for the normalization nucleic acid in the nucleic acid sample from the human subject; and detecting in the nucleic acid sample the presence of the normalization nucleic acid, wherein normalization nucleic acid has a variation from a transcription standard, wherein the normalization nucleic acid has a nucleotide sequence of or complementary to one of SEQ ID NOs: 1-4 and 301-303.

In some embodiments, the method can include generating a report, the report reciting the presence of the combination of nucleic acid biomarkers being present in the nucleic acid sample of the human subject being present in a biomarker amount that is varied from the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7g having a nucleotide sequence of or complementary to SEQ ID NO: 13 with a variation less than the transcription standard; miRNA-99b having a nucleotide sequence of or complementary to SEQ ID NO: 7 with a variation greater than the transcription standard; miRNA-99a having a nucleotide sequence of or complementary to SEQ ID NO: 6 with a variation greater than the transcription standard; and miRNA-548L having a nucleotide sequence of or complementary to SEQ ID NO: 5 with a variation greater than the transcription standard.

In some embodiments, a method of detecting a combination of nucleic acid biomarkers in a human subject can include: obtaining a nucleic acid sample from the human subject; selecting the combination of nucleic acid biomarkers; providing a transcription standard for each nucleic acid biomarker for the combination of nucleic acid biomarkers; analyzing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from the transcription standard, wherein the combination of nucleic acid biomarkers includes: miRNA-let-7g having a nucleotide sequence of or complementary to SEQ ID NO: 13 with a variation less than the transcription standard; miRNA-490 having a nucleotide sequence of or complementary to SEQ ID NO: 304 with a variation less than the transcription standard; miRNA-491 having a nucleotide sequence of or complementary to SEQ ID NO: 9 with a variation less than the transcription standard; miRNA-31 having a nucleotide sequence of or complementary to SEQ ID NO: 11 with a variation less than the transcription standard; miRNA-382 having a nucleotide sequence of or complementary to SEQ ID NO: 8 with a variation less than the transcription standard; miRNA-342 having a nucleotide sequence of or complementary to SEQ ID NO: 12 with a variation less than the transcription standard; miRNA-194 having a nucleotide sequence of or complementary to SEQ ID NO: 305 with a variation less than the transcription standard; miRNA-214 having a nucleotide sequence of or complementary to SEQ ID NO: 10 with a variation less than the transcription standard; miRNA-371 having a nucleotide sequence of or complementary to SEQ ID NO: 306 with a variation less than the transcription standard; and/or miRNA-519c having a nucleotide sequence of or complementary to SEQ ID NO: 307 with a variation less than the transcription standard.

In one embodiment, a kit includes purified or isolated nucleic acids, wherein the nucleic acids have the sequences of each of the nucleic acid biomarkers in the combination of biomarkers. As such, each recited combination can be uniquely included in a kit. In some aspects, the nucleic acid biomarkers are attached to a substrate of a biochip, where each nucleic acid biomarker can be in a unique position or a position can include one or more of the nucleic acid biomarkers of the combination.

As used herein, "nucleic acid biomarker" or "biomarker" is defined to be a nucleic acid, such as an RNA, that is present in an abnormal amount compared to a standard or normal amount. The biomarker thereby then serves as a tool to look for changes in the transcription thereof. For example, a biomarker can be present at a normal or standard level when there is no disease state or susceptibility of a disease state, but the biomarker is present at a changed level or a variation from the standard or normal amount. While SNPs may be detected by merely identifying the presence, the nucleic acid biomarkers described herein may always be present, but the change in the transcription thereof or change in the amount or concentration in blood or plasma provides the indication that the subject may have a condition that is marked by the biomarker. Thus, by using the term "biomarker" it is clear that the transcription thereof, amount thereof or concentration thereof is not normal, such that it is changed. Such a changed condition can be compared to subject (e.g., pregnant woman) prior to pregnancy or in early pregnancy (e.g., earlier than 12 weeks (PTB) or between 16-20 weeks (pre-eclampsia). Thus, by being defined as a biomarker, it is defined that the transcription thereof, amount thereof or concentration thereof is detectably different from a standard or normal person without the condition or the same subject prior to onset of the condition. In some aspects, a biomarker requires at least a fold change relative to the normal or standard amount or concentration or transcription, or at least a 1.3 fold change, or at least a 1.4 fold change, or at last a 1.5 fold change, or at least a 1.6 fold change, or at least a 1.7 fold change, whether the change is up regulation (increased transcription, amount or concentration) or down regulation (decreased transcription, amount or concentration) compared to a standard or normal amount or compared to that of the subject prior to being pregnant or prior to 10 weeks or prior to 12 weeks of gestation.

As used herein, "combination of biomarkers" or "combination of nucleic biomarkers" defines a unique combination of nucleic acids that are biomarkers under the definition of a biomarker provided herein. The combination of biomarkers provides an indication of a disease state in a pregnant woman or susceptibility thereto. In some instances, the disease state is preterm birth. In other instances the disease state is pre-eclampsia. The presence of the combination of biomarkers provides the indication of the disease state or susceptibility thereto.

In one embodiment, Group 1 is a combination of biomarkers that includes: miRNA-let-7g (SEQ ID NO: 13), accession number NR_029660; (SEQ ID NO: 68) Homo sapiens proteasome (prosome, macropain) activator subunit 2 (PA28 beta) (PSME2), mRNA, accession number NM_002818; (SEQ ID NO: 53) Homo sapiens apolipoprotein A-I (APOA1), mRNA, accession number NM_000039; (SEQ ID NO: 66) Homo sapiens apolipoprotein A-IV (APOA4), mRNA, accession number NM_000482; and (SEQ ID NO: 71) Homo sapiens nicotinamide phosphoribosyltransferase (NAMPT), mRNA, accession number NM_005746. This combination of biomarkers can be used for PTB and pre-eclampsia when detected to be present in a biomarker amount (e.g., not normal or not standard)

In one embodiment, Sub Group 1A can be used for sPTB less than 33 weeks: SEQ ID NO: 68) Homo sapiens proteasome (prosome, macropain) activator subunit 2 (PA28 beta) (PSME2), mRNA, accession number NM_002818; and (SEQ ID NO: 53) Homo sapiens apolipoprotein A-I (APOA1), mRNA, accession number NM_000039. Sub Group 1A is used for samples at about 12 weeks pregnancy, or from 10 to 15 weeks, or earlier than 16 weeks.

In one embodiment, Sub Group 1B can be used for sPTB less than 33 weeks; SEQ ID NO: 68) Homo sapiens proteasome (prosome, macropain) activator subunit 2 (PA28 beta) (PSME2), mRNA, accession number NM_002818; and miRNA-let-7g (SEQ ID NO: 13), accession number NR_029660. Sub Group 1B is used for samples at about 16 weeks pregnancy, or from 16 to 20 weeks, or earlier than 20 weeks.

In one embodiment, Sub Group 1C can be used for Early Onset Preeclampsia at less than 34 weeks: SEQ ID NO: 71) Homo sapiens nicotinamide phosphoribosyltransferase (NAMPT), mRNA, accession number NM_005746; and (SEQ ID NO: 53) Homo sapiens apolipoprotein A-I (APOA1), mRNA, accession number NM_000039. Sub Group 1C is used for samples less than 34 weeks.

In one embodiment, Sub Group 1D can be used for all PTB, spontaneous and iatrogenic: miRNA-let-7g (SEQ ID NO: 13), accession number NR_029660; (SEQ ID NO: 68) Homo sapiens proteasome (prosome, macropain) activator subunit 2 (PA28 beta) (PSME2), mRNA, accession number NM_002818; (SEQ ID NO: 53) Homo sapiens apolipoprotein A-I (APOA1), mRNA, accession number NM_000039; and (SEQ ID NO: 71) Homo sapiens nicotinamide phosphoribosyltransferase (NAMPT), mRNA, accession number NM_005746.

In one embodiment, Group 2 can be used for PTB or pre-eclampsia: miRNA-let-7g (SEQ ID NO: 13), accession number NR_029660; miRNA-99b (SEQ ID NO: 7), see accession number NR_029843; miRNA-99a (SEQ ID NO: 6), see accession number NR_029514; and miRNA-548L (SEQ ID NO: 5), see accession number NR_031630.

In one embodiment, Group 3 can be used for PTB or pre-eclampsia: miRNA-let-7g (SEQ ID NO: 13), accession number NR_029660; miRNA-490 (SEQ ID NO: 304) miRNA-491 (SEQ ID NO: 9), accession number NR_030166; miRNA-31 (SEQ ID NO: 11), accession number NR_029505; miRNA-382 (SEQ ID NO:8), accession number NR_029874; miRNA-342 (SEQ ID NO: 12), accession number NR_029888; miRNA-194 (SEQ ID NO: 305); miNRA-214 (SEQ ID NO: 10), accession number NR_029627; miRNA-371 (SEQ ID NO: 306); and miRNA-519c (SEQ ID NO: 307).

In one embodiment, Group 4 can be used for PTB or pre-eclampsia: (SEQ ID NO: 42) Homo sapiens keratin associated protein 6-2 (KRTAP6-2), mRNA, accession number NM_181604; (SEQ ID NO: 25) Homo sapiens splicing factor 3a, subunit 3, 60 kDa (SF3A3), mRNA, accession number NM_006802; (SEQ ID NO: 21) Homo sapiens cDNA FLJ16171 fis, clone BRHIP2003272, accession number AK131247; (SEQ ID NO: 22) Homo sapiens regenerating islet-derived 3 gamma (REG3G), transcript variant 1, mRNA, accession number NM_001008387; (SEQ ID NO: 24) Homo sapiens NADH dehydrogenase (ubiquinone) 1 alpha subcomplex, 2, 8 kDa (NDUFA2), nuclear gene encoding mitochondrial protein, transcript variant 1, mRNA, accession number NM_002488; (SEQ ID NO: 50) Homo sapiens coiled-coil-helix-coiled-coil-helix domain containing 10, (CHCHD10), mRNA, accession number NM_213720; (SEQ ID NO: 62) Homo sapiens olfactory receptor, family 4, subfamily D, member 1 (OR4D1), mRNA, accession numbers NM_012374 and XM_292627; (SEQ ID NO: 52) Homo sapiens biogenesis of lysosomal organelles complex-1, subunit 1 (BLOC1S1), mRNA, accession number NM_001487; (SEQ ID NO: 56) Homo sapiens PDZ domain containing 1 (PDZK1), mRNA, accession numbers NM_002614, XM_936907, XM_943050, XM_943061, and XM_943068; (SEQ ID NO: 58) Homo sapiens keratin 17 (KRT17), mRNA, accession number NM_000422; (SEQ ID NO: 61) Homo sapiens cysteine and glycine-rich protein 2 (CSRP2), mRNA, accession number NM_001321; (SEQ ID NO: 46) Homo sapiens pregnancy specific beta-1-glycoprotein 9 (PSG9), mRNA, accession number NM_002784; (SEQ ID NO: 48) Homo sapiens armadillo repeat containing 10 (ARMC10), transcript variant A, mRNA, accession number NM_031905; (SEQ ID NO: 54) Homo sapiens CD3e molecule, epsilon (CD3-TCR complex) (CD3E), mRNA, accession number NM_000733; (SEQ ID NO: 47) Homo sapiens guanylate cyclase activator 2B (uroguanylin) (GUCA2B), mRNA, accession number NM_007102; (SEQ ID NO: 64) Homo sapiens tumor necrosis factor receptor superfamily, member 13C (TNFRSF13C), mRNA, accession number NM_052945; (SEQ ID NO: 41) Homo sapiens hypothetical protein LOC643008 (LOC643008), transcript variant 1, mRNA, accession numbers NM_001162995 and NR_024379; (SEQ ID NO: 65) Homo sapiens mitochondrial ribosomal protein S21 (MRPS21), nuclear gene encoding mitochondrial protein, transcript variant 2, mRNA, accession number NM_018997; (SEQ ID NO: 57) Homo sapiens N-acetyltransferase 14 (GCNS-related, putative) (NAT14), mRNA, accession number NM_020378; (SEQ ID NO: 45) Homo sapiens proteinase 3 (PRTN3), mRNA, accession number NM_002777; (SEQ ID NO: 44) Homo sapiens olfactory receptor, family 2, subfamily A, member 2 (OR2A2), mRNA, accession number NM_001005480 and XM_498253; (SEQ ID NO: 63) *Homo sapiens* ribosomal protein L8 (RPL8), transcript variant 1, mRNA, accession number NM_000973; (SEQ ID NO: 60) *Homo sapiens* transmembrane protein 188 (TMEM188), mRNA, accession number NM_153261; (SEQ ID NO: 59) *Homo sapiens* ribosomal protein S19 binding protein 1 (RPS19BP1), mRNA, accession numbers NM_194326 and XM_039373; (SEQ ID NO: 67) *Homo sapiens* junctional sarcoplasmic reticulum protein 1 (JSRP1), mRNA, accession number NM_144616; and (SEQ ID NO: 26) *Homo sapiens* late cornified envelope 2A (LCE2A), mRNA, accession number NM_178428.

The following are combinations of biomarkers:

Group 1

| Gene Name | p-value | Sequence | Fold Change | Up or Down Regulation |
|---|---|---|---|---|
| hsa-let-7g | 0.00713887 | SEQ ID NO: 13 | -1.8 | Down Regulation |
| PSME2 | 0.00992433 | SEQ ID NO: 68 | -5.6 | Down Regulation |
| APOA1 | 0.00146359 | SEQ ID NO: 53 | -1.9 | Down Regulation |
| APOA4 | 0.00924241 | SEQ ID NO: 66 | -1.5 | Down Regulation |
| NAMPT | 0.00139273 | SEQ ID NO: 71 | -2.3 | Down Regulation |

Group 2

| Gene Name | p-value | Sequence | Fold Change | Up or Down Regulation |
|---|---|---|---|---|
| hsa-let-7g | 0.00713887 | SEQ ID NO: 13 | -1.8 | Down Regulation |
| hsa-mir-99b | 0.0457254 | SEQ ID NO: 7 | 1.7 | Up Regulation |
| hsa-mir-99a | 0.00464255 | SEQ ID NO: 6 | 1.6 | Up Regulation |
| hsa-mir-548l | 0.00160527 | SEQ ID NO: 5 | 1.5 | Up Regulation |

Group 3

| Gene Name | p-value | Sequence | Fold Change | Up or Down Regulation |
|---|---|---|---|---|
| hsa-let-7g | 0.00713887 | SEQ ID NO: 13 | -1.8 | Down Regulation |
| hsa-mir-490 | 0.00840327 | SEQ ID NO: 304 | -4.7 | Down Regulation |
| hsa-mir-491 | 0.000234436 | SEQ ID NO: 9 | -2.2 | Down Regulation |
| hsa-mir-31 | 0.0013245 | SEQ ID NO: 11 | -1.9 | Down Regulation |
| hsa-mir-382 | 9.49E-05 | SEQ ID NO: 8 | -1.8 | Down Regulation |
| hsa-mir-342 | 0.00601943 | SEQ ID NO: 12 | -1.5 | Down Regulation |
| hsa-mir-194 | 0.0079514 | SEQ ID NO: 305 | -1.5 | Down Regulation |
| hsa-mir-214 | 0.000512653 | SEQ ID NO: 10 | -1.5 | Down Regulation |
| hsa-mir-371 | 0.00779123 | SEQ ID NO: 306 | -1.4 | Down Regulation |
| hsa-mir-519c | 0.00510367 | SEQ ID NO: 307 | -1.3 | Down Regulation |

Group 4

| Gene Name | p-value | Sequence | Fold Change | Up or Down Regulation |
|---|---|---|---|---|
| KRTAP6-2 | 0.00046104 | SEQ ID NO: 42 | -2.1 | Down Regulation |
| SF3A3 | 0.00910645 | SEQ ID NO: 25 | 2.7 | Up Regulation |
| FLJ16171 | 0.00133126 | SEQ ID NO: 21 | 2.6 | Up Regulation |
| REG3G | 0.00207211 | SEQ ID NO: 22 | 1.9 | Up Regulation |
| NDUFA2 | 0.00749296 | SEQ ID NO: 24 | 1.6 | Up Regulation |
| CHCHD10 | 0.00106558 | SEQ ID NO: 50 | -2.6 | Down Regulation |
| OR4D1 | 0.00698767 | SEQ ID NO: 62 | -2.3 | Down Regulation |
| BLOC1S1 | 0.00118782 | SEQ ID NO: 52 | -2.2 | Down Regulation |
| PDZK1 | 0.00190269 | SEQ ID NO: 56 | -2.0 | Down Regulation |
| KRT17 | 0.00298912 | SEQ ID NO: 58 | -2.0 | Down Regulation |
| CSRP2 | 0.00626579 | SEQ ID NO: 61 | -1.8 | Down Regulation |
| PSG9 | 0.00064014 | SEQ ID NO: 46 | -1.8 | Down Regulation |
| ARMC10 | 0.00098666 | SEQ ID NO: 48 | -1.7 | Down Regulation |
| CD3E | 0.00152925 | SEQ ID NO: 54 | -1.7 | Down Regulation |
| GUCA2B | 0.00076153 | SEQ ID NO: 47 | -1.7 | Down Regulation |
| TNFRSF13C | 0.00814341 | SEQ ID NO: 64 | -1.6 | Down Regulation |
| LOC643008 | 0.00010597 | SEQ ID NO: 41 | -1.6 | Down Regulation |
| MRPS21 | 0.00911331 | SEQ ID NO: 65 | -1.6 | Down Regulation |
| NAT14 | 0.00231347 | SEQ ID NO: 57 | -1.6 | Down Regulation |
| PRTN3 | 0.00060814 | SEQ ID NO: 45 | -1.6 | Down Regulation |
| OR2A2 | 0.00059257 | SEQ ID NO: 44 | -1.6 | Down Regulation |
| RPL8 | 0.00750065 | SEQ ID NO: 63 | -1.5 | Down Regulation |
| TMEM188 | 0.00622275 | SEQ ID NO: 60 | -1.5 | Down Regulation |
| RPS19BP1 | 0.00571346 | SEQ ID NO: 59 | -1.5 | Down Regulation |
| JSRP1 | 0.0092973 | SEQ ID NO: 67 | -1.5 | Down Regulation |
| LCE2A | 0.012785 | SEQ ID NO: 26 | 2.3 | Up Regulation |

The combination of biomarkers can be detected to be present in a biomarker amount by hybridizing the biomarker with a biomarker primer (PCR) or biomarker probe (biochip). The combination of biomarkers can be qualitated or quantitated with a normalization nucleic acid during the detection of the biomarker amount thereof. The combination of biomarkers can be tied to a disease state. Once the disease state is identified for the combination of biomarkers, a treatment regimen can be provided to the subject, such as pregnant woman, that has the biomarker amount. The treatment regimen can then be implemented on the pregnant woman in an attempt to inhibit onset or progression of the disease state. The combination of biomarkers can be present as a kit in the combination. The kit may include instructions identifying the combination of biomarkers and the indication of the disease state thereof.

Transcriptome-typing can be performed with the combination of biomarkers. Transcriptome-typing is equivalent to genotyping for transcribed RNA.

In some embodiments, a method of detecting a combination of nucleic acid biomarkers in a human subject can include: obtaining a nucleic acid sample from the human subject; selecting the combination of nucleic acid biomarkers; transcriptome-typing a transcriptome of the human subject for the combination of nucleic acid biomarkers in the nucleic acid sample from the human subject; detecting in the nucleic acid sample the presence of the combination of nucleic acid biomarkers, wherein each nucleic acid biomarker in the combination of nucleic acid biomarkers has a variation from a transcription standard, wherein the combination of nucleic acid biomarkers includes at least two of: miRNA-let-7g having a nucleotide sequence of or complementary to SEQ ID NO: 13 with a variation less than the transcription standard; PSME2 having a nucleotide sequence of or complementary to SEQ ID NO: 68 with a variation less than the transcription standard; APOA1 having a nucleotide sequence of or complementary to SEQ ID NO: 53 with a variation less than the transcription standard; and NAMPT having a nucleotide sequence of or complementary to SEQ ID NO: 71 with a variation less than the transcription standard. In some aspects: the variation for miRNA-let-7g is about −1.8 fold change; the variation for PSME2 is about −5.6 fold change; the variation for APOA1 is about −1.9 fold change; and/or the variation for NAMPT is −2.3 fold change. In some aspects, the analyzing includes hybridizing each nucleic acid biomarker in the nucleic acid sample with a complementary nucleic acid configured as a primer or a probe, the method comprising detecting the hybridizing.

Combination Example 1 for sPTB Less than 33 Weeks:

The nucleic acid biomarkers of Group 1 were used in a validation study with 40 subjects, 20 being susceptible to PTB or having had a PTB, and 20 being controls without PTB or susceptibility thereto. The samples were obtained between 16-20 weeks gestation. The sensitivity was found to be 100%. The specificity was found to be 100%. The PPV was found to be 100%. The NPV was found to be 100%.

Combination Example 2 for sPTB Less than 33 Weeks:

The PSME2 and APOA1 nucleic acid biomarkers of Group 1 were used in a validation study with 60 subjects, 20 being susceptible to PTB or having had a PTB, and 40 being controls without PTB or susceptibility thereto. All subjects being G1P0 (first pregnancy). The samples were obtained at 12 weeks gestation. The APOA1 biomarker (MoM; multiple of the median) plus MA resulted in an AUC of 0.79, a P of 0.001, a FPR (false positive rate) 10% of 52, a FPR 20% of 61 and a FPR 30% being 75. The APOA1 biomarker and PSME2 biomarker combination resulted in an AUC of 0.796, a P of 0.05, a FPR 10% of 48, a FPR 20% of 66 and a FPR 30% being 72. The APOA1 biomarker and PSME2 biomarker (MoMs) combination resulted in an AUC of 0.793, a P of 0.04, a FPR 10% of 41, a FPR 20% of 61 and a FPR 30% being 78.

Combination Example 3 for sPTB Less than 33 Weeks:

The PSME2 and has-let-7g nucleic acid biomarkers of Group 1 were used in a validation study. The samples were obtained at 16-20 weeks gestation. The has-let-7g biomarker and PSME2 biomarker (MoMs) combination resulted in an AUC of 0.761, a P of less than 0.001, a FPR 10% of 50, a FPR 20% of 57 and a FPR 30% being 70. The has-let-7g biomarker and PSME2 biomarker (MoMs) combination resulted in an AUC of 0.841, a P of less than 0.001, a FPR 10% of 62, a FPR 20% of 76 and a FPR 30% being 79.

Combination Example 4 for Early Onset Preeclampsia Less than 34 Weeks:

The NAMPT and APOA1 nucleic acid biomarkers of Group 1 were used in a validation study. The samples were obtained at 16-20 weeks gestation. The NAMPT biomarker and APOA1 biomarker combination resulted in an AUC of 0.882, a P of less than 0.001, a FPR 10% of 67, a FPR 20% of 67 and a FPR 30% being 100.

Combination Example 5 for all PTB (Spontaneous and Iatrogenic Less than 33 Weeks:

The PSME2, has-let-7g, NAMPT and APOA1 nucleic acid biomarkers of Group 1 were used in a validation study. The samples were obtained at 16-20 weeks gestation. The PSME2, has-let-7g, NAMPT and APOA1 nucleic acid biomarker combination resulted in an AUC of 0.883, a P of less than 0.001, a FPR 10% of 58, a FPR 20% of 78 and a FPR 30% being 83.

Combination Example 6:

The APOA4 nucleic acid biomarker was used in combinations with PSME2, has-let-7g, NAMPT and APOA1 nucleic acid biomarkers in studies of Combination Examples 1-5. The combination of biomarkers with APOA4 produced data comparable with the data of Combination Examples 1-5. It has been found that APOA4 can also beneficially provide information regarding PTB and preeclampsia.

A method of quantification of cell free plasma (CFP) RNA can include: providing one or more normalization nucleic acids, each normalization nucleic acid having a CFP RNA normalization sequence; obtaining a biological sample from a subject; extracting biological sample CFP RNA from the biological sample, wherein the biological sample is cell free plasma RNA; introducing the biological sample CFP RNA to the one or more normalization nucleic acids; performing a polymerase chain reaction (PCR) with the biological sample CFP RNA in the presence of the one or more normalization nucleic acids; measuring the amount of the one or more normalization nucleic acids present in the biological sample CFP RNA; and determining the amount of biological sample CFP RNA based on the amount of the one or more normalization nucleic acids in the biological sample, wherein the CFP RNA normalization sequence and sample CFP RNA are miRNA or mRNA, wherein the CFP RNA normalization sequences have a continuous normalization sequence including or complementary to a continuous sequence of one or more of SEQ ID NOs: 1-4 and 301-303. This normalization can be done with a combination of nucleic acid biomarkers, which can be the nucleic acids having a continuous sequence of one or more of SEQ ID NOS: 5-300 and 304-307 or complement thereof.

A method for determining an amount of a biomarker nucleic acid in a cell free plasma (CFP) RNA transcriptome of a pregnant woman can include: providing one or more normalization nucleic acids, each normalization nucleic acid having a CFP RNA normalization sequence; providing one or more biomarker nucleic acids, each biomarker nucleic acid having a biomarker nucleic acid sequence; obtaining a biological sample from a subject; extracting biological sample CFP RNA from the biological sample; introducing the biological sample CFP RNA to the one or more normalization nucleic acids; performing a polymerase chain reaction (PCR) with the biological sample CFP RNA in the presence of the one or more normalization nucleic acids; measuring the amount of the one or more normalization nucleic acids present in the biological sample CFP RNA; determining the amount of biological sample CFP RNA based on the amount of the one or more normalization nucleic acids in the biological sample; determining an amount of each biomarker nucleic acid in the biological sample CFP RNA of the pregnant woman based on the amount of the one or more normalization nucleic acids in the biological sample, wherein the one or more biomarker nucleic acids each includes a continuous sequence of one or more continuous sequences of SEQ ID NOS: 5-300 and 304-307 or complement thereof as well as a combination of biomarkers as defined herein, wherein the CFP RNA normalization sequence and sample CFP RNA are miRNA or mRNA, wherein the CFP RNA normalization sequences have a continuous normalization sequence including or complementary to a continuous sequence of one or more of SEQ ID NOs: 1-4 and 301-303.

The methods may also include one or more of: extracting and isolating the CFP RNA from a body fluid of the pregnant woman at less than 32 weeks of pregnancy; extracting and isolating the CFP RNA at about 12 weeks to about 32 weeks of pregnancy; one or more biomarker nucleic acids includes a biomarker consisting of one or more sequences from one or more of SEQ ID NOs: 5-18 of complement thereof; the one or more biomarker nucleic acids includes a biomarker consisting of one or more sequences from one or more of SEQ ID NOs: 19-106 or complement thereof; the CFP RNA transcriptome includes a CFP miRNA PTB biomarker that is up-regulated in order to indicate susceptibility of PTB, the CFP miRNA PTB biomarker having a sequence of one or more of SEQ ID NOs: 5-7 or complement thereof; one or more biomarker nucleic acids includes a biomarker that is present in an amount less than a standard, the biomarker consisting of a sequence of one or more of SEQ ID NOs: 8-18 of complement thereof; the CFP RNA transcriptome includes a CFP small RNA PTB biomarker that is up-regulated in order to indicate susceptibility of PTB, the CFP small RNA PTB biomarker having a sequence of one or more of SEQ ID NOs: 19-41 and/or 107-142 or complement thereof; one or more biomarker nucleic acids includes a biomarker that is present in an amount less than a standard, the biomarker consisting of a sequence of one or more of SEQ ID NOs: 42-106 and/or 143-300 or complement thereof; using a primer or a probe that hybridizes with each of the biomarkers of the combination of biomarkers; extracting and isolating a first sample of the one or more CFP RNA PTB biomarkers of the CFP RNA transcriptome prior to 12 weeks of pregnancy and a second sample of the one or more CFP RNA biomarkers after 12 weeks of pregnancy, and comparing the amount of one or more CFP RNA PTB biomarkers from the first sample and second sample, wherein a change in amount indicates susceptibility to PTB.

A method for detecting spontaneous preterm birth in an asymptomatic subject comprising: (a) subjecting a sample from the subject to a procedure to detect polynucleotides (biomarkers); (b) detecting spontaneous preterm birth by comparing the amount of polynucleotides to the amount of such polynucleotides obtained from a control who does not suffer from preterm birth wherein the polynucleotides comprise at least one of, or are selected from Group 1, 2, 3, 4, or sub groups thereof, or any other combination group described herein.

A method where the procedure comprises detecting one or more polynucleotides in the sample by contacting the sample with oligonucleotides that hybridize to the polynucleotides (biomarkers); and detecting in the sample levels of nucleic acids that hybridize to the polynucleotides relative to a control, wherein a change or significant difference in the amount or status of the polynucleotides in the sample compared with the amount or status in the control is indicative of spontaneous preterm birth.

A method wherein the procedure comprises: contacting the sample with biomarkers that specifically bind to the polynucleotides under conditions effective to bind the biomarkers and form complexes; measuring the amount or status of the polynucleotides present in the sample by quantitating the amount of the complexes; and wherein a change or significant difference in the amount or status of polynucleotides in the sample compared with the amount or status obtained from a control subject who does not suffer from preterm birth is indicative of spontaneous preterm birth.

In any of the embodiments, the subject may be asymptomatic for a pregnancy complication, such as PTB or early onset preeclampsia.

The invention further relates to a method of assessing the efficacy of a therapy for preventing, inhibiting, or reducing spontaneous preterm birth in a patient. A method of the invention comprises comparing: (a) levels of a combination of biomarkers in a sample from the patient obtained from the patient prior to providing at least a portion of a therapy to the patient; and (b) levels of combinations of biomarkers in a second sample obtained from the patient following therapy. A significant difference between the levels of biomarkers in the second sample relative to the first sample is an indication that the therapy may be efficacious for inhibiting spontaneous preterm birth. In an embodiment, the method is used to assess the efficacy of a therapy for inhibiting spontaneous preterm birth where changes in amounts of biomarkers relative to the first sample, is an indication that the therapy may be efficacious for inhibiting the condition. In an embodiment, the method is used to assess the efficacy of a therapy for inhibiting spontaneous preterm birth where different levels of the combination of biomarkers relative to the first sample, is an indication that the therapy may be efficacious for inhibiting spontaneous preterm birth. A "therapy" may be any therapy for treating spontaneous preterm birth, in particular, including but not limited to therapeutics, procedures and interventions such as progesterone, cervical cerclage and pessary. A method of the invention can be used to evaluate a patient before, during, and after therapy.

Methods for diagnosing, detecting or monitoring spontaneous preterm birth are contemplated comprising detecting combinations of biomarkers associated with preterm birth. Thus, the present invention relates to a method for diagnosing and monitoring spontaneous preterm birth in a sample from a subject comprising isolating polynucleotides, in particular mRNA, from the sample; and detecting combinations of biomarkers in the sample. The presence of different levels of combinations of biomarkers in the sample compared to a standard or control may be indicative of spontaneous preterm birth and/or a positive prognosis.

The invention provides methods for determining the presence or absence of spontaneous preterm birth in a subject comprising detecting in the sample levels of polynucleotides that hybridize to one or more combinations of biomarkers, comparing the levels with a predetermined standard or cut-off value, and therefrom determining the presence or absence of spontaneous preterm birth in the subject. In an embodiment, the invention provides methods for determining the presence or absence of spontaneous preterm birth in a subject comprising (a) contacting a sample obtained from the subject with oligonucleotides that hybridize to one or more combinations of biomarkers; and (b) detecting in the sample a level of polynucleotides that hybridize to the combinations of biomarkers relative to a predetermined cut-off value, and therefrom determining the presence or absence of spontaneous preterm birth in the subject.

Within certain embodiments, the amount of polynucleotides that are mRNA are detected via polymerase chain reaction using, for example, oligonucleotide primers that hybridize to one or more combinations of biomarkers, or complements of such combinations of biomarkers. Within other embodiments, the amount of mRNA is detected using a hybridization technique, employing oligonucleotide probes that hybridize to one or more combinations of biomarkers, or complements thereof.

The invention contemplates the methods, compositions, and kits described herein comprising assessing one or more additional clinical factor or prognostic factor associated with spontaneous preterm birth. The additional factor may be additional markers of spontaneous preterm birth and/or clinical blood data. In an aspect the additional marker is fetal fibronection or phosphorylated insulin-like growth factor binding protein-1. The additional factor may be clinical factors comprising or chosen from or selected from the group consisting of history of abortion, history of PTB, alcohol consumption, anaemia, antepartum haemorrhage and urinary tract infection. The additional factor may be clinical factors comprising or chosen from or selected from the group consisting of history of abortion, history of PTB, alcohol consumption and urinary tract infection. Accordingly, the methods of this invention may be used in combination with other methods of preterm birth diagnosis or clinical factors including without limitation, clinical blood data, fetal fibronectin, phosphorylated insulin-like growth factor binding protein-1, and at least one of history of abortion, history of PTB, alcohol consumption, anaemia, antepartum haemorrhage and urinary tract infection, in particular history of abortion, history of PTB, alcohol consumption, and anaemia. Methods including additional markers can include reagents to detect the additional markers. In an aspect, the methods of this invention are used in combination with the clinical factors history of PTB, history of abortion, and anaemia. In an aspect, the methods of this invention are used in combination with the clinical factors history of PTB and history of abortion. In an aspect, the methods of this invention are used in combination with the clinical factors history of PTB, history of abortion, alcohol consumption, urinary tract infections and anaemia. In an aspect, the methods of this invention are used in combination with the clinical factors history of PTB, history of abortion and urinary tract infections, and optionally anaemia. In an aspect, the methods of this invention are used in combination with the clinical factors history of PTB, history of abortion and alcohol consumption. In an aspect, the methods of this invention are used in combination with the clinical factors history of abortion and anaemia.

The terms "sample", "biological sample", and the like mean a material known or suspected of expressing or containing one or more combinations of biomarkers. A test sample can be used directly as obtained from the source or following a pretreatment to modify the character of the sample. A sample can be derived from any biological source, such as tissues, extracts, or cell cultures, including cells, cell lysates, and physiological fluids, such as, for example, whole blood, plasma, serum, saliva, ocular lens fluid, cerebral spinal fluid, sputum, sweat, urine, milk, ascites fluid, synovial fluid, peritoneal fluid, and the like. A sample can be obtained from animals, preferably mammals, most preferably humans. A sample can be treated prior to use, such as preparing plasma from blood, diluting viscous fluids, and the like. Methods of treatment can involve filtration, distillation, extraction, concentration, inactivation of interfering components, the addition of reagents, and the like.

"Spontaneous preterm birth" or "SPTB" refers to birth at <37 weeks of gestation.

"Spontaneous preterm labor (SPTL)" is defined as spontaneous onset of labor <37 weeks of gestation resulting in preterm delivery.

The terms "subject", "individual" or "patient" refer to a warm-blooded animal such as a mammal. In particular, the terms refer to a human. A subject, individual or patient may be afflicted with or suspected of having or being predisposed to spontaneous preterm birth. The present invention may be particularly useful for determining spontaneous preterm birth development potential in at-risk patients suffering from particular spontaneous preterm birth predisposing conditions. Spontaneous preterm birth predisposing conditions include without limitation a previous history of preterm birth, previous history of abortion, anaemia, uterine factors such as uterine volume increase, uterine anomalies, trauma and infection. In aspects of the invention the predisposing conditions are history of preterm birth and history of abortion. In other aspects of the invention the predisposing conditions are history of abortion and anaemia. In embodiments of the invention "history of PTB" refers to any previous premature delivery, any type i.e. spontaneous or induced or medically instigated. In embodiments of the invention "history of abortion" refers to any previous abortion, any type i.e. spontaneous or induced. In embodiments of the invention "anaemia" refers to <120 g/L of haemoglobin occurring anytime during a current pregnancy prior to sampling (e.g., prior to 27-33 weeks).

The results of a subject's diagnosis, screening, prognosis or monitoring is typically displayed or provided to a user such as a clinician, health care worker or other caregiver, laboratory personnel or the patient. The results may be quantitative information (e.g. the level or amount of a marker compared to a control) or qualitative information (e.g. diagnosis of spontaneous preterm birth). The output can comprise guidelines or instructions for interpreting the results, for example, numerical or other limits that indicate the presence or absence of spontaneous preterm birth. The guidelines may also specify the diagnosis, for example whether there is a high risk of spontaneous preterm birth. The output can include tools for interpreting the results to arrive at a diagnosis, prognosis or treatment plan, for example, an output may include ranges or cut-offs for abnormal or normal status to arrive at a diagnosis, prognosis, or treatment plan. The output can also provide a recommended therapeutic plan, and it may include other clinical information and guidelines and instructions for interpreting the information.

Devices known in the art can be used to transmit the results of a method of the invention. Examples of output devices include without limitation, a visual output device (e.g. a computer screen or a printed paper), an auditory output device (e.g., a speaker), a printer or a patient s electronic medical record. The format of the output providing the results and related information may be a visual output (e.g., paper or a display on a screen), a diagram such as a graph, chart or voltammetric trace, an audible output (e.g. a speaker) or, a numerical value. In an aspect, the output is a numerical value, in particular the amount or relative amount of at least one marker in a subject's sample compared to a control. In an aspect, the output is a graph that indicates a value, such as an amount or relative amount, of the at least one marker in the sample from the subject on a standard curve. In an embodiment, the output (such as a graphical output) shows or provides a cut-off value or level that indicates the presence of high risk of spontaneous preterm birth. An output may be communicated to a user by physical, audible or electronic means, including mail, telephone, facsimile transmission, email or an electronic medical record.

The analytic methods described herein can be implemented by use of computer systems and methods described below and known in the art. Thus the invention provides computer readable media comprising one or more combinations of biomarkers, and optionally other markers (e.g. markers of preterm birth). "Computer readable media" refers to any medium that can be read and accessed directly by a computer. Thus, the invention contemplates computer readable medium having recorded thereon markers identified for patients and controls. "Recorded" refers to a process for storing information on computer readable medium. The skilled artisan can readily adopt any of the presently known methods for recording information on computer readable medium to generate manufactures comprising information on one or more combinations of biomarkers.

A variety of data processor programs and formats can be used to store information on one or more combinations of biomarkers, and other markers on computer readable medium. Any number of dataprocessor structuring formats (e.g., text file or database) may be adapted in order to obtain computer readable medium having recorded thereon the marker information.

By providing the combination of biomarker information in computer readable form, one can routinely access the information for a variety of purposes. For example, one skilled in the art can use the information in computer readable form to compare marker information obtained during or following therapy with the information stored within the data storage means.

The invention also provides in an electronic system and/or in a network, a method for determining whether a subject has spontaneous preterm birth or is at risk of spontaneous preterm birth, comprising determining the presence or absence of one or more combinations of biomarkers, and based on the presence or absence of the one or more combinations of biomarkers, determining whether the subject has a pre-disposition to spontaneous preterm birth and optionally recommending a procedure or treatment.

The invention further provides in a network, a method for determining whether a subject has a pre-disposition to spontaneous preterm birth comprising: (a) receiving phenotypic and/or clinical information on the subject and information on one or more combinations of biomarkers associated with samples from the subject; (b) acquiring information from the network corresponding to the one or more combinations of biomarkers; and (c) based on the phenotypic information and information on the one or more combinations of biomarkers, determining whether the subject has a pre-disposition to spontaneous preterm birth; and (d) optionally recommending a procedure or treatment.

The invention still further provides a system for identifying selected records that identify spontaneous preterm birth. A system of the invention generally comprises a computer; a database server coupled to the computer; a database coupled to the database server having data stored therein, the data comprising records of data comprising one or more combinations of biomarkers, and a code mechanism for applying queries based upon a desired selection criteria to the data file in the database to produce reports of records which match the desired selection criteria.

In an aspect of the invention a method is provided for detecting cells or tissues associated with spontaneous preterm birth using a computer having a processor, memory, display, and input/output devices, the method comprising the steps of: (a) creating records of one or more combinations of biomarkers, identified in a sample suspected of containing biomarkers associated with spontaneous preterm birth; (b) providing a database comprising records of data comprising one or more combinations of biomarkers of spontaneous preterm birth; and (c) using a code mechanism for applying queries based upon a desired selection criteria to the data file in the database to produce reports of records of step (a) which provide a match of the desired selection criteria of the database of step (b) the presence of a match being a positive indication that the markers of step (a) have been isolated from cells or tissue that are associated with spontaneous preterm birth.

The invention contemplates a method for determining whether a subject has a pre-disposition to spontaneous preterm birth comprising: (a) receiving phenotypic and/or clinical information on the subject and information on one or more combinations of biomarkers, associated with samples from the subject; (b) acquiring information from a network corresponding to one or more biomarkers; and (c) based on the phenotypic information, information on one or more combinations of biomarkers, and optionally other markers, and acquired information, determining whether the subject has a pre-disposition to spontaneous preterm birth; and (d) optionally recommending a procedure or treatment.

In an aspect of the invention, the computer systems, components, and methods described herein are used to monitor preterm birth or determine the stage or type of spontaneous preterm birth. The computer systems, components and methods may also include clinical variables, in particular history of PTB, history of abortion, consumption of alcohol, antepartum haemorrhage in first and/or second trimester, presence of Group B *streptococcus*, urinary tract infection and anaemia, more particularly history of PTB, history of abortion and anaemia.

In some instances, it may be important to determine whether or not an asymptomatic pregnant woman is susceptible to having preterm labor (PTL) or PTB. If the pregnant woman is asymptomatic, it is because there are no indications, physical or biochemical that have been diagnosed or detected that would lead a medical professional to believe she is at risk of PTL or PTB. However, such an asymptomatic pregnant woman indeed may be susceptible to PTL or PTB without them knowing or having any indication of such susceptibility. As such, the asymptomatic pregnant woman may need to be screened to determine whether or not she may have a susceptibility to PTL or PTB. If the asymptomatic pregnant woman is susceptible to PTL or PTB, then medical therapy can be performed to inhibit the PTL or PTB. If the asymptomatic pregnant woman is not susceptible to PTL or PTB, then normal care can be provided. However, determining whether an asymptomatic pregnant woman is susceptible to PTL or PTB may be difficult because there are no obvious symptoms.

In one aspect, the method includes defining the asymptomatic pregnant woman as being asymptomatic when having no physical indication of being susceptible to PTL or PTB. In one aspect, the method includes prior to obtaining the vaginal fluid sample: screening the asymptomatic pregnant woman for physical and/or biochemical indications of being susceptible to preterm labor; and determining the asymptomatic pregnant woman to be not susceptible to preterm labor. In one aspect, the asymptomatic pregnant woman has not previously had: a preterm birth; a complicated pregnancy; diagnosed physical abnormalities; diagnosed aneuploidy; or diagnosed genetic syndromes associated with preterm birth or complicated pregnancy. In one embodiment, when the asymptomatic pregnant woman is determined to be susceptible to PTB, providing instructions for the asymptomatic pregnant women to receive treatment to prevent the PTB. In one aspect, the method can include performing treatment on the asymptomatic pregnant woman to prevent the PTB. Such a treatment can include administering progesterone to the asymptomatic pregnant woman.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

A unique segment of a sequence in a sequence listing is a specific sequence segment that is found within the recited sequence of the SEQ ID NO, and substantially absent in the rest of the RNA transcriptome. That is, the unique segment of the sequence in the Sequence Listing identified by the SEQ ID NO can be used as a probe or a primer that is specific for that SEQ ID NO. The techniques available for identifying a primer or a probe available to one of ordinary skill in the art can be used to identify one or more unique segments of each SEQ ID NO recited in the Sequence Listing.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited or in the incorporated references herein are incorporated herein by specific reference in their entirety.

The invention claimed is:

1. A method comprising:
obtaining a plasma sample from a human subject, wherein the human subject is a pregnant female;
obtaining cell free nucleic acids from the plasma sample;
detecting in the cell free nucleic acids the presence of a combination of nucleic acid biomarkers comprising miRNA-let-7g, PSME2, APOA1, NAMPT, miRNA-491, miRNA-31, miRNA-382, miRNA-342, and miRNA-214, wherein detection comprises contacting the cell free nucleic acids with primers or probes that are complementary to miRNA-let-7g, PSME2, APOA1, NAMPT, miRNA-491, miRNA-31, miRNA-382, miRNA-342, and miRNA-214 and detecting hybridization between the primers or probes and the combination of nucleic acid biomarkers.

2. The method of claim 1, wherein the combination of nucleic acid biomarkers further includes APOA4.

3. The method of claim 1, wherein the combination of nucleic acid biomarkers further includes: miRNA-99b, miRNA-99a and miRNA-548L.

4. The method of claim 1, wherein the combination of nucleic acid biomarkers further includes: SF3A3, FLJ16171, REG3G, NDUFA2, LCE2A, KRTAP6-2, CHCHD10, OR4D1, BLOC1S1, PDZK1, KRT17, CSRP2, PSG9, ARMC10, CD3E, GUCA2B, TNFRSF13C, LOC643008, MRPS21, NAT14, PRTN3, OR2A2, RPL8, TMEM188, RPS19BP1 and JSRP1.

5. The method of claim 1, wherein the nucleic acid biomarkers are RNA.

6. The method of claim 1, further comprising quantitating the amount of each nucleic acid biomarker in the cell free nucleic acid sample.

7. The method of claim 6, further comprising generating a report, wherein the report recites the amount of each nucleic acid biomarker in the cell free nucleic acid sample.

8. The method of claim 1, further comprising providing the pregnant female a therapy to treat a pregnancy disorder.

9. A method comprising:
obtaining a plasma sample from a human subject, wherein the human subject is a pregnant female;
obtaining a cell free nucleic acid from the plasma sample;
detecting in the cell free nucleic acid sample the presence of a combination of nucleic acid biomarkers comprising miRNA-let-7g, PSME2, APOA1, and NAMPT, wherein detection comprises contacting the cell free nucleic acid with primers or probes that are complementary to miRNA-let-7g, PSME2, APOA1, and NAMPT, and detecting hybridization between the primers or probes and the combination of nucleic acid biomarkers; and detecting in the cell free nucleic acid sample the presence of a normalization nucleic acid, wherein the normalization nucleic acid is snRNA:U6:96A having the sequence of SEQ ID NO: 2 and wherein detection comprises contacting the cell free nucleic acid with primers or probes that are complementary to snRNA:U6:96A and detecting hybridization between the primers or probes and the normalization nucleic acid.

10. A method comprising:

obtaining a biological sample from a human subject, wherein the human subject is a pregnant female;

obtaining a nucleic acid sample from the biological sample;

detecting in the nucleic acid sample the presence of a combination of nucleic acid biomarkers comprising miRNA-let-7g, PSME2, APOA1, NAMPT, miRNA-491, miRNA-31, miRNA-382, miRNA-342, and miRNA-214, wherein detection comprises contacting the nucleic acid with primers or probes that are complementary to miRNA-let-7g, PSME2, APOA1, NAMPT, miRNA-491, miRNA-31, miRNA-382, miRNA-342, and miRNA-214 and detecting hybridization between the primers or probes and the combination of nucleic acid biomarkers.

11. The method of claim 10, wherein the combination of nucleic acid biomarkers further includes APOA4.

12. The method of claim 10, wherein the combination of nucleic acid biomarkers further includes miRNA-99b, miRNA-99a, and miRNA-548L.

13. The method of claim 10, wherein the combination of nucleic acid biomarkers further includes: SF3A3, FLJ16171, REG3G, NDUFA2, LCE2A, KRTAP6-2, CHCHD10, OR4D1, BLOC1S1, PDZK1, KRT17, CSRP2, PSG9, ARMC10, CD3E, GUCA2B, TNFRSF13C, LOC643008, MRPS21, NAT14, PRTN3, OR2A2, RPL8, TMEM188, RPS19BP1, and JSRP1.

14. The method of claim 10, wherein the biological sample is obtained from a pregnant female that has been pregnant for at least 12 weeks.

15. The method of claim 10, wherein the biological sample is a plasma sample and the nucleic acid sample is cell free nucleic acid obtained from the plasma sample.

16. The method of claim 10, further comprising quantitating the amount of each nucleic acid biomarker in the nucleic acid sample.

17. The method of claim 10, further comprising providing the pregnant female a therapy to treat a pregnancy disorder.

* * * * *

SEQUENCE LISTING

<160> NUMBER OF SEQ ID NOS: 307

<210> SEQ ID NO 1
<211> LENGTH: 2276
<212> TYPE: DNA
<213> ORGANISM: Homo sapiens

<400> SEQUENCE: 1

| | | | | | |
|---|---|---|---|---|---|
| gaacgtggta | taaaggggc | gggaggccag | gctcgtgccg | ttttgcagac | gccaccgccg | 60 |
| aggaaaaccg | tgtactatta | gccatggtca | accccaccgt | gttcttcgac | attgccgtcg | 120 |
| acggcgagcc | cttgggccgc | gtctccttg | agctgtttgc | agacaaggtc | ccaaagacag | 180 |
| cagaaaattt | tcgtgctctg | agcactggag | agaaaggatt | tggttataag | ggttcctgct | 240 |
| ttcacagaat | tattccaggg | tttatgtgtc | agggtggtga | cttcacacgc | cataatggca | 300 |
| ctggtggcaa | gtccatctat | ggggagaaat | ttgaagatga | gaacttcatc | ctaaagcata | 360 |
| cgggtcctgg | catcttgtcc | atggcaaatg | ctggacccaa | cacaaatggt | tcccagtttt | 420 |
| tcatctgcac | tgccaagact | gagtggttgg | atggcaagca | tgtggtgttt | ggcaaagtga | 480 |
| aagaaggcat | gaatattgtg | gaggccatgg | agcgctttgg | gtccaggaat | ggcaagacca | 540 |
| gcaagaagat | caccattgct | gactgtggac | aactcgaata | agtttgactt | gtgttttatc | 600 |
| ttaaccacca | gatcattcct | tctgtagctc | aggagagcac | ccctccaccc | catttgctcg | 660 |
| cagtatccta | gaatctttgt | gctctcgctg | cagttccctt | tgggttccat | gttttccttg | 720 |
| ttccctccca | tgcctagctg | gattgcagag | ttaagtttat | gattatgaaa | taaaaactaa | 780 |
| ataacaattg | tcctcgtttg | agttaagagt | gttgatgtag | gctttatttt | aagcagtaat | 840 |
| gggttacttc | tgaaacatca | cttgtttgct | taattctaca | cagtacttag | atttttttta | 900 |
| cttccagtc | ccaggaagtg | tcaatgtttg | ttgagtggaa | tattgaaaat | gtaggcagca | 960 |
| actgggcatg | gtggctcact | gtctgtaatg | tattacctga | ggcagaagac | cacctgaggg | 1020 |
| taggagtcaa | gatcagcctg | ggcaacatag | tgagacgctg | tctctacaaa | aaataattag | 1080 |
| cctggcctgg | tggtgcatgc | ctagtcctag | ctgatctgga | ggctgacgtg | ggaggattgc | 1140 |
| ttgagcctag | agtgagctat | tatcatgcca | ctgtacagcc | tgggtgttca | cagatcttgt | 1200 |
| gtctcaaagg | taggcagagg | caggaaaagc | aaggagccag | aattaagagg | ttgggtcagt | 1260 |
| ctgcagtgag | ttcatgcatt | tagaggtgtt | cttcaagatg | actaatgtca | aaaattgaga | 1320 |
| catctgttgc | ggttttttt | tttttttttt | cccctggaat | gcagtggcgt | gatctcagct | 1380 |
| cactgcagcc | tccgcctcct | gggttcaagt | gattctagtg | cctcagcctc | ctgagtagct | 1440 |
| gggataatgg | gcgtgtgcca | ccatgcccag | ctaattttg | tatttttagt | atagatgggg | 1500 |
| tttcatcatt | ttgaccaggc | tggtctcaaa | ctcttgacct | cagctgatgc | gcctgccttg | 1560 |
| gcctcccaaa | ctgctgagat | tacagatgtg | agccaccgca | ccctacctca | ttttctgtaa | 1620 |
| caaagctaag | cttgaacact | gttgatgttc | ttgagggaag | catattgggc | tttaggctgt | 1680 |
| aggtcaagtt | tatacatctt | aattatggtg | gaattcctat | gtagagtcta | aaaagccagg | 1740 |
| tacttggtgc | tacagtcagt | ctccctgcag | agggttaagg | cgcagactac | ctgcagtgag | 1800 |
| gaggtactgc | ttgtagcata | tagagcctct | ccctagcttt | ggttatggag | gctttgaggt | 1860 |
| tttgcaaacc | tgaccaattt | aagccataag | atctggtcaa | agggataccc | ttcccactaa | 1920 |
| ggacttggtt | tctcaggaaa | ttatatgtac | agtgcttgct | ggcagttaga | tgtcaggaca | 1980 |
| atctaagctg | agaaaacccc | ttctctgccc | accttaacag | acctctaggg | ttcttaaccc | 2040 |
| agcaatcaag | tttgcctatc | ctagaggtgg | cggatttgat | catttggtgt | gttgggcaat | 2100 |

```
tttgtttta ctgtctggtt ccttctgcgt gaattaccac caccaccact tgtgcatctc    2160
agtcttgtgt gttgtctggt tacgtattcc ctgggtgata ccattcaatg tcttaatgta    2220
cttgtggctc agacctgagt gcaaggtgga aataaacatc aaacatcttt tcatta        2276

<210> SEQ ID NO 2
<211> LENGTH: 107
<212> TYPE: DNA
<213> ORGANISM: Drosophila melanogaster

<400> SEQUENCE: 2
gttcttgctt cggcagaaca tatactaaaa ttggaacgat acagagaaga ttagcatggc    60
ccctgcgcaa ggatgacacg caaaatcgtg aagcgttcca cattttt                 107

<210> SEQ ID NO 3
<211> LENGTH: 107
<212> TYPE: DNA
<213> ORGANISM: Drosophila melanogaster

<400> SEQUENCE: 3
gttcttgctt cggcagaaca tatactaaaa ttggaacgat acagagaaga ttagcatggc    60
ccctgcgcaa ggatgacacg caaaatcgtg aagcgttcca cattttt                 107

<210> SEQ ID NO 4
<211> LENGTH: 107
<212> TYPE: DNA
<213> ORGANISM: Drosophila melanogaster

<400> SEQUENCE: 4
gttcttgctt cggcagaaca tatactaaaa ttggaacgat acagagaaga ttagcatggc    60
ccctgcgcaa ggatgacacg caaaatcgtg aagcgttcca cattttt                 107

<210> SEQ ID NO 5
<211> LENGTH: 86
<212> TYPE: DNA
<213> ORGANISM: Homo sapiens

<400> SEQUENCE: 5
tattaggttg gtgcaaaagt atttgcgggt tttgtcgtag aaagtaatgg caaaaactgc    60
agttacttgt gcaccaacca aatgct                                         86

<210> SEQ ID NO 6
<211> LENGTH: 81
<212> TYPE: DNA
<213> ORGANISM: Homo sapiens

<400> SEQUENCE: 6
cccattggca taaacccgta gatccgatct tgtggtgaag tggaccgcac aagctcgctt    60
ctatgggtct gtgtcagtgt g                                              81

<210> SEQ ID NO 7
<211> LENGTH: 70
<212> TYPE: DNA
<213> ORGANISM: Homo sapiens

<400> SEQUENCE: 7
ggcacccacc cgtagaaccg accttgcggg gccttcgccg cacacaagct cgtgtctgtg    60
ggtccgtgtc                                                           70
```

<210> SEQ ID NO 8
<211> LENGTH: 76
<212> TYPE: DNA
<213> ORGANISM: Homo sapiens

<400> SEQUENCE: 8
tacttgaaga gaagttgttc gtggtggatt cgctttactt atgacgaatc attcacggac    60 aacactttt tcagta                                                    76

<210> SEQ ID NO 9
<211> LENGTH: 84
<212> TYPE: DNA
<213> ORGANISM: Homo sapiens

<400> SEQUENCE: 9
ttgacttagc tgggtagtgg ggaacccttc catgaggagt agaacactcc ttatgcaaga    60
ttcccttcta cctggctggg ttgg                                          84

<210> SEQ ID NO 10
<211> LENGTH: 110
<212> TYPE: DNA
<213> ORGANISM: Homo sapiens

<400> SEQUENCE: 10
ggcctggctg gacagagttg tcatgtgtct gcctgtctac acttgctgtg cagaacatcc    60
gctcacctgt acagcaggca cagacaggca gtcacatgac aacccagcct              110

<210> SEQ ID NO 11
<211> LENGTH: 71
<212> TYPE: DNA
<213> ORGANISM: Homo sapiens

<400> SEQUENCE: 11
ggagaggagg caagatgctg gcatagctgt tgaactggga acctgctatg ccaacatatt    60
gccatctttc c                                                        71

<210> SEQ ID NO 12
<211> LENGTH: 99
<212> TYPE: DNA
<213> ORGANISM: Homo sapiens

<400> SEQUENCE: 12
gaaactgggc tcaaggtgag gggtgctatc tgtgattgag ggacatggtt aatggaattg    60
tctcacacag aaatcgcacc cgtcaccttg gcctactta                          99

<210> SEQ ID NO 13
<211> LENGTH: 84
<212> TYPE: DNA
<213> ORGANISM: Homo sapiens

<400> SEQUENCE: 13
aggctgaggt agtagtttgt acagtttgag ggtctatgat accacccggt acaggagata    60
actgtacagg ccactgcctt gcca                                          84

<210> SEQ ID NO 14
<211> LENGTH: 85
<212> TYPE: DNA
<213> ORGANISM: Homo sapiens

<400> SEQUENCE: 14

```
atggtgttat caagtgtaac agcaactcca tgtggactgt gtaccaattt ccagtggaga    60
tgctgttact tttgatggtt accaa                                          85

<210> SEQ ID NO 15
<211> LENGTH: 85
<212> TYPE: DNA
<213> ORGANISM: Homo sapiens

<400> SEQUENCE: 15
tggttcccgc ccctgtaac agcaactcca tgtggaagtg cccactggtt ccagtggggc     60
tgctgttatc tggggcgagg gccag                                          85

<210> SEQ ID NO 16
<211> LENGTH: 96
<212> TYPE: DNA
<213> ORGANISM: Homo sapiens

<400> SEQUENCE: 16
cgggccccgg gcgggcggga gggacgggac gcggtgcagt gttgttttt cccccgccaa     60 tattgcactc gtcccggcct ccggcccccc cggccc                              96

<210> SEQ ID NO 17
<211> LENGTH: 79
<212> TYPE: DNA
<213> ORGANISM: Homo sapiens

<400> SEQUENCE: 17
aattaatccc tctctttcta gttcttccta gagtgaggaa aagctgggtt gagagggcaa    60
acaaattaac taattaatt                                                 79

<210> SEQ ID NO 18
<211> LENGTH: 138
<212> TYPE: DNA
<213> ORGANISM: Homo sapiens

<400> SEQUENCE: 18
tgttattttt tgtcttctac ctaagaattc tgtctcttag gctttctctt cccagatttc    60
ccaaagttgg gaaagctgg gttgagaggg caaaaggaaa aaaaagaat tctgtctctg     120 acataattag atagggaa                                                 138

<210> SEQ ID NO 19
<211> LENGTH: 2368
<212> TYPE: DNA
<213> ORGANISM: Homo sapiens

<400> SEQUENCE: 19
gggtgactac ttccggtgca gtgaaggctc ggggctgaag cggggtaatt cctctcctgc    60
aattactttt ggatggaagt atgcccctt ctcagtagaa gatggtaatc ttggagaatg   120
accatggaga aggggatgag ttctggagaa gggctgcctt ccagatcatc tcaggtttcg   180
gctggtaaaa taacagccaa agagttggaa acaaagcagt cctataaaga gaaacgagga   240
ggctttgtgt tggtgcatgc aggtgcaggt tatcattctg aatccaaagc caaggagtat   300
aaacatgtat gcaaacgagc ttgtcagaag gcaattgaaa agctgcaggc cggtgctctt   360
gcaactgacg cagtcactgc agcactggtg gaacttgagg attctccttt tacaaatgca   420
ggaatgggat ctaatctaaa tctgttaggt gaaattgagt gtgatgccag cataatggat   480
```

```
ggaaaatcct taaattttgg agcagttgga gcactgagtg gaatcaagaa cccagtctcg    540
gttgccaaca gactcttatg tgaagggcag aagggcaagc tctcggctgg cagaattcct    600
ccctgctttt tagttggaga aggagcctac agatgggcag tagatcatgg aatacccctct    660 tgccctccta acatcatgac acaagattc agtttagctg catttaaaag aaacaagagg      720
aaactagagc tggcagaaag ggtggacaca gattttatgc aactaaagaa aagaagacaa    780
tcaagtgaga aggaaaatga ctcaggcact ttggacacgg taggcgctgt ggttgtggac    840
cacgaaggga atgttgctgc tgctgtctcc agtggaggct tggccttgaa acatccgggg    900
agagttgggc aggctgctct ttatggatgt ggctgctggg ctgaaaatac tggagctcat    960 aaccccctact ccacagctgt gagtacctca ggatgtggag agcatcttgt gcgcaccata  1020
ctggctagag aatgttcaca tgctttacaa gctgaggatg ctcaccaagc cctgttggag   1080
actatgcaaa acaagtttat cagttcacct ttccttgcca gtgaagatgg cgtgcttggc   1140
ggagtgattg tcctccgttc atgcagatgt tctgccgagc ctgactcctc ccaaaataag   1200
cagacacttc tagtggaatt tctgtggagc cacacgacgg agagcatgtg tgtcggatat   1260
atgtcagccc aggatgggaa agccaagact cacatttcaa gacttcctcc tggtgcggtg   1320
gcaggacagt ctgtggcaat cgaaggtggg gtgtgccgcc tggagagccc agtgaactga   1380
cccttcaggc tgagtgtgaa gcgtctcaga ggcatttcag aacctgagct tttgggggtt    1440
tttaactgaa gttggttgtt ttatctttct tgttttataa ttcctattgc aacctcgtgc    1500
actgctcgag acacaagtgc tgctgtagtt agcgcttagt gacacgcggg cctttggtgg   1560
gtgagcggga ctgtgtgtga gtgtgtgcgc gtatgtgcgc acatatgtgt atgtgtggag   1620
tatgtgtgtt tgcttctccg tggatgaaat agaaactcct cattgtgtga ccaggaatgg   1680
ttaaatcatc tttacaaaat gtgtgcttta actgtttaca agtaaaacct aaagttgcag    1740
gaaacatttt ttatttcgta aagaggtacc aactgtcgct gatgtgatat gtcagaactg    1800
aagagtaaat ctacttgttt aaatgacttg acagtggtag tgctccattt aataacagta    1860
ataagtaata aagtgttttt atttgttaac cagtttaagt ggatcctgtg gtaacttaaa    1920
ctgttgttct catcccttat atggggcatt tttctttaac aaagaatggt ttcagtgaaa   1980
caatctagca gagaattaat gtcagaacct ttttaaataa tagtctgatt gatacagttt    2040
gtacttattt catcaagctt ttctaagctt aaatattgca tagcttcgag ctgtatggac    2100
tatattatga agaatatgt aaagagaaca tacagtaatg cacagtcctt aatttgtgta     2160
taatggaaag ttatttacaa tataacactg taaataagaa agcaaagttt atgggaaaat    2220
tcaatattat ctttgttttt gtttaaatat attttttaaga taaaggcaca aaaataaaag   2280
aagcgtatta ctgggtatag tatgtgactc ctcttctcag actaataaat tatcttttga   2340
atccttggtt aaaaaaaaaa aaaaaaaa                                       2368

<210> SEQ ID NO 20
<211> LENGTH: 3111
<212> TYPE: DNA
<213> ORGANISM: Homo sapiens

<400> SEQUENCE: 20
atgtcttttt ggtctgaaaa atgtacaaga cttattctgt atgatttaaa aatagcactc       60
aaaaatggat cgttgacatt tgggatgtg accatagaat tcgctctgga ggagtggcaa      120
tgcctggaca tggctcagca gaatttatat aggaatgtta tgttagagaa ctacagaaac    180
ctggtcttcc tgggtatcgc tgtctctaag ctagacttga taacttgtct gaagcaaggg    240
```

```
aaagagcctt ggaatatgaa gagacatgag atggtaacta aacccccagt tattagttct      300
cattttacac aagactttg gccagatcag agcataaaag attctttcca agaaataata       360
ttgagaacat atgcaagatg tggacataag aatttacgat taagaaaaga ttgtgaaagt      420
gtcaatgagg gtaagatgca cgaagaagct tataataaac ttaaccaatg ttggacaact      480
acccagggaa aaatatttca gtgtaacaaa tatgtgaaag tctttcataa atattcaaat      540
tcaaatagat ataagataat tcatactggg aagaaaccat ataaatgtga agaatgtggc      600
aaagctttta agcaatcctc acaccttact agacataaag caattcatac tggagagaaa      660
ccctacaaat gcgaagaatg tggcaaagct tttaaccatt tctcagccct tagaaaacat      720
cagataattc atactggaaa gaaaccctac aaatgtgaag aatgtggcaa agcttttagc      780
cagtcctcaa cccttagaaa acatgagata attcatactg aagagaaacc ctacaaatat      840
gaagaatgcg gcaaagcttt tagcaatttg tcagccctta gaaaacatga gataattcat      900
actggacaga aaccctacaa atgtgaagaa tgtggtaaag cttttaagtg gtcctcaaaa      960
cttactgtac ataaggtaat tcatactgca gagaaaccct gcaaatgtga agaatgtggc     1020
aaagctttta agcgtttctc agcccttaga aaacataaga taattcatac tggaaagcaa     1080
ccctacaaat gtgaagaatg cagcaaagct tttagcaatt tttcagccct tagaaaacat     1140
gagataattc atactggaga gaaaccctac aaatgtgaag aatgtggtaa agcttttaag     1200
tggtcctcaa aacttactgt acataaggta attcatatgg aagagaaacc ttgcaaatgt     1260
gaagaatgtg gcaaagcttt taagcatttc tcagccctta gaaaacataa gataattcat     1320
actggaaaga aaccctacaa atgtgaagaa tgtggcaaag cttttaacaa ttcctcaacc     1380
cttatgaaac ataagataat tcatactggg aagaaaccat acaaatgtga agaatgtggc     1440
aaagctttta agcaatcttc acatcttact agacataaag caattcatac tggggagaaa     1500
ccctacaaat gtgaagaatg tggcaaagct tttaaccact tctcagccct tagaaaacat     1560
cagataattc atactggaaa gaaaccctac aaatgtgaag aatgtggcaa agcttttagc     1620
cagtcctcaa cccttagaaa acatgagata attcatactg gagagaaacc ctacaaatgt     1680
gaagaatgtg gtaaagcttt taagtggtcc tcacaccta ctagacataa agtaattcat      1740
actgaagaga aaccctacaa atgtgaagaa tgtggcaagg cttttaacca tttctcagcc     1800
cttaggaaac ataagataat tcatactgga agaaaccct acaaatgtga agaatgtggc      1860 aaagcttta gccagtcctc aactcttaga aacatgaga taattcatac tggagagaaa      1920
ccctacaaat gtgaagaatg tggtaaagct tttaagtggt cctcaaaact tactgtacat     1980
aaggtaattc atactgcaga gaaaccctgc aaatgtgaag aatgtggcaa agcttttaag     2040
catttctcag cccttagaaa acataagata attcatactg gaagagaaacc ctataaatgt    2100 gaagaatgtg gcaaagcttt taacaattcc tcaccccttta gaaaacatga gataattcat    2160
actggagaga atcctacaa atgtgaagaa tgtgcctta gaaaacatga gataattcat       2220
actggaaaga aaccctacaa atgtgaagaa tgtggcaaag cttttaacaa ttcctcaacc     2280
cttaggaaac ataagataat ttatactggg aagaaaccat acaaatgtga agaatgtggc     2340
aaagctttta agcagtcctc acaccttact agacataaag cagttcatac tggggagaag     2400
ccctacaaat gtggagaatg tggaaaagct tttaacaatt cctcaacct taagaaacat      2460 aagctaattc atactaggga gaatcgtac aaatgtgaag aatgtggcaa agcttttagc      2520
aatttctcag cccttaggaa acataagata attcatactg gggagaaacc atacaaatgt    2580
```

| | |
|---|---|
| gaagaatgtg aatgtggcaa agcttttaac aattcctcaa cccttatgaa acataagata | 2640 |
| attcatactg gggagaaacc gtacaaatgt gaagaatgtg gcaaaggttt taacaatttc | 2700 |
| tcgacccta tgaaacataa gataattcat actggggaga aaccgtacaa atgtgaagaa | 2760 |
| tgtggcaaag cttttaagca atcctcacac cttactaaac ataaatcaat tcatactgga | 2820 |
| gagaaaccct acaaatgtga agaacgtggc aaagctttta gccatttctc acgccttact | 2880 |
| aaacatagga taattcatac tggaaagaaa ccctacaaat gtgaagagtg tgagaaaccc | 2940 |
| tacaaatgtg aagaatgtgg caaagccttt aaccagtcct cacaccttac tcaacataaa | 3000 |
| acaattcata ctggagggaa aacctacaaa tgtgaagaat gtggcaaagc tttaaccat | 3060 |
| ctttcagccc ttactaaaca taagataatt catactgggg agaagcccta a | 3111 |

<210> SEQ ID NO 21
<211> LENGTH: 2142
<212> TYPE: DNA
<213> ORGANISM: Homo sapiens

<400> SEQUENCE: 21

| | |
|---|---|
| taactctcca aactcccatg agctgtaacc tagcttccct atgcagcaaa gttcttgaac | 60 |
| aaggtgctta ccatcctatc ctcattccct caccctctc tcctccctgg acccactgtg | 120 |
| cccaacatct gcgcccttgt acctgcaaag gctcatctca ctatggggac caacaacctc | 180 |
| gctcacaagt gttaaactcc aagatgctcc tttctgcttc tgtccttgac cttccagtg | 240 |
| ttgacagtga tgcctttgaa atcctcctct ccttggcttc catagcaata cgcactccta | 300 |
| gagtttgtca ccctctttg cccctccact tcattcttct tcacaagggc cagccttcac | 360 |
| atgttgaggt tctttgggat gctgcctggc tgttcttcat tgtggacttg atgttttcct | 420 |
| ctatcctgtt gtgcacattc ttacggcttc aatactttgt ctaagctgtt gatttcaaag | 480 |
| ttggcatttc atcccagctc tctcctgagt ttcagactgc cttttcaaaa gcctactggg | 540 |
| catctctatc cagtggtcac ccaggcacat caactcattc caaactggtg actctccagg | 600 |
| tatttctatc tcacccaccc caagatgctc aagcagaaca cctggcatct ccttgggtca | 660 |
| tctttttccc atctttatac ttattctcca tctaatccca tctacccatt acatgttttt | 720 |
| taaatccatc cacctcttt caaccccact gctcattccc tacatcatta acatctttct | 780 |
| cgtagactcc tgacctccct ccaaattctt gctgtggtct gaagaatttt tctaaagtgt | 840 |
| aaatctggcc aagtcagtcc cctgtgtaag gctctttcat ggtttctcat tgcttttagg | 900 |
| ataagttcaa gtccttatca aggatcttaa gacctacctt gcctggcccc aggttaccct | 960 |
| ccccaaccta actcatacca ctcccaaaca catattccaa gttctgacca tacagcactg | 1020 |
| ttttcaaatc cttgaacaag ccaagggtga cttgcctctg ggcttttc ctgccattct | 1080 |
| tcttcctgga acactttctc agaatcctgt ttctccacta attcctattt gtctttctga | 1140 |
| tgctactcca caggtcccct cctccaggaa gccctccgtg ttctcccagg ctagatgaga | 1200 |
| gcccctcctc tgtatcctat atttcttggg cacacaataa ttctgtacat ttgaagctca | 1260 |
| ttctactctt tctacttcct ctgtcccagc acttagtaca ggtgattgta gcagcctctt | 1320 |
| tatgggtcag agccgcctac aggaccgaaa gcttcatgaa gccagcaccc caacttccaa | 1380 |
| caccagcgtc cgcaatgccc aacagagatc ccaggtgagg aagctgaact gactttggtg | 1440 |
| acatatattc cccaagatct gacagctgat gagtgacaga gcacgtattc aaacccagag | 1500 |
| atgtgaattc gctatgctgc ctaggctggt cttgaactcc tgacttcaag taatcctccc | 1560 |
| accttcgctt gccaaagtgc tgggattata ggcgtgaact actgctccca gctgagagct | 1620 |

```
cacttttgtt tgctagtggt gttcttagta tcttttcata tttgaggttt tggtggtagt    1680
gctgaagtat tgtactcacc atccaaggtt tacaggactt ttgttttact atggaacaga    1740
tggaattgtt tagttctgca tctttgcaaa tatacaaaat gtgcctacca ggactctgct    1800
ttatatccat tgaaagcaag aagtaataca gtaaaacttt gcctggctag aggctttgaa    1860
agaatggact attctgattt aattgtatta acttggaagt atgaaggtga aaaaaattaa    1920
aaacttaaat ttcctgttga atgcaatttg aaaatatagc cattgattcc acttttattc    1980
tccagtaagt ctggacattc tgatatacct ggtgttttat tatagaactc ctagtgtgcc    2040
tgaagatcat tttctacaac tttaggtgta agaggatgta aatggtattg tatgagatca    2100
ggctggatga gaactgatac ttgtaaatac acttttttaga ct                      2142
```

<210> SEQ ID NO 22
<211> LENGTH: 947
<212> TYPE: DNA
<213> ORGANISM: Homo sapiens

<400> SEQUENCE: 22

```
ccatccctga gatcttttta taaaaaaccc agtctttgct gaccagacaa agcataccag      60
atctcaccag agagtcctag gggactacag aaggaaaaag acaagaggca gtaggatatc     120
tgtgtgtcct cccgctgacc acacttcctt tagtgacccg attgcctcct caagtcgcag     180
acactatgct gcctcccatg gccctgccca gtgtgtcctg gatgctgctt tcctgcctca     240
ttctcctgtg tcaggttcaa ggtgaagaaa cccagaagga actgccctct ccacggatca     300
gctgtcccaa aggctccaag gcctatggct cccctgcta tgccttgttt ttgtcaccaa     360
aatcctggat ggatgcagat ctggcttgcc agaagcggcc ctctggaaaa ctggtgtctg     420
tgctcagtgg ggctgaggga tccttcgtgt cctccctggt gaggagcatt agtaacagct     480
attcatacat ctggattggg ctccatgacc ccacacaggg ctctgagcct gatggagatg     540
gatgggagtg gagtagcact gatgtgatga attactttgc atgggagaaa aatccctcca     600
ccatcttaaa ccctggccac tgtgggagcc tgtcaagaag cacaggattt ctgaagtgga     660
aagattataa ctgtgatgca agttacccct atgtctgcaa gttcaaggac tagggcaggt     720
gggaagtcag cagcctgagc ttggcgtgca gctcatcatg gacatgagac cagtgtgaag     780
actcaccctg gaagagaata ttctccccaa actgccctac ctgactacct tgtcatgatc     840
ctccttcttt ttccttttc ttcaccttca tttcaggctt ttctctgtct ccatgtctt     900 gagatctcag agaataataa taaaaatgtt actttatacg taaaaaa                   947
```

<210> SEQ ID NO 23
<211> LENGTH: 942
<212> TYPE: DNA
<213> ORGANISM: Homo sapiens

<400> SEQUENCE: 23

```
atgtccatta tcaacacatc atatgttgaa atcaccacct tcttcttggt tgggatgcca      60
gggctagaat atgcacacat ctggatctct atccccatct gcagcatgta tcttattgct     120
attctaggaa atggcaccat tctttttatc atcaagacag agccctcctt gcatgggccc     180
atgtactatt ttctttccat gttggctatg tcagacttgg gtttgtcttt atcatctctg     240 ccactgtgt taagcatctt cctgttcaat gcccctgaaa cttcttctag tgcctgcttt     300
gcccaggaat tcttcattca tggattctca gtactggagt cctcagtcct cctgatcatg     360
```

| | |
|---|---|
| tcatttgata gattcctagc catccacaat cctctgagat acacctcaat cctgacaact | 420 |
| gtcagagttg cccaaatagg gatagtattc tcctttaaga gcatgctcct ggttcttccc | 480 |
| ttcccttcca ctttaagaag cttgagatat tgcaagaaaa accaattatc ccattcctac | 540 |
| tgtctccacc aggatgtcat gaagttggcc tgttctgaca acagaattga tgttatctat | 600 |
| ggcttttttg gagcactctg ccttatggta gactttattc tcattgctgt gtcttacacc | 660 |
| ctgatcctca agactgtacc gggaattgca tccaaaaagg aggagcttaa ggctctcaat | 720 |
| acttgtgttt cacacatctg tgcagtgatc atcttctacc tgcccatcat caacctggcc | 780 |
| gttgtccacc gctttgccgg gcatgtctct cccctcatta atgttctcat ggcaaatgtt | 840 |
| ctcctacttg tacctccgct gatgaaacca attgtttatt gtgtaaaaac taaacagatt | 900 |
| agagtgagag ttgtagcaaa attgtgtcaa tggaagattt aa | 942 |

<210> SEQ ID NO 24
<211> LENGTH: 726
<212> TYPE: DNA
<213> ORGANISM: Homo sapiens

<400> SEQUENCE: 24

| | |
|---|---|
| gcttcctgtt tttccctccg accaaccccg agcgcaaaga aattgacctc gcagcggtcc | 60 |
| tacaatactt ttatatcatt ggccaagctt taccccgccc ctgcctcatg cagcctatgg | 120 |
| gctaggcttt agggtccgcg gttggtcaga ccggagcact tggcctgaag acctggaatt | 180 |
| ggcgacttcg atattaacaa ggatggcggc ggccgcagca agtcgaggag tcggggcaaa | 240 |
| gctgggcctc gtgagattc gcatccactt atgtcagcgc tcgcccggca gccagggcgt | 300 |
| cagggacttc attgagaaac gctacgtgga gctgaagaag gcgaatcccg acctacccat | 360 |
| cctaatccgc gaatgctccg atgtgcagcc caagctctgg gcccgctacg catttggcca | 420 |
| agagacgaat gtcccttga caacttcag tgctgatcag gtaaccagag ccctggagaa | 480 |
| cgttctaagt ggtaaagcct gaagcctcca ctgaggatta agagcaacag ccccagagcc | 540 |
| tgggctctgc tggacttagt ataatgtgaa aaaaatgtgt tctcctattc ctcataaagc | 600 |
| ttgtgctgta aaatactttc tcagggtgtt cttgtcctca tctaccctct accccttact | 660 |
| gtgcaaccac tgaggcaaag tagcttaata taaaaataaa actttattct gtctcatcaa | 720 |
| aagcta | 726 |

<210> SEQ ID NO 25
<211> LENGTH: 2855
<212> TYPE: DNA
<213> ORGANISM: Homo sapiens

<400> SEQUENCE: 25

| | |
|---|---|
| ttccggcact cgcggaactt tggtgcagcc tgatgcgcaa cgtggggact caggcgcgct | 60 |
| gggcggcagg agttgcttcc ggccgtgttg gtggtctgaa ttgagaagcc gcgactaagg | 120 |
| gaagatggag acaatactgg agcagcagcg gcgctatcat gaggagaagg aacggctcat | 180 |
| ggacgtcatg gctaaagaga tgctccaccaa gaagtccacg ctccgggacc agatcaattc | 240 |
| tgatcaccgc actcgggcca tgcaagatag gtatatggag gtcagtggga acctgaggga | 300 |
| tttgtatgat gataaggatg gattacgaaa ggaggagctc aatgccattt caggacccaa | 360 |
| tgagtttgct gaattctata atagactcaa gcaaataaag gaattccacc ggaagcaccc | 420 |
| aaatgagatc tgtgtgccaa tgtcagtgga atttgaggaa ctcctgaagg ctcgagagaa | 480 |
| tccaagtgaa gaggcacaaa acttggtgga gttcacagat gaagagggat atggtcgtta | 540 |

```
tctcgatctc catgactgtt acctcaagta cattaacctg aaggcatctg agaagctgga      600
ttatatcaca tacctgtcca tctttgacca attatttgac attcctaaag aaaggaagaa      660
tgcagagtat aagagatacc tagagatgct gcttgagtac cttcaggatt acacagatag      720
agtgaagcct ctccaagatc agaatgaact ttttgggaag attcaggctg agtttgagaa      780
gaaatgggag aatgggacct ttcctggatg gccgaaagag acaagcagtg ccctgaccca      840
tgctggagcc catcttgacc tctctgcatt ctcctcctgg gaggagttgg cttctctggg      900
tttggacaga ttgaaatctg ctctcttagc tttaggcttg aaatgtggcg ggaccctaga      960
agagcgagcc cagagactat tcagtaccaa aggaaagtcc ctggagtcac ttgatacctc     1020
tttgtttgcc aaaaatccca agtcaaaggg caccaagcga gacactgaaa ggaacaaaga     1080
cattgctttt ctagaagccc agatctatga atatgtagag attctcgggg aacagcgaca     1140
tctcactcat gaaaatgtac agcgcaagca agccaggaca ggagaagagc gagaagaaga     1200
ggaagaagag cagatcagtg agagtgagag tgaagatgaa gagaacgaga tcatttacaa     1260
ccccaaaaac ctgccacttg gctgggatgg caaacctatt ccctactggc tgtataagct     1320
tcatggccta aatatcaact acaactgtga gatttgtgga aactcacct accgagggcc     1380 caaagccttc cagcgacact tgctgaatg gcgtcatgct catggcatga ggtgtttggg     1440
catcccaaac actgctcact tgctaatgt gacacagatt gaagatgctg tctccttgtg     1500
ggccaaactg aaattgcaga aggcttcaga acgatggcag cctgacactg aggaagaata     1560
tgaagactca gtgggaatg ttgtgaataa gaagacatac gaggatctga aaagacaagg     1620
actgctctag tgttcaggga tgtagctcag cttttgggct agcccaggct tccctaagat     1680 ctgcttttc tatttctccc aaccaaatcc tcttaaagac cctttgctat gtagtctcat     1740
ggtctagcat gcatcttgta gaaacaaggc atgctggcag attgcagggt tgagatgtgt     1800
tttatctgtt ttatatttta aaagattctg ccagaaaata aaaccagacc ttgttctaaa     1860
gcccagggtt atggaccaac tcagtgcttc aggtcttaac gcctccatac ctcttcctca     1920
ccaactttac tagtagctga gatttaatgg gcacctatta tgctacatat catgttaggt     1980
aaatctgacc tgacctcttt ccccaccctc ctttgttgct gcttccctga atgagtatta     2040
ccccaggatg aggtctgcca tcagcttagt tagccattga tgcaaatact agggaaagac     2100
taggaggatg agccagggtt gctactaagg actaagtgtc gcaccaaggt ttgccttttg     2160
tatttgcata agaaaggag ttggagctgg gtgcagtggc ttgtgcctgt agtcccagct     2220
acttgggagg ctgaggcagg aggggttgctt gagactagcc taggtaacat agtgagaccc     2280
tgtctcatta aaaaaaaaa aaaggcatgg tggcacgcac tgtagtccca gctactcagg     2340
agactgaggc tagaagatcc tttgaaccta ggagtttgag accagcctgg gcgatatagt     2400
gaggccccat ctcaaaaaaa aaaaagggg ggggggggg agttgggctg tgttggaatg     2460
ggcctgcagc ccaacaaaca agggaactag gaccgacagt gacttcacca gcttgctagg     2520
tcagaatgag agactggtgg gtctgtctac ctgtttcttc tacaagatcc ctatttgact     2580
gtaaaagtag ctaatactca catgttctcc aatcccaggt agccatggta gagttgggta     2640
gagttgagca gctgccccag gatccaaatg tggtgtctga aatggaaaga actaaggcaa     2700
ccaggaaggc actgatctgc cttataagca cagtcatctg aaagtcaggc ctgctgcagg     2760
acaggatccc ccagagaccc catttgcctc tcaacactca gaccttcaac tgtttttaa     2820 taaatctact ttttaaaaaa aaaaaaaaa aaaaa                                  2855
```

<210> SEQ ID NO 26
<211> LENGTH: 592
<212> TYPE: DNA
<213> ORGANISM: Homo sapiens

<400> SEQUENCE: 26

| | | | | | |
|---|---|---|---|---|---|
| ggacgtgtct | gtgctcctgt | gtgtgaccag | ggttgaaaaa | gtcgcactga | gatgtcctgc | 60 |
| cagcaaaacc | agcagcagtg | ccagccccct | cccaagtgcc | ccccaaaatg | cccacccaag | 120 |
| tgtcctccaa | agtgccgacc | tcagtgccca | gccccatgcc | acctccagt | ctcttcctgc | 180 |
| tgtggtccca | gctctggggg | ctgctgcggc | tccagctctg | ggggctgctg | cagctctggg | 240 |
| ggtggcggct | gctgcctgag | ccaccacagg | ccccgtctct | tccaccggca | ccggcaccag | 300 |
| agccccgatt | gttgtgagtg | tgaaccttct | gggggctctg | gctgctgcca | cagctctggg | 360 |
| gactgctgct | gaccagacct | cgaacatcac | agagcaaccc | ttatggagaa | acttgcaacc | 420 |
| aggacctgtc | ccagagtgat | gcttctcctg | cccctttttc | tcctttcctt | gggctgacac | 480 |
| accttgtgag | gtgttttgtc | tgttgtcatg | gcccaagagc | ccatcctgga | tcctgatctt | 540 |
| accttcccac | tttacctcat | acaacaataa | agctcttttg | cctcttcgtg | aa | 592 |

<210> SEQ ID NO 27
<211> LENGTH: 1057
<212> TYPE: DNA
<213> ORGANISM: Homo sapiens

<400> SEQUENCE: 27

| | | | | | |
|---|---|---|---|---|---|
| gtctcagcgg | ctgccaacag | atcatgagcc | atcagctcct | ctggggccag | ctataggaca | 60 |
| acagaactct | caccaaagga | ccagacacag | tgagcaccat | gggacagtgt | cggtcagcca | 120 |
| acgcagagga | tgctcaggaa | ttcagtgatg | tggagagggc | cattgagacc | ctcatcaaga | 180 |
| actttcacca | gtactccgtg | gagggtggga | aggagacgct | gacccccttct | gagctacggg | 240 |
| acctggtcac | ccagcagctg | ccccatctca | tgccgagcaa | ctgtggcctg | aagagaaaa | 300 |
| ttgccaacct | gggcagctgc | aatgactcta | aactggagtt | caggagtttc | tgggagctga | 360 |
| ttggagaagc | ggccaagagt | gtgaagctgg | agaggcctgt | ccgggggcac | tgagaactcc | 420 |
| ctctggaatt | cttgggggt | gttggggaga | gactgtgggc | ctggagataa | aacttgtctc | 480 |
| ctctaccacc | ccctgtacc | ctagcctgca | cctgtcctca | tctctgcaaa | gttcagcttc | 540 |
| cttccccagg | tctctgtgca | ctctgtcttg | gatgctctgg | ggagctcatg | ggtggaggag | 600 |
| tctccaccag | agggaggctc | aggggactgg | ttgggccagg | gatgaatatt | tgagggataa | 660 |
| aaattgtgta | agagccaaag | aattggtagt | agggggagaa | cagagaggag | ctgggctatg | 720 |
| ggaaatgatt | tgaataatgg | agctgggaat | atggctggat | atctggtact | aaaaaagggt | 780 |
| ctttaagaac | ctacttccta | atctcttccc | caatccaaac | catagctgtc | tgtccagtgc | 840 |
| tctcttcctg | cctccagctc | tgccccaggc | tcctcctaga | ctctgtccct | gggctaggc | 900 |
| aggggaggag | ggagagcagg | gttggggag | aggctgagga | gagtgtgaca | tgtggggaga | 960 |
| ggaccagctg | ggtgcttggg | cattgacaga | atgatggttg | ttttgtatca | tttgattaat | 1020 |
| aaaaaaaat | gaaaaagtg | aaaaaaaaaa | aaaaaaa | | | 1057 |

<210> SEQ ID NO 28
<211> LENGTH: 1330
<212> TYPE: DNA
<213> ORGANISM: Homo sapiens

<400> SEQUENCE: 28

```
gcggacgcgg ggcgccagca ggtggcgctg gacgcgcaac ggacaaggag gcggggcctg      60
cagctggctt ggaggctccg cgctctggag gctcaggcgc cgcgtggggc ccgcacctct     120
gggcagcagc ggcagccgag actcacggtc aagctaaggc gaagagtggg tggctgaagc     180
catactattt tatagaatta atggaaagca gaaaagacat cacaaaccaa gaagaacttt     240
ggaaaatgaa gcctaggaga aatttagaag aagacgatta tttgcataag gacacgggag     300
agaccagcat gctaaaaaga cctgtgcttt tgcatttgca ccaaacagcc catgctgatg     360
aatttgactg cccttcagaa cttcagcaca cacaggaact cttttcacag tggcacttgc     420
caattaaaat agctgctatt atagcatctc tgacttttct ttacactctt ctgagggaag     480
taattcaccc tttagcaact tcccatcaac aatattttta taaaattcca atcctggtca     540
tcaacaaagt cttgccaatg gtttccatca ctctcttggc attggtttac ctgccaggtg     600
tgatagcagc aattgtccaa cttcataatg gaaccaagta taagaagttt ccacattggt     660
tggataagtg gatgttaaca agaaagcagt ttgggcttct cagtttcttt tttgctgtac     720
tgcatgcaat ttatagtctg tcttacccaa tgaggcgatc ctacagatac aagttgctaa     780
actgggcata tcaacaggtc caacaaaata aagaagatgc ctggattgag catgatgttt     840
ggagaatgga gatttatgtg tctctgggaa ttgtgggatt ggcaatactg gctctgttgg     900
ctgtgacatc tattccatct gtgagtgact ctttgacatg gagagaattt cactatattc     960
agagcaagct aggaattgtt tcccttctac tgggcacaat acacgcattg attttttgcct    1020 ggaataagtg gatagatata aaacaatttg tatggtatac acctccaact tttatgatag    1080 ctgtttttcct tccaattgtt gtcctgatat ttaaaagcat actattcctg ccatgcttga    1140
ggaagaagat actgaagatt agacatggtt gggaagacgt caccaaaatt aacaaaactg    1200
agatatgttc ccagttgtag aattactgtt tacacacatt tttgttcaat attgatatat    1260
tttatcacca acatttcaag tttgtatttg ttaataaaat gattattcaa ggaaaaaaaa    1320
aaaaaaaaaa                                                           1330

<210> SEQ ID NO 29
<211> LENGTH: 1212
<212> TYPE: DNA
<213> ORGANISM: Homo sapiens

<400> SEQUENCE: 29
aatctttttt gcctctcaac ctgtctccca ggtagtgtac ctgtcaccat taataactct      60
ttagccgctc cctagtgatt tgacctatca gttgtcgttc acagaaaagt ggtgctctgg     120
cctgctattg aagcttatgc aggttctttc agctcctcag tcaccccagc agccatatac     180
ttgtaggaag ttgtgttggt gggcttcaca agcaggcagc tgaacacttc gtacagtttg     240
ataaaggtgg cattacattt tgaacaatag atgataagac tcccatttag accgcaaaac     300
agtgccacag gggtagacag gggtctgggg gagataagat gggtggtgag gatgaccaac     360
agcaaataaa cttccctgtc tctttgatgc taattatctc tttgcaccta attatcatgg     420
catcatcatc atcctctgat gtttgcaaac taagagttga tgtgtttgat caggttagtg     480
aatctgtcag gtatggcatt ctgcctgttt ctgaagctta agaatgagaa gccagtagct     540
atcatgcgga agatgtgaac tgcccccccag tcctcgtcct ttagcagtgt gtcattcctc     600
tgtttggaca tgtgctctct tgcttcctct cttccctct ctgttcctga agtgtgctgc     660
ttccaacact tccccagatt aattcctacc tgcatttagg tctcaaccta gccatcactt     720
```

```
tttcaggaaa ctgctactgc tctctctatt tggcattgac tgtaccaact aaaatgccca      780
tatggcagtt ttcatttatt tcttattatg ctctacaata actgcttgtt tacttgtctt      840
tttctcctac tggattgtaa gttttttcat ggatggtaca tagtgttgtt tgctatatcc      900
acgttctggg agtgtcatag aatctcaata aatttatttg aagagaatga gaatttattt      960
tttatgaact cactttccat tgacatatca tggtcacatc aatggggagt tcaggcaata     1020
aattatggca tatattgtct actgtatact gtgctggcac caggggttca gataggaaaa     1080
catttcgatt gctttttacc cttttagtga gtgactaatg gacatttctt tgtctgagga     1140
tatatcttgg cagtacagga tttcttcaga cgtggctcag gaaatggccg agagtaaggt     1200
gaatcacaag gc                                                         1212
```

<210> SEQ ID NO 30
<211> LENGTH: 2691
<212> TYPE: DNA
<213> ORGANISM: Homo sapiens

<400> SEQUENCE: 30

```
ggggaggggga aggagcggca catggggttg agcagaggag aaaatcagaa agatggctta       60
gagaagtcag cagtctgcga gtctgggggag gatggagagt ggtttggggt tttgggtcgg      120
ggtctaaggt gatcagatgc agaagcatta cacagtggcc tggtttcttt actcagcccc      180
tggggtagat cccagccccc catgtaggtc ccttggctgg aaaaggaaga gggagtggtc      240
agatgaatct gaggaggagc cggagaagga gctcgcccct gagcctgagg agacctgggt      300
agtggagacg ctgtgtgggc tcaagatgaa gctgaagcaa cagcgagtgt cacccatcct      360
ccttgagcac cacaaggact tcaacagtca gcttgcccct ggggtagatc ccagcccccc      420
gcataggtcc ttttgctgga aaaggaagat ggagtggtgg gacaaatctg aggagtcgga      480
ggaggagcca cggaaggtgc tcgcccctga gcctgaggag atctgggtgg cggagatgct      540
gtgtggcctc aagatgaagc tgaagcgacg gcgagtgtcg ctcgtgctcc ctgagcacca      600
cgaggccttc aacaggctgc ttgaggatcc tgtcattaaa agattcctgg cctgggacaa      660
agatctgagg gtgtcggaca gtatctcctt gctatggtc atagcgtatt tcagccgagc      720
cggcttcccc tcctggcaat accaacgcct tcatttcttc ctggctctct acctggccaa      780
tgacatggag gaggacgacg aggactccaa acaaaacatc ttccacttcc tgtatgggaa      840
gaaccgctct cgcatacccet tgctccgtaa gcgtcggttc cagttatacc gttccatgaa      900
cccgagggcc aggaagaacc gctctcacat acccttggtc cgtaagcgtc ggttccagtt      960
acgccgttgc atgaacccga gggccaggaa gaaccgctct cagatagtcc tgttccagaa     1020
acgtcggttc cacttcttct gttccatgag ctgcagggct tgggttccc cagaggagtt     1080 ggaggagatc caggcttatg acccagagca ctgggtgtgg gcgcgagatc gcgctcgcct     1140
ttcctagagc tccagggacc gtggaggcct gaggtcatcg gcctgagaga gaacaccgg      1200 acccagggga gatgtggatt ttcagcagga actttattcc aatgctaatg gcagacacca     1260
ggaaggagga gaggaaccat ttgtgcagat catctagaag aacctggacc attcttgatg     1320
gagctgaata cagtgatcac gttgtcctcc taggagcagg ggtgggggga ggggatggg      1380 gtccttctag gagtccttgg agaaaagtaa gaaaccagga gtgtttccag ttccacccctt     1440 tcctggggca ccaccaccct ttttatattg ctgaattcca acctccctgg ggcggaacct     1500
ggaggtcctg tttcttacgg acttggttgc cacagtccag gagcatttga aggcacaatg     1560
caggggctca gattggcaca gaattctttt gtgaaatatc agtgccacag attgtaacag     1620
```

```
atagcttcat gcacactctg cattttattg gtttgtttgg aaaatgttgg ccattgaatt    1680
attcatagat ttatttcaaa tagtttggaa attgttgtac ttttgaaaac atgctgttcc    1740
tgtagttttt tgatgagagt tatagttgtt atatatacat aaagataatt ttcttttcat    1800
ttttgagaca attcttttta tcctaaatat tttatcatct ttaaatttgt ttctgtatta    1860
ttatatgtgc tcctgaagcg agcactcttt ttatctatga tacttccata ataatctctt    1920
ctatttatag ctattggtag ttcccctaaa ttctgacgat agaaatttt atttgctgtt    1980 taggtttgtg actgaattgt gagaattcag ttgtgatttt taacatgtgt cagatatata    2040
tactaacacg tctaatatat actattttat tggtttattt tgaaaaacat gggtatagaa    2100
ttatttaaat attattttat ttatttaaat atttattaaa tatatttatt tatttaaatg    2160
ttattattac tttaaatatt attttaaata ttttggaaat actggtattt ttgaatagat    2220
gctgtttcta taaagctgtg tgatggtatt ataactgtta tatacacata catataattt    2280
tgttttcctt tttaagagag gattcttttc atcctaaatc ttttaccttt caatctttgt    2340
atctattatt acacgtgctg ctgaagggag catggttttt atctatgata cttagttaac    2400
atatatatta catttatagc tatgtagtag ttcccctaaa ttcttgtaaa ataaaatttt    2460
tatttgatat ttcatctatg tttgaaatgt gagaattcag atgtaatttt ttaccttgat    2520
ttggcatgtt tgtatgttac tttaaagagg atgtgtgttc taaaggagga catgagctgt    2580
gtgttttcaa gagaacaata gagtgtgtct cttggggaaa cgtaataaaa atgaacttt     2640 ctcaccttca aaaaaaaaaa aaaaaaaaa aaaaaaaaa aaaaaaaaa a                2691

<210> SEQ ID NO 31
<211> LENGTH: 1463
<212> TYPE: DNA
<213> ORGANISM: Homo sapiens

<400> SEQUENCE: 31
cttagaggga gctgtgtttt ggtgacctct gaaactcagt actgcagcga atgagctcct     60
gaccttgagg agtacttaac agaattatgt ctcgaagaat cattgtggga acccttcaaa    120
gaacccagcg aaacatgaat tctggaatct cgcaagtctt ccagagggaa ctcacctgcc    180
ccatctgcat gaactacttc atagacccgg tcaccataga ctgtgggcac agcttttgca    240
ggccctgttt ctacctcaac tggcaagaca tcccaattct tactcagtgc tttgaatgca    300
taaagacaat acagcagaga aacctcaaaa ctaacattcg attgaagaag atggcttccc    360
ttgccagaaa agccagtctc tggctattcc tgagctctga ggagcaaatg tgtggcattc    420
acagggagac aaagaagatg ttctgtgaag tggacaggag cctgctctgt ttgctgtgct    480
ccagctctca ggagcaccgg tatcacagac actgtcccgc tgagtgggct gctgaggaac    540
actgggagaa gcttttaaag aaaatgcagt ctttatggga aaaagcttgt gaaaatcaga    600
gaaacctgaa tgtggaaacc accagaatca gccactggaa ggcttttgga gacatatat    660 acaggagtga gtccgtgctg ctgcacatgc cccagcctct gaatctagcg ctcagggcag    720
ggcccatcac tggactgagg gacaggctca accaattctg agtggatatt actctgcatc    780
acaatgaagc caacagtcat atcttccgat gtggagattt gagaagcatt tgtattggat    840
gtgaccgtca aaatccgccc catatcactg caacacctac aagttttctt gcatggggtg    900
ctcagacttt cacctctggc aaatattact gggaggtcca tgtggggac tcttggaatt    960 gggcttttgg tgtctgtaat aagtattgga aagggaagaa tcagaatggc aatatatatg    1020
```

| | |
|---|---|
| gagaggaggg actctttagt cttgggtgtg ttaagaacga cattcagtgc agtctcttta | 1080 |
| ccacctcccc aattacactg cagtatgtcc caagacctac caaccatgta gaattattcc | 1140 |
| tggattgtga agctagaact gtgagcttcg ttgatgttag tcaaagctcc cctatataca | 1200 |
| ccatccctaa ttgctccttc tcacttcctc tcagacctat cttttctgt attctcctct | 1260 |
| gaccagagac aaatcagaaa tgtgttcatc tgctgtggga accccttat cccagaaagc | 1320 |
| cctcttcctt gtgccttatc aaacaggaca aataggttcg gttttatgtc ttgaattgca | 1380 |
| ttctaatgtt attaaaactc atttattgtg ttactattaa atgtagtaaa aacactaaaa | 1440 |
| gtataaaaaa aaaaaaaaaa aaa | 1463 |

<210> SEQ ID NO 32
<211> LENGTH: 828
<212> TYPE: DNA
<213> ORGANISM: Homo sapiens

<400> SEQUENCE: 32

| | |
|---|---|
| gtgcgccttt ttttttttt ccttcttagt cgtgtgtaca tcattgggaa tggagggaaa | 60 |
| taaatgactg gatggtcgct gcttttaag tttcaaattg acattccaga caagcggtgc | 120 |
| ctgagcccgt gcctgtcttc agatcttcac agcacagttc ctgggaaggt ggagccacca | 180 |
| gcctctcctt gtcctggagg ctggaagtgc aaaaggaagg tgtcggcaag atcgttttt | 240 |
| tctgagagct ctctccttgg cttgcagatg cagcctgct cctggcacag tcttttctct | 300 |
| actcatgccc aaagttacgg aggacccagc aaccatctcc tgcagcccct ggaaacctct | 360 |
| tgactcttct gtgatgtccc cagtgatcca gcagccctgg ccttcttttg atggcttgaa | 420 |
| catttggtct tcattgaaca gtttgtatat tggaaacttg ccagcctcca tccacattcc | 480 |
| aacctccgtc tgcatccctc gaataactgg gagatgaaac aggaagctct atgacacact | 540 |
| tgatcgaata tgacagacac cgaaaatcac gactcagccc cctccagcac ctctacctgt | 600 |
| tgcccgccga tcacagccgg aatgcagctg aaagattccc tggggcctgg ttccaaccgc | 660 |
| ccactgtgga ctctgaggcc tctgcatttg cgggtggtct gcctgtgata ttttggtcat | 720 |
| gggctggtct ggtcggtttc ccatttgtct ggccagtctc tatgtgtctt aatcccttgt | 780 |
| ccttcattaa aagcaaaact aaagaaaaaa aaaaaaaaaa aaaaaaaa | 828 |

<210> SEQ ID NO 33
<211> LENGTH: 2212
<212> TYPE: DNA
<213> ORGANISM: Homo sapiens

<400> SEQUENCE: 33

| | |
|---|---|
| agttggcctt cagcccctgc ctcggccaga ggtttcattt ttaactgaat atttacgaaa | 60 |
| gctgaaagcg tgcgaggggg gtggggtgga aatagcggct gcttcttttc caaggattta | 120 |
| tttaatgggg atgtgttcaa ggcaagaccg aattcagaag gatatcgacg tcgtgatcca | 180 |
| gaagtccaga gctgaggact gcctgttgc agggctcttc aaaggcctaa agctaaagg | 240 |
| cgaggatgga ttaattcaac aagtcctagt cgtgcgccct ggtgagtgcc agaccctgct | 300 |
| ccccgcgagg ggaccccatga gccaccctca ccacgatccc tgcccggtg gagccccgt | 360 |
| gcgggacaca ggatccgaag atggcagcgg aagttcctca gcggcctcaa aagtgactgg | 420 |
| gcagagtggg cacaggctcc ctcactgggt gaaggaggcg caaagaacgg gaagagccat | 480 |
| cccgggagcc caccggcctt tcagtttccc ttgggccccc aggcggttca ggtatgtgtc | 540 |
| ggggccgggg cgtttccggc agcttttgat gaaggcgagg ggcaaggtcg tcctggttcc | 600 |

```
agaatctccc aacctgcgga tctccaatga gactaacacg attcaccact ctaatctctt      660
cagttttcca aagccttgca cagttgtact gtctggtggg ctctgaggtt gggacggttg      720
ggggagtgtt tggtgagtgc acccttccta tagtgcccag aagaaggtac aatacctgtc      780
tctgtggcac aatcggttag cgcgttcggc tgttaatcta gaggttggtg gttagagccc      840
actgagggat gcctcctcca gattttttt tttttttttc tgagacagag tcttgctctg      900
tcgccaggct ggagtgcagt ggcgcgatct cggctcactg caacatccgc ctccctggtt      960
caagcgattc ccctgcctca gtctcccgag tagctgagaa tacaggcgag cgccaccccg     1020
cccggctaat gttttgtatt ttagtagaga cagaggtttc accttattgg ccaggatggt     1080
ctcgatcagc tgacctcgtg atccacccgc cttggcctcc caaagtgctg ggattacagg     1140
tgtaagcaac cgcgccctgc ccggctgcct gcttcagctt ttaaagcgtt catgcattat     1200
caatcactag ataaacggcg gagattatat cttcccagag tcctaagcca ctagggttgt     1260
gtctctgtgg cacaatcagt tgtcgcatcc aaaaggccta gctaacttt gtatttttg     1320 tagagaaagg gtttcattat gttgcccatg ctggtcccca aactcctggg ctcgggcacc     1380
tccgaggtct cccaaagtgc taggattaca ggcatgagcc actgcacagg gccttataca     1440
atgcttctaa tttcagcaca tttagcaaac ttatcttctg cgggagaggt accaaatcac     1500
attccagttt atttctcaac tctaataatg tcccttcttt catttacttg ctgacacaac     1560 aaatttctc ccctcccgta cttttgttt tgagactagg tgtcactcta tcacccaaga     1620
tggagtgcag tggcatgatc tcatgtcact gcaaactcac cgcccctgca accatggcac     1680
tagtgatcct ccagaagagc tggaactaca gagaggacat cttgctgtgt tttccaggct     1740
ggacctgaat gaactcctgg gctcaatcaa tccttccacc tcagcctaac atttacactg     1800
ggagcagaga tgcatttgga catataaact gttaacatga ggtaagcgcc aaggtctaga     1860
gaaggcagtg gaagagatgg caaactccgg caccatgtct gcgtgtccag tgtgctctgc     1920
tggagcagca cattttgta cattgctgta tttgaaaaaa ccctgcaaga atcatgaaac     1980
tggacgacca tctttataac actcccagtg ataaaacaag taagaatggc tggtttgtag     2040
tcatctgagc agcctctcta gtttcgtaga tatggtttct ctctgatatc gaacgacttc     2100
caatgtcaag cggaatgcta catcacaagg ataaccgtat gtgaaaagaa ccagttttct     2160
ttgtaatcct gaactttcta gtttgcgcat taaaagacat tatttgaaga ag            2212

<210> SEQ ID NO 34
<211> LENGTH: 2747
<212> TYPE: DNA
<213> ORGANISM: Homo sapiens

<400> SEQUENCE: 34
agacactctc caaaaagcag agacagcagg aagaggggag tggaggcagc ccattcacct       60
ggggaaatga ctgggttgtc gatgacggt ggcggcagcc ccaaggggga cgtgacccg      120 ttctactatg gtaagcctgg gcccctgcgc acccttcctg agccctcagg accccttcca      180
ccaagcagcg gcctctccca gccccaggtc catgctctgt gccccttatc tcccctggtt      240
accacgggct gctgcgggca ggctgcggag agagacagct gctgggagag accacccatc      300
ccgctcctct tgccctctct ttccggagac tatgagaccg ttcgcaatgg gggcctgatc      360
ttcgctggac tggccttcat cgtggggctc ctcatcctcc tcagtaagtg gggtggcctc      420
cagggaaggg gtgctgacca gggcacctct cttctcaagg ccgctgagca ggctggcttt      480
```

```
cgggagttgc caagggaggg gtgagcctcc ccaccacgcc ccccactgca ggatgtggga     540
atgggtgccc ggtgggtgc caggctcgct gggagcacag tgtgaggttc ctgcttgctc      600
aagtgcaccc tccagtgggc ccgggaggag ccgcagaagt gagagcaaac ccacggggta     660
actgggtaac cggagggcca gacagggga ctaggccccc cgctgctaac catggtccca     720
aactcatttg ttaaataggg atgatcccac ctgcctcaca agattagggc tagcatccaa     780
agacatggca gtcaggacag cgctctgaga acggtccagt gcagactcgg agtgttctgg     840
gggagacaaa gagagttatg tatcctcaag ccccgagggg cacacagcag gagcttaata     900
actgcacatt gacttgtttt ggtccaaccc aaagaaaaat acacagaaaa cacaacccat     960
ggaaagaaga tacagcaagc acacctgtgg gctctggact tctaatgcac gtgtgccact    1020
gccaccccac cccaaggctc gggcacagt cctgcgggtc tccccatttt cccgtgttgc    1080
ccatggcagc tctctctacg tgtgccactg ccagcccacc ccaaggctcg ggccacagtc    1140
ctgcaggtct ccccattttc acatgttgcc cgtggcagct cccggagggc agtgccgggt    1200
ggcagctgat cacataggca caggaggcag gtggcctaag caaggggctc cactttggag    1260
ttgctgccat ccttctccag gtgttcatcg ggcagctgtg ctgggggcac catgatggcc    1320
cagtctctgc tgctactctc gatatgccaa cagaccaccg tggatctgct ccagtaaata    1380
tttgctgact gactgactga cttaggttct taaatgccta tggtccagcc ttatataaag    1440
agagagaagg ctgggcgtgg tggctcatgc ctgtaatgcc ggcatattag gaggccaagg    1500
caggaggatc tcttgagacc aggagtttaa gaccagcctg gtcaatacag tgagacccga    1560
tctatacaaa aaaaattt tttaattagc tgggcatggt gacatgtacc tatagtccca    1620
gctacttggg aggctgaggc aggaggatta cttgagccca ggagtttgag gctgcagtga    1680
gctacgatcc caccactgca ctccagcctg ggtgacagag taagacccg tctcaaaaaa    1740 taaaataaaa taaaatataa aataaaatag agacagtcaa acgtggcctc caagcctgac    1800
cctgcgatga tactggcagg agggaggtag gagagactgg aagaattttg agtcttccag    1860
ggtctccttg gaaaattagt ccatggaaac aaatctcctt ttctcttttc aaggcagaag    1920
attccgctgt gggggcaata agaagcgcag gtgagcgctg cctggggtga ccgatgaggg    1980
ggttggggct ggagaaggag gggcgggctg aggattttgt ctctgacaca gtggaggatc    2040
cccagcctca gagatcccta gacccacccc tcccctgcc ctctcacctg ttgcttttcc    2100
ttcccccacc aggcaaatca atgaagatga gccgtaacag caggtatgct aggagggcct    2160
ggggaaggtg cggggagggc agggcaggct tgggagcaac agggaagaat tctggctcct    2220
ggactcggta aataagaatt ttagggtcgt ccacacatca gccaggtggt ctgtcaccca    2280
tcgtgtgttt aaaatgatgg ccaagggcct ggcgtggagt gtgtgccgca ggagatcaca    2340
gaggagccct ggagaaaagt gagatggaca agggggaagt aaaacccaa cctctgctgc    2400 ctcccaccca accccatcct gcctttgtct tctcagcctc ggcggtgcca cccactgcac    2460
tggggccagc tgggaagcca agcatggccc tgcctctggc gcctcccctt cttccctggg    2520
ctttagacct ttgtccccgt cactgccagc gcttgggctg aaggaagctc cagactcaat    2580
gtgaccccca ggtggcatcg ccaactcctg cctcgtgcca cctcatgctt ataataaagc    2640
cggcgtcaga gaccgctgct tccctcacct gcctgcctgt ctccctcctc tgtcaccacc    2700
agcctctcca agctcaagta caaatacagc cgggaaaaaa aaaaaaa               2747

<210> SEQ ID NO 35
<211> LENGTH: 1710
```

```
<212> TYPE: DNA
<213> ORGANISM: Homo sapiens

<400> SEQUENCE: 35
ggcccgagct gcacaggcca aggaattcca cagagggtgt gacccaaagc ccctaacaac      60
agactcgctg ggaccccta gacttggcat ggaggctggg tgcagaccta aagacagag      120
gtggtgaagc ccggccagtg aggacaagag ctgcggggaa ggacaccgag gtgacttgac     180
ggcagcagca ggcctgaagg ctctggctgc tttggaagat atttcaatga gatgcaaatc     240
gcaatcgact gaccattagt ttccactgca gtgtttgcag atggagtcga atgtaacccc     300
ccgggaatgg agccgggagg gtcagagaac gcggctgcgc tctggatctc cgaagggggg     360
cgggggcctg gaagaggtcc gggcccagaa tggacctcca ggtccctgct gccgcaatct     420
ggccctgccc tccagcctac cccttactcc cagaggaagg gacccaggga gacccaccca     480
gatgccctga aggaggtgg aggatggggg tgggcaata cgcagagttt gtctggtgaa       540
tgcaggaaag gggtggggc tggagaggaa aaggatggag cagccgtcag cttgtcaact      600
ccgcatctgc tggctgcctc ggccgggctc cagcctgcgc cctcgcccct cggaacagcg     660
gtatgtccat tctctccgca ttcgtctcca tcgttcagcc accaccgcac ctttctcta     720
ttcatttctc ctgctcccctt gtcctgcccc gccctcgtg cccaggtcca tcggtctaca    780
cccatgggcc gagccctcct caccagggtc tcctggaac cgctccggcc ttgggcttgt     840
ccgcggctcc cacggtcccc gccggcggg gcacagagcg ggaggggagg ggcactagca     900
caacctaccc tgcgctgcgc agctgcaccc ctgcgcgcat gggcgtggcg tagctcagac     960
ccgcccccag cgtttagcgt cttttgtcac ccacctagag ggtttgatat atcctaagct    1020
tttggcccct gggtcctggt tccgtgcagc gagtcctccc agcacccac cctgcacatt     1080
ctggaaagtg ccagactctg gctgggccga gcaagaacag aaccacaaga aggttacacg    1140
attatttatt gagagcctcc tctccccgcc cttgcaatct ctaggtcact ttctccgctt    1200
gtagattttg cgcgcaagcc ccagaaagac ggctggggc agggtgctg cgtactgttc      1260
aatgagagcc ataatgtggc tgtaactgtc ttcctcatat tgcaagaaca ctgctggcag    1320
atccagctcc tcatatagcg ccttcacccg ggccactttc tcagcctcct tctgccgta    1380
attttcctgg aagaggttga agacaggaa aacgggcttg gccttcccca gagcctccag    1440
gaccctcca ctcccctcat tcacatattc cagaacatct ccaaagccac ccactccttt    1500
cctcccctcca atttcaagt gtctctacgt agctaaaatc ccaagcttcc cttccctatc    1560
ccaaatattg cctcatacca ggcatcctct actccagggt ttctccacct tggcactatt    1620
gaaatttggg accagaaaaa aaaaaaaaa aaaaaaaaaa aaaaaaaaa aaaaaaaaaa      1680
aaaaaaaaaa aaaaaaaaa aaaaaaaaaa                                      1710

<210> SEQ ID NO 36
<211> LENGTH: 2221
<212> TYPE: DNA
<213> ORGANISM: Homo sapiens

<400> SEQUENCE: 36
ggccaggaac gccagccgtt cacgcgttcg gtcctccttg gctgactcac cgccctggcc      60
gccgcaccat ggacgccccc aggcaggtgg tcaactttgg gcctggtccc gccaagctgc     120
cgcactcagt gttgttagag atacaaaagg aattattaga ctacaaagga gttggcatta    180
gtgttcttga aatgagtcac aggtcatcag attttgccaa gattattaac aatacagaga    240
```

```
atcttgtgcg ggaattgcta gctgttccag acaactataa ggtgattttt ctgcaaggag      300
gtgggtgcgg ccagttcagt gctgtcccct taaacctcat tggcttgaaa gcaggaaggt      360
gtgctgacta tgtggtgaca ggagcttggt cagctaaggc cgcagaagaa gccaagaagt      420
ttgggactat aaatatcgtt caccctaaac ttgggagtta tacaaaaatt ccagatccaa      480
gcacctggaa cctcaaccca gatgcctcct acgtgtatta ttgcgcaaat gagacggtgc      540
atggtgtgga gtttgacttt atacccgatg tcaagggagc agtactggtt tgtgacatgt      600
cctcaaactt cctgtccaag ccagtggatg tttccaagtt tggtgtgatt tttgctggtg      660
cccagaagaa tgttggctct gctggggtca ccgtggtgat tgtccgtgat gacctgctgg      720
ggtttgccct ccgagagtgc ccctcggtcc tggaatacaa ggtgcaggct ggaaacagct      780
ccttgtacaa cacgcctcca tgtttcagca tctacgtcat gggcttggtt ctggagtgga      840
ttaaaaacaa tggaggtgcc gcggccatgg agaagcttag ctccatcaaa tctcaaacaa      900
tttatgagat tattgataat tctcaaggat tctacgtttg tccagtggag ccccaaaata      960
gaagcaagat gaatattcca ttccgcattg gcaatgccaa aggagatgat gctttagaaa     1020
aaagatttct tgataaagct cttgaactca atatgttgtc cttgaaaggg cataggtctg     1080
tgggaggcat ccgggcctct ctgtataatg ctgtcacaat gaagacgtt cagaagctgg      1140
ccgccttcat gaaaaatttt tggagatgc atcagctatg aacacatcct aaccaggata      1200
tactctgttc ttgaacaaca tacaaagttt aaagtaactt ggggatggct acaaaaagtt      1260
aacacagtat ttttctcaaa tgaacatgtt tattgcagat tcttcttttt tgaaagaaca     1320
acagcaaaac atccacaact ctgtaaagct ggtgggacct aatgtcacct taattctgac     1380
ttgaactgga agcattttaa gaaatcttgt tgcttttcta acaaattccc gcgtattttg     1440
cctttgctgc tactttttct agttagattt caaacttgcc tgtggactta ataatgcaag     1500
ttgcgattaa ttatttctgg agtcatggga acacacagca cagagggtag gggggccctc     1560
taggtgctga atctacacat ctgtggggtc tcctgggttc agcggctgtt gattcaaggt     1620
caacattgac cattggagga gtggtttaag agtgccaggc gaagggcaaa ctgtagatcg     1680
atctttatgc tgttattaca ggagaagtga cataccttat atatgttat attagcaagg      1740
tctgttttta ataccatata ctttatattt ctatacatttt atatttctaa taatacagtt    1800
atcactgata tatgtagaca cttttagaat ttattaaatc cttgaccttg tgcattatag     1860
cattccatta gcaagagttg taccccctcc ccagtcttcg ccttcctctt tttaagctgt     1920
tttatgaaaa agacctagaa gttcttgatt catttttacc attctttcca taggtagaag     1980
agaaagttga ttggttggtt gtttttcaat tatgccatta aactaaacat ttctgttaaa     2040
ttaccctatc ctttgttctc tactgttttc tttgtaatgt atgactacga gagtgatact     2100
ttgctgaaaa gtcttcccc  tattgtttat ctattgtcag tattttatgt tgaatatgta    2160
aagaacatta aagtcctaaa acatctaaaa aaaaaaaaaa aaaaaaaaaa aaaaaaaaa      2220
a                                                                    2221
```

<210> SEQ ID NO 37
<211> LENGTH: 4601
<212> TYPE: DNA
<213> ORGANISM: Homo sapiens

<400> SEQUENCE: 37

```
cgggccgggg cgcgcaggtc ccgtcgccgg tgagcacggg ctccctctcg cgtggcctcg      60
ccgggtccgc ctggcctgcc cacctccgga gccacctctg cccccgcatg ggctggcgaa     120
```

```
gttgggagga gcgagctgga gccagagcgc gcgccgggcg cgccccgtcg ctgcctgact    180
cggcgcccgc agttcgggcg cagcacgccg gccgcaggag cacggatgcc ccccggagcc    240
gcgggctggc aggtctgggg tcctgaggct gctggcagac tatgggtaca acggccagca    300
cagcccagca gacggtctcg gcaggcaccc catttgaggg cctacagggc agtggcacga    360
tggacagtcg gcactccgtc agcatccact ccttccagag cactagcttg cataacagca    420
aggccaagtc catcatcccc aacaaggtgg ccctgttgt gatcacgtac aactgcaagg     480
aggagttcca gatccatgat gagctgctca aggctcatta cacgttgggc cggctctcgg    540 acaacaccccc tgagcactac ctggtgcaag gccgctactt cctggtgcgg gatgtcactg   600
agaagatgga tgtgctgggc accgtgggaa gctgtggggc ccccaacttc cggcaggtgc    660
agggtgggct cactgtgttc ggcatgggac agcccagcct ctcagggttc aggcgggtcc    720
tccagaaact ccagaaggac ggacataggg agtgtgtcat cttctgtgtg cgggaggaac    780
ctgtgctttt cctgcgtgca gatgaggact ttgtgtccta cacacctcga gacaagcaga    840
accttcatga gaacctccag ggccttggac ccggggtccg ggtggagagc ctggagctgg    900
ccatccggaa agagatccac gactttgccc agctgagcga gaacacatac catgtgtacc    960
ataacaccga ggacctgtgg ggggagcccc atgctgtggc catccatggt gaggacgact   1020
tgcatgtgac ggaggaggtg tacaagcggc ccctcttcct gcagcccacc tacaggtacc   1080
accgcctgcc cctgcccgag caagggagtc ccctggaggc ccagttggac gccttttgtca  1140 gtgttctccg ggagacccccc agcctgctgc agctccgtga tgcccacggg cctcccccag   1200
ccctcgtctt cagctgccag atgggcgtgg gcaggaccaa cctgggcatg gtcctgggca   1260
ccctcatcct gcttcaccgc agtgggacca cctcccagcc agaggctgcc cccacgcagg   1320
ccaagcccct gcctatggag cagttccagg tgatccagag cttctccgc atggtgcccc    1380 agggaaggag gatggtggaa gaggtggaca gagccatcac tgcctgtgcc gagttgcatg   1440
acctgaaaga agtggtcttg gaaaaccaga agaagttaga aggtatccga ccggagagcc   1500
cagcccaggg aagcggcagc cgacacagcg tctggcagag ggcgctgtgg agcctggagc   1560
gatacttcta cctgatcctg tttaactact accttcatga gcagtacccg ctggcctttg    1620
ccctcagttt cagccgctgg ctgtgtgccc accctgagct gtaccgcctg cccgtgacgc   1680
tgagctcagc aggccctgtg ctccgagggg acctcatcgc caggggctcc ctacgggagg   1740
acgatctggt ctccccggac gcgctcagca ctgtcagaga gatggatgtg gccaacttcc   1800
ggcgggtgcc ccgcatgccc atctacggca cggcccagcc cagcgccaag gccctgggga   1860
gcatcctggc ctacctgacg gacgccaaga ggaggctgcg gaaggttgtc tgggtgagcc   1920 ttcggggagga ggccgtgttg gagtgtgacg ggcacaccta cagcctgcgg tggcctgggc   1980 ccctgtggc tcctgaccag ctggagaccc tggaggccca gctgaaggcc catctaagcg    2040
agcctccccc aggcaaggag ggccccctga cctacaggtt ccagacctgc cttaccatgc    2100
aggaggtctt cagccagcac cgcagggcct gtcctggcct cacctaccac cgcatccca    2160 tgccggactt ctgtgccccc cgagaggagg actttgacca gctgctggag ccctgcggg    2220 ccgccctctc caaggaccca ggcactggct tcgtgttcag ctgcctcagc ggccagggcc    2280
gtaccacaac tgcgatggtg gtggctgtcc tggccttctg gcacatccaa ggcttccccg   2340
aggtgggtga ggaggagctc gtgagtgtgc ctgatgccaa gttcactaag ggtgaatttc    2400
aggtagtaat gaaggtggtg cagctgctac ccgatgggca ccgtgtgaag aaggaggtgg   2460
```

| | | | | |
|---|---|---|---|---|
| acgcagcgct | ggacactgtc | agcgagacca | tgacgcccat | gcactaccac | ctgcgggaga | 2520 |
| tcatcatctg | cacctaccgc | caggcgaagg | cagcgaaaga | ggcgcaagaa | atgcggaggc | 2580 |
| tgcagctgcg | gagcctgcag | tacttggagc | gctatgtctg | cctgattctc | ttcaacgcgt | 2640 |
| acctccacct | ggagaaggcc | gactcctggc | agaggccctt | cagcacctgg | atgcaggagg | 2700 |
| tggcatcgaa | ggctggcatc | tacgagatcc | ttaacgagct | gggcttcccc | gagctggaga | 2760 |
| gcggggagga | ccagcccttc | tccaggctgc | gctaccggtg | gcaggagcag | agctgcagcc | 2820 |
| tcgagccctc | tgccccgag | gacttgctgt | aggggggcctt | actccctgtc | cccccaccca | 2880 |
| cagggcccca | cgcaggcctg | gggtgtctga | ggtgctcttg | gctgggagcg | gccctgaggg | 2940 |
| gtgctggcct | tgaaatgatt | ccccacttc | ctggagagac | tgagcggagt | tgggagcctt | 3000 |
| tttagaaaga | acttttata | ggacagggag | acagcacagc | catcccttgc | aaaccaccaa | 3060 |
| ggtgtgtggc | tgacctccag | ggaggagcac | tcactggagt | gctcacaagg | tgcacactgc | 3120 |
| tgtgtgtacc | ttgcagacag | gccggcgttc | agcctccaag | gggctcactc | ccccagttgc | 3180 |
| caaacactgt | ggatctctct | gtcctcttct | ccctctctc | agattggcct | ggcagcccct | 3240 |
| ggcacagagc | agaccggcc | actggtagct | ccccacttcc | ttactcctgc | tgctctgcca | 3300 |
| ttgccgctcc | ccttgttgct | gcccaagcac | tgccctcggg | cgtctggcag | cctgaggtgg | 3360 |
| gtggagggga | cagtgttctg | gatagatcta | ttatgtgaaa | ggcagcttca | cccagttttc | 3420 |
| tggactctca | tgccccatc | tccgacctgg | gagacttcag | gaatgacaac | ctacccagcc | 3480 |
| tggtggggct | ggcaggatgg | tggaggtttc | tcaaggagct | ggagacttca | gggagcccct | 3540 |
| ctcatgggga | ggaaagagct | tccaggggc | gaacgcagca | cagaggaaga | ggcctgctcc | 3600 |
| acttgtctgg | gaacctgggc | aggaggcaca | gaggaagcca | aggcctggag | ctgcaggtcc | 3660 |
| cccggcatct | ctctctgtcc | cggcagccca | ggatggcctg | gtgcccccac | ctgctgcagc | 3720 |
| aggagcccca | aggagtgcta | gctgagggtg | gttgctgggg | tggtcctcat | ggacagtgag | 3780 |
| gtgtgcaagg | gtgcactgag | ggtggtggga | ggggatcacc | tgggttccag | gccatccttg | 3840 |
| ctgagcatct | ttgagcctgc | cttccggtgg | gagcagaaaa | ggccagaccc | tgctgagtta | 3900 |
| gaggctgctg | ggatccactg | tttccacaca | gcgggaaggc | tgctgggaac | aggtggcaga | 3960 |
| gaagtgccat | gtttgcgttg | agccttgcag | ctcttccagc | tggggactgg | tgcttgctga | 4020 |
| aacccaggag | ctgaacagtg | aggaggctgt | ccaccttgct | tggctcactg | ggaccaggaa | 4080 |
| agcctgtctt | tggttaggct | cgtgtacttc | tgcaggaaaa | aaaaaaaagg | atgtgtcatt | 4140 |
| ggtcatgata | tttgaaaagg | ggaggaggcc | gaagttgttc | ccatttatcc | agtattggaa | 4200 |
| aatatttgac | ccccttggct | gaattctttt | gcagaactac | tgtgtgtctg | ttcactacct | 4260 |
| tttcaggttt | attgttttta | tttttgcatg | aattaagacg | ttttaatttc | tttgcagaca | 4320 |
| aggtctagat | gcggagtcag | agatgggact | gaatggggag | ggatcctttg | tgttctcatg | 4380 |
| gttggctctg | actttcagct | gtgttgggac | cactggctga | tcacatcacc | tctctgcctc | 4440 |
| agtttcccca | tctgtaaaat | gggagaataa | tacttgccta | cctacctcac | aggggtgttg | 4500 |
| tgaggattca | tttgtgattt | tttttttttt | tgtacagagc | ttttaagcat | taaaaacagc | 4560 |
| taaatgtgaa | aaaaaaaaaa | aaaaaaaaaa | aaaaaaaaa | a | | 4601 |

<210> SEQ ID NO 38
<211> LENGTH: 924
<212> TYPE: DNA
<213> ORGANISM: Homo sapiens

<400> SEQUENCE: 38

```
atgctacgtg tagtggaagg catcttcatt tttgttgtag ttagtgagtc agtgtttggg      60
gttttgggga atggatttat tggacttgta aactgcattg actgtgccaa gaataagtta     120
tctacgattg gctttattct caccggctta gctatttcaa gaattttttct gatatggata    180 ataattacag atggatttat acagatattc tctccaaata tatatgcctc cggtaaccta     240
attgaatata ttagttactt tgggtaatt ggtaatcaat caagtatgtg gtttgccacc     300
agcctcagca tcttctatttt cctgaagata gcaaattttt ccaactacat atttctctgg   360
ttgaagagca gaacaaatat ggttcttccc ttcatgatag tattcttact tatttcatcg    420
ttacttaatt ttgcatacat tgcgaagatt cttaatgatt ataaaacgaa gaatgacaca    480
gtctgggatc tcaacatgta taaaagtgaa tactttatta aacagatttt gctaaatctg    540
ggagtcattt tcttctttac actatcccta attacatgta ttttttttaat catttccctt   600 tggagacaca acaggcagat gcaatcgaat gtgacaggat tgagagactc caacacagaa    660
gctcatgtga aggcaatgaa agttttgata tctttcatca tcctctttat cttgtattt     720 ataggcatgg ccatagaaat atcatgtttt actgtgcgag aaaacaaact gctgcttatg    780 tttgaatga caaccacagc catctatccc tggggtcact catttatctt aattctagga    840
aacagcaagc taaagcaagc ctctttgagg gtactgcagc aattgaagtg ctgtgagaaa    900
aggaaaaatc tcagagtcac atag                                           924

<210> SEQ ID NO 39
<211> LENGTH: 857
<212> TYPE: DNA
<213> ORGANISM: Homo sapiens

<400> SEQUENCE: 39
atatttcctg ttccggggcg tgtgggaccc ggatgcaagc gtgctatata agcgttgctc     60
aagtcccacc cctttctttt tgaggaagac gcggtcgtaa gggctgagga ttttggtcc     120 gcacgctcct gctcctgact caccgctgtt cgctctcgcc gaggaacaag tcggtcagga    180
agcccgcgcg caacagccat ggcttttaag gataccggaa aaacaccgt ggagccggag    240 gtggcaattc accgaattcg aatcacccta acaagccgca acgtaaaatc cttggaaaag    300
gtgtgtgctg acttgataag aggcgcaaaa gaaaagaatc tcaaagtgaa aggaccagtt    360
cgaatgccta ccaagacttt gagaatcact acaagaaaaa ctccttgtgg tgaaggttct    420
aagacgtggg atcgtttcca gatgagaatt cacaagcgac tcattgactt gcacagtcct    480
tctgagattg ttaagcagat tacttccatc agtattgagc aggagttga ggtggaagtc     540 accattgcag atgcttaagt caactatttt aataaattga tgaccagttg ttaacttctg    600
ttggttttta ttcagaatac tggcagattt taggaatata aaggtgtact atgagacttc    660
cacttttcag gtggaatata tgggtatctt agagtggtct atcctgtttt cgttgtcgtt    720
tgagtcattt gaaaactgga ttccgttaac tacataatat gtgagacctg actggtttta   780
ttggacactg gcagtttata actttggcat actctagata aattctgatt ggtatgggga    840
aaaaaaaaaa aaaaaaa                                                   857

<210> SEQ ID NO 40
<211> LENGTH: 2840
<212> TYPE: DNA
<213> ORGANISM: Homo sapiens

<400> SEQUENCE: 40
```

```
ggctctcggg gctgccttttt agccggacgc gcggaggtgg gcaatccgct ccttcccttg      60
agcagtccac gccttgtggc ggctttgcgg agctgctgct ttggcgggag ttggaagctg     120
gtgtgaggtg agaggcgcgg tggtcgctcc ccggcgaggc caggtttctg tggggagaag     180
gagagtgcca gaggtgactg gttcatggtt cttctaggct ctcatggcca ccatgttgga     240
aggcagatgc caaactcagc caaggagcag ccccagtggc cgagaggcta gcctgtggtc     300
gtcaggcttt gggatgaagc tggaggctgt cactccattc ctggggaagt atcgcccctt     360
tgtgggtcgc tgttgccaga cctgcacccc caagagctgg gagtccctct tccacagaag     420
cataacggac ctaggcttct gcaatgtgat cctggtgaag gaggagaaca caaggtttcg     480
gggctggctg gttcggaggc tctgctattt cctgtggtcc ctggagcagc catccccccc     540
ctgccaggat gtcccacaga agatcatgga aagcaccggg gtgcagaacc tcctctcagg     600
gagggtccca ggaggcactg gggaaggcca ggtgcctgac cttgtgaaga aggaggtaca     660
gcgcatcctg ggtcacatcc aggccccacc ccgtcccttc ctggtcaggc tgttcagctg     720
ggcgctgctg aggttcctga actgcctgtt cctgaatgtg cagctccaca agggtcagat     780
gaagatggtc cagaaggccg cccaggcagg cttgccgctt gtcctcctct ctactcacaa     840
aaccctcctg gatgggatcc tgctgccctt tatgctgctc tcccagggcc tgggtgtgct     900
tcgtgtggcc tgggactccc gcgcctgctc ccctgccctc agagctctgc tgaggaagct     960 tgggggggctt ttcctgcccc cagaggccag cctctccctg gacagctctg aggggctcct    1020
tgccagggct gtggtccagg cggtcataga gcagctgctg gttagtgggc agcccctgct    1080
catcttcctg gaggaacctc ctggggctct ggggccacgg ctgtcagccc tgggccaggc    1140
ttgggtgggg tttgtggtgc aggcagtcca ggtgggcatc gtcccagatg ctctgctggt    1200
accagtgggc gtcacctatg acctggttcc ggatgcaccg tgtgacatag accatgcctc    1260 ggccccctg gggctgtgga caggagctct ggctgtccta cgtagcttgt ggagccgctg    1320
gggctgcagc caccggatct gctcccgggt gcacctagct cagcccttttt ccctgcagga    1380 atacatcgtc agtgccagaa gctgctgggg cggcagacag accctggagc agctactgca    1440
gcccatcgtg ctgggccaat gtactgctgt cccagacact gagaaggagc aggagtggac    1500
ccccataact gggcctctcc tggccctcaa ggaagaggac cagctcctgg tcaggagact    1560
gagctgtcat gtcctgagtg ccagtgtagg gagctctgcg gtgatgagca cggccattat    1620
ggcaacgctg ctgctcttca agcatcagaa gctcctgggg gagttctcct ggctgacgga    1680
ggagatactg ttgcgtggct ttgatgtagg cttctctggg cagctgcgga gcctgctgca    1740
gcactcactg agcctgctgc gggcgcacgt ggccctgctg cgcatccgtc agggtgactt    1800
gctggtggtg ccgcagcctg gcccaggcct cacacacctg gcacaactga gtgctgagct    1860
gctgcccgtc ttcctgagcg aggctgtggg cgcctgtgca gtgcgggggc tgctggcagg    1920
cagagtgccg cccagggc cctgggagct gcagggcata ttgctgctga gccagaatga    1980
gctgtaccgc cagatcctgc tgctgatgca cctgctgccg caagacctgc tgctgctaaa    2040
gccctgccag tcttcctact gctactgtca ggaggtgctg gaccggctca tccaatgcgg    2100
gctcctggtt gctgaggaga ccccaggctc ccggccagcc tgtgacacag gcgacagcg    2160 attgagcaga aagctgctgt ggaaaccgag tggggacttt actgatagtg acagtgatga    2220
cttcggagag gctgacggcc ggtacttcag gctcagccag cagtcacact gcccagattt    2280
ctttcttttc ctctgccgcc tgctcagccc gctgctcaag gcctttgcac aggctgccgc    2340
cttcctccgc cagggccagc tgcccgatac tgagttgggc tacacagagc agctgttcca    2400
```

| | | |
|---|---|---|
| gttcctgcag gccaccgccc aggaagaagg gatcttcgag tgtgcggacc caaagctcgc | 2460 |
| catcagtgct gtctggacct tcagagacct aggggttctg cagcagacgc cgagccctgc | 2520 |
| aggccccagg ctccacctgt cccctacttt tgccagcctg acaatcagg aaaaactaga | 2580 |
| acagttcatc cggcagttca tttgtagcta aactgtgag gaggagcctg tgctgagact | 2640 |
| tctcagcccc agaacacagc tgtgtcctag agccagaaga tggagaggag gctgcaaacc | 2700 |
| cttagctgct ctataaatat aatcattgag gcttgattgt cccttgccat ctcttgcttt | 2760 |
| ttcccttctt tgatgtgata aacaagggga cgagacgagt tgtctttcc ccagcccagc | 2820 |
| agcaaaaaaa aaaaaaaaaa | 2840 |

<210> SEQ ID NO 41
<211> LENGTH: 1566
<212> TYPE: DNA
<213> ORGANISM: Homo sapiens

<400> SEQUENCE: 41

| | | |
|---|---|---|
| cacagcccca gcagaaggcc ctcacctcac aaggaacatg aggcgccttg ccgggcgcgc | 60 |
| aggccactcc caggtcactc aggattccaa gttctccccc aagacgcctt cagatgctga | 120 |
| gcggcacaag ggcctcccca gggactggtt gcaaagcctc ctgctcagct tgagagggcc | 180 |
| accagctccc cactgtttac tgttgttcct gagagaggcc agaggagg accagccagg | 240 |
| gagtggccag agggacagaa ggggtggcct tcctgagggc agggtgggtg ccccagacct | 300 |
| gagagcgctg caggactccc ctccacaggc tcaggtggag cctccccagg gtcctcctgg | 360 |
| ccaggaaggc agagagccga cttctttctt cagctcccaa cccaggccca gcccacggcg | 420 |
| tgggagtcgg ggagagggag aggaggagga aggaggagga gagagggagc ttgtcttgtc | 480 |
| cctgagcagc gctctcaggg cagaggtgag gcaccgggac atgaagttgg aggacaagtt | 540 |
| cccaagcagg gcttcctcgg gctccccctc gcgacggtaa tttgacactt ggatctccag | 600 |
| gacgaccaac aacaaaaaag ccaggcagag acagcagctg gctgtcagca gaggagctgg | 660 |
| gctgaggcgc ccaggggagc agcggcgccc acgaaggaag tacgaggaca gcacgtggag | 720 |
| gctccgcgct ggggcactgc tgctcagccc caacacctg agctcccaga gcccggcagg | 780 |
| agccccaaca ggaagccagc gcggcatggc tgccaccgac ttcgtgcagg agatgcgcgc | 840 |
| cgtgggcgag aggctgctgc tcaagctgca gagactgccc caggctgagc ccgtggagat | 900 |
| cgtggccttc tcagtcatca tccttttcac agctactgtt ctgctgttgc tgctgatagc | 960 |
| ctgcagctgc tgctgcactc actgctgctg ccctgagcgg agaggcagga aggtccaggt | 1020 |
| gcagccgaca ccaccatgac ggacgggcga tggctgagga aagctggag aggagatggc | 1080 |
| caatgccatg acacaggcca tcagcctggc cctgcagccc ttacccctca agaccaggct | 1140 |
| cccctggccc cagctctggc ccagcccagg tacctggaca ctgacaactt gagccctacc | 1200 |
| aaggaaacaa gggctggtat aggtgcaaac ctctcatctg ccagtggaca ctgggtgctg | 1260 |
| gggagtcagc tgtttcaaag actgggtcaa ctgcctgggc ttcttcgcct acctgcactt | 1320 |
| tttaacaaaa caaggaagta ggggtcccca taccttgatg gagaacagtc cccacctgtg | 1380 |
| ggcaattggc ccttgggact ctgctgatac atgccaaaga ggagcaaggc aatcagaggg | 1440 |
| gctttgtgca atagcttctg catccgagct cccgccagag cgtgagcatg tcagtattct | 1500 |
| agtccagtat ttgccagttt ccaagtaaaa gcttttgtgt tacgtgttaa aaaaaaaaa | 1560 |
| aaaaaa | 1566 |

<210> SEQ ID NO 42
<211> LENGTH: 189
<212> TYPE: DNA
<213> ORGANISM: Homo sapiens

<400> SEQUENCE: 42

```
atgtgcggca gctactacgg aaactactac ggcgaccatg gctatgggtg ctgtggatac      60
gaaggcctag gctatggcta tggaagcctg cgctgtggct atagctcctg ctgtggctat     120
ggtcatggct acggctcccg cttcttctgt ggctgtggct atggatgcgg ctctggctac     180
tactattga                                                             189
```

<210> SEQ ID NO 43
<211> LENGTH: 445
<212> TYPE: DNA
<213> ORGANISM: Homo sapiens

<400> SEQUENCE: 43

```
gcatgtgtct gctgctccct agtctgggcc atgagtgagg gtggaggcca agtctcatgc      60
atttttgcag cccccacaag actgtgcagg tggccggccc tcattgaatg cggggttaat     120
ttaactcagc ctctgtgtga gtggatgatt caggttgcca gagacagaac cctcagctta     180
gcatgggaag tagcttccct gttgaccctg agttcatctg aggttggctt ggaaggtgtg     240
ggcaccattt ggcccagttc ttacagctct gaagagagca gcaggaatgg ggctgagcag     300
ggaagacaac tttccattga aggcccattt cagggccaga actgtccctc ccaccctgca     360
gctgccctgc ctctgcccat gagggggtgag agtcaggcga cctcatgcca agtgtagaaa     420
ggggcagacg ggagccccag gttat                                           445
```

<210> SEQ ID NO 44
<211> LENGTH: 957
<212> TYPE: DNA
<213> ORGANISM: Homo sapiens

<400> SEQUENCE: 44

```
atggaaggca accagacatg gatcacagac atcaccctgc tgggattcca ggttggtcca      60
gcactggcga ttctcctctg tggactcttc tctgtcttct atacactcac cctgctgggg     120
aatgggtca tctttgggat tatctgcctg gactctaagc ttcacacacc catgtacttc     180
ttcctctcac acctggccat cattgacatg tcctatgctt ccaacaatgt tcccaagatg     240
ttggcaaacc taatgaacca gaaaagaacc atctcctttg ttccatgcat aatgcagact     300
tttttgtatt tggcttttgc tgttacagag tgcctgattt tggtggtgat gtcctatgat     360
aggtatgtgg ccatctgcca ccctttccag tacactgtca tcatgagctg gagagtgtgc     420
acgatcctgg ttctcacgtc ctggtcatgt gggtttgccc tgtccctggt acatgaaatt     480
ctccttctaa ggttgccctt ctgtgggccc gggatgtga accacctctt ctgtgaaatt     540
ctgtctgtcc tcaagctggc ctgtgctgac acctgggtta accaagtggt catatttgct     600
acctgtgtgt ttgtcttagt cgggcctctt tccttgattc tggtctccta catgcacatc     660
ctcgggccaa tcctgaagat ccagacaaag gagggccgca taaaggcctt ctccacctgc     720
tcctcccacc tgtgtgtggt tggactattc tttggcatag ccatggtggt ttacatggtc     780
ccagactcta atcaacgaga ggagcaggag aaaatgctgt ccctgttcca cagtgtcttt     840
aatccaatgc tgaacccct gatctacagc ctgaggaatg ctcagttgaa gggcgccctc     900
cacagagcac tccagaggaa gaggtccatg agaacggtgt atgggctttg cctttaa       957
```

<210> SEQ ID NO 45
<211> LENGTH: 1001
<212> TYPE: DNA
<213> ORGANISM: Homo sapiens

<400> SEQUENCE: 45

| | | | | | |
|---|---|---|---|---|---|
| cgtgggtgca | ccctggaccc | caccatggct | caccggcccc | ccagccctgc | cctggcgtcc | 60 |
| gtgctgctgg | ccttgctgct | gagcggtgct | gcccgagctg | cggagatcgt | gggcgggcac | 120 |
| gaggcgcagc | cacactcccg | gccctacatg | gcctccctgc | agatgcgggg | gaacccgggc | 180 |
| agccacttct | gcggaggcac | cttgatccac | cccagcttcg | tgctgacggc | cgcgcactgc | 240 |
| ctgcgggaca | taccccagcg | cctggtgaac | gtggtgctcg | gagcccacaa | cgtgcggacg | 300 |
| caggagccca | cccagcagca | cttctcggtg | gctcaggtgt | ttctgaacaa | ctacgacgcg | 360 |
| gagaacaaac | tgaacgacgt | tctcctcatc | cagctgagca | gcccagccaa | cctcagtgcc | 420 |
| tccgtcgcca | cagtccagct | gccacagcag | gaccagccag | tgcccacgg | cacccagtgc | 480 |
| ctggccatgg | gctggggccg | cgtgggtgcc | cacgacccc | cagcccaggt | cctgcaggag | 540 |
| ctcaatgtca | ccgtggtcac | cttcttctgc | cggccacata | acatttgcac | tttcgtccct | 600 |
| cgccgcaagg | ccggcatctg | cttcggagac | tcaggtggcc | cctgatctg | tgatggcatc | 660 |
| atccaaggaa | tagactcctt | cgtgatctgg | ggatgtgcca | cccgcctttt | ccctgacttc | 720 |
| ttcacgcggg | tagccctcta | cgtggactgg | atccgttcca | cgctgcgccg | tgtggaggcc | 780 |
| aagggccgcc | cctgaaccgc | ccctcccaca | gcgctggccg | ggaccccgag | cctggctcca | 840 |
| aaccctcgag | gcggatcttt | ggacagaagc | agctcttccc | cgaacactgt | ggcgtccggg | 900 |
| acggccccac | ccgtcccccc | acactccctc | ccacgggggct | ccgggagaca | ggccggccct | 960 |
| gcacctcacc | ccaccgtgac | ctcaataaac | gttgaaactc | c | | 1001 |

<210> SEQ ID NO 46
<211> LENGTH: 1706
<212> TYPE: DNA
<213> ORGANISM: Homo sapiens

<400> SEQUENCE: 46

| | | | | | |
|---|---|---|---|---|---|
| acagaaggag | gaaggacagc | acagctgaca | gccgtgctca | gacagcttct | ggatcccagg | 60 |
| ctcatctcca | cagaggagaa | cacacaggca | gcagagacca | tggggcccct | cccagcccct | 120 |
| tcctgcacac | agcgcatcac | ctggaagggg | ctcctgctca | cagcatcact | tttaaacttc | 180 |
| tggaacccgc | ccaccactgc | cgaagtcacg | attgaagccc | agccaccaa | agtttctgag | 240 |
| gggaaggatg | ttcttctact | tgtccacaat | ttgccccaga | atcttcctgg | ctacttctgg | 300 |
| tacaaagggg | aaatgacgga | cctctaccat | tacattatat | cgtatatagt | tgatggtaaa | 360 |
| ataattatat | atgggcctgc | atacagtgga | agagaaacag | tatattccaa | cgcatccctg | 420 |
| ctgatccaga | atgtcacccg | gaaggatgca | ggaacctaca | ccttacacat | cataaagcga | 480 |
| ggtgatgaga | ctagagaaga | aattcgacat | ttcaccttca | ccttatactt | ggagactccc | 540 |
| aagccctaca | tctccagcag | caacttaaac | cccagggagg | ccatggaggc | tgtgcgctta | 600 |
| atctgtgatc | ctgagactct | ggacgcaagc | tacctatggt | ggatgaatgg | tcagagcctc | 660 |
| cctgtgactc | acaggttgca | gctgtccaaa | accaacagga | ccctctatct | atttggtgtc | 720 |
| acaaagtata | ttgcaggacc | ctatgaatgt | gaaatacgga | acccagtgag | tgccagtcgc | 780 |
| agtgacccag | tcaccctgaa | tctcctcccg | aagctgccca | tcccctacat | caccatcaac | 840 |

```
aacttaaacc ccagggagaa taaggatgtc ttagccttca cctgtgaacc taagagtgag    900
aactacacct acatttggtg gctaaacggt cagagcctcc ccgtcagtcc cggggtaaag    960
cgacccattg aaaacaggat actcattcta cccagtgtca cgagaaatga aacaggaccc   1020
tatcaatgtg aaatacggga ccgatatggt ggcctccgca gtaacccagt catcctaaat   1080
gtcctctatg gtccagacct ccccagaatt taccttcat tcacctatta ccgttcagga   1140
gaaaacctcg acttgtcctg cttcacgaaa tctaacccac cggcagagta ttttggaca   1200 attaatggga agtttcagca atcaggacaa aagctcttta tcccccaaat tactagaaat   1260
catagcgggc tctatgcttg ctctgttcat aactcagcca ctggcaagga aatctccaaa   1320
tccatgacag tcaaagtctc tggtccctgc catggagacc tgacagagtc tcagtcatga   1380
ctgcaacaac tgagacactg agaaaaagaa caggctgata ccttcatgaa attcaagaca   1440
aagaagaaaa aaactcaatg ttattggact aaataatcaa aaggataatg ttttcataat   1500
tttttattgg aaaatgtgct gattctttga atgttttatt ctccagattt atgaactttt   1560
tttcttcagc aattggtaaa gtatactttt gtaaacaaaa attgaaatat ttgcttttgc   1620
tgtctatctg aatgccccag aattgtgaaa ctattcatga gtattcatag gtttatggta   1680
ataaagttat ttgcacatgt tccgta                                        1706

<210> SEQ ID NO 47
<211> LENGTH: 597
<212> TYPE: DNA
<213> ORGANISM: Homo sapiens

<400> SEQUENCE: 47
gacagcggca gggggaaccc agggagcgcg atgggctgca gggctgcatc agggctcctg     60
ccaggagtgg ccgtggtcct cctgctgctg ctgcagagca cagtcagt ctacatccag    120 taccaaggct tccgggtcca gctggaatcc atgaagaagc tgagtgacct ggaggcacag    180
tgggcaccca gcccccgcct gcaggcccag agcctcctgc ccgccgtgtg ccaccaccct    240
gctctgcctc aggaccttca gcctgtctgc gcctcgcagg aggcttccag catcttcaag    300
accctgagga ccatcgctaa cgacgactgt gagctgtgtg tgaacgttgc gtgtaccggc    360
tgcctctgag atagccctgg gtaccctgag cccaccaggg acacctcgcc cttcagccca    420
ccaccctggc aggcttccat ccccgtccat gctcaagatg ggtccctggc caccatggtc    480
atcaccaccc ttccagggcc tgagcagctg gatctggtac aaagcaatcg gacatagagt    540
tggaggggga ggcccctgag gcagcccagc tcctgaataa agattctaca acacacg       597

<210> SEQ ID NO 48
<211> LENGTH: 2629
<212> TYPE: DNA
<213> ORGANISM: Homo sapiens

<400> SEQUENCE: 48
accgccccgc gctccgctgc caggggcggg agggaggaat ggttgcttca cgccccgggg     60
gaagagacgg gaagctcggc tctgggttgc gggccccggc gtctccgcgt ggggcgcacc    120
gtccgacccc cccctcccgg tgtgcagcgc ccgcaccgc ccgcctcgc ctgggagaag     180 ccgccgggac gcgccgggct ggagtgggcg gttataggct ttgagctagg ccgtttccgg    240
gaggcggagc tcagaccccg tttcctttct ccacatccag gtcaggtggc gtttgctgtg    300
gcggctaggc ccgcgtgcgc tggagacctc cgcgctggcc ccgcgagcc tcctgccctg    360 gccccggcgct gcggctctgc cgcggcggca gcatgggtgg ccccccggggc gcgggctggg    420
```

```
tggcggcggg cctgctgctc ggcgcgggcg cctgctactg catttacagg ctgacccggg      480
gtcggcggcg gggcgaccgc gagctcggga tacgctcttc gaagtccgca ggtgccctgg      540
aagaagggac gtcagagggt cagttgtgcg ggcgctcggc ccggcctcag acgggaggta      600
cctgggagtc acagtggtcc aagacctcgc agcctgaaga cttaactgat ggttcatatg      660
atgatgttct aaatgctgaa caacttcaga aactccttta cctgctggag tcaacggagg      720
atcctgtaat tattgaaaga gctttgatta ctttgggtaa caatgcagcc ttttcagtta      780
accaagctat tattcgtgaa ttgggtggta ttccaattgt tgcaaacaaa atcaaccatt      840
ccaaccagag tattaaagag aaagctttaa atgcactaaa taacctgagt gtgaatgttg      900
aaaatcaaat caagataaag atatacatca gtcaagtatg tgaggatgtc ttctctggtc      960
ctctgaactc tgctgtgcag ctggctggac tgacattgtt gacaaacatg actgttacca     1020
atgaccacca gcacatgctt cacagttaca ttacagacct gttccaggtg ttacttactg     1080
gaaatggaaa cacgaaggtg caagttttga aactgctttt gaatttgtct gaaaatccag     1140
ccatgacaga aggacttctc cgtgcccaag tggattcatc attcctttcc ctttatgaca     1200
gccacgtagc aaaggagatt cttcttcgag tacttacgct atttcagaat ataaagaact     1260
gcctcaaaat agaaggccat ttagctgtgc agcctacttt cactgaaggt tcattgtttt     1320
tcctgttaca tggagaagaa tgtgcccaga aataagagc tttagttgat caccatgatg     1380
cagaggtgaa ggaaaaggtt gtaacaataa tacccaaaat ctgattggtc atatttttcc     1440
aaagagtaat gcagtctgga tataaacgta ttttctgtct tccttataag gggattctcc     1500
cagctgctaa atttaaacag taaatatcac attttgtcat taacacagct ataacttgcc     1560
gtggttctca gatttatttt ggactatttt gatgccaagt gaatataaga gcttgtactg     1620 aaaccatttta tttctttcta ttttgctatt tgcaaatgct tgttatcttc cctacatgaa     1680
gtggcagtaa cctttttcac atttaagcta cccttctacc ttttgaagtg atttgcagtt     1740
actcatctga gacagcatca gtatttgact aaatcattgt ttcacaactg aatagtcttg     1800
ttcttttagt agcaacgaaa tcctaagctc ttgaggccat tcacctgcca acctgaccat     1860
actgctttca aaagtctttt ctcatcagta gaatctattt tggtcacttc tagtcaatga     1920
aaaatgtaaa cttttaggag agaatgtttc ttaggactca cccactccat tcaatgttat     1980
atataaaata gtgtgatcaa tcacaatgtc catctttaga cagttggtta aataaattat     2040
ctggtctttg aaaagaccgt gctgggcgcg gtggctcttg cctgtaatcc cagcactttg     2100
ggaggctgag gcgggcagat cacctgagat cgggagtttg agaccaagcc tgaccaatat     2160
ggagaaaccc tgtctctact aagaacacaa aattagctgg gcatggtggt gcatgcctgt     2220
aatcccagct acttgggagg ccgaggcagg agaattgctt gaacccggga ggcagaggtt     2280
gcagtgagct gagatagcgc cattgcactc cagcctgggc aacaagagca aaactctgtc     2340
tcaaaaaaaa aaaaaaatga tggagctccg aatgtgctta agtggaaaga tatctatgaa     2400
atatggtggt tttttaaaac acaaaaatta tagaatatgg gatcccgtgt gtgtgtgtgt     2460
gtgtttgaat gaaaaatgct tatgtattga cagaacactt ctagaatgat acccaaactc     2520
ctggagtggg agtggggaat gccttctacg tacacactgt tctactgttt gaattttta     2580 atatgagccc aaattgtata atctttttttt aataaggggg agaaaaatc              2629

<210> SEQ ID NO 49
<211> LENGTH: 1198
<212> TYPE: DNA
```

<213> ORGANISM: Homo sapiens

<400> SEQUENCE: 49

```
ggggtattga ctgaggcggc caagcggctc cgggacaggg ggtacggggg gtggggcgg      60
gtggttgcct gcgggaggcc gccgcgggtc atgtgaccgg aagggctcct cacggacgcc    120
gtccctcctc ggcgcggcct gagcgcccgg cccgaccccg gccatggggt gctgctacag    180
cagcgagaac gaggactcgg accaggaccg agaggagcgg aagctgctgc tggaccctag    240
cagcccccct accaaagctc tcaatggagc cgagcccaac taccacagcc tgccttccgc    300
tcgcactgat gagcaggccc tgctctcttc catccttgcc aagacagcca gcaacatcat    360
tgatgtgtct gctgcagact cacagggcat ggagcagcat gagtacatgg accgtgccag    420
gcagtacagc acccgcttgg ctgtgctgag cagcagcctg acccattgga agaagctgcc    480
accgctgccg tctcttacca gccagcccca ccaagtgctg gccagtgagc ccatcccgtt    540
ctctgatttg cagcaggtct ccaggatagc tgcttatgcc tacagtgcac tttctcagat    600
ccgtgtggac gcaaaagagg agctggttgt acagtttggg atcccatgaa gagagggggtc   660
cttggacagc tcttctcctc tcttcatccc atctctaccc cacccccttg gcccccagcc    720
tcactgcggc ttatacagta ccctaacctg ctactaatca cagagaaaaa tgtgaagaag    780
gaggagaaga ggaaggctag aagcctgagc aagtgagggt agaacctttt gggactggcc    840
tttgaagctc tggccaggga tggggtgggg gccaaaagga cagagcctgg tatgtcttca    900
tagtcattga gaatgtggag ataccagttt gggtgggggg tgatcaccag gggacctagg    960
gagatcccct tcccacccct ctgttggcc tcagagtcac tcctgccccc tctccctgac    1020
ttggtgctca catgcacctc actagggttt gtgaccaggg tctggatgag cttgaatttg    1080
aatgaattga gtttgtattt ctagaaccct gggttttttac atgtttggtc ttttttttgtt   1140
ttggtttgtc accctcgata aggaagtat attcatccaa aaaaaaaaaa aaaaaaaa     1198
```

<210> SEQ ID NO 50
<211> LENGTH: 749
<212> TYPE: DNA
<213> ORGANISM: Homo sapiens

<400> SEQUENCE: 50

```
gacaagcgct gcggcatttg tccccgcgac agcaccgctg ccgccgtctc taaggtcgcc     60
cgggtcccac cgccgccacc atgcctcggg gaagccgcag cgcggcctcc cggccagcca    120
gccgcccagc cgcgccctct gcccaccgc ccgcgcaccc accgccctcg gcagccgccc    180
cagcccccgc cccttcgggc cagccggggc tcatggctca gatggcgacc acggccgcag    240
gggtagccgt gggctcggct gtgggacacg tcatgggcag cgccctgacc ggagccttca    300
gcggggggag ctcggagccc tcccagcctg ctgtccagca ggcccccacc ccgctgccc    360
cccagccct gcagatgggg ccctgcgcct acgagatcag gcagttcctg gactgttcca    420
ccactcagag tgacctgtcc ctgtgtgagg gcttcagcga ggccctgaag cagtgcaagt    480
actaccatgg tctgagctcc ctgccctgaa gaggtcggtg cagactcggg ggccagtcct    540
gcacccacct ctaccctcg ccgacagcca gaccacaaca ccagattgta cccagatagc    600
tgggattgga agtgaggagg tttctcaccc cacagataac ccaagacaca aatgtgcaat    660
taaaagttta tttttagacca caaaaaaaaa aaaaaaaaaaa aaaaaaaaaa aaaaaaaaaa   720
aaaaaaaaaa aaaaaaaaaa aaaaaaaaa                                     749
```

<210> SEQ ID NO 51
<211> LENGTH: 2080
<212> TYPE: DNA
<213> ORGANISM: Homo sapiens

<400> SEQUENCE: 51

| | | | | | |
|---|---|---|---|---|---|
| gtacagggct | ggatgattga | agcaccagcg | ggaactagtc | ggacctccga | gctcttaaa | 60 |
| ctgtcctcag | ctcggctggt | tctccacgag | ctccgggcag | acggcggggg | gtgggtcggc | 120 |
| gtttaagtca | aaggccttgg | ggctccgagt | cccttcctct | ccccgtcctg | tgaaggcacg | 180 |
| acccagttca | gctgtctgta | aagtggagcc | attagtccct | gcctcgtagt | gggaaaactg | 240 |
| ggaggcggaa | cgaggaggcc | gccggtccca | acccggccca | ggagcatctt | tctccgcaga | 300 |
| ccgtttcctg | gcgagatcct | gcgcagccga | ggctgtgtta | gcgccaagga | cttccagcag | 360 |
| ctgttagcag | aggctgctgc | cagggctgct | gccccgctcc | ctcctcctcc | ttcccctgga | 420 |
| gtcagtggtg | ggaagcttcc | caggagagtc | ctcagcaacc | tctggaacac | aggacttggc | 480 |
| catgactgtc | tcctgtccct | gtgtgggccc | agatggttga | gcttgagcag | gaggtggagc | 540 |
| ggcggcagcg | gctggggcag | gagtcagcag | ctaggaaagc | cctcatcgcg | agttcctacc | 600 |
| acccggcacg | gcctgaggtc | tacgactcac | tgcaggatgc | agctctggcc | ccgagttcc | 660 |
| tggccgtgac | tgagtacagc | gtgtccccag | acgcagacct | caagggcctt | ctccagcggc | 720 |
| tggagacagt | atcggaggag | aagcgcatct | accgggtgcc | tgttttcaca | gcgcccttct | 780 |
| gccaggccct | gctggaagag | ctggagcact | tcgagcaatc | ggacatgcct | aaggggaggc | 840 |
| ccaacaccat | gaacaactac | ggggtgctgc | tgcacgagct | cgggctggac | gagccgctga | 900 |
| tgacaccact | gcgggagcgc | ttcctgcagc | cgctgatggc | cctgctgtac | cctgactgtg | 960 |
| gcggggccg | gctcgacagc | caccgggcct | ttgtggtcaa | atacgcaccg | ggccaggacc | 1020 |
| tggagctggg | ctgccactat | gataatgccg | agctcaccct | caatgtggcc | ttgggcaagg | 1080 |
| tcttcacagg | gggcgccctg | tattttgggg | gcctcttcca | ggcacccaca | gccctgacgg | 1140 |
| agcccctgga | ggtggagcac | gtggtgggcc | agggtgtcct | ccaccgtggc | ggccagctgc | 1200 |
| atggagcccg | gcccttgggc | actggtgagc | gttggaacct | tgtcgtctgg | ctccgagcct | 1260 |
| ctgctgtgcg | caacagcctc | tgtcccatgt | gctgccgtga | gccgacctg | gtggacgatg | 1320 |
| agggcttcgg | tgatggcttc | acccgagagg | agcccgccac | ggtggatgta | tgtgcgctca | 1380 |
| cctgagcttg | cttgggccca | gtgtgggggt | ggcaggcagg | tgagggctcc | gttgccttgg | 1440 |
| tctgggggca | gaaataaaat | ccccgcagcc | tactgcactt | cttggctcaa | cggtgtgcca | 1500 |
| gcttctgggt | cattctatgg | gcaaagatgc | tgccttagtt | caggtttgtc | agaagcaggg | 1560 |
| tctggaatgg | ggcttcagcg | agggagtcag | ggaagcaggg | gaggggaggg | agcagctggg | 1620 |
| caaggaagtg | gcttcagagg | acgtccagcc | tcagctggcc | ccacggagag | ctccaggcag | 1680 |
| agcccacagt | accacagtgt | gcccacacca | ccggttactg | gctcctggat | gaggggcca | 1740 |
| gagaggagtg | aataacttcc | cagacactta | cctccagggc | agggtgcctt | ccagtagcca | 1800 |
| agggaagcct | ccagagagca | cagatgtgaa | ccctcagcag | caggcatcac | ccccagtgg | 1860 |
| actcgggtgg | gccaccagta | gcatcttcta | gatggcaggg | gggtgaatgg | cagggccagg | 1920 |
| aaccaggctg | cccgggttcc | cattctgctt | ctgccacttc | cagctgtgtg | gctttaggtg | 1980 |
| agccttcacc | ttttggtgcc | ttcgtttcct | catttagcac | ctacctccta | gagctgtttt | 2040 |
| gggagtcaaa | tgcgctgacg | tatataaagt | gctttgcaag | | | 2080 |

<210> SEQ ID NO 52

<211> LENGTH: 590
<212> TYPE: DNA
<213> ORGANISM: Homo sapiens

<400> SEQUENCE: 52

```
acagcggtca cgtgacatgg ccccggggag ccgaggtgag cgttccagct tccggagccg      60
gaggggggccc ggcgtaccca gccccagcc cgacgtgacc atgctgtccc gcctcctaaa     120
agaacaccag gccaagcaga atgaacgcaa ggagctgcag gaaaagagga ggcgagaggc     180
tatcactgca gcgacctgcc tgacagaagc tttggtggat cacctcaatg tgggtgtggc     240
ccaggcctac atgaaccaga gaaagctgga ccatgaggtg aagacctac aggtccaggc      300
tgcccaattt gccaagcaga caggccagtg gatcggaatg gtgagaact tcaaccaggc      360
actcaaggaa attggggatg tggagaactg ggctcggagc atcgagctgg acatgcgcac     420
cattgccact gcactggaat atgtctacaa agggcagctg cagtctgccc cttcctagcc     480
cctgttccct ccccaaccc tatccctcct acctcacccg caggggaag gagggaggct       540
gacaagcctt gaataaaaca caagcctccg ttaaaaaaaa aaaaaaaaa                 590
```

<210> SEQ ID NO 53
<211> LENGTH: 897
<212> TYPE: DNA
<213> ORGANISM: Homo sapiens

<400> SEQUENCE: 53

```
agagactgcg agaaggaggt ccccacggc ccttcaggat gaaagctgcg gtgctgacct       60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag agatgggagc tctaccgcca aaggtggag ccgctgcgcg      480
cagagctcca agagggcgcg cgccagaagc tgcacgagct gcaagagaag ctgagcccac     540
tgggcgagga gatgcgcgac cgcgcgcgcg cccatgtgga cgcgctgcgc acgcatctgg     600
cccccctacag cgacgagctg cgccagcgct tggccgcgcg ccttgaggct ctcaaggaga   660
acggcggcgc cagactggcc gagtaccacg ccaaggccac cgagcatctg agcacgctca     720
gcgagaaggc caagcccgcg ctcgaggacc tccgccaagg cctgctgccc gtgctggaga     780
gcttcaaggt cagcttcctg agcgctctcg aggagtacac taagaagctc aacacccagt     840
gaggcgcccg ccgccgcccc ccttcccggt gctcagaata aacgtttcca aagtggg         897
```

<210> SEQ ID NO 54
<211> LENGTH: 1534
<212> TYPE: DNA
<213> ORGANISM: Homo sapiens

<400> SEQUENCE: 54

```
tatttgtcaga gtcctcttgt ttggccttct aggaaggctg tgggacccag ctttcttcaa     60
ccagtccagg tggaggcctc tgccttgaac gtttccaagt gaggtaaaac ccgcaggccc    120
agaggcctct ctacttcctg tgtggggttc agaaaccctc ctcccctccc agcctcaggt    180
gcctgcttca gaaaatgaag tagtaagtct gctggcctcc gccatcttag taaagtaaca    240
```

-continued

```
gtcccatgaa acaaagatgc agtcgggcac tcactggaga gttctgggcc tctgcctctt    300
atcagttggc gtttgggggc aagatggtaa tgaagaaatg ggtggtatta cacagacacc    360
atataaagtc tccatctctg gaaccacagt aatattgaca tgccctcagt atcctggatc    420
tgaaatacta tggcaacaca atgataaaaa cataggcggt gatgaggatg ataaaaacat    480
aggcagtgat gaggatcacc tgtcactgaa ggaattttca gaattggagc aaagtggtta    540
ttatgtctgc tacccagag gaagcaaacc agaagatgcg aacttttatc tctacctgag    600
ggcaagagtg tgtgagaact gcatggagat ggatgtgatg tcggtggcca caattgtcat    660
agtggacatc tgcatcactg ggggcttgct gctgctggtt tactactgga gcaagaatag    720
aaaggccaag gccaagcctg tgacacgagg agcgggtgct ggcggcaggc aaaggggaca    780
aaacaaggag aggccaccac ctgttcccaa cccagactat gagcccatcc ggaaaggcca    840
gcgggacctg tattctggcc tgaatcagag acgcatctga ccctctggag aacactgcct    900
cccgctggcc caggtctcct ctccagtccc ctgcgactc cctgtttcct gggctagtct    960
tggaccccac gagagagaat cgttcctcag cctcatggtg aactcgcgcc tccagcctg   1020 atccccgct ccctcctccc tgccttctct gctggtaccc agtcctaaaa tattgctgct   1080
tcctcttcct ttgaagcatc atcagtagtc acaccctcac agctggcctg ccctcttgcc   1140
aggatattta tttgtgctat tcactccctt ccctttggat gtaacttctc cgttcagttc   1200
cctccttttc ttgcatgtaa gttgtccccc atcccaaagt attccatcta cttttctatc   1260
gccgtcccct tttgcagccc tctctgggga tggactgggt aaatgttgac agaggccctg   1320
ccccgttcac agatcctggc cctgagccag ccctgtgctc ctccctcccc caacactccc   1380
taccaacccc ctaatcccct actccctcca cccccctcc actgtaggcc actggatggt   1440
catttgcatc tccgtaaatg tgctctgctc ctcagctgag agagaaaaaa ataaactgta   1500
tttggctgca agaaaaaaaa aaaaaaaaa aaaa                                1534
```

<210> SEQ ID NO 55
<211> LENGTH: 415
<212> TYPE: DNA
<213> ORGANISM: Homo sapiens

<400> SEQUENCE: 55

```
aaacttgacg ccatgaagat cccggtcctt cctgccgtgg tgctcctctc cctcctggtg     60
ctccactctg cccagggagc caccctgggt ggtcctgagg aagaaagcac cattgagaat    120
tatgcgtcac gacccgaggc ctttaacacc ccgttcctga catcgacaa attgcgatct    180 gcgtttaagg ctgatgagtt cctgaactgg cacgccctct ttgagtctat caaaaggaaa    240 cttccttttcc tcaactggga tgcctttcct aagctgaaag gactgaggag cgcaactcct    300
gatgcccagt gaccatgacc tccactggaa gaggggcta gcgtgagcgc tgattctcaa    360
cctaccataa ctctttcctg cctcaggaac tccaataaaa catttccat ccaaa         415
```

<210> SEQ ID NO 56
<211> LENGTH: 2131
<212> TYPE: DNA
<213> ORGANISM: Homo sapiens

<400> SEQUENCE: 56

```
gagcagctcc tcttccatct ccagggtctc attctgttgc ccaggctgga gtgcagtggt     60
gcgatctcgg ctcacagcaa cctctctgcc tccagaaatg acctccacct tcaaccccg     120
```

-continued

```
agaatgtaaa ctgtccaagc aagaagggca aaactatggc ttcttcctgc gaattgagaa        180
ggacaccgag ggccacctgg tccgggtggt tgagaagtgt agcccagcag agaaggctgg        240
ccttcaagat ggagacagag ttcttaggat caatggtgtc tttgtggaca agaagaaca         300 tatgcaggtt gtggatctgg tcagaaagag tgggaattca gtgactttac tagttctgga        360
tggggattcc tatgagaaag cagtgaaaac acgggtggac ttgaaagagt tgggtcaaag        420
tcagaaggag caaggtttga gtgataatat actttcccct gtgatgaatg gaggtgtgca        480
aacttggacc cagccccggc tctgctatct cgtgaaggaa ggaggcagct atggcttctc        540
tctgaaaact gtccaaggta aaaggggggt gtacatgact gatattacac ctcaaggtgt        600
ggctatgaga gctggagttc tggctgatga tcacttgatt gaagtgaatg gagagaatgt        660
agaggatgcc agccatgagg aagtggttga aaaggtgaag aagtcaggaa gccgtgtcat        720
gttcctgctg gtggacaaag aaactgacaa gcgtcatgtt gagcagaaga tacaattcaa        780
aagagaaaca gccagtttga aactgttacc ccaccagccc cgaattgtgg agatgaagaa        840
aggaagcaat ggctatggtt tctatctgag ggcaggctca gaacagaaag gtcaaatcat        900
caaggacata gattctggaa gtccagcaga ggaggctggc ttgaagaaca atgatctggt        960
agttgctgtc aacggcgagt ctgtggaaac cctggatcat gacagtgtgg tagaaatgat       1020
tagaaagggt ggagatcaga cttcactgtt ggtggtagac aaagagacgg acaacatgta       1080
cagactggct catttttctc catttctcta ctatcaaagt caagaactgc ccaatggctc       1140
tgtcaaggag gctccagctc ctactcccac ttctctggaa gtctcaagtc caccagatac       1200
tacagaggaa gtagatcata agcctaaact ctgcaggctg gctaaaggtg aaaatggcta       1260
tggctttcac ttaaatgcga ttcggggtct gccaggctca ttcatcaaag aggtacagaa       1320
gggcggtcct gctgacttgg ctgggctaga ggatgaggat gtcatcattg aagtgaatgg       1380
ggtgaatgtg ctagatgaac cctatgagaa ggtggtggat agaatccaga gcagtgggaa       1440
gaatgtcaca cttctagtct gtggaaagaa ggcctatgat tatttccaag ctaagaaaat       1500
ccctattgtt tcctccctgg ctgatccact tgacacccct ccagattcta agaaggaat          1560 agtggtggag tcaaaccatg actcgcacat ggcaaaagaa cgggcccaca gtacagcctc       1620
acattcttct tccaattctg aagatacaga gatgtgatga aaacaagtaa tagctttggc       1680
tgtttatttg atagctgttt ctgggtattt aataggaatc cttctcaag gaatgagttg        1740 tgacctgttt actgtctctt tagaagaaaa actccactgg aaaccattca ccatgtgtga       1800
ttgtcttctg ttatcatttg tcttacaggc ggctattgca gacggctaat ttatgcttaa       1860
cttaggaaga gataaggcaa gagctagatt ttttcatgt gatctttcc aagcttcaac         1920 ttaacttaac tacatttctc tgtatgatga tgtctcttac ttctacaggt tccttgagca       1980
ccaaagatga ttcataactc tgtataggtg acagctgctt ataaaagcat cttagcagat       2040
aagcctatta aaattgtgct tttgtaacaa tgttgtggtt gctagaataa ataccattaa       2100
caaatgcaaa aaaaaaaaaa aaaaaaaaa a                                       2131
```

<210> SEQ ID NO 57
<211> LENGTH: 1368
<212> TYPE: DNA
<213> ORGANISM: Homo sapiens

<400> SEQUENCE: 57

```
ttccgcccgc gaccccttc cagacccgct cccgaaacct tgtcgaagga ccaaaggcga         60
ccggtgcagg tgcacgacgc cagctccctt ctgggggggcc ggggcctggg ggttgccatg       120
```

```
gcccccagcc acctgtcagt gcgggagatg agggaagatg agaagcccct ggtgctggag      180
atgctgaagg ccggcgtgaa ggacacggaa aaccgcgtgg ccctccatgc cttgacacgg      240
ccgccggccc tgctcctcct ggcggcggcc agcagcggcc tgcgctttgt cctggcttcc      300
ttcgccctgg ccctcctcct gccggtgttc ctggctgtgg ccgccgtgaa gctgggcctg      360
cgggcccgat ggggctcgct gcctccgccg ggtggcctgg ggggcccctg ggtggccgtg      420
cggggctccg gtgacgtgtg tggggtcctg gctctggccc ctggcacaaa tgcaggggac      480
ggggcccggg tcacccgcct gtctgtctct cgctggcacc gccgcggggc cgtgggcagg      540
aggctgctgg ccttcgcgga ggcccgggct cgggcctggg ctgggggcat gggggagccc      600
cgggcccggc tcgtggtccc cgtggctgtg gccgcctggg gggtgggagg gatgctggag      660
ggctgtggct accaggccga ggggggctgg ggctgcctgg gctacacgct ggtgagggaa      720
ttcagcaaag acctgtgaag ctacagactg acagccaggg caggggagga gggaggggcg      780
ccagcacctg atgatcgcct actgtctgcg ggttctttta cctgctctcc ctcagtgagt      840
cctcaaccac cctgggccca gaaacagagg cctgccgagg ggaggagcct ggcctctgtc      900
cacccgtcag cagtgtgaag tctgttgtgt ttgagcttct cagagtggaa tgactccttt      960
tccttcctgg ccctcggggg cctctcgagg tcagcctctc aacccctac ctcagctcct     1020 gtctgcactg agaaacctcc ccgggtgatg tctgcaaagt ctgtgctgtc cgtgccccag     1080
gctgggagag ctatctgggg aggggagag gaggccgagc agaatacacc ccagagttag     1140
ggtttgcgac tccgcctccc tgggacctgg attgggtcag atgcctgtcc ttggagggga     1200
caaggttgac tgcttaggag gcgcgacgca cagggctgcc aggcctggcc cctctctggg     1260
aaggttgaga gctgagacgg gcagcccgt cccttcctcc agatccgtct ggttttttac     1320
accgtttgtt aataaagcct gaaaccgctg aaaaaaaaaa aaaaaaa                   1368
```

<210> SEQ ID NO 58
<211> LENGTH: 1574
<212> TYPE: DNA
<213> ORGANISM: Homo sapiens
<400> SEQUENCE: 58

```
atcgctacgc ccacttggtg gcctataaag gaagcgggcg aaccccggca gccctacaca       60
acttggggcc cctctcctct ccagcccttc tcctgtgtgc ctgcctcctg ccgccgccac      120
catgaccacc tccatccgcc agttcacctc ctccagctcc atcaagggct cctccggcct      180
gggggggcgg tcgtcccgca cctcctgccg gctgtctggc ggcctgggtg ccggctcctg      240
caggctggga tctgctggcg gcctgggcag caccctcggg ggtagcagct actccagctg      300
ctacagcttt ggctctggtg gtggctatgg cagcagcttt gggggtgttg atgggctgct      360
ggctggaggt gagaaggcca ccatgcagaa cctcaatgac cgcctggcct cctacctgga      420
caaggtgcgt gccctggagg aggccaacac tgagctggag gtgaagatcc gtgactggta      480
ccagaggcag gccccggggc ccgcccgtga ctacagccag tactacagga caattgagga      540
gctgcagaac aagatcctca cagccaccgt ggacaatgcc aacatcctgc tacagattga      600
caatgcccgt ctggctgctg atgacttccg caccaagttt gagacagagc aggcctgcg      660 cctgagtgtg gaggccgaca tcaatggcct gcgcagggtg ctggatgagc tgaccctggc      720
cagagccgac ctggagatgc agattgagaa cctcaaggag gagctggcct acctgaagaa      780
gaaccacgag gaggagatga acgccctgcg aggccaggtg ggtggtgaga tcaatgtgga      840
```

| | |
|---|---|
| gatggacgct gccccaggcg tggacctgag ccgcatcctc aacgagatgc gtgaccagta | 900 |
| tgagaagatg gcagagaaga accgcaagga tgccgaggat tggttcttca gcaagacaga | 960 |
| ggaactgaac cgcgaggtgg ccaccaacag tgagctggtg cagagtggca agagtgagat | 1020 |
| ctcggagctc cggcgcacca tgcaggcctt ggagatagag ctgcagtccc agctcagcat | 1080 |
| gaaagcatcc ctggagggca acctggcgga gacagagaac cgctactgcg tgcagctgtc | 1140 |
| ccagatccag gggctgattg gcagcgtgga ggagcagctg gcccagcttc gctgcgagat | 1200 |
| ggagcagcag aaccaggaat acaaaatcct gctggatgtg aagacgcggc tggagcagga | 1260 |
| gattgccacc taccgccgcc tgctggaggg agaggatgcc cacctgactc agtacaagaa | 1320 |
| agaaccggtg accacccgtc aggtgcgtac cattgtggaa gaggtccagg atggcaaggt | 1380 |
| catctcctcc cgcgagcagg tccaccagac cacccgctga ggactcagct accccggccg | 1440 |
| gccacccagg aggcagggag gcagccgccc catctgcccc acagtctccg gcctctccag | 1500 |
| cctcagcccc ctgcttcagt cccttcccca tgcttccttg cctgatgaca ataaagcttg | 1560 |
| ttgactcagc tatg | 1574 |

<210> SEQ ID NO 59
<211> LENGTH: 952
<212> TYPE: DNA
<213> ORGANISM: Homo sapiens

<400> SEQUENCE: 59

| | |
|---|---|
| ccacgcgtcc ggcacttccg cccatccccc tccggatccc tctgttcggg ctcgggtttc | 60 |
| cgccgagacg acagggactg ccaggtcgga agtagtgtga ggctcgtggg cggagccaag | 120 |
| cgccgccatg tccgccgccc tgctgcggcg gggcctggag ctgctggcgg cgtccgaggc | 180 |
| cccccggac cctccaggtc aggccaagcc gagaggggct ccggtgaaac ggccccggaa | 240 |
| gacgaaggca attcaggccc agaaactgcg gaactcggcc aagggaaagg tgcccaagtc | 300 |
| ggcactggac gagtaccgga agcgagagtg tcgagaccac ctcagagtaa acctgaagtt | 360 |
| tctgaccagg acgagaagca ccgtggctga gtctgtgagc cagcagattt tgcgccagaa | 420 |
| ccggggccgc aaggcctgtg accggcctgt ggccaagacc aagaagaaga aggctgaggg | 480 |
| caccgtgttc accgaggaag acttccagaa gttccagcag gaatacttcg gcagctaggc | 540 |
| tccctggagg gcacggtgaa gaggccttca agccctgcag cctccgactc ctgctggctc | 600 |
| caggaaccgg ccgtgccgcg cggccagcag atggcgatgc aggaccagcc tggctcgagg | 660 |
| aagccgcgga gctgagccga gtggaggctg aatggagct ggtgggccgg aagtcctggg | 720 |
| gaggatttac acacagaccg gagctggctt ccgcaggcct gggcagagca tctgcacctg | 780 |
| ccggaaagga acgtatctgt tttgtttgct tttgcccagg tggggcctct gggctgtttg | 840 |
| ctgtggagca aggctaattc ctgagccctt ggggacgaca gctccaggag taggaagaag | 900 |
| ggtgggcttc caagttacaa taaatgtgaa cccaagaaaa aaaaaaaaa aa | 952 |

<210> SEQ ID NO 60
<211> LENGTH: 2129
<212> TYPE: DNA
<213> ORGANISM: Homo sapiens

<400> SEQUENCE: 60

| | |
|---|---|
| ggacagggca gcggcggtga cccgagctgc cgcccgacat gaactcgctg gagcaggcgg | 60 |
| aagccccgcg agttgtatcc ctgattcctg cggtggtttc cggtaactgc caagatctca | 120 |
| aggcttttga gaggagactt actgaatata ttcattgttt gcaacctgct actggacgct | 180 |

```
ggagaatgct tcttatagtg gtatctgtct gtacagctac tggtgcctgg aactggttaa      240
tagaccctga gacacaaaag gtgtccttct tcacatcatt atggaatcac ccatttttca      300
ccattagctg tatcactcta ataggcttgt tctttgctgg aatacacaag agagtagttg      360
caccatcaat tatagctgct cgatgtcgaa cggtattagc agaatacaat atgtcttgtg      420
atgatacagg aaaactaatt ttgaaaccta ggcctcatgt tcaatgacaa tcttcactca      480
ttgttatggg acttaaaata gccttttctt gaataagtga tacagcaaaa agccataaag      540
gattcctttt gcggttggat atgtaaaggt catagcagca actgacaaga agtgtgcaat      600
atttacctgg attatcttga tgatggtgac tcattatcag tgctttggta cttttgatta      660
cctgtgtttc agtattagtg tcactttagt acttcagatc ctgcaaatat ttttgcagat      720
gaagtatgta tgtatgttac taagttaaac ttagaaacag aacctcattc agtttttata      780
atgtattttt gcaaactact gtaaatagca aatcaatgcc aatgttaaac aaagaggaaa      840
acgttgtgtg gactttgttc tcttgcaccg gtatttcagg aacatctgct tgccatcccc      900
acagctcttt aaaactggct attatgtgtg cctttcattc ttacatttct aatcatactg      960
caggaaaaac attggattca gcttagactg aggaaaactc tccattatgt tgtaagaaat     1020
tatagatgtt ttgagagaca cttttgtta aaccagatat tgaactccag caactattgt       1080
ggttatattt ttagttcatt gttctcattt aatgctaaat atcctttata ttgctttaat     1140
aattttcttt tttttttttt ttttttaga cggagtctcg ctctgttgcc aggctggagg      1200
gcagtggcac gatcttggct ttctgcaacc tctgcctccc aggttcaagc gattctcctg     1260
cttcagcctt ccgagtagct gggactacag gcgcatgcca ccatgcccag ctaattttt      1320 tgtatttta gtagagacgg ggtttcacca cgttggccag gatggtttcg atctcctgac      1380
ctcgtgatcc tcctgcctca tcctcccaaa atgctgggat tacaggcata agccaccgtg     1440
cctggcctct ttaataattt ttaaaatacc ctaaaggctt gtgaatatac aagtctactg      1500
ataaattatg tattgtctgg gaatttgata gtcattgttt tagataactg gattttacgc     1560
tgtggtagac aggctgtgac actagtgttg cacaggtgta attggtcatc ctatgccttc     1620
accagaataa cttgggagtg gtgccagaaa ctagagtcta caattctcac tgtttagaga    1680
gtgttaatga catactgtgt atgcataata gccgcatgta ctataatagc ccttaaaatt     1740
aaactattgg gattgctgta aatattttaa agtactggag gtgccttta cctgtttatt      1800 agattttgaa aaggtttaaa ttatttcatg agcaatcttt taaatttcat ttaacataaa     1860
gctgaaaatt caataacagg ataaaaaagc tttttaacaa ggctgccatt taacttaaat    1920
gtgttcatct tagctttcac ttgtataaaa tttgattctt tgaactgcag caataaaacc     1980
ctcagctcct aagaagtctt aagagggtat tctatatatt ctgctttgtt ttattttctg     2040
taaattttgt aggtaaatat gtgcattaaa aataaatact ttatatataa ctcgtgaaaa    2100
aaaaaaaaaa aaaaaaaaa aaaaaaaa                                        2129

<210> SEQ ID NO 61
<211> LENGTH: 901
<212> TYPE: DNA
<213> ORGANISM: Homo sapiens

<400> SEQUENCE: 61
gggatctcgg actccctgga ccctccctcc agcccagcct cgctagctcc gcctgcggta       60
cgtgctcccg cctccgactc aaaatgcctg tctggggagg tggaaacaag gtgggggcct      120
```

| | |
|---|---|
| gtgggaggac cgtgtaccac gcagaagagg tgcagtgtga tggcaggagc ttccaccgct | 180 |
| gctgctttct ctgcatggtt tgcaggaaaa atttagatag cacaacagtg gcaattcacg | 240 |
| atgaagagat ctactgcaaa tcctgctacg gaaagaagta tgggccaaaa ggctacggtt | 300 |
| atggccaggg cgctggcacg cttaacatgg accgtggcga gaggctgggc atcaaaccag | 360 |
| agagtgttca gcctcacagg cctacaacaa atccaaacac ttctaaattt gctcagaaat | 420 |
| atggaggtgc tgagaagtgt tccagatgtg gggattctgt atatgctgcc gagaagataa | 480 |
| ttggagctgg aaagccctgg cacaaaaact gtttccgatg tgcaaagtgt gggaagagtc | 540 |
| ttgaatcaac aactctgact gaaaaagaag gtgaaatcta ttgtaaagga tgctatgcaa | 600 |
| agaactttgg gcccaaggga tttggctatg gccaaggagc aggggctctt gttcatgccc | 660 |
| agtaagatgt aaaccctgaa ctaaacatca cacactgaga atctcttcat aatctaggca | 720 |
| cagataatct ttaacactaa actactgtga aattctacca gcattaagta ctgtatatcg | 780 |
| ccctgtactt ggataggctg gctaactcgt aggaagagag cactgtatgg tatccttttg | 840 |
| ctttattcac cagcattttg ggggaacatt tcttttacat tttaaataaa acttcagctt | 900 |
| g | 901 |

<210> SEQ ID NO 62
<211> LENGTH: 933
<212> TYPE: DNA
<213> ORGANISM: Homo sapiens

<400> SEQUENCE: 62

| | |
|---|---|
| atggaaccac agaacaccac acaggtatca atgtttgtcc tcttagggtt ttcacagacc | 60 |
| caagagctcc agaaattcct gttccttctg ttcctgttag tctatgttac caccattgtg | 120 |
| ggaaacctcc ttatcatggt cacagtgact tttgactgcc ggctccacac acccatgtat | 180 |
| tttctgctcc gaaatctagc tctcatagac ctctgctatt ccacagtcac ctctccaaag | 240 |
| atgctggtgg acttcctcca tgagaccaag acgatctcct accagggctg catggcccag | 300 |
| atcttcttct tccacctttt gggaggtggg actgtctttt ttctctcagt catggcctat | 360 |
| gaccgctaca tagccatctc ccagcccctc cggtatgtca ccatcatgaa cactcaattg | 420 |
| tgtgtgggcc tggtagtagc cgcctgggtg gggggctttg tccactccat tgtccaactg | 480 |
| gctctgatac ttccactgcc cttctgtggc cccaatatcc tagataactt ctactgtgat | 540 |
| gttcccccaag tactgagact tgcctgcact gatacctccc tcctggagtt cctcatgatc | 600 |
| tccaacagtg ggctgctagt tatcatctgg ttcctcctcc ttctgatctc ttatactgtc | 660 |
| atcctggtga tgctgaggtc ccactcggga aaggcaagga ggaaggcagc ttccacctgc | 720 |
| accacccaca tcatcgtggt gtccatgatc ttcattccct gtatctatat ctatacctgg | 780 |
| cccttcaccc cattcctcat ggacaaggct gtgtccatca gctacacagt catgacccc | 840 |
| atgctcaacc ccatgatcta caccctgaga aaccaggaca tgaaagcagc catgaggaga | 900 |
| ttaggcaagt gcctagtaat ttgcagggag taa | 933 |

<210> SEQ ID NO 63
<211> LENGTH: 903
<212> TYPE: DNA
<213> ORGANISM: Homo sapiens

<400> SEQUENCE: 63

| | |
|---|---|
| agataaggcc gctcgctgac gccgtgtttc ctctttcggc cgcgctggtg aacaggaccc | 60 |
| gtcgccatgg gccgtgtgat ccgtggacag aggaagggcg ccgggtctgt gttccgcgcg | 120 |

```
cacgtgaagc accgtaaagg cgctgcgcgc ctgcgcgccg tggatttcgc tgagcggcac      180
ggctacatca agggcatcgt caaggacatc atccacgacc cgggccgcgg cgcgcccctc      240
gccaaggtgg tcttccggga tccgtatcgg tttaagaagc ggacggagct gttcattgcc      300
gccgagggca ttcacacggg ccagtttgtg tattgcggca agaaggccca gctcaacatt      360
ggcaatgtgc tccctgtggg caccatgcct gagggtacaa tcgtgtgctg cctggaggag      420
aagcctggag accgtggcaa gctggcccgg catcaggga actatgccac cgttatctcc       480
cacaaccctg agaccaagaa gacccgtgtg aagctgccct ccggctccaa gaaggttatc      540
tcctcagcca acagagctgt ggttggtgtg gtggctggag gtggccgaat tgacaaaccc      600
atcttgaagg ctggccgggc gtaccacaaa tataaggcaa agaggaactg ctggccacga      660
gtacggggtg tggccatgaa tcctgtggag catcctttg gaggtggcaa ccaccagcac       720
atcggcaagc cctccaccat ccgcagagat gcccctgctg ccgcaaagt gggtctcatt       780 gctgcccgcc ggactggacg tctccgggga accaagactg tgcaggagaa agagaactag      840
tgctgagggc ctcaataaag tttgtgttta tgccaaaaaa aaaaaaaaaa aaaaaaaaa       900 aaa                                                                    903

<210> SEQ ID NO 64
<211> LENGTH: 934
<212> TYPE: DNA
<213> ORGANISM: Homo sapiens

<400> SEQUENCE: 64
agctcagcct cagtccccgc agcttgtgcg gcggcgtcgg caccatgagg cgagggcccc       60
ggagcctgcg gggcagggac gcgccagccc ccacgccctg cgtcccggcc gagtgcttcg      120
acctgctggt ccgccactgc gtggcctgcg ggctcctgcg cacgccgcgg ccgaaaccgg      180
ccggggccag cagccctgcg cccaggacgg cgctgcagcc gcaggagtcg gtgggcgcgg      240
gggccggcga ggcggcgctg ccctgcccg ggctgctctt tggcgcccc gcgctgctgg        300 gcctggcact ggtcctggcg ctggtcctgg tgggtctggt gagctggagg cggcgacagc      360
ggcggcttcg cggcgcgtcc tccgcagagg ccccgacgg agacaaggac gccccagagc       420
ccctggacaa ggtcatcatt ctgtctccgg gaatctctga tgccacagct cctgcctggc      480
ctcctcctgg ggaagaccca ggaaccaccc cacctggcca cagtgtccct gtgccagcca      540
cagagctggg ctccactgaa ctggtgacca ccaagacggc cggccctgag caacaatagc      600
agggagccgg caggaggtgg cccctgccct ccctctggac cccagccag gggcttggaa       660 atcaaattca gctcttcact ccagcatgca catgccctct ttctgggacc aggctaactc      720
tgcagaagca cagacactac agaccacagc attcagcccc catggagttt ggtgtgcttg      780
cctttggctt cagacctcac catctttgac agcccttgaa ggtggtagcc cagctcctgt      840
tcctgtgcct tcaaaaggct ggggcactat gagtaaaaga ccgcttttaa aatggggaag      900
gcaccattaa gccaaaatga atctgaaaaa agac                                  934

<210> SEQ ID NO 65
<211> LENGTH: 945
<212> TYPE: DNA
<213> ORGANISM: Homo sapiens

<400> SEQUENCE: 65
gcttccggta gtgagaaccc ttccggtggg ctaggtactg agcgcgcgag gtgaggagtt       60
```

```
gtgcagggtt tggggaaagg aaggctggct tggcgagagg gcaggtttgc gggctttcgc    120 cccctttttcc aaagaccaac aaagagtcct tccccaactc ccaactcaac ccctttttgga   180 actatgtgtg gtggttggga ccctgtggcg catccttgtc gctcgtgtcc ttctcatgcc    240
cggcgacgcg tctttgtggt aacgccctgc tgccatctct tttcttctct atgcgaggat    300
ttggactggc agtgagaata agagacaacg attcacgtct actttctagg atgacttcca    360
tgtgctccat ctcgcgcgtc cctgagcatg ttgaatttcc aaatcctaaa taagccgcgc    420
ggtgtagttt gtattatgtt gcgtttctct ttctgctttc ctcgcccttt ctccatcatc    480
ctttaggctc tacagagtga aggtttaaat ccaaggtcat ggcaaaacat ctgaagttca    540
tcgccaggac tgtgatggta caggaaggga acgtggaaag cgcatacagg accctaaaca    600
gaatcctcac tatggatggg ctcattgagg acattaagca tcggcggtat tatgagaagc    660
catgccgccg gcgacagagg gaaagctatg aaaggtgccg gcggatctac aacatggaaa    720
tggctcgcaa gatcaacttc ttgatgcgaa agaatcgggc agatccgtgg cagggctgct    780
gaggcctgtg ggtgggacac ccagtgcgaa accctcatcc agttttctct ccatctcttt    840
tctttgtaca atcccatttc ctattaccat tctctgcaat aaactcaaat cacatgtctg    900
caagaaggcc tccaaatata gaaacaatcc cattagtcaa aaaaa                    945

<210> SEQ ID NO 66
<211> LENGTH: 1460
<212> TYPE: DNA
<213> ORGANISM: Homo sapiens

<400> SEQUENCE: 66
tgcagcgcag gtgagctctc ctgaggacct ctctgtcagc tcccctgatt gtagggagga     60
tccagtgtgg caagaaactc ctccagccca gcaagcagct caggatgttc ctgaaggccg    120
tggtcctgac cctggccctg gtggctgtcg ccggagccag ggctgaggtc agtgctgacc    180
aggtggccac ggtgatgtgg gactacttca gccagctgag caacaatgcc aaggaggccg    240
tggaacatct ccagaaatct gaactcaccc agcaactcaa tgccctcttc caggacaaac    300
ttggagaagt gaacacttac gcaggtgacc tgcagaagaa gctggtgccc tttgccaccg    360
agctgcatga acgcctggcc aaggactcgg agaaactgaa ggaggagatt gggaaggagc    420
tggaggagct gagggcccgg ctgctgcccc atgccaatga ggtgagccag aagatcgggg    480
acaacctgcg agagcttcag cagcgcctgg agccctacgc ggaccagctg cgcacccagg    540
tcagcacgca ggccgagcag ctgcggcgcc agctgaccec ctacgcacag cgcatggaga    600
gagtgctgcg ggagaacgcc gacagcctgc aggcctcgct gaggccccac gccgacgagc    660
tcaaggccaa gatcgaccag aacgtggagg agctcaaggg acgccttacg ccctacgctg    720
acgaattcaa agtcaagatt gaccagaccg tggaggagct gcgccgcagc ctggctccct    780
atgctcagga cacgcaggag aagctcaacc accagcttga gggcctgacc ttccagatga    840
agaagaacgc cgaggagctc aaggccagga tctcggccag tgccgaggag ctgcggcaga    900
ggctggcgcc cttggccgag gacgtgcgtg gcaacctgag gggcaacacc gagggggctgc    960 agaagtcact ggcagagctg ggtgggcacc tggaccagca ggtggaggag ttccgacgcc    1020
gggtggagcc ctacggggaa aacttcaaca agccctggt gcagcagatg gaacagctca    1080
ggcagaaact gggcccccat gcgggggacg tggaaggcca cttgagcttc ctggagaagg    1140 acctgagggda caaggtcaac tccttcttca gcaccttcaa ggagaaagag agccaggaca    1200
agactctctc cctcccctgag ctggagcaac agcaggaaca gcagcaggag cagcagcagg    1260
```

```
agcaggtgca gatgctggcc cctttggaga gctgagctgc ccctggtgca ctggccccac   1320
cctcgtggac acctgccctg ccctgccacc tgtctgtctg tctgtcccaa agaagttctg   1380
gtatgaactt gaggacacat gtccagtggg aggtgagacc acctctcaat attcaataaa   1440
gctgctgaga atctagcctc                                                1460

<210> SEQ ID NO 67
<211> LENGTH: 1145
<212> TYPE: DNA
<213> ORGANISM: Homo sapiens

<400> SEQUENCE: 67
tcctccgtcc tgtccacaag gctcagcaaa gcggctggcg gcctggcctg ggacctgctg     60
ctgctccagc catgtccatg acaaccgagc ctggggagga gctggatggc ggcctgggca    120
gctgccaggc cctggaggac cactctgcgc tggccgagac ccaggaggac agggcttcag    180
cgacacccag gctggccgac tccgcagcg tgccccacga ctctcaggtg ctgaaggcc     240 ccagtgtgga caccaggccc aagaagatgg aaaaagagcc tgccgccagg gggacccccag   300 gaacggggaa ggagaggctg aaagccgag cgagccctcg gagcgtcccc gcgcgcaaga    360
aggcgcagac cgcgccgccc ctgcagccgc cgccgccgcc cccggccctg agcgaggagc    420
tgccctgggg agacctgtcg ctcaacaagt gcctggtgct cgcctcgctg gtggcgctgc    480
tgggctcggc tttccagctg tgccgcgacg ccgtccctgg ggaggcagca ctccaagcac    540
gtgtgcccga gcctgggtc ccgccaagct cagccccgag ggagccatcg tcgcccctgc     600
ctaagttcga ggcccaggcg cctccatcag cgccgcctgc ccccgggcc gaggcagagg    660 tcagacccaa gattcccggg agtcgggagg ctgcagagaa cgacgaagag gagcccggcg    720
aggccaccgg agaggccgtc cgggaggacc gtgtgaccct cgcagaccgg ggacccaagg    780
agaggcctcg gagagagggg aagccgcgga aggagaagcc gcggaaggag gagagaccta    840
agaaagagag gccgcggaaa gaggagaggc cacgggccgc cagggagccc cgggaagccc    900
taccccagcg ctgggagtca cgcgaagggg gccaccggcc gtgggcacgg gactccaggg    960
acgccgagcc caggaagaag caggcctggg tgtccccgag gcgtcccgac gaggagcagc   1020
ggcctgggag tcgccagaag ctccgcgcag gcaaggggcg ggactgagcc ggccccgcgc   1080
cggagtccag gggccccttc tggacgcccc gcgactctgg cgaaataaag cgagtgctgc   1140
ggccg                                                              1145

<210> SEQ ID NO 68
<211> LENGTH: 829
<212> TYPE: DNA
<213> ORGANISM: Homo sapiens

<400> SEQUENCE: 68
tggggagtga aagcgaaagc ccgggcgact agccgggaga ccagagatct agcgactgaa     60
gcagcatggc caagccgtgt ggggtgcgcc tgagcgggga agcccgcaaa caggtggagg    120
tcttcagaca gaatcttttc caggaggctg aggaattcct ctacagattc ttgccacaga    180
aaatcatata cctgaatcag ctcttgcaag aggactccct caatgtggct gacttgactt    240
ccctccgggc cccactggac atccccatcc cagaccctcc acccaaggat gatgagatgg    300
aaacagataa gcaggagaag aaagaagtcc ataagtgtgg attctctccct gggaatgaga    360 aagtcctgtc cctgcttgcc ctggttaagc cagaagtctg gactctcaaa gagaaatgca    420
```

```
ttctggtgat tacatggatc caacacctga tccccaagat tgaagatgga aatgattttg      480
gggtagcaat ccaggagaag gtgctggaga gggtgaatgc cgtcaagacc aaagtggaag      540
ctttccagac aaccatttcc aagtacttct cagaacgtgg ggatgctgtg gccaaggcct      600
ccaaggagac tcatgtaatg gattaccggg ccttggtgca tgagcgagat gaggcagcct      660
atggggagct cagggccatg gtgctggacc tgagggcctt ctatgctgag ctttatcata      720
tcatcagcag caacctggag aaaattgtca acccaaaggg tgaagaaaag ccatctatgt      780
actgaacccg ggactagaag gaaaataaat gatctatatg ttgtgtgga              829

<210> SEQ ID NO 69
<211> LENGTH: 4654
<212> TYPE: DNA
<213> ORGANISM: Homo sapiens

<400> SEQUENCE: 69
agagtgctgc ggcgaactgg ctggaggagc taggggacta gaggcggggt gggagggggg      60
cgggtggaag ggggaggaag tcccgtaacg gagacgctgg tcaggacgtt cccacctcct     120
ctgacactgc cgagtccgat cggagagggg tcaccgcctc cttcagcgag gaggaggggg     180
gcggagcccg actcaggatc atggattttc tggtcacttt gaacaaatc ttccagcagc     240 tgaactacca gagacttcat ggccagctct gtgattgtgt cattgtagtg gggaatagac     300
actttaaagc ccaccgctcc gtgctggcag catgcagcac gcatttccga gccctgttct     360
cagtggcaga aggagatcag accatgaaca tgatccagct ggatagcgag gtggtgacag     420
cagaggcctt tgctgcactg attgacatga tgtataccctc caccctcatg ctggggggaga     480 gcaatgtaat ggatgtctta ttggcagcct ctcacctgca tttgaactct gttgttaagg     540
catgtaaaca ttacttaacg acaaggacgc tgcccatgtc tccccccagt gagcgcgttc     600
aggagcagag cgcccgcatg cagcgctcct ttatgctaca gcagctggga ctaagcatcg     660
tgagctcagc cctcaattcc agccagaatg gcgaggagca gccagccccc atgagctctt     720
ccatgcgcag taacctggat cagcgcacgc ccttccccat gagacgcctt cataagcgca     780
agcagtctgc agaggagcgg gccaggcagc gcctccgacc ctccatagat gagtctgcca     840
tttcagatgt tacaccggag aatgggcctt caggggttca ttctcgggag gagttctttt     900
caccagattc tctgaaaatt gtggataatc taaagctga tggaatgact gataaccagg     960
aagatagtgc gatcatgttt gatcagtctt ttggcactca agaagatgcc caggtgccca    1020
gccagtctga taacagtgct ggcaacatgg cacagttgtc catggcctct cgtgcaactc    1080
aggttgagac tagttttgat caggaagctg cacctgagaa aagtagtttt cagtgtgaaa    1140
accctgaggt tggccttggt gagaaggagc acatgagagt ggtggttaaa tctgagcccc    1200
tgagctcacc tgagcctcag gatgaagtga gcgatgtgac ctcacaagca gaaggcagcg    1260
agtctgtgga agtggaagga gttgtggtca gtgccgagaa gatagacctc agccctgaaa    1320
gcagtgatcg gagttttttca gatccccagt ctagcacaga cagggtaggt gatatccata    1380
ttttggaagt cacaaataac ctagagcata gtccacttt tagtatttcg aattttctta    1440
acaagagcag aggaaataac tttactgcaa atcagaacaa tgatgataat attccaaaca    1500
ccactagtga ctgcaggctg gagagtgagg ccccctattt gttgagtcca gaggctgggc    1560
ctgcaggtgg gccctcctct gcccctggct cccatgtaga gaacccattt agtgaacctg    1620
cagactccca cttcgtcagg cctatgcagg aggtgatggg cctgccgtgt gtgcagactt    1680
caggctacca aggaggagaa cagtttggga tggacttttc caggtctggt ttgggcctcc    1740
```

```
actcctccttt ctccagggta atgataggtt ccccaagggg aggagccagt aactttcctt    1800
actaccgccg catagctccc aaaatgccag ttgtaacttc cgtcaggagc tcacagatcc    1860
cagaaaactc taccagttct cagctaatga tgaatggagc tacgtcctca tttgaaaatg    1920
gccatccttc ccagcctggc cctccacagt tgaccaggga atctgcagat gttctgtcaa    1980
agtgcaagaa ggccttatca gagcacaatg ttttggttgt agagggagct cgcaagtatg    2040
cctgcaaaat ctgctgcaaa acttttctga ctttgacaga ttgcaagaag cacatccgtg    2100
ttcacacagg tgaaaagcct tacgcctgcc tgaagtgtgg caagaggttt agtcagtcca    2160
gccacctgta taagcactca aagactacct gcctgcgctg gcagagcagc aatcttccca    2220
gcactttgct ctagctgttt gtccttacaa gacaacgctg aggccagttg tcagactgaa    2280
tttcttttgg taagcagtta atgcctttgg gttcgaggct tccagctgcc cagtggctct    2340
taaacagttt agcaactaat aaccggagaa ctaacatgta gtatttgtgc tgctgcattt    2400
ctgagtgaag tgcacgtctt gggaaaggga tgcaatccct gaaaccaggt gcttccttgg    2460
ggttgagtaa tgcagtcaga aagtagtttg taattgatat taaaagtggc acatttaaaa    2520
atttaaaaat tgaagtgcaa aaaaaatttt ttagcaattt ttgtaaaact gtgtagcatt    2580
taaatttcct ataccttctg atgggagtat tatatccctg tatagtgatg caaaatgcac    2640
ttatgtgtaa ccagtggtga tttggtgcct gtcttaaagg aaggcctttg aggacacacc    2700
tgtctgccac aaatgcttta aagtgtatca tgagctagtc ctaggcctca aagtactgta    2760
ttttttattt ttacctgatt tgcagtcata aacactgcac tttggtgctg acactgggtc    2820
cagagtgagc attctcttgg actattagat gtatatactt ttgaatacat cactgttgga    2880
tagatgtttt aacagttttt tctggtttaa aaaccaaatt gtaaatggag tgtgtacttg    2940
tagagagtga caaggtattg tttccctatg tgctgtttga gcagtatttt aaccaacttg    3000
tattacagat gttacagttc catgttagga agtcagaaaa gacttgtgtt tgtctttgtt    3060
ctgctgatgt ggagtcatgt tttgtggggt cttccatggc acatttacct gttgctccgt    3120
ccagatgttg agggccagtc taggctgaca catcctaccc gaggacaagc tgttctccca    3180
tttcttcact ctcccctccc catatagcaa ctctcccagg tttagattac cgttttcgac    3240
gacagattaa ccaaaaatgc cccacacagg ttttattact gttatatact atacttttaa    3300
cagtacagac cctaaatttt attatttgtt gctcccccaa tctgatacca aatgtttaaa    3360
gttgtttgaa atccaaacat ggtagtgttc atgggtaaat attttctagg ctatgtaaga    3420
gttagcagcc catagcatag aagtaatcaa gtagcatctg agactgttgg aggcactagg    3480
gcctctctgg gcctacagc ctcacttccc cagcctcacc ttgctgtcct ctgacactgc    3540
catcagggct gttagtggca cctgtatgag gccaagtgtg cgtccagggg aacagcacag    3600
gttaatgcgt ctccctagaa ctcatgaagt cagtttaatt catgcatgaa catgagttca    3660
ttttatgttt tatatagctt tcttagacat accaaaccat cattcataaa tcagataaat    3720
tattcagttt ttgtgtttag aaagctaagt atgtgtagct ggaaacaaaa atgagcgtgt    3780
tttctctcct gttaatctag agtgtgcagt tacacatgtg tggataattt catgttccag    3840
gggcgcttgg catctcccat ggactgattc ccaggaagaa aagcccaaag ggaaacccac    3900
gattcctttc gagtagatgt gggaaagagc ccattggagg atatgaggtc ctgtgaaatt    3960
cagttgtgtg tgtggctcct tgttagcagt catgttgaca tggtgttagg aggctcccca    4020
tccacccttt acatgatgta gggaccagtg tcttgtgaga ttaaccttgg gacacagtgg    4080
```

-continued

```
gttagcctgg agaaaatgag aggccctgcc tggacccagg gagaggagcc agtgacacag    4140
gcagagcggt gcagccctcc ttcccttcca tttggaggag gtggtgccag gagcctgccc    4200
gcttacctct gctgaagcat aagtggactt tgcttttggg gcttatctct gatacatgct    4260
ggagccctgc ctctccactg ctagatggaa cctggaatct ctcatctacc tcttagtctg    4320
tcagtttcta cgtgtgagaa gcaagcttgt gggccagtgt ccttgtacat gctgtagcac    4380
ttaaaaaata attccagggt tccctggaaa accagtccca gggttcctat gatctgtagt    4440
ttctacctgg attataactg gttttgggta cctgaatttt gattggttag ccttaattat    4500
agtctggcgt gatcatgtag aatcttttct ggtgaacaga tcataaagtt ctatcaagga    4560
gttctatcaa ggcatccatg tcagtggtgc tatgctggtt acaacttgag attttttgaaa   4620 taaaaaattt gtcatattca tgcctctaaa aaaa                                4654
```

<210> SEQ ID NO 70
<211> LENGTH: 864
<212> TYPE: DNA
<213> ORGANISM: Homo sapiens

<400> SEQUENCE: 70

```
aggagtggct gaggcagggc atggagcgga gcaacgcagc tacaaagtgc ggagaggagc     60
cccgctctgg atcccgccgg ctccccaagg ctgaaggaga caagtctgga tccgcaggag    120
cccccagtaa gaacagcagc cgcctggggg gccgaccatg tatgtgtaca gctggccgcc    180
gcccaaacag ggcgtctggc cgccgccgcc gcagctgctc acctgcacct acctggccgc    240
ccctctgctg ctaccccag tccaggccca cagcttccgc agccggcccg ggagcctgca    300
tgcgggcgag tgggcggccc cacgggaata ccaccgcttc tacggccccg ccgcgccacc    360
cgaggccgcg ccgccctggt gggcctgccc tccggcctac gccacgaccc tgcgccggcc    420
ctgcgccgcc gccggcatct cgggactgtc gctgcaggcg cccgcggcgg tggccgagag    480
ctgggcgccg tggccggagg gcgggagcct gcaaaccgag ctgcgctggg gccgcgtgga    540
gcgcgcgcgg ggccccctc tgcagctacc ggacttcgtg cgccgggagc tgcggcgcgc    600
gtacggcacc taccccccgcg ccgacgtgcg cgtcacccag cgccgcggcc agttcctgct    660
gcaggcgacg ccgcgcgtgc tcgagcccga ccaccgcgtg gagtggcgcg tgcggcgccg    720
gcccgacagc ggcgacagca gcccagcccg ggaagccgcg gagcgcggcc gccccaggaa    780
gagcaagggc ctgagctgaa gccgccgcaa ggcctagggg cgggcccgcg tgcacgcgct    840
tggctctttc ctgtgtgtgc cgcc                                            864
```

<210> SEQ ID NO 71
<211> LENGTH: 4593
<212> TYPE: DNA
<213> ORGANISM: Homo sapiens

<400> SEQUENCE: 71

```
gctgccgcgc ccgccctttt ctcggccccc ggagggtgac ggggtgaagg cgggggaacc     60
gaggtgggga gtccgccaga gctcccagac tgcgagcacg cgagccgccg cagccgtcac    120
ccgcgccgcg tcacggctcc cgggcccgcc ctcctctgac ccctcccctc tctccgtttc    180
cccctctccc cctcctccgc cgaccgagca gtgacttaag caacgagcg cggtgaagct    240 catttttctc cttcctcgca gccgcgccag ggagctcgcg gcgcgcggcc cctgtcctcc    300
ggcccgagat gaatcctgcg gcagaagccg agttcaacat cctcctggcc accgactcct    360
acaaggttac tcactataaa caatatccac ccaacacaag caaagtttat tcctactttg    420
```

```
aatgccgtga aaagaagaca gaaaactcca aattaaggaa ggtgaaatat gaggaaacag    480
tattttatgg gttgcagtac attcttaata agtacttaaa aggtaaagta gtaaccaaag    540
agaaaatcca ggaagccaaa gatgtctaca aagaacattt ccaagatgat gtctttaatg    600
aaaagggatg gaactacatt cttgagaagt atgatgggca tcttccaata gaaataaaag    660
ctgttcctga gggctttgtc attcccagag gaaatgttct cttcacggtg gaaaacacag    720
atccagagtg ttactggctt acaaattgga ttgagactat tcttgttcag tcctggtatc    780
caatcacagt ggccacaaat tctagagagc agaagaaaat attggccaaa tatttgttag    840
aaacttctgg taacttagat ggtctggaat acaagttaca tgattttggc tacagaggag    900
tctcttccca agagactgct ggcataggag catctgctca cttggttaac ttcaaaggaa    960
cagatacagt agcaggactt gctctaatta aaaaatatta tggaacgaaa gatcctgttc   1020
caggctattc tgttccagca gcagaacaca gtaccataac agcttggggg aaagaccatg   1080
aaaaagatgc ttttgaacat attgtaacac agttttcatc agtgcctgta tctgtggtca   1140
gcgatagcta tgacatttat aatgcgtgtg agaaaatatg gggtgaagat ctaagacatt   1200
taatagtatc aagaagtaca caggcaccac taataatcag acctgattct ggaaaccctc   1260
ttgacactgt gttaaaggtt ttggagattt taggtaagaa gtttcctgtt actgagaact   1320
caaagggtta caagttgctg ccaccttatc ttagagttat tcaaggggat ggagtagata   1380
ttaataccct acaagagatt gtagaaggca tgaaacaaaa aatgtggagt attgaaaata   1440
ttgccttcgg ttctggtgga ggtttgctac agaagttgac aagagatctc ttgaattgtt   1500
ccttcaagtg tagctatgtt gtaactaatg gccttgggat taacgtcttc aaggacccag   1560
ttgctgatcc caacaaaagg tccaaaaagg gccgattatc tttacatagg acgccagcag   1620
ggaattttgt tacactggag gaaggaaaag gagaccttga ggaatatggt caggatcttc   1680
tccatactgt cttcaagaat ggcaaggtga caaaaagcta ttcatttgat gaaataagaa   1740
aaaatgcaca gctgaatatt gaactggaag cagcacatca ttaggcttta tgactgggtg   1800
tgtgttgtgt gtatgtaata cataatgttt attgtacaga tgtgtggggt ttgtgttttta   1860 tgatacatta cagccaaatt atttgttggt ttatggacat actgcccttt cattttttt    1920 cttttccagt gtttaggtga tctcaaatta ggaaatgcat ttaaccatgt aaaagatgag   1980
tgctaaagta agctttttag ggcccttgc caataggtag tcattcaatc tggtattgat    2040
cttttcacaa ataacagaac tgagaaactt ttatatataa ctgatgatca cataaaacag   2100
atttgcataa aattaccatg attgctttat gtttatattt aacttgtatt tttgtacaaa   2160
caagattgtg taagatatat ttgaagtttc agtgatttaa cagtctttcc aacttttcat   2220 gattttatg agcacagact ttcaagaaaa tacttgaaaa taaattacat tgccttttgt    2280
ccattaatca gcaaataaaa catggcctta acaaagttgt tgtgttatt gtacaatttg     2340 aaaattatgt cggacatac cctatagaat tactaacctt actgcccctt gtagaatatg    2400
tattaatcat tctacattaa agaaaataat ggttcttact ggaatgtcta ggcactgtac   2460
agttattata tatcttggtt gttgtattgt accagtgaaa tgccaaattt gaaaggcctg   2520
tactgcaatt ttatatgtca gagattgcct gtggctctaa tatgcacctc aagattttaa   2580
ggagataatg ttttagaga gaatttctgc ttccactata gaatatatac ataaatgtaa    2640
aatacttaca aaagtggaag tagtgtattt taaagtaatt acacttctga atttattttt   2700
catattctat agttggtatg acttaaatga attactggag tgggtagtga gtgtacttaa   2760
```

| | |
|---|---|
| atgtttcaat tctgttatat ttttttattaa gtttttaaaa aattaaattg gatattaaat | 2820 |
| tgtatggaca tcatttatta attttaaact gaatgccctc aataagtaat actgaagcac | 2880 |
| attcttaaat gaagataaat tatctccaat gaaaagcatg acatgtgttt caatagaaga | 2940 |
| atcttaagtt ggctaaattc aaagtgcttg acatcaaaat gttctagagt gattagctac | 3000 |
| tagattctga atcatacatc acatctgact agagaccagt ttctttcgaa tgattctttt | 3060 |
| atgtatgtag atctgttctt ctgaggcagc ggttggccaa ctatagccca aaggccaaat | 3120 |
| ttggacttct ttttataaat gcagattgtc tatggctgct ttcccactac tccagcctaa | 3180 |
| ggtaaacagc tgcaatagaa gccaaatgag aatcgcaaag cccaaaatgt ttattaacct | 3240 |
| gccctttaca caaaattaca caaaaagttt cctgatctct gttctaagaa aaggagtgtg | 3300 |
| ccttgcattt aaaaggaaat gttggttttct agggaaggga ggaggctaaa taattgatac | 3360 |
| ggaattttcc tcttttgtct tctttttttct cacttaagaa tccgatactg aagactgat | 3420 |
| ttagaaaagt ttttaacatg acattaaatg tgaaatttta aaaattgaaa agccataaat | 3480 |
| catctgtttt aaatagttac atgagaaaat gatcactaga ataacctaat tagaagtgtt | 3540 |
| atcttcatta aatgtttttt gtaagtggta ttagaaagaa tatgttttttc agatggttct | 3600 |
| ttaaacatgt agtgagaaca ataagcatta ttcacttttta gtaagtcttc tgtaatccat | 3660 |
| gatataaaat aattttaaaa tgatttttta atgtatttga gtaaagatga gtagtattaa | 3720 |
| gaaaaacaca catttcttca caaaatgtgc taaggggcgt gtaaagaatc aaaagaaact | 3780 |
| attaccaata atagttttga taatcaccca taattttgtg tttaaacatt gaaattatag | 3840 |
| tacagacagt attctctgtg ttctgtgaat ttcagcagct tcagaataga gtttaattta | 3900 |
| gaaatttgca gtgaaaaaag ctatctcttt gttcacaacc ataaatcagg agatggagat | 3960 |
| taattctatt ggctcttagt cacttggaac tgattaattc tgactttctg tcactaagca | 4020 |
| cttggtattt ggccatctcc attctgagca ccaaacggtt aacacgaatg tccactagaa | 4080 |
| ctctgctgtg tgtcacccctt aaatcagtct aaatcttcca gacaaaagca aatggcattt | 4140 |
| atggatttaa gtcattagat tttcaactga cattaattaa tccctcttga ttgattatat | 4200 |
| catcaagtat ttatatctta aataggaggt aggattctg tgttaagact cttatttgta | 4260 |
| ccctataatt aaagtaaaat gttttttatg agtatcccctt gttttcccctt cttaaattgt | 4320 |
| tatcaaacaa ttttttataat gaaatctatc ttggaaaatt agaaagaaaa atggcaaggt | 4380 |
| atttattgtt ctgtttgcca taatttagaa ctcacactta agtattttgt agttttacat | 4440 |
| tcctttttaa cccattcagt ggagaatgtc agcttttctc ccaagttgta tgttaagtct | 4500 |
| attctaatat gtactcaaca tcaagttata aacatgtaat aaacatggaa ataaagttta | 4560 |
| gctctattag tgaagtgtta aaaaaaaaaa aaa | 4593 |

<210> SEQ ID NO 72
<211> LENGTH: 1038
<212> TYPE: DNA
<213> ORGANISM: Homo sapiens

<400> SEQUENCE: 72

| | |
|---|---|
| atgagcagca attcatccct gctggtggct gtgcagctgt gctacgcgaa cgtgaatggg | 60 |
| tcctgtgtga aaatccccctt ctcgccggga tcccgggtga ttctgtacat agtgtttggc | 120 |
| tttggggctg tgctggctgt gtttggaaac ctcctggtga tgatttcaat cctccatttc | 180 |
| aagcagctgc actctccgac caattttctc gttgcctctc tggcctgcgc tgatttcttg | 240 |
| gtgggtgtga ctgtgatgcc cttcagcatg gtcaggacgg tggagagctg ctggtatttt | 300 |

```
gggaggagtt tttgtacttt ccacacctgc tgtgatgtgg catttgtta ctcttctctc        360 tttcacttgt gcttcatctc catcgacagg tacattgcgg ttactgaccc cctggtctat        420
cctaccaagt tcaccgtatc tgtgtcagga atttgcatca gcgtgtcctg gatcctgccc        480
ctcatgtaca gcggtgctgt gttctacaca ggtgtctatg acgatgggct ggaggaatta        540
tctgatgccc taaactgtat aggaggttgt cagaccgttg taaatcaaaa ctgggtgttg        600
acagattttc tatccttctt tatacctacc tttattatga taattctgta tggtaacata        660
tttcttgtgg ctagacgaca ggcgaaaaag atagaaaata ctggtagcaa gacagaatca        720
tcctcagaga gttacaaagc cagagtggcc aggagagaga gaaaagcagc taaaaccctg        780
ggggtcacag tggtagcatt tatgatttca tggttaccat atagcattga ttcattaatt        840
gatgccttta tgggctttat aaccctgccc tgtatttatg agatttgctg ttggtgtgct        900
tattataact cagccatgaa tcctttgatt tatgctttat tttacccatg gtttaggaaa        960
gcaataaaag ttattgtaac tggtcaggtt ttaaagaaca gttcagcaac catgaatttg       1020
ttttctgaac atatataa                                                     1038

<210> SEQ ID NO 73
<211> LENGTH: 758
<212> TYPE: DNA
<213> ORGANISM: Homo sapiens

<400> SEQUENCE: 73
gtcatcggga cgtactaaga ctagggttgg gccgagagtc ggagccatta ctgcaggaaa         60
aggtcccgga gagctgagca gtcaagatgt gtgacttcac cgaagaccag accgcagagt        120
tcaaggaggc cttccagctg tttgaccgaa caggtgatgg caagatcctg tacagccagt        180 gtgggggatgt gatgagggcc ctgggccaga accctaccaa cgccgaggtg ctcaaggtcc        240
tggggaaccc caagagtgat gagatgaatg tgaaggtgct ggactttgag cactttctgc        300
ccatgctgca gacagtggcc aagaacaagg accagggcac ctatgaggat tatgtcgaag        360
gacttcgggt gttgacaag gaaggaaatg gcaccgtcat gggtgctgaa atccggcatg        420
ttcttgtcac actgggtgag aagatgacag aggaagaagt agagatgctg gtggcagggc        480
atgaggacag caatggttgt atcaactatg aagcgtttgt gaggcatatc ctgtcggggt        540
gacgggccca tggggcggag ctcgtccgca tggtgctgaa tggctgagga ccttcccagt        600
ctccccagag tccgtgcctt tccctgtgtg aattttgtat ctagcctaaa gtttccctag        660
gctttcttgt ctcagcaact ttcccatctt gtctctcttg gatgatgttt gccgtcagca        720
ttcaccaaat aaacttgctc tctgggccct cggtaaaa                                758

<210> SEQ ID NO 74
<211> LENGTH: 898
<212> TYPE: DNA
<213> ORGANISM: Homo sapiens

<400> SEQUENCE: 74
ccacgttacg gatcggctta ctccgcggag ttggcctcat ttctgcagtc ggcgctccct         60
gtagtttctc ctctcgaacg ccaggtggag caaccggccg gataccgcca cagccctggc        120
aggcggcgct gtgatgcctg agctgatcct gtatgttgca atcactctat ccgtggctga        180
gcgactcgtt ggcccgggtc acgcatgcgc tgagccttcc tttcgctctt cccgctgctc        240
cgcccctctc tgtcttctct gcagtgggag cagctctcct gccacagctc ctcaccccct        300
```

```
gaaaatgttc gcctgctcca agtttgtctc cactccctcc ttggtcaaga gcacctcaca      360
gctgctgagc cgtccgctat ctgcagtggt gctgaaacga ccggagatac tgacagatga      420
gagcctcagc agcttggcag tctcatgtcc ccttacctca cttgtctcta gccgcagctt      480
ccaaaccagc gccatttcaa gggacatcga cacagcagcc aagttcattg gagctggggc      540
tgccacagtt ggggtggctg gttctggggc tgggattgga actgtgtttg ggagcctcat      600
cattggttat gccaggaacc cttctctgaa gcaacagctc ttctcctacg ccattctggg      660 cttttgccctc tcggaggcca tggggctctt ttgtctgatg gtagccttc tcatcctctt      720 tgccatgtga aggagccgtc tccacctccc atagttctcc cgcgtctggt tggccccgtg      780
tgttcctttt cctatacctc cccaggcagc ctggggaacg tggttggctc agggtttgac      840
agagaaaaga caaataaata ctgtattaat aagatgtttc ttgaaaaaaa aaaaaaaa       898
```

<210> SEQ ID NO 75
<211> LENGTH: 1632
<212> TYPE: DNA
<213> ORGANISM: Homo sapiens
<400> SEQUENCE: 75

```
gctcgccccg ccccgctcg ccccgcccct ggatttgctc cctcaaagcg gaggtgaggc       60
cggactgagg ctcttacagt ggtccctgct ggcccttggt gacgggtcgc gtcagttccg      120
acccggaccc gtacgctgct cgcgctgacgt ggctcctgga agcagggctg gcgtagggcc      180
gccatgttgc agcaggatag taatgatgac actgaagatg tttcactgtt tgatgcggaa      240
gaggagacga ctaatagacc aagaaaagcc aaaatcagac atccagtagc atcgttttc       300 cacttattct ttcgagtcag tgcaatcatc gtctgtcttc tctgtgagtt gctcagcagc      360
agctttatta cctgtatggt tacaattatc ttgttgttgt cgtgtgactt ttgggcagtg      420
aagaatgtca caggtagact aatggttggc ctacgttggt ggaatcacat tgatgaagat      480
ggaaagagcc attgggtgtt tgaatctaga aaggagtcct ctcaagagaa taaaactgtg      540
tcagaggctg aatcaagaat cttttggttg ggacttattg cctgttcagt actgtgggtg      600
atatttgcct ttagtgcact cttctccctc acagtaaagt ggctgagacg gtctcgccac      660
attgcccaga ctggtctgaa agtcttgggc tcaagagatc ctcccgcttc cgccttccaa      720
agcgctggga taacaggcgt gagccgctgc ccggggccatc cctcgaggaa gttcatcag      780 gtagacatta attctttcac gaggatcacg gatcgagctc tttactggaa acctgcgccc      840
cgccttagtt ctccacctct tcgtgcggct ccaggcaact gccaacagat ggcgcccgcc      900
cgcctatttc tctccttgcg gctttgggcc tggaggggag gtggggagag tcccaatagc      960
agaggaactg gtgagcccgg gccaaaattt catctggcat ccggaatgca ttaaaaacaa     1020
cccacaaatc tgaagctcct cgcaggagag agagagagag agagagagga gagagaggag     1080
agaggagaga ggggagggaag agagtgacgg agaaggagag aaagacggg gagagaggag     1140 agagaaagag agagagagga gagagagaaa gaacgaacga acagggaact tgtaaaacta     1200
aggggaaaag ggcagaagag aggcagcagc gtggtccctg caagcgtccg cttttcctggc    1260 caagcagccc ccagcacgcc tgctttgtgg ggcagggcca tgcggccccg aggaaggatg     1320
cggtgagcca gagggttcca gacaaaggag gggatcccca aggctctggg ccagccagtc     1380
cctgttttac tggcaccacg gtccctcctta ggcgaggacg aagagggaag gggtggagac    1440
ctccaccttc tctgcgtgtg gctgcgtccc tttacagaat gacaggccct tacttccgag     1500
ggcggggact aatgtgtaag gcttaacaga tccaattcca gaaattatct gtgttttttt     1560
```

| | |
|---|---|
| caatcaccct cttgtgcccc cccaccccc attaaatttc atcttttatc ttttaaaaaa | 1620 |
| aaaaaaaaaa aa | 1632 |

<210> SEQ ID NO 76
<211> LENGTH: 3794
<212> TYPE: DNA
<213> ORGANISM: Homo sapiens

<400> SEQUENCE: 76

| | |
|---|---|
| gactcagatc tcacctccta ccactcccct aggagagctg ggggccactg tttcctggat | 60 |
| tatcctaaaa gcttctgagg ccgtgaggac ttggcagcat ccctgctccc tccttcacct | 120 |
| cccccttggg cactgcctgt cacctccttt ataaagcctg gctcttttat caccgccact | 180 |
| tggccctcac tgccgccgcc agctctgggc tccatggact ggtcccgtct gaggtgcccc | 240 |
| tgaccgtccc tgccctcacc ccaccccgga tcccggcaat gctaaccgct gtctgcggct | 300 |
| ctctgggcag ccagcacacg gaagcgccgc acgcctcccc gccgcgcctc gacctgcagc | 360 |
| ctctccaaac ttaccagggc cacacgagcc ctgaggccgg ggactacccc tccccgctgc | 420 |
| agcctggaga gctgcagagc ctcccgctgg gcccggaggt ggacttctcg cagggctatg | 480 |
| agctgccagg ggcctcctcg cgggtaacct gcgaggacct ggaaagcgac agtcccttgg | 540 |
| ccccgggccc cttttccaag ctcctgcagc cggacatgtc acaccattat gaatcgtggt | 600 |
| tcaggccgac tcacccaggc gcggaggatg gctcgtggtg ggaccttcat ccgggcacca | 660 |
| gctggatgga cctcccccac actcaggcg cgctgacctc acctggccac ccgggggcgc | 720 |
| ttcaggcggg cttggggggc tacgtcggag accaccagct ttgtgccccg ccaccccacc | 780 |
| cgcatgcgca ccacctcctt ccagctgccg gagggcagca tctcctaggg ccgcccgacg | 840 |
| gggctaaggc cttggaagta gccgcccggg agtctcaagg gctggattcc agcctggacg | 900 |
| gggcggcgcg tcccaaaggc tcccggcggt cggtgcccg cagctcaggc cagaccgtct | 960 |
| gtcgctgccc caactgtctg gaggcggagc gactggggc tccatgtggg cccgatgggg | 1020 |
| gcaagaagaa gcatttgcac aactgccaca tcccgggctg cgggaaagcc tacgccaaga | 1080 |
| cgtcgcacct gaaggcgcac ctgcgctggc acagcggcga ccgtcccttc gtgtgcaact | 1140 |
| ggctcttctg cggcaagcgc ttcacgcgct cggacgagct gcagcgccac ctccagaccc | 1200 |
| acaccggcac caagaagttc ccctgtgcag tctgcagccg cgtcttcatg cgcagcgacc | 1260 |
| acctggccaa gcacatgaaa cccacgagg gcgccaagga ggaggcggct ggggcggcct | 1320 |
| cgggagaggg caaggccggc ggcgcagtgg agccccccgg gggcaaaggc aaacgcgagg | 1380 |
| ccgagggcag cgtggctccc tccaactgag ctcctcagtg ccgcctccct gcgggtatcc | 1440 |
| cggggggcac tggatgcgag cccccaggtc tgacgtcctt gggggtggct tgaggaagag | 1500 |
| gggaaggtgc gtatttattc agggaggagg aaaagtggtg cagggacagg gagatggggc | 1560 |
| gctagggggtt cttagtctct ggggctacta ggcaggatga atttgactgg gtcggtagga | 1620 |
| gctgcgcaat gcccctctgt tctcccctgc ctcacagttt ccctcgcccc tgggctgggg | 1680 |
| ggttggggtg ggacaccgt accgcggctg gctggcgggg acaggctaga ggagacagca | 1740 |
| agtcccagtc cccggagcag agagaagtgg ggccggcccg gggcgctggt ggtggctgtc | 1800 |
| tggacacgtc cttagcgcct gggaaccagg acataaaagc gcctccggag ccgccctgcg | 1860 |
| gcggggtccc tttcatccca cttaaagtgc ttctgcccct agggtttccg gagggagagc | 1920 |
| cgagatggga tggggagcc tggggtccc ccttggcagg ggtgtctctt tctggtttgg | 1980 |

```
agggttgttg ctgtaaaaat aactcctttg atgagcttcc ttattaaccc tttcagaccc      2040
agtctgttgg agccatgaag gaagagggaa agagggctgc cattcctgac agcctcccag      2100
ccagggctgg cgataaagga ccgagataga tggagggggc gagtagggaa gtcctcttct      2160
aaaatgagag atagggatttt ggtggggtat ggaaggaact aaccccttcc ctctccacct      2220
ctgattcagc ccttaattct tggtctatga taaataaagt tcagtagtct cacattcccc      2280
atctattacc ctaggtgtgt tttcaaggca gccagcggta gaatccatgt agttcccacc      2340
agttgccttc ccctcaggga tggaaggaag agggtttctt gggctggttg agggcagatt      2400
gggggtgtct catcagaggg acctccactg gttcccactc agagtggagg cctgcagcct      2460
acctgaccat ctctttagct gtcaccaaga aaataaaccc cactgtctct ctagcttggc      2520
ccttgtcttt cccttgcccc tgccatagca tgttcattag gggattcctt cctcccctc      2580 atctcacagg ggaagggaga ggaaagagtt gttctcccac tggaagggt tctgccttct      2640 gaggtgacat ccaggaagct gtccccattc ccttctcctt tagatgctag aaacacattt      2700
tgattctgat catgggtgg gggagagagg aaaggaggga ggggagaagc ccagcagaag      2760
ctgagccagg cagaggggaa agaagctgat atgaggaagg gtctgacagg ccacagccct      2820
tgcagccgga gggctttccc acactcaaga gaggggcctt acagtccctc tgacacccct      2880 ccccccttccc ctcgctccct ttcttcaccc ggagccctct gcagagatta gctgtgtatt      2940 gattttaag ttataagcaa agggtatttt atttaatatt aggttatgtg tgtgcatgtt       3000
gtgtgtacct gtgtgcatgt atgtgtgttt ctctactgag cctgggtctc ctagccaggg      3060 agacccatc ttattcacca tgtccaagat cctgggatct gggcccagca tctcttcctc       3120
ctttgtagat gctggagccc agccaaggtc tgggagctat atgggaagtg ggggctggga      3180
tctgggtggg aatatgtgtt tgtatacaaa ggggccctcc ttaaaaggga caggatgacc      3240
ttcccgagga actcattggc ctggggtagt ttaagaagta atgttctttc tttctttctc      3300 ttttcccta ctcctgctaa cccaaccaga gatccccttc cttgctgaga gggttggggg      3360
caggaggaga tttggcagtg cctgcaggtt gcctggccag gtggagaggg ggaaagagga      3420
agggcaccgt gggtgtaaga tgcctttctc ctccacccat cgaaaccagc cacccccttcc      3480 ctgtgccacc aagacagcct tttccagtgg ccatcctaag gggaactccc aaatgggtgt      3540
tgctggtgga cacagatgct cccccaatg gaagccccaa gctctgaggt atgcgggtag       3600
aggctttgga taggtttct tctgctcccc tcttttatag atctaggctg cttggctgcc       3660
tgtctttcta ggcagtcccc ctagaggaaa aatgtaggaa tttatttttt ctttaactgc      3720
tgtgaactca ctttgagggg gtaggaggag ggagaaacag cctgtgtttt ttatgcaata      3780
aagtcatcaa ctac                                                        3794

<210> SEQ ID NO 77
<211> LENGTH: 4725
<212> TYPE: DNA
<213> ORGANISM: Homo sapiens

<400> SEQUENCE: 77
cgccccgcgc cgccaggag ccaccgtccg agccttgcgg agcgcggcag tgggcgccgg         60
ctgcccgcag cccctgaccc ggccccggac ggagcgccgg ccgcaccacc gccctctggc      120
cgttgcctca ccggctcggc aagatgtcgg tgaaggaggg cgcacagcgc aagtgggcag      180
cgctgaagga gaagctgggg ccacaggatt cggaccccac ggaggccaac ctggagagcg      240
cggaccccga gctgtgcatc cggctgctcc agatgccctc tgtggtcaac tactccggcc      300
```

```
tgcgcaagcg cctggagggc agcgacggcg gctggatggt gcagttcctg gagcagagcg    360
gcctggacct gctgctggag gcgctggcgc ggctgtcggg ccgcggcgtt gcacgtatct    420
ccgacgccct gctgcagctc acctgcgtca gctgcgtgcg cgccgtcatg aactcgcggc    480
agggcatcga gtacatcctc agcaaccagg gctacgtgcg ccagctctcc caggccctgg    540
acacatccaa cgtgatggtg aagaagcagg tgtttgagct actggctgcc ctgtgcatct    600
actctcccga gggccacgtg ctgaccctgg acgccctgga ccactacaag acggtgtgca    660
gccagcagta ccgcttcagc attgtcatga cgagctctc cggcagcgac aacgtgccct     720
acgtggtcac cctgcttagc gtgatcaacg ccgtcatctt gggccccgag acctgcgcg     780
cgcgcaccca gctgcggaac gagtttatcg gctgcagct gctggacgtc ctggctcgcc     840
tgcgagacct ggaggatgcc gacctgctga tccagctgga ggctttcgag gaggctaagg    900
ccgaggacga ggaggagctg ctgcgagtct ctggcggggt cgacatgagc agccaccagg    960
aggtctttgc ctccctgttc cacaaggtga gctgctcccc ggtgtctgcc cagctcctgt   1020
cggtgctgca gggcctcctg cacctggagc ccaccctccg ctccagccag ctgctctggg   1080
aggccctgga gagcctcgtg aaccgggccg tgctcctggc cagcgatgcc caggaatgca   1140
ccctggagga agtggttgag cggctcctgt ctgtcaaggg gcgacccaga ccgagccccc   1200
tggtcaaggc ccataaaagc gtccaggcca acctagacca gagccagagg ggcagctccc   1260
cgcaaaacac tacaaccccc aagcccagcg tggagggcca gcagccagca gcagctgctg   1320
cctgcgagcc cgtggaccac gcccagagtg agagcatcct gaaagtttcg cagcccagag   1380
ccctggagca gcaggcgtcc accccacccc cacccccacc cccacccctg ctccctggtt   1440
ccagtgccga gcccctccc cctccccac caccccccct gcccagtgtg ggggctaagg    1500
ccctcccaac agcaccccg cccccacccc tgccaggcct gggggccatg gcccccccag    1560
cacctcctct accaccaccc ctgccaggct cctgtgagtt cctgccccca ccacctccac   1620
cactcccggg cttgggatgc ccgccccac ccccacccct gctgcctggt atgggctggg    1680
gccctcctcc accccacct ccactactgc cctgcacctg cagccccccc gtggcgggag    1740
gcatggagga ggtcatcgtg gcccaggtgg accatggctt gggctcagca tgggtcccca   1800
gccatcggcg ggtgaaccca cccacactgc gcatgaagaa gctgaactgg cagaagctgc    1860
catccaacgt ggcacgtgag cacaaactcta tgtgggcgtc cctgagcagc ccgacgccg    1920
aggctgtgga gcccgacttc tccagcatcg agcgactatt ctccttccct gcagccaagc    1980
ccaaggagcc caccatggtg gccccccggg ccaggaagga gccaaggag atcacttttcc    2040
tcgatgccaa gaagagcctg aacctcaaca tcttcctgaa gcaatttaag tgctccaacg    2100
aggaggtcgc tgctatgatc cgggctggag ataccaccaa gtttgatgtg gaggttctca    2160
aacaactcct taagctcctt cccgagaagc acgagattga aaacctgcgg gcattcacag    2220
aggagcgagc caagctggcc agcgccgacc acttctacct cctcctgctg gccattccct    2280
gctaccagct gcgaatcgag tgcatgctgc tgtgtgaggg cgcggccgcc gtgctggaca    2340
tggtgcggcc caaggcccag ctggtgctgg ctgcctgcga aagcctgctc accagccgcc    2400
agctgccat cttctgccag ctgatcctga gaattgggaa cttcctcaac tacggcagcc    2460
acaccggtga cgccgacggc ttcaagatca gcacattgct gaagctcacg gagaccaagt    2520
cccagcagaa ccgcgtgacg ctgctgcacc acgtgctgga ggaagcggaa aagagccacc    2580
ccgacctcct gcagctgccc cgggacctgg aacagccctc gcaagcagca gggatcaacc    2640
```

| | |
|---|---|
| tggagatcat ccgctcagag gccagctcca acctgaagaa gcttctggag accgagcgga | 2700 |
| aggtgtctgc ctccgtggcc gaggtccagg agcagtacac cgagcgcctc caggccagca | 2760 |
| tctcggcctt ccgggcactg gatgagctgt ttgaggccat cgagcagaag caacgggagc | 2820 |
| tggccgacta cctgtgtgag gacgcccagc agctgtccct ggaggacacg ttcagcacca | 2880 |
| tgaaggcttt ccgggacctt ttcctccgcg ccctgaagga gaacaaggac cggaaggagc | 2940 |
| aggcggcgaa ggcagagagg aggaagcagc agctggcgga ggaggaggcg cggcggcctc | 3000 |
| ggggagagga cgggaagcct gtcaggaagg ggcccgggaa gcaggaggag gtgtgtgtca | 3060 |
| tcgatgccct gctggctgac atcaggaagg gcttccagct gcggaagaca gcccggggcc | 3120 |
| gcggggacac cgacgggggc agcaaggcag cctccatgga tcccccaaga gccacagagc | 3180 |
| ctgtggccac cagtaaccct gcaggagatc ccgtgggcag cacgcgctgt cccgcctctg | 3240 |
| agcccggcct tgatgctaca acagccagcg agtcccgggg ctgggacctt gtagacgccg | 3300 |
| tgaccccccgg ccctcagccc acctggagc agttggagga gggtggtcca cggcccctgg | 3360 |
| agaggcgttc ttcctggtat gtggatgcca gcgatgtcct aaccactgag gatccccagt | 3420 |
| gccccccagcc cttggagggg gcctggccgg tgactctggg agatgctcag gccctgaagc | 3480 |
| ccctcaagtt ctccagcaac cagccccctg cagccggaag ttcaaggcaa gatgccaagg | 3540 |
| atcccacgtc cttgctgggc gtcctccagg ccgaggccga cagcacaagt gagggggtgg | 3600 |
| aggacgctgt ccacagccgt ggtgccagac cccctgcagc aggcccaggt ggggatgagg | 3660 |
| acgaggacga ggaggacacg gccccagagt ccgcactgga cacatccctg gacaagtcct | 3720 |
| tctccgagga tgcggtgacc gactcctcgg ggtcgggcac actccccagg gcccgggggcc | 3780 |
| gggcctcaaa ggggaccggg aagcgaagga gaagcgtcc ctccaggagc caggaagagg | 3840 |
| ttcccccctga ttctgatgat aataaaacaa agaaactgtg tgtgatccag taaggcctca | 3900 |
| ggcccaggcc caaggccaag tgagagagcc caggccacag acatgctgc cattctgcca | 3960 |
| agagaggctc ttctgggggc caggctggga ctgggcccg gaaaccaaaa ctccgtgcct | 4020 |
| tacccagccg gggccctcct ggagccttct tggggtgttg tggctgggaa cccgacaggc | 4080 |
| accagtgccc tgccaggcct ggtgccctcc tggaccgcct gcacgtgcca gcctcccacc | 4140 |
| tgcttcctaa aggcaaccct ggcccacacc cgcatgcgcc cggtgcagcc tgccaagggc | 4200 |
| cagtcggggg gtgctgcgtc ctgccagtgt ccaccacagc tctgcctgcc cttcagccca | 4260 |
| gcaaggttta atcaaaatgc aatgctttgc aagtctttac tgcttggagg tggctgagtt | 4320 |
| gggggccctg gcagggggta agctggcagg cagtgccatg gcaggccagg gtcccctccc | 4380 |
| atggggtctg gccccgttc cagcatgtcc agccctgaa gttggagtgg ggcggtct | 4440 |
| gcctttgctg ccactgccag gcctctgccc tgcagctgaa acttggccat cacatcaaca | 4500 |
| gaaaacccct cccagtgcca gctgcccagc gtgggcaggc cctggggaca atacaggtcc | 4560 |
| acctgagggg ctgcagggtg acacccagca gccgctgccc cctcactgcc cacccagcga | 4620 |
| gggcagccta cccgagcctg cccctgcca ggtgtgtgcc ctgaggctgg cggctggatg | 4680 |
| cgtggccaat aaaagcaga cctagcccgg aaaaaaaaa aaaaa | 4725 |

<210> SEQ ID NO 78
<211> LENGTH: 1956
<212> TYPE: DNA
<213> ORGANISM: Homo sapiens

<400> SEQUENCE: 78

| | |
|---|---|
| gagcggaagt ctcgtgaccc cggaagtgac aggcagggcg ggcggggcgg ccgacgacgt | 60 |

```
tcgtcattta gtgcgggagg gatcctgaac cgcgcggccg aaccctccgg tgtcccgacc    120
caggctaagc ttgagcatgg ctgagcagga gcccacagcc gagcagctgg cccagattgc    180
agcggagaac gaggaggatg agcactcggt caactacaag cccccggccc agaagagcat    240
ccaggagatc caggagctgg acaaggacga cgagagcctg cgaaagtaca aggaggccct    300
gctgggccgc gtggccgttt ccgcagaccc caacgtcccc aacgtcgtgg tgactggcct    360
gaccctggtg tgcagctcgg ccccgggccc cctggagctg gacctgacgg cgacctggga    420
gagcttcaag aagcagtcgt tgtgctgaaa ggagggtgtg gagtaccgga taaaaatctc    480
tttccgggtt aaccgagaga tagtgtccgg catgaagtac atccagcata cgtacaggaa    540
aggcgtcaag attgacaaga ctgactacat ggtaggcagc tatgggcccc gggccgagga    600
gtacgagttc ctgaccccg tggaggaggc acccaagggt atgctggccc ggggcagcta    660
cagcatcaag tcccgcttca cagacgacga caagaccgac cacctgtcct gggagtggaa    720
tctcaccatc aagaaggact ggaaggactg agcccagcca gaggcgggca gggcagactg    780
acggacggac gacggacagg cggatgtgtc ccccccagcc cctcccctcc ccataccaaa    840
gtgctgacag gccctccgtg cccctcccac cctggtccgc ctccctggcc tggctcaacc    900
gagtgcctcc gaccccctc ctcagccctc ccccaccac aggcccagcc tcctcggtct    960
cctgtctcgt tgctgcttct gcctgtgctg tgggggagag aggccgcagc caggcctctg   1020
ctgccctttc tgtgccccc aggttctatc tccccgtcac acccgaggcc tggcttcagg   1080
agggagcgga gcagccattc tccaggcccc gtggttgccc ctggacgtgt gcgtctgctg   1140
ctccggggtg gagctggggt gtgggatgca cggcctcgtg ggggccgggc cgtcctccag   1200
ccccgctgct ccctggccag ccccccttgtc gctgtcggtc ccgtctaacc atgatgcctt   1260
aacatgtgga gtgtaccgtg gggcctcact agcctctaac tccctgtgtc tgcatgagca   1320
tgtggcctcc ccgtcccttc cccggtggcg aacccagtga cccagggaca cgtggggtgt   1380
gctgctgctg ctccccagcc caccagtgcc tggccagcct gcccccttcc ctggacaggg   1440
ctgtggagat ggctccggcg gcttggggaa agccaaattg ccaaaactca agtcacctca   1500
gtaccatcca ggaggctggg tattgtcctg cctctgcctt ttctgtctca gcgggcagtg   1560
cccagagccc acacccccc aagagccctc gatggacagc ctcacccacc ccacctgggc   1620
ccagccagga gccccgcctg gccatcagta tttattgcct ccgtccgtgc cgtccctggg   1680
ccactggcct ggcgcctgtt ccccaggct ctcagtgcca ccaccccgg caggccttcc   1740 ctgacccagc caggaacaaa caagggacca agtgcacaca ttgctgagag ccgtctcctg   1800
tgcctccccc gccccatccc cggtcttcgt gttgtgtctg ccaggctcag gcagaggcgc   1860
ctgtccctgc ttcttttctg accgggaaat aaatgcccct gaaggaaaaa aaaaaaaaa   1920 aaaaaaaaa aaaaaaaa aaaaaaaaa aaaaaa                                1956
```

<210> SEQ ID NO 79
<211> LENGTH: 1689
<212> TYPE: DNA
<213> ORGANISM: Homo sapiens

<400> SEQUENCE: 79

```
agcaaatttc aactcccgct tgccattcaa catcatggat gatccgaaga gtgaacagca     60
gcgcatactg cgccgccacc aacgcgagag gcaggagctg caggcccaga tccggagctt    120
aaaaaactcg gtccccaaga ccgacaagac gaaaagaaag cagttgctcc aagacgtggc    180
```

```
ccgcatggag gccgagatgg ctcagaagca ccggcaggag ctggagaagt tccaagacga    240
cagtagcatt gaatctgtcg tcgaagacct ggccaagatg aatctggaaa accggcctcc    300
ccgctcctcc aaagcccaca gaaagagaga agaatggag tccgaggaga gggagcgcca     360
ggagagcatc ttccaggctg agatgtcgga gcacctggcc ggcttcaagc gcaggaggag    420
ggagaagctc gccgccatcc tgggagccag gggtctggag atgaaagcga tcccggccga    480
cggccactgc atgtaccgcg ccatccaaga ccagctggtg ttcagcgtgt ctgtggagat    540
gctgcgctgc cgcaccgcca gctacatgaa gaagcacgtc gacgagttcc tgcccttctt    600
cagcaacccc gagaccagcg actccttcgg ctacgacgac ttcatgatct actgcgacaa    660
catcgtgcgc accacggcat ggggaggcca gctggagctg agggccctgt cgcacgtcct    720
gaagaccccc atcgaggtga tccaggccga ctcgcccacc ttgatcatcg ggaggagta    780 cgtcaagaag ccgatcatcc tggtctacct gcgctatgcc tacagcctcg gcgagcacta    840
caactccgtg acaccgctcg aggccggcgc cgccgggggc gtgctcccgc gtctcctgta    900
ggccccaagg cgctgagcag ccccgggaaa ctgtcgccgt cgccgcatct cctcagtagg    960
ctcagtttat tttcccctt  tgcttttctc tgttttttctt ttccttcctt ttaatcaaaa   1020
ctacccgccc ccgcccgcc  cccgctttcc taaccttgct gctttcacag ggtgggaaac    1080
gaaattcgag ggaaattccc cggaaatatg agggaaatct ctgcattgca ccaccagagg    1140
ggcataaatt tgaaagttct aacctcttct tgcccttaag ggtcttttac ctccctcacc    1200
aactaagatt tggtcatgtt gcgtataact tcaccacaaa aatggaaata ttggccgggc    1260
gcggtggctc acgcctgtaa tcccagcact ttgggaggcc gaggcgggcg gatcacgagg    1320
tcaggagttc gagaccagcc tggccaacat ggtgaaaccc cacctctaca aaaaatacaa    1380
aaattagccg ggcgtggtgg caggcacctg tagtcccaga tactcgggag gctaaggcag    1440
gagaatcgct tgacgggaag cggaggttgc agtgagccga gatcgtgcct ttgcactcca    1500
gcgtggaaga cagtgagact ccgtctcaaa aaaatgaaaa attagccagg caggttggcg    1560
ggggcctgta atcctagcta cttggggtgc tgaggcagga gaatcaactg aacccgggag    1620
gcggaggctg cagtgggccg ggatcatact actgcactcc agcatggaag acagcgagac    1680
tccgtctcc                                                           1689
```

<210> SEQ ID NO 80
<211> LENGTH: 1865
<212> TYPE: DNA
<213> ORGANISM: Homo sapiens

<400> SEQUENCE: 80

```
cgcccacgcg gagccggccc cgcgcgcgcg cgcgtcccgt gcatcccgc gcctgcgcgc      60 tgcccaggcc ctgcccgtgt gtgggggtcg ctgccggccc cgggggggggg tggggaaaat    120 aagggattaa aaaacagcg cgcggaaccg ggccagggtt gcccacccc gccacaatgg      180 cctctggggt ggaagtcctg cgcttccagc tgccccggcca cgaggccgca acgctacgga    240
acatgaacca gctccgggca gaggagcggt tctgcgacgt gaccattgtg gccgacagcc    300
tcaagtttcg aggccacaag gtcatcttgg ccgcctgctc accccttcctg cgggaccagt    360 tcctgctgaa ccccagctcg gagctgcagg tctccctgat gcacagtgca cgcatcgtgg    420
ccgacttgct cctctcctgc tacacggggcg ccttggaatt cgctgttagg gacatcgtca    480
actaccttac agccgcctcc tacctgcaga tggagcacgt ggtggagaaa tgccggaatg    540
ccctcagcca gttcattgag cccaaaatag gcctcaaaga ggatggggtc agtgaggcta    600
```

| | |
|---|---|
| gccttgtgag cagcatcagc gccaccaagt ccctcctccc tccagccagg accccaaagc | 660 |
| cagccccgaa gcccccaccc ccacctcctc taccccctcc actcctgcgg ccagtgaagc | 720 |
| tggagttccc actggatgaa gacttggagc tgaaagccga ggaagaggat gaggatgagg | 780 |
| atgaggacgt gtctgacatc tgcatcgtca aggtggagtc ggccctggag gtggcacacc | 840 |
| ggctcaaacc ccctggaggc ctgggagggg gtctgggcat tggaggctcc gtgggtggcc | 900 |
| accttgggga gctggcccag agcagcgttc ccccagcac tgtagcccca ccgcagggtg | 960 |
| tggtgaaggc ctgctatagc ctgtcggaag atgcagaagg ggagggcctg ctgttgattc | 1020 |
| ccggaggccg ggccagcgtg ggggccacct cgggcctggt ggaagcagca gcggtggcca | 1080 |
| tggctgcccg gggggcgggg ggcagcctgg gggcggggggg cagccgggga cccctgcctg | 1140 |
| ggggcttctc agtggaaaac cccttaaaga acatcaagtg caccaagtgc ccggaagtgt | 1200 |
| tccagggcgt ggagaagctg gtcttccaca tgcgggcgca gcacttcatc ttcatgtgcc | 1260 |
| ctcgctgtgg caagcagttc aaccacagca gcaacctcaa ccgccacatg aacgtgcatc | 1320 |
| gtggtgtcaa gtcacactcg tgcggcatct gcggcaagtg cttcacacag aagtccaccc | 1380 |
| ttcacgacca cctcaacctg cactcgggag cgcggcccta ccgctgctcc tactgcgacg | 1440 |
| tgcgcttcgc ccacaagcct gccattaggc ggcacctcaa ggagcaacac ggcaagacca | 1500 |
| cggccgagaa cgtgctggag gccagtgtgg ccgagattaa cgtcctcatc cgctagccgc | 1560 |
| gcaggcgtgg aggccaggag gctggggccc ctgggctgcg tggaaaaagg gctctttggc | 1620 |
| ccaggagaat tggggggtgg ggggtctggg gcagaaaggt aagagtggga ggctgagcag | 1680 |
| atgcacacat cctgagagag ggaagatgat tccttggaga gacttgctct tgagagtgca | 1740 |
| agaatctgga gctgggaaaa gggttcttgg aggccagggg aatacgggt cccagagaaa | 1800 |
| gatttccttc tcttagaagt gcatgtatat gtggagggag ggaaaagggt cctatagaat | 1860 |
| gaggg | 1865 |

<210> SEQ ID NO 81
<211> LENGTH: 967
<212> TYPE: DNA
<213> ORGANISM: Homo sapiens

<400> SEQUENCE: 81

| | |
|---|---|
| tttcttgaaa gaggcattta ccgagcgccc aatgtatgcc tggcactggg ctgggtgctg | 60 |
| ccacctaagc gagcacgacc aatgcagtct atcagggagg cccagatcgc caagcagcgg | 120 |
| accccctgcgt tccgccatgc cactcccggc tcctagagcg ccgctcagca caccgtgagc | 180 |
| gcccaataac tgttgggctt caatgacgcc gcggaggcgg ccccgtcccc gcgctcccgc | 240 |
| ccctcccgcc agggcagccc gggaggccag acgttgacgc tgcagggaga gggtggtggg | 300 |
| cgcagccgct aggggggcgcg gcggggcgga gcgcacctt ccgcgggccg cggggatggc | 360 |
| ggcgcagggc gtagggcctg gccgggggtc ggcggcgccc ccggggctgg aggcggcccg | 420 |
| gcagaagctg gcgctgcggc ggaagaaggt gctgagcacc gaggagatgg agctgtacga | 480 |
| gctggcgcag gcggcggggcg gcgctatcga ccccgacgtg ttcaagatcc tggtggacct | 540 |
| gctgaagctg aacgtggccc cctcgccgt cttccagatg ctcaagtcca tgtgtgccgg | 600 |
| gcagaggcta gcgagcgagc cccaggaccc tgcggccgtg tctctgccca cgtcgagcgt | 660 |
| gcccgagacc cgagggagaa acaaaggcag cgctgccctc gggggagcat ggccctggc | 720 |
| ggaacgcagc agccgcgaag gatccagcca gaggatgcca cgccagccca gcgctaccag | 780 |

| | |
|---|---:|
| gctgcccaag ggggcgggc ctgggaagag ccctacacgg ggcagcacct aggatggggc | 840 |
| agagacttgt tgcatctttg tccccagcaa aggctacatg ttacctcctt caattgataa | 900 |
| taaacctttc tgagatgcag agggtccagg tcaaaaaaaa aaaaaaaaaa aaaaaaaaa | 960 |
| aaaaaaa | 967 |

<210> SEQ ID NO 82
<211> LENGTH: 978
<212> TYPE: DNA
<213> ORGANISM: Homo sapiens

<400> SEQUENCE: 82

| | |
|---|---:|
| atgttccttc ccaatgacac ccagtttcac ccctcctcct tcctgttgct ggggatccca | 60 |
| ggactagaaa cacttcacat ctggatcggc tttcccttct gtgctgtgta catgatcgca | 120 |
| ctcataggga acttcactat tctacttgtg atcaagactg acagcagcct acaccagccc | 180 |
| atgttctact tcctggccat gttggccacc actgatgtgg gtctctcaac agctaccatc | 240 |
| cctaagatgc ttggaatctt ctggatcaac ctcagaggga tcatctttga agcctgcctc | 300 |
| acccagatgt tttttatcca caacttcaca cttatggagt cagcagtcct tgtggcaatg | 360 |
| gcttatgaca gctatgtggc catctgcaat ccactccaat atagcgccat cctcaccaac | 420 |
| aaggttgttt ctgtgattgg tcttggtgtg tttgtgaggg ctttaatttt cgtcattccc | 480 |
| tctatacttc ttatattgcg gttgcccttc tgtgggaatc atgtaattcc ccacacctac | 540 |
| tgtgagcaca tgggtcttgc tcatctatct tgtgccagca tcaaaatcaa tattatttat | 600 |
| ggtttatgtg ccatttgtaa tctagtgttt gacatcacag tcattgccct ttcttatgtg | 660 |
| catattcttt gtgctgtttt ccgtcttcct actcatgaag cccgactcaa gtccctcagc | 720 |
| acatgtggtt cacatgtgtg tgtaatcctt gccttctata caccagccct cttttccttt | 780 |
| atgactcatc gctttggccg aaatgtgccc cgctatatcc atatactcct agccaatctc | 840 |
| tatgttgtgg tgccaccaat gctcaatcct gtcatatatg gagtcagaac caagcagatc | 900 |
| tataaatgtg tgaagaaaat attattgcag gaacaaggaa tggaaaagga agagtaccta | 960 |
| atacatacga ggttctga | 978 |

<210> SEQ ID NO 83
<211> LENGTH: 11868
<212> TYPE: DNA
<213> ORGANISM: Homo sapiens

<400> SEQUENCE: 83

| | |
|---|---:|
| agtctggctg gagctggacc ggctggtggc gccaggcagt gccaagcacc cctggcagcc | 60 |
| ctgcagaggg ttctcaaatc cagatttcat tctgcagtcc cggcagtgtt ttgacgactg | 120 |
| cctcactaaa ggaagctaaa agctgtgctg atgcctccca gacgagcctc gttggaagca | 180 |
| cagaaccttc acggctcgga gccgctgaca ccgtgacaaa gggagccctg ctcaggagaa | 240 |
| agagcaaatg agaggcagtt gcacttttc aggtgtcagg ctgaggaag ccacttgaag | 300 |
| atgaatctac ctctgcctta ggattgcctg atggcctgtg ccattccatg ttatatctac | 360 |
| tgatttgctc cctgtattca aagatttttt tttttactt aattctctct tactgaccct | 420 |
| gagagtgacc atatttttaa ccaatttggt cttcagcctc aaaacttagc tctttccttt | 480 |
| tgtggtcccc gaatcctatc acgtgtcatg gtggctgtga agatgtttgc caagcctgct | 540 |
| gagaaggctc atctgtggca tccaaaagca gagatttcaa ctctggaccc ctgtgacctg | 600 |
| cctttgtaat tatggatacc cagcactgtt ttgaaatatc agtggacatc cagttttaa | 660 |

```
aagccctcag agctttggga gacacccctt tatctctctg gcatgtcaga gaaccgattc    720
aacccttctc atctcctcct ccttccctct cttgggccat caggatgcgg cagcaactca    780
ctgtgcatgt ttttacagct cttctccagt aatgctgcca tttccactgc agaccacagg    840
ataaaaggac cgcttcaccg tggcccagga tacccttttta agtaggaggt aactattcag    900
tttcgtagtg gcccatacat aaacttgatt atgttcttcg ttgctccaat atactatttg    960
tgtgttttgt ttttccaga gggagaagaa agtactgctt tgatctaaaa ttaagcaaac    1020
gttcttcaat aaacccacca tgagacttga ccactaatgg tgaccagcag tggctttgtc    1080
atggccctgc ccactggggg caggcacatg ccggggccag ggcaggctgc cagctggtga    1140
gcacgaatag gtggctggtg gagcgcatgc agtgggaagg gcagatggct ccattttgat    1200
ttgttagcag gccacttcct cggaaggggc tttcccttca gtggggtctg caccgccagc    1260
ctcagctgtc ttggagcaga tgtgtatagt tagagatggg gaccttttca ctgtaaatac    1320
tgctcacatg ttcctaggct gactttacta tgtgcagagc ctcttctcaa atatccaaat    1380
cccctctgtt gggtactaca gaacagatgt taccctgcct cctattacat taatttacga    1440
actttacata tgctgagtta cggaccctaa gctgttgcat gtgcttggct cttatgttcc    1500
aaaaagtaca tttgtatggt tttgtggaaa ctgtgctgtt ctgcttttgc agtctgtgag    1560
attctgattt tttttttctc atcagcaatt atccttgtct tggaacatca gagcttgaag    1620
aaagggattc tagcagccca cctctctcct tcctaatcca gatggttaga ggcttagaga    1680
gaggtggtgg ttgctctgag tttaccagat tcagtgacaa accccttcta atttctaatc    1740
aatctggcag ccttcattta ccaaaagttg acttttgata gtataacttt tatacaccgt    1800
gagacaactt atttttaaaaa acagtttaga aatatttaat ttttttttga aagacttttt    1860
aaggtcaggc accatgggtc atgcctatca tctcaacgct ttgaggactg aagtgggagg    1920
atcatttgag gccaagattt caagatcagc ttgggcaaca tagtgagact ctgtctctaa    1980
aaaattaaaa aaaaaaatag ccaggtgtgg tggcgcatgc ctgtagtccc agctacttcg    2040
gaggctgaag tgggaggatc cattgagcct aagagatggc gattgagtaa gccatgattg    2100
caccactgca ctccagcctg gacgacagag atgtcagaaa aaaattagtt ttattattat    2160
tagtttataa taatattatt ttaatattaa tattatttaa taatttcata ttatttatta    2220
ttattagttt tattattagc aaaactgagt ggaaggcaca gagattttcc atattcttcc    2280
tgcctctcca acaaacatgt ctccctcatt atcaacattt cttcccagag tggtacactt    2340
tttataattg atgatcctac actgacacat catcatcaca atgagttcat agttgacgcc    2400
agggttcact cttggtgttg tacattccag gcatttggac aaatgtataa tgacatgact    2460
ccaccatttt agtatcatac agacgagttt cactgcccta aaatcctctg tgctccactg    2520
atacttactc cttcatcccc ttgctccctc agcccctgac aaccactgat cttttttattg    2580 tctccatagt ttggtcttat ttaatatttt ttgaggttgc actgttgccc caggacatcg    2640
tatgagtaga gggttaacca ccttagccaa gagtaaatttg gtctggtgag ttctccacct    2700
tcaggacaaa agcatttcag aaccatccta acaatagtgt tcccataagt aaccagacac    2760
tgtttgtatc catagcaaca tggctccatg agccctgctt ccgaggagca gctgccctc    2820 ctgggcactg tcaagagttg ttcttctctg acatccacac ccttctttac ctggcacata    2880
ccccagccca ggaccaggc atccagggcc ttctatggct gtccggatgc attccttcac    2940
agctggaatg tggttggctt gttgacttct gttcccagca tagtgaacag tgggcactat    3000
```

```
aagccagtag gcactcaatt gatgattctt caatgaaata attgatgcca cttttaggtc   3060
agtctttctt gtacgttaca ccttctgttg ttcaacagag ccccacaata tcccagaact   3120
tggaggtctt atctcggggt ttctcagatg ttggagtacc caggtatcac ctgctgagcc   3180
agtttccctg gcctcacctg caggggctct gagtcagtaa atctgggca ggcccagtac    3240 tttgcatgtg agcacagacc caggtgtttc tgaacctggt ggtccaggga ctgctgcagg   3300
aaggagccaa taggactgca tgccttagag gcagtgggtc tcatccatcc ctatctatgg   3360
cactgactac aggccatgtc caggccacat gggcacatgc tattataatt attttgtgtg   3420
atggatgagt tacagaactg gagccctaag acctgagttc tagtttcagc tctgccagtt   3480
gctggctgat tgaaactgaa caagccacct gccttccctg agactgtctc ttctcctgtg   3540
aaattagggc attagaatac atgaagaccc ctttatgtcc ttaataacct gtaagtttaa   3600
gaacctaggg aatctccatg ctggtggctg cggttatatc cccttatcct caactcgtga   3660
agaaagagtc aaaatggca gcagggttgt gtcaactgct ctcctcagca gctatcataa    3720
gggaattgcc tttgtcattt tccccagcca tcaccacact cccacacggc caccatcacc   3780
taaaccatct ggcagtgggg gttacctcct aaatctaaga cgcagagacc caccgcaggc   3840 cttttctttct ggctgccctc cactcccacc cagaggctca gttttgctgg gctgcacacc  3900
tccgaggact cagttctttg tgtttcatgt tgtttcatat ccactagtgt tacagaaact   3960
gctgcaaacc agggaccaaa agtccatagg ttctaattct agctgtgaca ctagtgagat   4020
gagtgactgc tggcaagtta ctttatctat ctgacctcac ctcccatgta caaaattggg   4080
tctgtatgca catttgtggt tctaaatcct ggagtccaaa tcagagttct ttgtgcaaaa   4140
tatacgtagc taggtcctaa cctcggagat cctgactcag tctggggaaa ggcgcagatc   4200
ttggggagaa acaactctc tagaagagtc tcgccttcag tgagtgacaa gatctctcct    4260
gtctctcggt tcacaatgtt accctaacta atccatcctc tgatgtcacc tgctaacaac   4320 ttccctgtg gcatcaaacc agtagcccat ttgcagctag tacaaacact tctttacatt    4380
taagttttgt ttacgagatt tagcctacaa tcatagaggc tgccagctgg gtttcaaatg   4440
tgtatgttcc attgctaata ggaaaaactg catctattag aaaaattctc tctgggagct   4500
gagcacagag gcaggccttg tattgcaaac atttgaaaag ccataagcag gtattctgga   4560
ctgtgtttta gatcacctga gaacatttct tgaacactag tatttgctta gagtgacaaa   4620
cctattaagt ggttctttca ggtaagtttg catccaagca atgtcgtctg aatcgcagga   4680
ggaagtcagg agttgtgtct ggcttttctgg ccatacaaat ggcatatggg aaagtcattg   4740
tatattatta atatcctttg atgtatatta ttatgacttt ctcacggtag taatgttgtt   4800 ggttttatt aatgttattt ttatagcaat gctaatatta tgagctaaaa gtttctgagc    4860
atctgctggg tgccaaaaat tcttataaat gctttacatg cattagctcc taacaacact   4920
ttgaagtaat tcttattgtc cttacttgac atatacagga ataaaaacct gaccattaga   4980
ccgagcgtgg tggctcacgc ctgtaatccc aacactttgg gaggccgagg caggcggatc   5040
acctgaggtc aggagtttga ccagcctg gccaccatgg tgagacccg tctctactaa      5100 aaacacacaa aaaattagcc gggcgtggtg gtgggtactt gtaatctcag ctacccggga   5160
ggctaatgca ggagaatcgc ttgaacccag gaggcggagg ttgcagtgag ccaagattgc   5220
gccattgcac tccagcctgg gcaacaagag caaaactctt tcaaataaac aaacaaaacc   5280
taagcatttg aggggtttgg cctgggcagt ggagcttgtg agctatatga gctggaatct   5340
gagtcaaggc tgggctggtg aaaggagttc actcaagttc ccaaggtatt ctgtcctcca   5400
```

```
ggactctgaa tcacctggga ggagaaggaa ttgtggcggg cctaacacct tttctttccc    5460
aaacaccaag agcaggttct ttctgttaca tccattgagg tcacattctt gaagtgcatt    5520
ttgaggaagt cattattttc gctacagcag ggactgatgt atcagtctat tagaattcag    5580
aaaaaagtaa gcaaacaaaa aacgtgttgg aattattctc ttctagcatt ttgaaatgta    5640
caatggttaa tgttaactat agccaccatg atgtattgaa gaccaggtct tattctttt    5700
atctaactgt acatttgtac ccattaacct aatgctcata gcatcaagaa aagatcaata    5760
tttaaggtga caaatatccc aattatgctg atttgattat atgaatgtgt tgaattatca    5820
tatgtactcc caaaatatgc acatctaaga tgtatcaata aaaataaaga caaaaattaa    5880
agcttttaca gtagaaaaaa ggttttagag aaattatgat tacttgattc acctaaactg    5940
acagtcttgc ttggaatgaa ttactgcttt ttgtaacata gttttagaag agagattcac    6000
atttaatgtt actttgtgct aagcactgta atccatgcct gggtgctcac agcgctcctc    6060
tgggaccagg catcaccatc tcctctgtaa aaggaaggtc agcctgttgc caagaccaca    6120
ggataaacgg cttggctgat ttaggaaacc cagttggtct tatgacaaaa catgcgcatt    6180
tgcccttcac caggtgattt ttctgtaggg ttatcttcaa cagtccgaca aagctgtgtt    6240
ccaccagctc aggcaggctg tgaccaggat caccagccat gtggcatcag gaagaagggg    6300
ctgtgtggcc aggctcaatc tctggtcctg cagccttctg cctttggctt tctgaagcga    6360
gctgaactag agattgggcc cagctcggca gcgcagtttc aggagagcca ggatacaaac    6420
catcccagtc tctgttccca caaggagaaa gctaaaccat ttttatttg cccattctaa    6480
gtgctaagtg atatgcaact gcttcacata agccttccag ccttccagcc gactctgctt    6540
tcaggagata tccttatgtc ccttttgcat ggcttaggag agtgaagcac gtgagaattg    6600
aacgaggggt caagggtcac ataacacatg agcacgaaac cgggactctc ctggggtatc    6660
agacccaaa gccagtggtc tgcgcttgat cttgctaac gtccgagaag caataagtcc    6720
agggctcttg acacattatt gtgcatttta ctttgggagg gactgtgggt ccactctgct    6780
tttaacagga ggaaattaaa tatttacatt tgattccagt ttggccccat gactgtccgg    6840
cttctttcct gtcaaaggcc caaattccct gttttaaagt agagggtgaa tttgtgtaat    6900
gaggatggat cgggcacgtg tagaacacac tctttcacct gcagattcac actccaaaca    6960
caaagaaata ctgatcata tatggtatat tttaaaagat gccataggca tacttaaaaaa    7020
gcacaacaga attctatttt ctcacgtcag agggcagagt cttatgagct attgagagga    7080
aaactgtatc ttagggggttg agagcctaac gtctgcttgg gggtgtttgt ggccctggca    7140
gctgttgtgt gcagtgcaca ttagaactga gcagctttat aaagccagga acaagggtag    7200
agtccctgtg tctctgaata gaaattagcg atgcttagcc ttctgtacca aggaatgcat    7260
cacaaaagct aatgctggga ctgggcctgg tgtgggatag gagtcacaca gaggagtcag    7320
aacgccaact gtggctggtg taaggggcct ccattcacac tgtctttgct gtttggaaaa    7380
tctgagcaag aatttaaggt aaaagctgat gtggaacagc ttgcaaccca aaagtctcaa    7440
gcccagcata aaaatcattg ctccagtgaa gatgcctgca gagctcaagg catttctgag    7500
actccatggg agaatgattc ctaaggaagg tgtgcccca gcacctgtgg agactcatca    7560
ccttgagggc aaacagactc tgtaaaagga gaattcacct ctaaggagct gcagacaata    7620
gagggattaa aatgggcctt tgatcattca aaaagcattt taaggaaaaa aataaagtaa    7680
cataatccaa attccaacag gagacttgaa aaagaaggta ataacaaaat ggaaaataaa    7740
```

```
gtcactgaaa taaagcaagt gagttggact atgaatgtct cctgtccatt agctgtgtcc    7800
ccggctgcaa ggtccatggg gactgtgcct cccttgacct tgaatctcaa tgccttagca    7860
aagtgcctgg ttctgggtag gttcacagta cacatgtacc tcccaaatgg atggattgcc    7920
aacttaaatg ttcataggaa ggtgctattt tcaggcactt caggtgtgga catcggtgtt    7980
gtcagatctt ttctgttcta gccaggcatt gtggacatca ccttactatg tgagggaaca    8040
agctgcattg gtggagagga aaccagcagg agcacaatag tgacccattt ctcttgtctt    8100
atgcactgca gtggaaatag cccagtgtgc atggtggatt ttattatggt gccagtagaa    8160
agataggggg tttcctctat gagctggctg acttacatga gctcattctc tgcagcattt    8220
ctctagccat ctcctgtcac atcgtttatt gtgttcacta gtcctgtgct aacgaggatc    8280
tttgaaaaat gactggtatg gtaatgatct acggaactta ctgtagatag caattaaata    8340
tcgttaacgg cgggttacgc tgacacatta aaaggcctac aggctgcgat ttatgaagac    8400
agctctgctg cctcctttgt atgtgatgca tttctctggt ttcggcttag gctgtctggt    8460
ctcagaaggg aatgatttcc aggctttccc catcatcact ccagttgcca ggccacccac    8520
aatcacatta gcaagcttta ttgtccctat tgcacctcct aatgccctca gggtgcttga    8580
ggtagctttt atcaaggtaa ggcctaggtc aacattttgt tgtgcagaaa aggcatctgc    8640
tttcagagga gaaatttag atacaatatt gaggtgaatc ttataagtga tgtaagataa    8700
tttgatgaca agaattgaga ttatatgctg agatcttact gtcttaaact ttgttgattt    8760
ctgaaaataa tagaaatgca atcctagcta aggaagaga agtagtctag ctcaccagtg    8820
gccagcaaac tctgtaaaga agtattgcct tcatgcagca atctcaccta atatgagact    8880
ccagatagaa gatagctcct gagaagtcaa acacaaacc aatatcatgt aaattactct    8940
cacgtgaaaa atagacaaga gataaccaac ccagtcccaa ccgtctcaca cccccactgg    9000
cctcctgcac tcatggatgc cacattcttc aacatttgta cttctgttaa cagagttaaa    9060
gtagagcaaa cataggctct tttaccaaga gcgtatggac taaatacaga tgcaatgcta    9120
ataaccacat gggaaaaaca agatcctgag acactgttat gttttctcc ctcttttgtg    9180 gccaagagtg tgtgctctct tgcctttgta gattttgctc acgtttttgg gtgataggac    9240
caaaagcagt agtgtctagg ccactaggag acaaggcaaa ccattatctg tgaaagcctg    9300
ggttttctga gaggaagcat gctggacact gccagtagag ggagaagtca tggtgtgaag    9360
ttttccatga tgagagataa ggacagctag gcatgggga tgcagaggat gttcttgttg    9420
ttgatggtgt tgtggaggtt gtaccccaag tctctgggat aagacagccc catgcacata    9480
gaggtcatga aaaatgtgag gaccctggac actgagtgtc acggctttgg ggacagtgat    9540
gacatgtccc tgtgtccaaa cagctcagtc agcttatcta aagggatgg agagtacttc    9600 tgtgggaaca gttggagctg aagaacagag aacatttcct ttgatgtttg gactctacgg    9660
aatctttggg aattgtgttc aagtccagga ggaatggctg aaaacatgat tgagataaat    9720
ttgcagccag gaggttgaag acaaattagg atctgatttt attcaactgg gagtaaccat    9780
ggccaagcat aattcttctg gtggattctg aagttatttg gaatttgccc ataagatgaa    9840
ttttcctgaa gaaggaagga tgtggaggct gatactgagg ccccatttcc acatgtgaac    9900
ttctaagaaa ccacagcttt catccagagt ggagatgaat ggcactgggg tccacgttgc    9960
cagaatgcct ggggacaagg aatgaggact tgtcacccaa ggcacgagat ccatagtggc    10020
tacgggaatg aagccactgc ctttgtggaa atgactaatt cacccaaatc caaggtgttt    10080
tccacaactg agaggcctgg gctgaggata gagatttgag ccttaactga gacatcctac    10140
```

```
tgggaagttg catcagtggt cagtatctga ggccacagaa aatgtcacat gatggtgtgt    10200
cacagggctc cacatttagg acatttgtgt actcaaagag aatctttgac gaccatgact    10260
cagagaaatt tttaatgact taaaacaggt tttggatcat gttgatgatg acagatggtg    10320
caagccacct acctaaatcc ctctggggag gggtggtatt tctgcattgt tctcagagca    10380
gaaatgtgac atggatgtgg aggctctgga cagtgagatg tgaagctgga ggcatggctt    10440
ggcctcccta gaatgggtgt ggccagggca agctgggac atcctcaacc caaaggtttg     10500
cataactgga tttgaactcc ttatagatat tcctaaacag tggtgatacg aagggagag     10560 gaggaggaaa aaaggatggc tcttcatcaa gagcaaaagc aagagattca gataggagat    10620
ttcacttggc ttttctagtc ttgggtgggg acccattatg gaagtgaaga gctctggaat    10680
cttccagaga acaagcatg ggtatccttt aacaggtccc agatagccag ttaccgcaga     10740
acaatgtcct gttaccagaa gcttattgca gaccttgtaa cctgaatcat tgtgttggcc    10800
cagggcacac ccaggagggt ggcttgggaa ggagattcca ggctgaggta aataccgaca    10860
tctgatttcc tgacattgag taggaaagca tttcagagac aagctccaag agctttggaa    10920 agggaacat tcacccactt cccacaattt ataaggggggc tggcagtggt tgttttgggg    10980
aggataataa tgggaaaaga gaacgggggta tgttatggca cacagaacca aaaatgaaga    11040
ttcctaagta gtaatctatt agtgagggaa ttcttgggca atttcaaaaa actcaaaacg    11100
tgttacagag aggagcccct tggactttgt aggagactcg tttgtctatc tggccccaag    11160
gcccagaagt agctgacaaa gagacccagt tgtcccctgg atgccaaact tggggagaga    11220
atggtcctgg gtggcagccc ctccccatcc agcctcagtc agagctctcc agcaagtcag    11280
cctgcaggta gctatggagt tgcagtgtag tcctgttatt aatggctttc tgctttggct    11340
ggatttcaga cataaagaag agaagaagga aaggtctggg tgatctgcct cttctgataa    11400
cactaaagtt gcacacatca cctcagctca tatttgatgg gctgggactt agtcactaag    11460
ccacacccat ctgcaaaagt gctggaaagc gttgcactct ctgatgacca catgcccagc    11520
taaatattga ggtcatatat tcctatataa taagacataa gcaaagtgca gtcactgaga    11580
atcactagca gtttacacca cgagtatctt cacagcccag aaaagacact gggttgagtt    11640
aaaatgaaaa ctggaataaa tacaatgaga agatagaaag cctgctgaga acactggggt    11700
acttgagtgg aactttaaac agtgtctttg ctaatgtgta tggtaactgt tcagattgtc    11760 tgtttctttta agctaattgt tttctgattg ttgaagcaat aataactcat atcttgcttg    11820
agaaaaaatt aaaaagtatg aaaaatcaaa tataattatc acactacc                11868
```

<210> SEQ ID NO 84
<211> LENGTH: 3275
<212> TYPE: DNA
<213> ORGANISM: Homo sapiens

<400> SEQUENCE: 84

```
gggccgcacg ccgccaccca gcagccaggg ccgcctctta aagggaggtg gccggcctta        60
aaggaccccc gcgcgcccag ccggcgggag cgcggcggcc cggctcccgc agggccgcgc       120
cgaggcaggc gagcccccgc ggcgcccagg cgcgggcccg ggcccccgcc gccgccgccg       180
ccgccgggcg cggcattttt attcaggcga cgcttaaggg agcccggccg cgcccggtgc       240
attgtgggag cggcccgcgg cccgtttttcg ggaggaggcg gagggcgcaa agcgagccgg       300
tggatccata aagaacccag ccaacccgca gagggagggg aggggctgag ctgtgaggag       360
```

```
agcggggccc aagaaccatg tctacgcggg agtcctttaa cccggaaagt tacgaattgg    420
acaaaagctt ccggctaacc agattcactg aactgaaggg cacaggctgc aaagtgcccc    480
aagatgtcct gcaaaaattg ctggaatctt tacaggagaa ccacttccaa gaagatgagc    540
agtttctggg agccgttatg ccaaggcttg cattggaat ggatacttgt gtcattcctt    600
tgaggcacgg tgggctttcc ttggttcaaa ccacagatta catttacccg atcgtagacg    660
acccttacat gatgggcagg atagcgtgtg ccaatgtcct cagtgacctc tatgcaatgg    720
gggtcacgga atgtgacaat atgctgatgc tccttggagt cagtaataaa atgaccgaca    780
gggaaaggga taaagtgatg cctctgatta tccaaggttt taaagacgca gctgaggaag    840
caggaacatc tgtaacaggc ggccaaacag tactaaaccc ctggattgtc ctgggaggag    900
tggctaccac tgtctgccaa cccaatgaat ttatcatgcc agacaatgca gtgccagggg    960
acgtgctggt gctgacaaaa cccctgggga cacaggtggc agtggctgtg caccagtggc   1020
tggatatccc tgagaaatgg aataagatta aactagtggt cacccaagaa gatgtagagc   1080
tggcctacca ggaggcgatg atgaacatgg cgaggctcaa caggacagct gcaggactca   1140
tgcacacgtt caatgcccac gccgccactg acatcacggg cttcgggatt ttgggccatg   1200
cgcagaacct ggccaagcag cagaggaacg aggtgtcgtt tgtaattcac aacctcccgg   1260
tgctggccaa gatggctgcg gtgagcaagg cctgcggaaa catgttcggc ctcatgcacg   1320
ggacctgccc ggagacttca ggcggccttc tgatctgttt accacgtgag caagcagctc   1380
ggttctgtgc agagataaag tcccccaaat atggtgaagg ccaccaagca tggattattg   1440
ggattgtaga gaagggcaac cgcacagcca gaatcataga caaacccgg atcatcgagg    1500
tcgcaccaca agtggccact caaaatgtga atcccacacc cggggccacc tcttaatcta   1560
gacagaaata gctgtttggt tttgttttta aatagatcta tttcccttat cacttcaatt   1620
aaagactata acaacaaaa atctcattgt gtctacacat cggggtgacc ttaggtcggt    1680
ttgtaagtgg atacaattaa taaaataaaa tccattgcct ttttttcctg ttacattaac   1740
tgaagatgca cctaatcttg aggcagcttc tgagttgaga attatattgt tatccaatac   1800
tgttgattca ttttgaatct ttagacactt atctcttgcc gcataggctt tttaaaggtg   1860
ctttcacata gcacaggcat tacccgtagt cgtgtcaaat agcagttggt gtcttcattt   1920
tatgtatatt tatcatataa gtctgatttt tttttttaag cgtcttgaat ggttttctgg   1980
agagacagca ttggtaagtg gcacatgacg gtatcccagt cataagaggg ttgcatgatt   2040
cctttgagtg tttgatttga aaagcctagt cttgtctctc aagagcatct cggacccaga   2100
acattctcca gtagtgcatt cagttcaaca cagcaagtgc ttcattgcat ggaaaacact   2160
ttgaagacaa aaaagaaatc ttatttcttt ttttgtagcc ttcctgatat ttacagtaat   2220
accattaact gttttatcga tagcaaaaaa ggatacttt tgcaatgtta ttagatgttc    2280
tatagtgcta caaggaattg ccttccgaat ggaggttcat gtataatact catttacaat   2340
tcaatatata attacacaaa taatttttaa atataatcaa tagtaaagac tgttctgtgg   2400
atggtagtgt ttaatacatt ttctattttg tacagtgatt tcaggccttt tgtttctta    2460
aaatcagcag ctgtttggcc taattcttag cattattttg tcctttgcgc cagtactttt   2520
ttgtgcacgc ttttttgtgat ctgtgttaaa aacctgcatt gccaacattg cagctcgaac   2580
ttaaacttgt tattcaaata aatatttaat tttttaaatt gctcttgtat aatcagatgc   2640
ccctttagt attattttag aagcgttggg aggtttttgc ctaaagtaca atttatcggg    2700
aaaaactaga ttttagtttt ataaaacttt taagtctttc atgggaccta tatttcttg    2760
```

```
aattaaattt tgtagttcta gaataaatag gcaatctaaa aaggtgttct ctgtgttatg      2820
taaagtggag gcttccttat attttaacct actaagcaat gaggagggat tcctgtcatt      2880
aagcacaagg gcgctggatc ctcaagtgcc catcttcgtg agagaaaaag cagcacatcc      2940
tgcccatttc tggtgctttc tgctcacagg caccaaagct gcacatgtaa actgacttct      3000
tgccaaagga aatgacccct gggaagttca agctcctgga agaggcttta actcggacgc      3060
gccctcctcc aggaaccagt gggcagggca gccttcatgc atgtgtaact ggacctccag      3120
ccataagcat ggtgtgcagt atggaagagc ctgctacgga actgaaagtg attggacatt      3180
ttataggaat tgatagagat gttggtcctc aaaagctaca aaccagtggt ctgcaaaata      3240
aagtgtgttg gaaacctcta aaaaaaaaaa aaaaa                                3275

<210> SEQ ID NO 85
<211> LENGTH: 1179
<212> TYPE: DNA
<213> ORGANISM: Homo sapiens

<400> SEQUENCE: 85
ccagtgttcc cagttcccac cagtccaact gcgaggagtg cgacgtgagt ctgagtctga        60
tccctccgaa aaccgtactt ccggcgctgt ctcggaggcc tcccgtcccc tcccttgtcc       120
gtcttctaac tcttccccac gccaggtccg tcaagcctaa gtccttgagt tccgggtccg       180
ggcagcagag aaaggaagtc ctctccctgg aggcctatct ccctcagaac tgcgcgagaa       240
gcgagacctt agaaggcagg gcttcccgcg aaggaccgga aaggagcgcc tactaaggac       300
gccgtcgagg tccggggcgc ctcaactcta tagctctaac tggctagaag tgcccaacgt       360
ggaatgtttc ttttttaaag gcggctcttg aagcgacccg gaagcggaag tggaagaaag       420
ttctagtggc ttgaggtatc cgcaggagcg gccgggtggc gggaggaacc gttacgggaa       480
ctgaagttgc ggattaagcc tgatcaagat gacaacctcc caaaagcacc gagacttcgt       540
ggcagagccc atgggggaga agccagtggg gagcctggct gggattggtg aagtcctggg       600
caagaagctg gaggaagggg gttttgacaa ggccctatgt tgtccttggcc agtttctggt       660 gctaaagaaa gatgaagacc tcttccggga atggctgaaa gacacttgtg gcgccaacgc       720
caagcagtcc cgggactgct tcggatgcct tcgagagtgg tgcgacgcct tcttgtgatg       780
ctctctggga agctctcaat ccccagccct catccagagt ttgcagccga gtagggactc       840
ctcccctgtc ctctacgaag gaaaagattg ctattgtcgt actcacctcc gacgtactcc       900
ggggtctttt gggagttttc tcccctaacc atttcaactt tttttttggat tctcgctctt       960 gcatgcctcc cccgtccttt ttcccttgcc agttccctgg tgacagttac cagctttcct      1020
gaatggattc ccgccccat ccctcacccc caccctcact ttcaatccgt ttgataccat      1080
ttggctcctt ttttggcaga acagtcactg tccttgtaaa gttttttaga tcaataaagt      1140
cagtggcttt caaaaaaaaa aaaaaaaaa aaaaaaaa                              1179

<210> SEQ ID NO 86
<211> LENGTH: 1651
<212> TYPE: DNA
<213> ORGANISM: Homo sapiens

<400> SEQUENCE: 86
acgactgcgt gggtgagtcg tctataaaaa ctcatctctg cgcgtctctt cgccacattc        60
gcttcctgct ttcggtgtgt ctgttgtgtc ttgttgcggg caccgcagtc gccgtgaaga       120
```

```
tggcgtctac cagccgtttg gatgctcttc caagagtcac atgtccaaac catccagatg      180
cgattttagt ggaggactac agagccggtg atatgatctg tcctgaatgt ggcttggttg      240
taggtgaccg ggttattgat gtgggatctg aatggcgaac tttcagcaat gacaaagcaa      300
caaaagatcc atctcgagtt ggagattctc agaatcctct tctgagtgat ggagatttgt      360
ctaccatgat tggcaagggc acaggagctg caagttttga cgaatttggc aattctaagt      420
accagaatcg gagaacaatg agcagttctg atcgggcaat gatgaatgca ttcaaagaaa      480
tcactaccat ggcagacaga atcaatctac ctcgaaatat agttgatcga acaaataatt      540
tattcaagca agtatatgaa cagaagagcc tgaaggaag agctaatgat gctatagctt      600
ctgcttgtct ctatattgcc tgtagacaag aaggggttcc taggacattt aaagaaatat      660
gtgccgtatc acgaatttct aagaaagaaa ttggtcggtg ttttaaactt attttgaaag      720
cgctagaaac cagtgtggat ttgattacaa ctggggactt catgtccagg ttctgttcca      780
acctttgtct tcctaaacaa gtacagatgg cagctacaca tatagcccgt aaagctgtgg      840
aattggactt ggttcctggg aggagcccca tctctgtggc agcggcagct atttacatgg      900
cctcacaggc atcagctgaa agaggaccc aaaaagaaat tggagatatt gctggtgttg      960
ctgatgttac aatcagacag tcctatagac tgatctatcc tcgagcccca gatctgtttc     1020
ctacagactt caaatttgac accccagtgg acaaactacc acagctataa attgaggcag     1080
ctaacgtcaa attcttgaat acaaaacttt gcctgttgta catagcctat acaaaatgct     1140
gggttgagcc tttcatgagg aaaaacaaaa gacatggtac gcattccagg gctgaatact     1200
attgcttggc attctgtatg tatatactag tgaaacatat ttaatgattt aaatttctta     1260
tcaaatttct tttgtagcaa tctaggaaac tgtattttgg aagatatttg aaattatgta     1320
attcttgaat aaaacatttt tcaaaactca gttttttgtt atatgttaca tgtaacttat     1380
gatacataat tacaaataat gcaaatcatt gcagctaata aagctgatag actttatttc     1440
cattacttat atatacatag ttttttattt taataaattt atggaaagag caaaagcttt     1500
tgagaaccat tgttaacatc aacatcatag tttccagttt gaaaggatgt gtatgtgaga     1560
tttattatgt atattattaa acaagaagtg atgagcttgg gccttgaaag gcaccagctt     1620
gagagacatt aaaatgttct aagtaaaaaa a                                    1651
```

<210> SEQ ID NO 87
<211> LENGTH: 3227
<212> TYPE: DNA
<213> ORGANISM: Homo sapiens

<400> SEQUENCE: 87

```
cccactctgc agttgtctcc cgagcgctgg ctgcgccgcc cgagccgctg ggccggggaa       60
gcactggccg ttcgctcccg ggccggctcc gccaggcgct cgcaggcatg cagcccggga      120
gcaggaggcg ctccccgggc cgctgctgag ccggccgggg cggcggggac cagcgccagc      180
ggagcccctc ccaccttgcc ccggggcaga cgagcggcgc cccgacaccc cctcttctcc      240
cgcagccccg ccagcgccac ccccgcggg ccgcaggggc tcatgcagcc gccaagggag       300
aggctagtgg taacaggccg agctggatgg atgggtatgg ggagagggc aggacgttca       360 gccctgggat tctggccgac cctcgccttc cttctctgca gcttcccgc agccacctcc       420 ccgtgcaaga tcctcaagtg caactctgag ttctggagcg ccacgtcggg cagccacgcc      480
ccagcctcag acgacacccc cgagttctgt gcagccttgc gcagctacgc cctgtgcacg      540
cggcggacgg cccgcacctg ccgggggtgac ctggcctacc actcggccgt ccatggcata      600
```

```
gaggacctca tgagccagca caactgctcc aaggatggcc ccacctcgca gccacgcctg    660
cgcacgctcc caccggccgg agacagccag gagcgctcgg acagcccga gatctgccat    720 tacgagaaga gctttcacaa gcactcggcc accccaact acacgcactg tggcctcttc    780
ggggacccac acctcaggac tttcaccgac cgcttccaga cctgcaaggt gcagggcgcc    840
tggccgctca tcgacaataa ttacctgaac gtgcaggtca ccaacacgcc tgtgctgccc    900
ggctcagcgg ccactgccac cagcaagctc accatcatct tcaagaactt ccaggagtgt    960
gtggaccaga aggtgtacca ggctgagatg gacgagctcc cggccgcctt cgtggatggc   1020
tctaagaacg gtggggacaa gcacgggcc aacagcctga agatcactga aaggtgtca   1080 ggccagcacg tggagatcca ggccaagtac atcggcacca ccatcgtggt gcgccaggtg   1140
ggccgctacc tgacctttgc cgtccgcatg ccagaggaag tggtcaatgc tgtggaggac   1200
tgggacagcc agggtctcta cctctgcctg cggggctgcc ccctcaacca gcagatcgac   1260
ttccaggcct tccacaccaa tgctgagggc accggtgccc gcaggctggc agccgccagc   1320
cctgcaccca cagcccccga gaccttccca tacgagacag ccgtggccaa gtgcaaggag   1380
aagctgccgg tggaggacct gtactaccag gcctgcgtct tcgacctcct caccacgggc   1440
gacgtgaact tcacactggc cgcctactac gcgttggagg atgtcaagat gctccactcc   1500
aacaaagaca aactgcacct gtatgagagg actcggacc tgccaggcag gcggctgcg   1560 gggctgcccc tggccccccg gcccctcctg ggcgccctcg tcccgctcct ggccctgctc   1620
cctgtgttct gctagacgcg tagatgtgga gggaggcgcg ggctccgtcc tctcggcttc   1680
cccatgtgtg ggctgggacc gcccacgggg tgcagatctc ctggcgtgtc caccatggcc   1740
ccgcagaacg ccagggaccg cctgctgcca agggctcagg cacggacccc tccccttcta   1800
gtgcacgtga caaggttgtg gtgactggtg ccatgatgtt tgacagtaga gctgtgtgag   1860
agggagagca gctcccctcg ccccgccct gcagtgtgaa tgtgtgaaac atcccctcag   1920
gctgaagccc cccaccccca ccagagacac actgggaacc gtcagagtca gctccttccc   1980
cctcgcaatg cactgaaagg cccggccgac tgctgctcgc cgatccgtgg ggcccctgt   2040 gcccgccaca cgcacgcaca cactcttaca cgagagcaca ctcgatcccc ctaggccagc   2100
ggggacaccc cagccacaca gggaggcatc cttgggggctt ggcccaggc agggcaaccc   2160 cggggcgctg cttggcacct tagcagactg ctggaacctt ttggcagta ggtcgtgccc   2220 gcctggtgcc ttctggcctg tggcctcccct gcccatgttc acctggctgc tgtgggtacc   2280
agtgcaggtc ccggttttca ggcacctgct cagctgcccg tctctggcct gggccctgc   2340 cccttccacc ctgtgcttag aaagtcgaag tgcttggttc taaatgtcta aacagagaag   2400
agatccttga cttctgttcc tctctctcct gcagatgcaa gagctcctgg gcaggggtgc   2460
ctgggcccca gggtgtggca ggagacccag tggatggggc cagctggcct gccctgatcc   2520
tctgcttcct cctcacaacc caagagccc cagcccgt ccatccacgt ctggagtctg   2580
gggagaggag cagggtctta ggactctcag ctctgagcat ccctggcagg gtcttcaacc   2640
tctaatctct tcccttaagc cctgtggcca cacagccagg agagacttgc cgctggctcc   2700
cgcctcattt cagcccaggg tgctcatcca ggggcccaga acagtccac ctgtgctgct   2760 gtgcccacag cacaaagcca ggcttcactc ccaaaagtgc agccaggccc tggagggtga   2820
tcctgccagc agccctacag ctccacaccc tacccaccca tcggcagccc ctctgctgtt   2880
ccccagggac ctctcatca ctggccagga ggctgcagaa cgtgtgtctc ccctccctc   2940
```

```
caagaggtcc tgctccctct gccagaaccg tgtgtgggcg ggtgggaggg cgctcggggc    3000
ccggcccctc cctctccctg ctggttttag ttggtcccta tgttggaagt aaaaagtgaa    3060
gcactttatt ttggttgtgt ttgctcacgt tctgcttgga agtggggacc cctcactgcg    3120
tccacgtgtc tgcgacctgt gtggagtgtc accgcgtgta catactgtaa attatttatt    3180
aatggctaaa tgcaagtaaa gtttggtttt tttgttattt tcttttta                 3227
```

<210> SEQ ID NO 88
<211> LENGTH: 1980
<212> TYPE: DNA
<213> ORGANISM: Homo sapiens

<400> SEQUENCE: 88

```
atttggatcc gttcagctcc cgcggagaag cgagaccgga tcaccgacgt gggcagagga      60
ctaccgaggg ccagcagaaa ttctgcccct tcttcccgcg agtgctttcc cgctctccaa     120
accccactcc caggtggcca tggcctcatc gaccactcgg ggcccaggg tttctgactt      180 attttctggg ctgccgccgg cggtcacaac tcccgccaac cagagcgcag aggcctcggc    240
gggcaacggg tcggtggctg gcgcggacgc tccagccgtc acgcccttcc agagcctgca    300
gctggtgcat cagctgaagg ggctgatcgt gctgctctac agcgtcgtgg tggtcgtggg    360
gctggtgggc aactgcctgc tggtgctggt gatcgcgcgg gtgcgccggc tgcacaacgt    420
gacgaacttc ctcatcggca acctggcctt gtccgacgtg tcatgtgca ccgcctgcgt     480 gccgctcacg ctggcctatg ccttcgagcc acgcggctgg gtgttcggcg cggcctgtg    540 ccacctggtc ttcttcctgc agccggtcac cgtctatgtg tcggtgttca cgctcaccac    600
catcgcagtg gaccgctacg tcgtgctggt gcaccgctg aggcggcgca tctcgctgcg    660
cctcagcgcc tacgctgtgc tggccatctg ggcgctgtcc gcggtgctgg cgctgcccgc    720
cgccgtgcac acctatcacg tggagctcaa gccgcacgac gtgcgcctct gcgaggagtt    780
ctggggctcc caggagcgcc agcgccagct ctacgcctgg gggctgctgc tggtcaccta    840
cctgctccct ctgctggtca tcctcctgtc ttacgtccgg gtgtcagtga agctccgcaa    900
ccgcgtggtg ccgggctgcg tgacccagag ccaggccgac tgggaccgcg ctcggcgccg    960
gcgcaccttc tgcttgctgg tggtggtcgt ggtggtgttc gccgtctgct ggctgccgct    1020
gcacgtcttc aacctgctgc gggacctcga ccccacgcc atcgacccctt acgcctttgg    1080 gctggtgcag ctgctctgcc actggctcgc catgagttcg gcctgctaca ccccttcat    1140 ctacgcctgg ctgcacgaca gcttccgcga ggagctgcgc aaactgttgg tcgcttggcc    1200
ccgcaagata gcccccatg gccagaatat gaccgtcagc gtggtcatct gatgccactt    1260
agccaggcct tggtcaagga gctccacttc aactggcctc ctagggcacc actcgaggtc    1320
aatctggtgc ttattctcag caccagagct agctaagcca acatagggca acatttccag    1380
cccagccctc ttgtccggct gtctgtcttg tccttgtgtg tttgtaaaat gttaagcggg    1440
ctttggtgag agtcttgctc tttgcttggg ggaggccaaa gagagggaag aggatttctt    1500
atttcttctt tatgcccttg aaggacaaac aaaacttttt ctccacgttc agaaaagtat    1560
ttcagaacca cgattgcctt cctggcgtcc cctcctcctg ctcgttggtg aaatgaacaa    1620
tatgaatggg atttaaaagg aatgcattgg gcttggtaaa gattttcagt ttgcctttag    1680
aaaaaggacc cagctgagag taccatgata ttgcttagtc catttgaacc cttgcattcc    1740
tagaatttca ggtaaatatg tattaaaact ctacatctag gatttcagca tttcctgagt    1800 aagacctttta tatgccaaaa gggtttcgtt ttaaaaccac ttgagtttat agtacaaaaa    1860
```

-continued

| | |
|---|---|
| cacctacaag ctcccttag aaaggtcttg ctattgtttc tcccctttcc tccccaacta | 1920 |
| ctatttaaaa atgatgagac gaattagtca atgaagagat agataaataa agaggaaaag | 1980 |

<210> SEQ ID NO 89
<211> LENGTH: 3700
<212> TYPE: DNA
<213> ORGANISM: Homo sapiens

<400> SEQUENCE: 89

| | |
|---|---|
| atttcacagt cgccatgacg accaggaggt ccgctagtca acggctcgtc aacggctgcg | 60 |
| gggacaagtc cgttgaggct gccaggcgag tcaggccttt ctggacctcg cctgactcgg | 120 |
| ctgggctgtg cctgaaattg acccagctcc actaggaatt atgaagaaac aaggactccg | 180 |
| ggaagaggtg cacgaactgc aggcgcggtg gttcccccagc agaaccactc tgcatcgggg | 240 |
| aattgaaaac aaggaattcc ccaaccaaac aggggcacag gctgtgtttg cagctcctgt | 300 |
| aaaagctcca tacccagagc cgtgtctccc agctcccagc cgtctttgtg gcaattctac | 360 |
| attggttaca tttagtaaca cttttttgaaa atgatcatca tttctctcac ctctcatctt | 420 |
| tggaacggga gatgactttt tgcattgaaa cggttaggtt tcttcttcta acgaattaat | 480 |
| ttgtggttta agaatagcca gaccgagagg tgacagcatg ctggcagtcc tcagagccct | 540 |
| tgcttgctct cggcacctcc cctgcctggg ctcccgcttt ggtggcattt gaggagccct | 600 |
| tcagtccccc actgcactgt gggagcccct ttctgggctg gccaaggccg gagcccactc | 660 |
| cctcagcttg cagggaggtg tggagggaga gacacgagcg ggaaccgggg ctgtgtgctg | 720 |
| cacttgcggg ccatctggag ttccgggtgg gcgtgggctt ggtgggcccc gcactcagag | 780 |
| cagccagcca gccctgctgg ccccgggcaa tgggggactt agcacctggg ccagtggctg | 840 |
| cggagggtgt actgagtccc ccagcagtgc tggcccaccg gcgctgcgct cgatttctcg | 900 |
| ctgggccttg gctgccttcc cacggggcag ggctcgggac ctgcagcccg ccatgcctga | 960 |
| gcctcctacc caatccatgg gctcctgtgc ggcctgagcc tccccgacga gcaccacccc | 1020 |
| ctgctccacg gcgcccagtc ccatcgacca cgcaagggct gaggaatgcg agcgcccggc | 1080 |
| acaggactgg caggcagctc cacctgcagc cccagtgcag gatccactag gtgaagccag | 1140 |
| ctgggctcct gagtctggtg gggacgtgga gagtctttat atctagctca gggattgtaa | 1200 |
| atacaccaat cagcaccctg tgtttagctc aaggtttgtg agtgcaccag tcaacactct | 1260 |
| gtatctagct gctctggtga gggcgtggag agtctttatg tctagctcaa ggattgtaaa | 1320 |
| tacaccaatc agcactctgt gtctagctca aggattgtaa atacaccaat cggcactctg | 1380 |
| tatctagctc aaggtttgta aacacaccaa tcagcaccct gtgtttagct caaggtttgt | 1440 |
| gagtgcacca gtcgacactc tgtatctagc tgccctgatg gggacgtgga gaacctttgt | 1500 |
| atctagctca gggattgtaa acgcaccaat cagcgccctg acgaaacagg ccactcggct | 1560 |
| ctaccaatca gcaggatgta ggtgggggcca gataagagaa taaaagcggg ctgcccgagc | 1620 |
| cagcattggc aacccgctcg ggtccccttc cacactgtgg aagctttgtt ctttcgctct | 1680 |
| ttgcaataaa tcttgctact gctcactctt tgggtccacg ctgcttttgt gagctgtaac | 1740 |
| actcaccatg aagatctgca gcttcactcc tgagcccagc gagaccacga gcccaccggg | 1800 |
| aggaacgaac aactccagac acgccacctt aagagctgta acactcaccg cgagggtcca | 1860 |
| ccgcttcatt cttgaagtca gtgagaccaa gaacccacca attccggaca caagactatg | 1920 |
| agggacttta ttattcttac ttcaagacca ttattgaagc accttcattt ttgggaggac | 1980 |

```
tgtggatgat tatgaatgac aggcttactg aatatcctct tgtaattaat gcagtaaaac    2040
gcttccatat ttatccagag aattctggag tccaaggaag accaagatca aggcgccagc    2100
agatttggtg tctggtgaag gctgctctcc gcttccaaga tggtgccttg atgttgcatc    2160
ttcctgaagg agaggaacac tgtgtcctca catggcagac agtaggagag taatcatagc    2220
ctcctggtat cgcacattca tgggaatagt gaatttattt ggactagaaa ctaagacctg    2280
ctggaatgtc accagaatag aacctcttaa tgaagttcaa agctgtgaag gattgcgaga    2340
tcctgcttgc ttttatgttg gtgtaatctt tattttaaat ggactaatga tgggattgtt    2400
cttcatatat ggaacatacc taagtggtac tgaactggga ggtcttatta cagtactgtg    2460 cttcttttc aaccatggag aggccacctg tgtgatgtgg acaccacctc tccgtgaaag    2520 ttttcctat cctttccttg tacttcagat gtatgtttta actttgattc tcaggacctc    2580
aagcaatgat agaaggccct tcattgcact ctgtctttcc aatgttgctt ttatgcttcc    2640
ctggcaattt gctcagttta tacttttac acagatagca tcattattc ccatgtatgt    2700 tgtgggatac attgaaccaa gcaaatttca gaagatcatt tatatgaaca tgatttcagt    2760 taccctagt ttcattttga tgtttggaaa ttcaatgtac ttatcttctt attattcttc    2820
atctttgtta atgacatggg caataattct aaagagaaat gaaattcaaa aactgggagt    2880
atctaaactc aactgctggc taattcaagg tagtgcctgg tggtgtggaa caatcatttt    2940
gaaatttctg acatctaaaa tcttaggcgt ttcagaccat atttgcctga gtgatcttat    3000
agcagccgga atcttaaggt atacagattt tgatacttta aaatacacct gttctcccga    3060
atttgacttc atggaaaaag cgactctgct gatatacaca aagacattat tgcttccagt    3120
tgttatggtg attacatgtt ttatctttaa aaagactgtt ggtgatattt cgcgtgtttt    3180
agctacaaac gtttatctaa gatgctgtct ttgcaggtgc catgcctaca atggcaagtg    3240
tcaagctgtc tacacttcat cccattgtga atcatccaca ttacgaagat gcagacttga    3300
ggcctggttg cagcatgctt gaaatctggg atgtggaaga cccttccaat gcagctaacc    3360
ctcccttatg tagcgtcctc cttgagccga gattgtgcca ctgcactcca gcctgggcga    3420
caaatcaaga ccccgtctcc aaaaaaaaaa aaaacaaaac ttgattggga tccaaaatca    3480
tacaactata cactaaaatc agtgaatatt accttatgta aattaaaaat taggaaatca    3540
aaagaaaagc atacatataa aaaacagttt tttctaagca tttctcattt gtagggtgtt    3600
tgaattacgt tgtatgttgt ctcatttcac ccccataaca aatctatgaa agaggtactt    3660
ttatccccat gttaacgtga ataaacccag gtttggaaaa                           3700
```

<210> SEQ ID NO 90
<211> LENGTH: 1109
<212> TYPE: DNA
<213> ORGANISM: Homo sapiens

<400> SEQUENCE: 90

```
gcttcgccgg ggccgggcgg ccggcgcccc cggctgctcc cgccgccgcc cggacccgcg     60
ccccgccggg gcagcggtgg tgagagcccc gactccccgg acgccgcccg ccgtgccatg    120
gggttcccgg ccgcggcgct gctctgcgcg ctgtgctgcg gcctcctggc cccggctgcc    180
cgcgccggct actccgagga gcgctgcagc tggaggggca gcggcctcac ccaggagccc    240
ggcagcgtgg ggcagctggc cctggcctgt gcggagggcg cggttgagtg gctgtacccg    300
gctggggcgc tgcgcctgac cctgggcggc cccgatccca gagcgcggcc cggcatcgcc    360
tgtctgcggc cggtgcggcc cttcgcgggc gcccaggtct tcgcggagcg cgcaggggc    420
```

```
gccctggagc tgctgctggc cgagggcccg ggcccggcag ggggccgctg cgtgcgctgg      480
ggtccccgcg agcgccgggc cctcttcctg caggccacgc cgcaccagga catcagccgc      540
cgcgtggccg ccttccgctt tgagctgcgc gaggacgggc gccccgagct gccccccgcag     600 gcccacggtc tcggcgtaga cggtgcctgc aggccctgca cgacgctga gctgctcctg       660 gccgcatgca ccagcgactt cgtaattcac gggatcatcc atggggtcac ccatgacgtg      720
gagctgcagg agtctgtcat cactgtggtg gccgcccgtg tcctccgcca gacaccgccg      780
ctgttccagg cggggcgatc cggggaccag gggctgacct ccattcgtac cccactgcgc      840
tgtggcgtcc acccgggccc aggcaccttc ctcttcatgg gctggagccg ctttggggag      900
gcccggctgg gctgtgcccc acgattccag gagttccgcc gtgcctacga ggctgcccgt      960 gctgccacc tccaccctg cgaggtggcg ctgcactgag gggctgggtg ctggggaggg       1020
gctggtagga gggagggtgg gcccactgct ttggaggtga tgggactatc aataagaact      1080
ctgttcacgc aaaaaaaaaa aaaaaaaa                                         1109

<210> SEQ ID NO 91
<211> LENGTH: 923
<212> TYPE: DNA
<213> ORGANISM: Homo sapiens

<400> SEQUENCE: 91
cggcggcccc atggacctgc cccgcagct ctccttcggc ctctatgtgg ccgcctttgc       60
gctgggcttc ccgctcaacg tcctggccat ccgaggcgcg acggcccacg cccggctccg      120 tctcaccct agcctggtct acgccctgaa cctgggctgc tccgacctgc tgctgacagt      180
ctctctgccc ctgaaggcgg tggaggcgct agcctccggg gctggcctc tgccggcctc       240 gctgtgcccc gtcttcgcgg tggcccactt cttcccactc tatgccggcg ggggcttcct     300
ggccgccctg agtgcaggcc gctacctggg agcagcctcc ccttgggct accaagcctt     360 ccggaggccg tgctattcct gggggtgtg cgcggccatc tgggccctcg tcctgtgtca      420
cctgggtctg gtcttttggg tggaggctcc aggaggctgg ctggaccaca gcaacacctc     480
cctgggcatc aacacaccgg tcaacggctc tccggtctgc ctggaggcct gggacccggc     540
ctctgccggc ccggcccgct tcagcctctc tctcctgctc ttttttctgc ccttggccat      600
cacagccttc tgctacgtgg gctgcctccg ggcactggcc cgctccggcc tgacgcacag     660
gcggaagctg cgggccgcct gggtggccgg cggggccctc ctcacgctgc tgctctgcgt     720
aggaccctac aacgcctcca acgtggccag cttcctgtac cccaatctag gaggctcctg     780
gcggaagctg gggctcatca cgggtgcctg gagtgtggtg cttaatccgc tggtgaccgg    840
ttacttggga aggggtcctg gcctgaagac agtgtgtgcg gcaagaacgc aagggggcaa     900
gtcccagaag taacgccact gct                                              923

<210> SEQ ID NO 92
<211> LENGTH: 708
<212> TYPE: DNA
<213> ORGANISM: Homo sapiens

<400> SEQUENCE: 92
ccccgcaggc tgagggcagg tgggaagcaa acccggacgc atcgcagcag cagcagcagc     60
agcagaagca gcagcagcag cctccgcagt ccctccagag acatggatcc ccagacagca     120
ccttcccggg cgctcctgct cctgctcttc ttgcatctgg ctttcctggg aggtcgttcc    180
```

| | |
|---|---|
| cacccgctgg gcagcccgg ttcagcctcg gacttggaaa cgtccgggtt acaggagcag | 240 |
| cgcaaccatt tgcagggcaa actgtcggag ctgcaggtgg agcagacatc cctggagccc | 300 |
| ctccaggaga gcccccgtcc cacaggtgtc tggaagtccc gggaggtagc caccgagggc | 360 |
| atccgtgggc accgcaaaat ggtcctctac accctgcggg caccacgaag ccccaagatg | 420 |
| gtgcaagggt ctggctgctt tgggaggaag atggaccgga tcagctcctc cagtggcctg | 480 |
| ggctgcaaag tgctgaggcg gcattaagag gaagtcctgg ctgcagacac ctgcttctga | 540 |
| ttccacaagg ggcttttcc tcaaccctgt ggccgccttt gaagtgactc attttttaa | 600 |
| tgtatttatg tatttatttg attgttttat ataagatggt ttcttacctt tgagcacaaa | 660 |
| atttccacgg tgaaataaag tcaacattat aagctttaaa aaaaaaa | 708 |

<210> SEQ ID NO 93
<211> LENGTH: 1535
<212> TYPE: DNA
<213> ORGANISM: Homo sapiens

<400> SEQUENCE: 93

| | |
|---|---|
| cctccgctca gtccgggagc gcacgtgggc cgcggcgctc cgacctccgc tttcccaccg | 60 |
| cccgcagctg aagcacatcc cgcagcccgg cgcggactcc gatcgccgca gttgccctct | 120 |
| ggcgccatgt cgcagaacgg agcgcccggg atgcaggagg agagcctgca gggctcctgg | 180 |
| gtagaactgc acttcagcaa taatgggaac ggggcagcg ttccagcctc ggtttctatt | 240 |
| tataatggag acatggaaaa aatactgctg gacgcacagc atgagtctgg acggagtagc | 300 |
| tccaagagct ctcactgtga cagcccacct cgctcgcaga caccacaaga taccaacagg | 360 |
| gcttctgaaa cagataccca tagcattgga gagaaaaaca gctcacagtc tgaggaagat | 420 |
| gatattgaaa gaaggaaaga agttgaaagc atcttgaaga aaaactcaga ttggatatgg | 480 |
| gattggtcaa gtcggccgga aaatattccc cccaaggagt tcctctttaa cacccgaag | 540 |
| cgcacggcca ccctcagcat gaggaacacg agcgtcatga gaaagggggg catattctct | 600 |
| gcagaatttc tgaaagtttt ccttccatct ctgctgctct ctcatttgct ggccatcgga | 660 |
| ttggggatct atattggaag gcgtctgaca acctccacca gcacctttg atgaagaact | 720 |
| ggagtctgac ttggttcgtt agtggattac ttctgagctt gcaacatagc tcactgaaga | 780 |
| gctgttagat cctggggtgg ccacgtcact tgtgtttatt tgttctgtaa atgctgcgtt | 840 |
| cctaatttag taaaataaaa gaatagacac taaaatcatg ttgatctata attcaccta | 900 |
| tgggatcaat aagcatgtca gactgattaa tgtctactgt gaaaatttgg tagtaaattt | 960 |
| tcatttgata ttagatataa atatctgaat ataataatt ttaatatact agtcatgatg | 1020 |
| tgtgttgtat tttaaaaatt atctgcaacc ttaattcagc tgaagtactt tatatttcaa | 1080 |
| aagaatgaat aacattgata ataaaatcgc tactttaagg ggtttgtcca aaataaatat | 1140 |
| tgtggcctta tatcacac tattgtagaa agtattattt aatttaaatg gatgcaggtt | 1200 |
| gtctactaaa gaaagattat atataactat gctaattgtt cataatcaac agaaaccaag | 1260 |
| atagagctac aaactcagct gtacagttcg tacactaaac tcttcttgct tttgcattat | 1320 |
| aaggaattaa gtctccgatt attaggtgat caccctggat gatcagtttt ctgctgaagg | 1380 |
| caccctactca gtatctttc ctctttatca ctctgcattg gtgaatttaa tcctctcctt | 1440 |
| tgtgttcaac ttttgtgtgc ttttaaaatc agctttattc taagcaaatc tgtgtctact | 1500 |
| ttaaaaaact ggaaatggaa aaaaaaataa atctt | 1535 |

<210> SEQ ID NO 94
<211> LENGTH: 706
<212> TYPE: DNA
<213> ORGANISM: Homo sapiens

<400> SEQUENCE: 94

```
agctccaagg gcctcacctt cctgccgcca cctcctagga cagccagtcc agggccatga     60
agaccaagaa ccggccccca cggcgccggg ccccggtgca ggacacagag gccaccccg    120
gggaggggac gcccgacggg tccctgccga accgggggcc agagccggcc aagggtctgc    180
ggagccggcc ggcccgggcc gcagcaaggg ctccgggcga gggcaggcgc aggcggccag    240
gaccctccgg gcccggtggc cgtcgtgaca gcagcatcca gcggcggctg gagagcaacg    300
agagggagcg gcagcggatg cacaagctaa ataacgcctt ccaggccctg cgtgaagtca    360
tcccccacgt gcgcgcggac aagaagctct ccaagatcga gacgctcacg ctggccaaga    420
actacatcaa atcgctgacg gccaccatcc tgaccatgtc cagcagccgc ctcccaggcc    480
tggaggggcc gggccccaag ctctaccagc actaccagca gcagcagcag gtggctgggg    540
gtgcgttggg ggccacggag gcccagcccc agggccacct gcagaggtac tccacgcaga    600
tccacagctt ccgagagggc acctagcgcc cagtcctggg tggggtggcc ggtggccgca    660
gctgcctggc ctgctcctcc cagccccagt ccctccaagc cacgag               706
```

<210> SEQ ID NO 95
<211> LENGTH: 579
<212> TYPE: DNA
<213> ORGANISM: Homo sapiens

<400> SEQUENCE: 95

```
gcgcggtcgc tcagcagtga cgtgacacgc agcccacggt ctgtactgac gcgccctcgc     60
ttcttcctct ttctcgactc catcttcgcg gtagctggga ccgccgttca gtcgccaata    120
tgcagctctt tgtccgcgcc caggagctac acaccttcga ggtgaccggc caggaaacgg    180
tcgcccagat caaggctcat gtagcctcac tggagggcat tgccccggaa gatcaagtcg    240
tgctcctggc aggcgcgccc ctggaggatg aggccactct gggccagtgc ggggtggagg    300
ccctgactac cctggaagta gcaggccgca tgcttggagg taaagtccat ggttccctgg    360
cccgtgctgg aaaagtgaga ggtcagactc taaggtggc caaacaggag aagaagaaga    420
agaagacagg tcgggctaag cggcggatgc agtacaaccg gcgctttgtc aacgttgtgc    480
ccaccttttgg caagaagaag ggccccaatg ccaactctta gtcttttgt aattctggct    540
ttctctaata aaaaagccac ttagttcagt catcgaaaa                       579
```

<210> SEQ ID NO 96
<211> LENGTH: 730
<212> TYPE: DNA
<213> ORGANISM: Homo sapiens

<400> SEQUENCE: 96

```
ctaaaaaagg gtagttgtgg ttggctctgc ctttgctgtc tttacctgaa tagaggtcag     60
gcccgggtcc aggggagcgt cccacggtcc cttcagcagc agcatctcta ggggaagtgg    120
ccggctgcag ggactgcacg gtgaggcaat ctgtgagcag gtctggatgg agctctgtgc    180
tggaccgcaa ctaagaggac aaaacggaag agacatcgat aaggagagcc ggtccttgga    240
atattttcct gggaaggcat catgctctat cagtgcaact cagcccacaa aaatttatca    300
agcagcaact acgggtcctc tgaacgggcc acaccacggt tgagccattg tgaccctgc    360
```

```
gacacacagg tccaggcctc ctggagtcac aaagctttga gcaacaggag aaccactaaa    420
gaagaagaaa cagctagctc ctgccttaac tgattaaccg aacttgcaac attccaccat    480
tgtgatatgt tcctgcccta ccctaaataa tcaatcggcc ttgtgatatc ctgccatgtg    540
aactccctcc acctcgtgac tacgcacctt gtgacattct tcccctgccc gaaaagactg    600
ccccaactgt aaccttccac tacctatccc aaacctataa aaccagttcc actcccaccg    660
cccttcgctg actccctttt cagactcagc ccgctcgcac cggagtgaat aaacagcctt    720
gttgctcaca                                                           730

<210> SEQ ID NO 97
<211> LENGTH: 524
<212> TYPE: DNA
<213> ORGANISM: Homo sapiens

<400> SEQUENCE: 97
cctttctcgt tccccggcca tcttagcggc tgctgttggt tgggggccgt cccgctccta     60
aggcaggaag atggtggccg caaagaagac gaaaaagtcg ctggagtcga tcaactctag    120
gctccaactc gttatgaaaa gtgggaagta cgtcctgggg tacaagcaga ctctgaagat    180
gatcagacaa ggcaaagcga aattggtcat tctcgctaac aactgccag cttt gaggaa    240 atctgaaata gagtactatg ctatgttggc taaaactggt gtccatcact acagtggcaa    300
taatattgaa ctgggcacag catgcggaaa atactacaga gtgtgcacac tggctatcat    360
tgatccaggt gactctgaca tcattagaag catgccagaa cagactggtg aaaagtaaac    420
cttttcacct acaaaatttc acctgcaaac cttaaacctg caaaattttc ctttaataaa    480
atttgcttgt tttaaaaaca ttgtaaaaaa aaaaaaaaa aaaa                      524

<210> SEQ ID NO 98
<211> LENGTH: 1348
<212> TYPE: DNA
<213> ORGANISM: Homo sapiens

<400> SEQUENCE: 98
gcggggggcg cgcgacgtga ccacccggac tcgaagcccg ccccgccccc gcccggctcg     60
ccggctccgg ggtctgctcc gggggtcgcg gacgcggggc cgggcggcgg agccggcgcc    120
agagcatgcg gggcgcggcg cgggcggcct ggggcgcgc ggggcagccg tggccgcgac    180 ccccgcccc gggcccgccc ccgccgccgc tcccgctgct gctcctgctc ctggccgggc    240
tgctgggcgg cgcggggcgcg cagtactcca gcgaccggtg cagctggaag gggagcgggc    300
tgacgcacga ggcacacagg aaggaggtgg agcaggtgta tctgcgctgt gcggcgggtg    360
ccgtggagtg gatgtaccca acaggtgctc tcatcgttaa cctgcggccc aacacccttct    420 cgcctgcccg gcacctgacc gtgtgcatca ggtccttcac ggactcctcg ggggccaata    480
tttatttgga aaaaactgga gaactgagac tgctggtacc ggacggggac ggcaggcccg    540
gccgggtgca gtgttttggc ctggagcagg gcggcctgtt cgtggaggcc acgccgcagc    600
aggatatcgg ccggaggacc acaggcttcc agtacgagct ggttaggagg cacagggcgt    660
cggacctgca cgagctgtct gcgccgtgcc gtccctgcag tgacaccgag gtgctcctag    720
ccgtctgcac cagcgacttc gccgttcgag gctccatcca gcaagttacc cacgagcctg    780
agcggcagga ctcagccatc cacctgcgcg tgagcagact ctatcggcag aaaagcaggg    840
tcttcgagcc ggtgcccgag ggtgacggcc actggcaggg gcgcgtcagg acgctgctgg    900
agtgtggcgt gcggccgggg catggcgact tcctcttcac tggccacatg cacttcgggg    960
```

| | |
|---|---|
| aggcgcggct cggctgtgcc ccacgcttca aggacttcca gaggatgtac agggatgccc | 1020 |
| aggagagggg gctgaaccct tgtgaggttg gcacggactg actccgtggg ccgctgccct | 1080 |
| tcctctcctg atgagtcaca ggctgcggtg ggcgctgcgg tcctggtggg gccgtgcggt | 1140 |
| gagggccgcg cgctgggagc cgcatgccct gggcccaggc ctgaccctgg taccgaagct | 1200 |
| gtggacgttc tcgccacact caaccccatg agcttccagc caaggatgcc ctggccgatt | 1260 |
| ggaaatgcta taaatgcaa actaagttat tatatttttt tttggtaaaa aagaaatgtc | 1320 |
| cataggaaac aaaaaaaaaa aaaaaaaa | 1348 |

<210> SEQ ID NO 99
<211> LENGTH: 537
<212> TYPE: DNA
<213> ORGANISM: Homo sapiens

<400> SEQUENCE: 99

| | |
|---|---|
| aacttccgct tccggttcct agcgttaact gcgaccgggg ttcagcgctc gggtgaggag | 60 |
| ctggtggcgt cggcaggttc gaggcgattc gaggtgaggg ggtcaagcgg agaggctcgg | 120 |
| agtcggagaa agctgtcgcg acccagccac ccagggtctg gggtcggtgg gagctccagc | 180 |
| taggatgatc gaggttgttt gcaacgaccg tctggggaag aaggtccgcg ttaaatgcaa | 240 |
| cacggatgat accatcgggg accttaagaa gctgattgca gcccaaactg gtacccgttg | 300 |
| gaacaagatt gtcctgaaga agtggtacac gattttaag gaccacgtgt ctctggggga | 360 |
| ctatgaaatc cacgatggga tgaacctgga gctttattat caatagatga gaatcctcat | 420 |
| cttcctgccc cgctttcctc tcccatcctc atccccaca ctgggataga tgcttgtttg | 480 |
| taaaaactca ccttaataaa gacttagatg ttgctttgta aaaaaaaaa aaaaaaa | 537 |

<210> SEQ ID NO 100
<211> LENGTH: 2063
<212> TYPE: DNA
<213> ORGANISM: Homo sapiens

<400> SEQUENCE: 100

| | |
|---|---|
| gagcggcgcg ggacggccgg gacgcgcgga gaccccaaga cccacgcgca gaccgagcgg | 60 |
| cagccgggga ggggagcgcg ggccggccgg ccgagttcgc gggcagggg cgccgggact | 120 |
| cccctctccg cgcccgggac gccgcccgcc ggatcgcgcc ttgggatgta gcgcccgctc | 180 |
| gccgcctccc ggactctcgt cggaccctcc gcccagcggc cctgcgtctt cccaggtgac | 240 |
| cacgccggct tcaggacatg cacggacaca gccgcaacgg ccaggccac gtgccccggc | 300 |
| ggaagcgccg caaccgcttc gtcaagaaga acggccaatg caacgtgtac ttcgccaacc | 360 |
| tgagcaacaa gtcgcagcgc tacatggcgg acatcttcac cacctgcgtg gacacgcgct | 420 |
| ggcgctacat gctcatgatc ttctccgcgg ccttccttgt ctcctggctc ttttccggcc | 480 |
| tcctcttctg gtgtatcgcc ttcttccacg gtgacctgga ggccagccca ggggtgcctg | 540 |
| cggcgggggg cccggcggcg ggtggtggcg gagcagcccc ggtggcccc aagccctgca | 600 |
| tcatgcacgt gaacggcttc ctgggtgcct tcctgttctc ggtggagacg cagacgacca | 660 |
| tcggctatgg gttccggtgc gtgacagagg agtgcccgct ggcagtcatc gctgtggtgg | 720 |
| tccagtccat cgtgggctgc gtcatcgact ccttcatgat tggcaccatc atggccaaga | 780 |
| tggcgcggcc caagaagcgg gcgcagacgt tgctgttcag ccaccacgcg gtcatttcgg | 840 |
| tgcgcgacgg caagctctgc ctcatgtggc gcgtgggcaa cctgcgcaag agccacattg | 900 |

| | |
|---|---|
| tggaggccca cgtgcgggcc cagctcatca agccctacat gacccaggag ggcgagtacc | 960 |
| tgccCctgga ccagcgggac ctcaacgtgg gctatgacat cggcctggac cgcatcttcc | 1020 |
| tggtgtcgcc catcatcatt gtccacgaga tcgacgagga cagcccgctt tatggcatgg | 1080 |
| gcaaggagga gctggagtcg gaggactttg agatcgtggt catcctggag ggcatggtgg | 1140 |
| aggccacggc catgaccacc caggcccgca gctcctacct ggccagcgag atcctgtggg | 1200 |
| gccaccgctt tgagcctgtg gtcttcgagg agaagagcca ctacaaggtg gactactcac | 1260 |
| gttttcacaa gacctacgag gtggccggca cgccctgctg ctcggcccgg gagctgcagg | 1320 |
| agagtaagat caccgtgctg cccgcccac cgcccctcc cagtgccttc tgctacgaga | 1380 |
| acgagctggc ccttatgagc caggaggaag aggagatgga ggaggaggca gctgcggcgg | 1440 |
| ccgcggtggc cgcaggcctg ggcctggagg cgggttccaa ggaggaggcg ggcatcatcc | 1500 |
| ggatgctgga gttcggcagc cacctggacc tggagcgcat gcaggcttcc ctcccgctgg | 1560 |
| acaacatctc ctaccgcagg gagtctgcca tctgacctcc aggcccggcc ctcaccactg | 1620 |
| cccacaagag cctctgccgg gggtgggatg ccaggacacc ccctcccaca ctcaggacag | 1680 |
| agccaaccct ggctccgtgg accttctgga ggaaggtggg ggtttcaaag actgggggac | 1740 |
| cccttcctcc tgactccagc acccaggcct gggaagagct cggccccgat cagcctgagt | 1800 |
| tccgccagcg cctacttctg gtggctctag gtccccggat ccaccaccct tcccccactg | 1860 |
| actcttcaag gacgtgccct ctttgctctc agaaccttgg ggaaggtggc tggactgctg | 1920 |
| ggcggggggac atctcggggt ttcagggtgg gcagggggtt agtttgggga ggggggggtg | 1980 |
| cgtttctttt gcatgactgt ggcctgttgc tcatgacttt cttttgtaaa tatctataaa | 2040 |
| tggagacaga tggagacacc aaa | 2063 |

<210> SEQ ID NO 101
<211> LENGTH: 6650
<212> TYPE: DNA
<213> ORGANISM: Homo sapiens

<400> SEQUENCE: 101

| | |
|---|---|
| ggagtctgct tagttctgag gactgcgtgg gtccgcgcag agagctcctg ctaggcctgc | 60 |
| gcgtcccgtt ctaaattctt acccttagt ccttgtcacc accccgccg tgggaacggc | 120 |
| ctgacagtca ctcgtcaaag gaagtggctg ccggcagctc ttgacccgga atcggatcct | 180 |
| agtcccaccc cctccgctcc aggcttcctt ctgcaacagg cgtgggtcac gctctcgctc | 240 |
| ggtctttctg ccgccatctt ggttccgcgt tccctgcaca aaatgcccgg cgaagccaca | 300 |
| gaaaccgtcc ctgctacaga gcaggagttg ccgcagcccc aggctgagac agctgtgcta | 360 |
| cctatgtctt cagccttgag tgtcactgct gccttagggc agcctggacc taccctcccc | 420 |
| cctccttgct ctcctgcccc acaacagtgc cctctctcag ctgctaacca ggcttcccca | 480 |
| ttcccttccc cctctactat tgcctcgacc cctttagaag ttcctttttcc ccagtcatcc | 540 |
| tctggaacag ccctaccttt gggaactgcc cctgaagccc aaccttcct accaaaccta | 600 |
| atagggcctc ccatctcccc agctgcctta gctctagcct ctcccatgat agctccaact | 660 |
| ctgaaaggga cccttcctc ttcagctccc ttagctctgg ttgccctggc tccccactca | 720 |
| gttcagaaga gttctgcttt tccacctaac cttcttactt cacctccttc agtggctgta | 780 |
| gctgagtcag ggtcagtgat aactctgtca gctcccattg ctccctcaga accaaagact | 840 |
| aatcttaata agttccctc tgaggtagtc cctaatccaa aaggcacccc cagccctcca | 900 |
| tgtatagtca gtactgttcc ttaccactgt gtgactccca tggcctctat tcaatctgga | 960 |

```
gtggcctccc ttcctcagac aacacccaca actaccctag ccatcgcttc ccctcaagtc   1020
aaagatacca ccatttcctc agttctgatt tctccacaaa acccaggaag cctcagcctg   1080
aaggggcctg ttagtccacc tgctgcctta tctctttcaa ctcagtctct tcctgtggtg   1140
acctcttctc aaaagactgc gggtcccaac acccccccag attttcccat ttctctgggc   1200
tctcatcttg cacctttaca tcagagttct tttggttctg tccaacttt aggtcaaaca    1260 ggtcctagtg ctttgtcaga ccctacagtg aagaccattt ctgtagatca ttcttccaca   1320
ggggcctctt atccttctca gagatctgta attcctcccc ttccttccag aaatgaggta   1380
gttcctgcta ctgtggctgc cttccagtg gtggctccat ctgttgacaa aggtccctct    1440
accatctcta gcataacctg cagcccttct ggctccttaa atgtagctac ctcttttca    1500 ttatctccta caacctctct cattctcaaa agctctccta atgccactta tcattatcct   1560
ttagtggccc aaatgcccgt tcttctgtt ggaaccaccc cacttgtggt gactaacccc    1620
tgtacaattg ctgcagcacc tactactacc tttgaggtag ctacttgtgt ttctcctcca   1680
atgtcatcag gtcccataag taacatagaa ccaacttccc ctgctgcctt ggttatggca   1740
cctgtggctc ccaaagagcc ttctactcaa gtagcaacca ctctgaggat accagtctct   1800
cctcctctgc cagaccctga agacctcaaa aatctcccca gttcagtatt ggttaaattt   1860
ccaacacaaa aagacctcca aactgtacct gcctctcttg aaggagcccc tttctctcca   1920
gcccaagcag gactcaccac caagaaagac cctactgtat taccgttagt ccaggcagcc   1980
cctaaaaatt ccccttcttt ccaaagtaca tcctcttctc cagagatacc tctttctcct   2040
gaagccaccc tagcaaagaa aagccttggg gagcctctcc ctataggtaa gccagccagc   2100
agtatgacct cccctctggg tgttaactcc tcggcctctg taatcaagac agattcttat   2160
gcaggcccag actctgctgg tccgcttctc aaaagttctc tcattacccc aacagtggct   2220
gcatttcctt tggaaagtgc tgaccctgcc ggggtggctc ccacaactgc caaaggtacc   2280
tcaacttata caactacagc cagccctttt ctagaaggaa ctgtctcttt agctcctaaa   2340
aaccacccag ttaaggaagg tactcttact actttacct tggttcctac agcttcagaa    2400
aattgccctg tggctccatc ccccagaat acctgtgctc tctggctac cttagtgctg     2460 gcccctgaaa tcccaaagtc tgtgccctca ccctctcttc ccccagctgg gactcctcca   2520
ggtacaaaaa aggttgatgg tatttctcat acttcagcat tggcacctgt tgcttcctct   2580
cccaaagagt gcccaactga ggactctggt gcttctgcta ctgcatcttc caaggaact    2640 ctgacttacc tagctgattc cccatctcct ttaggggtta gtgtgtctcc tcagactaaa   2700
agacctccaa ccaagaaggg ttctgctggc cctgatactc ctattggaaa tctctcatcc   2760 cctgttctc cagttgaagc ttcatttctt ccagagaata gtctttcttt ccaaggctct    2820
aaagactcac cagccacgac gcattctccc actcctccat ccccaaagg ggcccctact    2880 ccctcagctg tgactcctct gtctcccaaa ggagtaacac taccccccaa agagaccccc   2940
actccttcag tggtgaatct gcccttcccc aaagagggtc cagctactcc agcacccaaa   3000
caggctcctg ctctatccat gacttcttcc tcccccaaaa aggcccgagc aactccagcc   3060
cctaaaggaa tccagcttc cccatccccc aaggggccc ccacacccc agctgcaact      3120 cctccctccc ctaaaggagg cccagctacc ccatcccga aatgggcccc cacaccccca    3180
gctgcaactc ctccctcccc aaaggaggt ccagctactc catccccaa aggggcccc      3240 acacccccag ctgcaactcc tccctccccc aaaggaggtc cagctactcc atcccccaaa   3300
```

```
ggggccccca caccccagc tgtgactcct ccctccccca aggaagtcc agcagctacc    3360
ccattcccca aggggcatc cacaccccca gctgcaactc ctccctcccc caaaggaagt    3420
ccagcagcta ccccactccc caaaggggcc cccacaaccc cagctgcaac tcttccctcc    3480
ccaaaaggag gtccagctac cccatccctc aggggggccc ccactccccc agctgcgact    3540
cctcctccc caaaggagg cccagctacc ccatccccca agggggcccc catgccccca    3600
gctgcaactc ctccctcccc aaaggaggt ctagctaccc caccccacaa agggcaccc    3660
acaaccccag ctgcaactcc tccctcccca aaaggaggtc tagctacccc accccaaaa    3720
ggggccccca caacccagc tgcaactcct ccttccccaa aaggaggtct agctaccccca   3780
ccccaaaaag gggccccac aacccagct gcaactcctc cttccccaaa aggaggtcta    3840
gctaccccat ccccaaagg ggccccaca accccagctg caactcctcc ctccccaaaa    3900
ggaggtctag ctaccccatc cccaaaggg gccccacaa cccagctgc aactcctccc    3960
tccccaaaag gaggtctggc taccccatcc cccaaagggg ccccacaac ccagctgca    4020
actcctccct ccccaaaagg aggcccagct accccacccc caaagggc cccactccc     4080
ccagctgcaa ctcctccctc cctaaaagga ggtctagcta ccccacccca caaaggggcc    4140
cccaatcccg cagttgtaac tcctccctct ccaaaaggag gccagctac ctcaccccccc   4200
aaggggccc ccactcctcc agctgcaact cctccctccc caaaggaag cccaggtacc    4260
ccaccccca aggggcccc cactcccca gctgtaactc ctccctcccc taagggacc    4320
cctactctcc cagctacaac tccctcctct aaaggaggcc caactactcc atcctccaaa    4380
gagggcccca ctcccagc tgcaacccc tcccacaaag gaggtccgc tatgactcct    4440
ccctccccca aagaggacc agctatccca tctcccaaag gggaccccac ttccccagca    4500
gtgattcctc tctccccaa aaggctcca gcaactccag tcaccagag aggcgcagcc     4560
accccatcca aaggagatct cactcccca gcagtgactc ctgtctccct caaaaggcc    4620
ccagcaactt cagcccccaa aggaggccca gctaccccat cctccaaagg ggatcccacc    4680
ctcccagcag tgactcctcc ttccccaag gagccccag ccccaaaaca gttgccact    4740
tcttcctctc ccaaaaaggc cccagcaact ccagccccca tggggcccc cactctgcca    4800
gctgtgattc cttcttcccc caaagaggtc ccagctaccc catcctccag aagggacccc    4860
attgccccaa cagcgactct ctctctaaaa agaccccag caactctagc ccccaaagag    4920
gccctcattc ccccagctat gactgttccc tccctaaaa agacccagc aattccaacc    4980
cccaaagaag cccagctac ccatcctcc aaagaggct ccagtccccc agcagtgact    5040
ccttccactt acaagggc cccatccccc aaagagctcc tcattccacc agctgtgact    5100
tctccttccc ccaaagaggc acctactcct ccagctgtga ctcctccatc ccccgaaaag    5160
ggcccagcaa ctcagccccc caaagggact cccacttccc cacctgtgac tccttcctcc    5220
ctcaaagact cccctacttc cccagcttct gtcacatgta aatgggggc cactgttcct    5280
caagcatcta aagggcttcc agcaaagaaa ggccccacag ctctgaaaga agtacttgtt    5340
gccccagctc cagaaagcac gccaatcatc acagctccca ctcggaaagg tccacagacc    5400
aaaaagagtt ctgctacttc acctcctata tgcccagatc cctcagctaa gaatggttct    5460
aaggacccc tttccacagt ggctccagcc cctctactcc ctgttcagaa agactcttca    5520
aagacagcaa aagggcaaaga tgcttctcat tccccaaagg gcccttggc tcctcctgag    5580
tctaaggcgt ccacccctct aacagcagct gcctttgaga aggtccttcc taaacctgaa    5640
tcagcatctg tctctgcagc accctcccca ccagtctctc tgcctcttgc tccctcccca    5700
```

```
gttcccactc tgcctcctaa acagcaattt ctgccgtcct ctcctgggct ggtgttggaa      5760
tcaccctcta aaccccttgc ccctgctgat gaggatgagc tgctgcctct gattccccg       5820 gaaccaatct ctgggggagt gcctttccag tcggtcctcg tcaacatgcc caccccctaaa    5880 tctgctggaa tccctgtccc aaccccctct gccaagcaac ctgttacgaa gaacaacaag    5940
gggtctggaa cagaatctga cagtgatgaa tcagtaccag agcttgaaga acaggattcc    6000
acccaggcaa ccacacaaca agcccagctg gcggcagcgc tgaaattga tgaagaacca    6060 gtcagtaaag caaaacagag tcggagtgaa aagaaggcac ggaaggctat gtccaaactg    6120
ggtcttcggc aggttacagg agttactaga gtcactatcc ggaaatctaa gaatatcctc    6180
tttgtcatca caaaaccaga tgtctacaag agccctgctt cagatactta catagttttt    6240
ggggaagcca agatcgaaga tttatcccag caagcacaac tagcagctgc tgagaaattc    6300
aaagttcaag gtgaagctgt ctcaaacatt caagaaaaca cacagactcc aactgtacaa    6360
gaggagagtg aagaggaaga ggtcgatgaa acaggtgtag aagttaagga cattgaattg    6420
gtcatgtcac aagcaaatgt gtcgagagca aaggcagtcc gagccctgaa gaacaacagt    6480
aatgatattg taaatgcgat tatgaattaa caatgtaac catatggaag caactttttt    6540
tggtgtctca aaggagtaac tgcagcttgg tttgaaattt gtactgtttc tatcataaat    6600
aaagttatgg cttcttgttg gatgaattca aaaaaaaaa aaaaaaaaaa              6650

<210> SEQ ID NO 102
<211> LENGTH: 2611
<212> TYPE: DNA
<213> ORGANISM: Homo sapiens

<400> SEQUENCE: 102
aggaacgact gtgctacgtt gccagaaggg gcgggacctg caacgtccga cagaacgagg      60
ggacgtaacg gaggcaggtt ggagccgctg ccgtcgccat gacccgcggt aaccagcgtg     120
agctcgcccg ccagaagaat atgaaaaagc agagcgactc ggttaaggga aagcgccgag     180
atgacgggct ttctgctgcc gcccgcaagc agagggactc ggagatcatg cagcagaagc     240
agaaaaaggc aaacgagaag aaggaggaac ccaagtagct ttgtggcttc gtgtccaacc     300
ctcttgccct tcgcctgtgt gcctggagcc agtcccacca cgctcgcgtt tcctcctgta     360
gtgctcacag gtcccagcac cgatggcatt ccctttgccc tgagtctgca gcgggtccct     420
tttgtgcttc cttcccctca ggtagcctct ctcccctgg ccactcccg ggggtgaggg       480 ggttacccct tcccagtgtt ttttattcct gtggggctca ccccaaagta ttaaaagtag     540
ctttgtaatt ccttgagcgc ctggtttgac tggggacttg gggggatggg gttggaagaa     600
tgactgccct ttcccaccaa aaaagggaga actctttaga ttcagattgt gggtatgtag     660
acttaataag tgaaacatca cagaagaagc ctttattata caatgacaac caaacaagta     720
ctccggatat gcagtagagg aatcctctaa gaaccataga gacttctttt ctgtgatttt     780
tgttccccac ccttgaacac catctctagg atggagttgg cctaagagtg aatgctgcaa     840
gatctgtgtt tatgcctctt ttcctcattc ttcctcagtt tgttcgtctg cttgaaagtt     900
ggccaaaaaa tcctgctgct caccgacttc ccgtggtcag ctgctgtcaa gcgttcactt     960
tctcttctgt cattcctcat ggaatgaggg tggttttgtc ttcccgcttc ccttgacctc    1020
aaaatcagga ttaaacctg gggtagcctc tgtgctcctt tcttctatgc cctggtttgt     1080
tctgtggttc tgggcttctt atatccgtgt gcccagggct gaactcctta ttttcctttc    1140
```

| | |
|---|---:|
| tccaagggca gagccgagtc ttcagtccct gttggtcttt ccccaccccc acttccagcc | 1200 |
| caagagccag gaaagggctg gtgccacact gtctgctggg atcagcggtg gttctttgag | 1260 |
| ctgctgattt gggtgttagg ctcttgagct gggatgcaga tgtaacagta gctccagtga | 1320 |
| gtcagacact ctgcccagca cattagactg tgtttgacca cttcttccag ttcatagtat | 1380 |
| tgacttcagc ccaaacggag ataactccct gtgtgtcctt gaggtattga gctgggctgg | 1440 |
| acagctcccc ttgagccaac tctaggagta caatgtcagg ggaacccag tttgtgaaaa | 1500 |
| ggacttagac tggaggatat tgttatctg gggatatgat gcggtggcgg cggcgcctca | 1560 |
| agataagggg ctggggtttc tgggtggggg gccaacagag tggtgccagt aacagcccca | 1620 |
| gatagaggag tacgcaggcc cagcatgagg caaccttgac ccagaaggtg gcccagctac | 1680 |
| ccttgatgaa ggtctttttcc agttctgctc cctcatagct gtgtaaccaa aggctctggt | 1740 |
| tagagaatat gaagggcctt agcttttaga cctgttctac ctcctcacca aatataatgg | 1800 |
| cagacccatg tgtgtctgga atggccttga attgctcttt ccttaaaata gctagctctt | 1860 |
| caggagagta tctaaggccc actccatctt acctgaacca gttggtaagg gtaaccatga | 1920 |
| catagagtga ggcaaggaag aagacgaagt ggaaggcaga atagttgtag gaaagatgct | 1980 |
| ggacttggac tggaggagct ggaggggttt cttggtcagc tggcctcgca gccccacccc | 2040 |
| tttgccctgg agaggaaa tggctgctgg gagcagagct gctgaaacac ctcttcccct | 2100 |
| ctcccccaac taccctttgtt aaggctcttg agggttctta tggcactcca cagagatcta | 2160 |
| ccacttctta tggttcctca cttggcactc acctttgtct gcctccactg tttcagggca | 2220 |
| gcagaaacac agtgagggct tctgcaaaac agaacgcagg ttttggaatg gtcttaaaag | 2280 |
| atgtgagggt gttaatctag gaaacttccc ccgtgaaaag attggtctag tattaaaaag | 2340 |
| tggaggcaca cctgggttca aattctagct ccagcatata agtggctgtg cagactttgg | 2400 |
| taagatgttt aatctttttgt gcctcgattt ctccatttgt aaaatggagc aaataacctac | 2460 |
| ctcacagggt tgttgtgagg gttaaattaa atgagattat gtaaaagtat ctagcacagt | 2520 |
| tgcctagcac attgtgggta ctcaataaaa ggtaacagca gctataatct gagcattctg | 2580 |
| ggtagaggtt ggtaaaaaaa aaaaaaaaaa a | 2611 |

<210> SEQ ID NO 103
<211> LENGTH: 1348
<212> TYPE: DNA
<213> ORGANISM: Homo sapiens

<400> SEQUENCE: 103

| | |
|---|---:|
| gtttgtcctg gagcccagat ggactgtggc cgggcaagtg gatcacaggc ctggccagcc | 60 |
| taggagttgc cacatgtgag gggccgaggg gctcaaggag gggaacatcg gggagaggag | 120 |
| cctactgggt ggaggctggg ggtcccagca ggaaatggtg agacaaaggg cgctggctgg | 180 |
| caggaagaca gcacaggaag gtcctagagg ttcctcagtg cagctggact ctcctggaga | 240 |
| ccttcacaca ccctgacatc tgggcccgc gccacgaggg tgctttcact ggtctgcacc | 300 |
| atggcccagg ccctgggatt ttgaacagct ccgcaggtga atgaaaggaa catggagctg | 360 |
| atccaggaca tctctcgccc gccactggag tacgtgaagg gggtcccgct catcaagtac | 420 |
| tttgcagagg cactggggcc cctgcagagc ttccaggccc ggcctgatga cctgctcatc | 480 |
| agcacctacc ccaagtccgg caccacctgg gtgagccaga ttctggacat gatctaccag | 540 |
| ggcggtgacc tggaaaagtg tcaccgagct cccatcttca tgcgggtgcc cttccttgag | 600 |
| ttcaaagtcc cagggattcc ctcagggatg gagactctga aaaacacacc agccccacga | 660 |

```
ctcctgaaga cacacctgcc cctggctctg ctcccccaga ctctgttgga tcagaaggtc    720
aaggtggtct atgttgcccg caacgcaaag gatgtgcgg tttcctacta ccacttctac    780
cacatggcca aagtgtaccc tcaccctggg acctgggaaa gcttcctgga aagttcatg    840 gctggagaag tgtcctatgg gtcctggtac cagcacgtgc aagagtggtg ggagctgagc    900
cgcacccacc ctgttctcta cctcttctat gaagacatga aggagaaccc caaaagggag    960
attcaaaaga tcctggagtt tgtgggcgc tccctgccag aggagactgt ggacctcatg    1020
gttgagcaca cgtcgttcaa ggagatgaag aagaaccta tgaccaacta caccaccgtc    1080
cgccgggagt tcatggacca cagcatctcc cccttcatga ggaaaggcat ggctggggac    1140
tggaagacca ccttcaccgt ggcgcagaat gagcgcttcg atgcggacta tgcggagaag    1200
atggcaggct gcagcctcag cttccgctct gagctgtgag aggggttcct ggagtcactg    1260
cagagggagt gtgcgaatca agcctgacca agaggctcca gaataaagta tgatttgtgt    1320
tcaaaaaaaa aaaaaaaaaa aaaaaaa                                       1348

<210> SEQ ID NO 104
<211> LENGTH: 945
<212> TYPE: DNA
<213> ORGANISM: Homo sapiens

<400> SEQUENCE: 104
atgaccctgg gatccctggg aaacagcagc agcagcgttt ctgctacctt cctgctgagt     60
ggcatccctg ggctggagcg catgcacatc tggatctcca tcccactgtg cttcatgtat    120
ctggtttcca tcccgggcaa ctgcacaatt cttttttatca ttaaaacaga gcgctcactt    180
catgaaccta tgtatctctt cctgtccatg ctggctctga ttgacctggg tctctcccct    240
tgcactctcc ctacagtcct gggcatcttt tgggttggag cacgagaaat tagccatgat    300
gcctgctttg tcagctctt tttcattcac tgcttctcct tctcgagtc ctctgtgcta    360 ctgtctatgg cctttgaccg ctttgtggct atctgccacc ccttgcacta tgtttccatt    420
ctcaccaaca cagtcattgg caggattggc ctggtctctc tgggtcgtag tgtagcactc    480 attttttccat tacctttat gctcaaaaga ttccccctatt gtggctcccc agttctctca    540
cattcttatt gtctccacca agaagtgatg aaattggcct gtgccgacat gaaggccaac    600
agcatctacg gcatgtttgt catcgtctct acagtgggta tagactcact gctcatcctc    660
ttctcttatg ctctgatcct gcgcaccgtg ctgtccatcg cctccagggc tgagagattc    720
aaggccctta acacctgtgt tcccacatc tgtgctgtgc tgctcttcta cactcccatg    780
attggcctct ctgtcatcca tcgctttgga aagcaggcac cccacctggt ccaggtggtc    840
atgggtttca tgtatcttct ctttcctcct gtgatgaatc ccattgtcta cagtgtgaag    900
accaaacaga tccgggatcg agtgacgcat gccttttgtt actaa                    945

<210> SEQ ID NO 105
<211> LENGTH: 1262
<212> TYPE: DNA
<213> ORGANISM: Homo sapiens

<400> SEQUENCE: 105
tgtgtcactt ccggcctccc tttagctgcc atcttgcgtc ccgcgtgtg tgcgcctaat      60 ctcaggtggt ccacccgaga cccttgagc accaacccta gtccccgcg cggccccttt     120 ttcgctccga caaggtacaa aaaggctctg gacggcggcg tggtaggagg acgggagcgg    180
```

```
gggcgggaag ttccctgaag gagcgagaca gggagggaca gggcagagga ggagaggaag      240
gcgatgcgac ggacaggcgc acccgctcag gctgactctc gggggcgagg tcgagccagg      300
ggcggctgcc ctgggggcga ggcgacgctg tctcaacctc cacctcgcgg cggaacccga      360
ggacaggagc ctcagatgaa agaaacaatc atgaaccagg aaaaactcgc caaactgcag      420
gcacaagtgc gcattggtgg gaaaggaact gctcgcagaa agaagaaggt ggttcataga      480
acagccacag cagatgacaa aaaacttcag ttctccttaa agaagttagg ggtaaacaat      540
atctctggta ttgaagaggt gaatatgttt acaaaccaag gaacagtgat ccactttaac      600
aaccctaaag ttcaggcatc tctggcagcg aacactttca ccattacagg ccatgctgag      660
acaaagcagc tgacagaaat gctacccagc atcttaaacc agcttggtgc ggatagtctg      720
actagtttaa ggagactggc cgaagctctg cccaaacaat ctgtggatgg aaaagcacca      780
cttgctactg gagaggatga tgatgatgaa gttccagatc ttgtggagaa ttttgatgag      840
gcttccaaga atgaggcaaa ctgaattgag tcaacttctg aagataaaac ctgaagaagt      900
tactgggagc tgctatttta tattatgact gcttttttaag aaattttttgt ttatggatct      960 gataaaatct agatctctaa tatttttaag cccaagcccc ttggacactg cagctctttt     1020 cagttttttgc ttatacacaa ttcattcttt gcagctaatt aagccgaaga agcctgggaa     1080
tcaagtttga aacaaagatt aataaagttc tttgcctagt atacagtttt attttttttat     1140 ttcattgaca ccgatctgta cacagtaaaa aaaattgctt atagaaagct aatcatggca     1200
tgtaatatgg ctgataaacct ttggaatttg attaaagatt taaaatcaca aaaaaaaaaa     1260
aa                                                                   1262

<210> SEQ ID NO 106
<211> LENGTH: 869
<212> TYPE: DNA
<213> ORGANISM: Homo sapiens

<400> SEQUENCE: 106
ggacagagcg gcccggtcgc cggcatggtt tctccgtcct gctgcagccg gcgggaggca       60
gccagtccag gcgcccgcta gcttcggcgg cgacccagac ggggaaagcg gaaggaatgt      120
cgcgtgcaag caggcagctg gtgtggaaga atggcggtga gccattcagt gaaggagcgg      180
accatctctg agaacagcct gatcatccta ctgcagggcc tccagggccg ggtaaccact      240
gtggacctgc gggatgagag cgtggcccac ggacgcatag acaatgtcga tgcttttcatg      300 aacatccgcc tggccaaagt cacctacacg gaccgttggg ggcatcaggt caagctggat      360
gacctctttg tgacaggccg caatgtccgc tacgtccaca tcccagatga cgtgaacatc      420
acctcgacca ttgagcagca gctgcagatt atccatcggg tgcgaaactt tggtggcaag      480
ggccaaggcc ggtgggaatt tcccccaaaa aactgtaagt gaggccctca gcaagccctg      540
gccccaactc ggagtcctcc agtgatctcc agagctagtt ccctgccctc acaccctgtc      600
tggtacccga gaagaaagca gggccaggcc agaagctggt gtccaacaga cacccacctgt      660 caaagctgcc tttcacaggg ttccacctcc cagactcact ctgggaccca gaatcctata      720
tgtggccttg gggtaggtga caatccccct ttttgatgat ctgaatctct gacttattga      780
ttatggaacc tgtcaagtag ttttcaactc tcccagtgag gataattaaa catgctcagc      840
ctgagccacc aaaaaaaaaa aaaaaaaa                                          869

<210> SEQ ID NO 107
<211> LENGTH: 43
```

```
<212> TYPE: DNA
<213> ORGANISM: Homo sapiens

<400> SEQUENCE: 107
ttggggtccg aactgctggc tggaccatct gcctggcagg gac         43

<210> SEQ ID NO 108
<211> LENGTH: 24
<212> TYPE: DNA
<213> ORGANISM: Homo sapiens

<400> SEQUENCE: 108
tccaatgacc acagtgcaaa ataa                              24

<210> SEQ ID NO 109
<211> LENGTH: 24
<212> TYPE: DNA
<213> ORGANISM: Homo sapiens

<400> SEQUENCE: 109
cctttctttt ccatccaaca atta                              24

<210> SEQ ID NO 110
<211> LENGTH: 24
<212> TYPE: DNA
<213> ORGANISM: Homo sapiens

<400> SEQUENCE: 110
tagcaacaag acggatgggg aagc                              24

<210> SEQ ID NO 111
<211> LENGTH: 24
<212> TYPE: DNA
<213> ORGANISM: Homo sapiens

<400> SEQUENCE: 111
ccctccccaa gagtgtaggt gaat                              24

<210> SEQ ID NO 112
<211> LENGTH: 24
<212> TYPE: DNA
<213> ORGANISM: Homo sapiens

<400> SEQUENCE: 112
gaagagcctg cgctccgagg accc                              24

<210> SEQ ID NO 113
<211> LENGTH: 25
<212> TYPE: DNA
<213> ORGANISM: Homo sapiens

<400> SEQUENCE: 113
tatgatgcag tcagggggga tggtc                             25

<210> SEQ ID NO 114
<211> LENGTH: 59
<212> TYPE: DNA
<213> ORGANISM: Homo sapiens

<400> SEQUENCE: 114
gacctcagct gaccccttct accagaacac acctcacagc agccgctgcg tggcacaca  59

<210> SEQ ID NO 115
```

```
<211> LENGTH: 39
<212> TYPE: DNA
<213> ORGANISM: Homo sapiens

<400> SEQUENCE: 115
gctcctcccg cagcatggcg agctcctgtt gcagggcct                              39

<210> SEQ ID NO 116
<211> LENGTH: 34
<212> TYPE: DNA
<213> ORGANISM: Homo sapiens

<400> SEQUENCE: 116
gtactctgcc tcctgctaca atggctctga agga                                   34

<210> SEQ ID NO 117
<211> LENGTH: 25
<212> TYPE: DNA
<213> ORGANISM: Homo sapiens

<400> SEQUENCE: 117
tgctccccca acaaagccgc ctacc                                             25

<210> SEQ ID NO 118
<211> LENGTH: 30
<212> TYPE: DNA
<213> ORGANISM: Homo sapiens

<400> SEQUENCE: 118
ctggctggac agtcaatgtg gagggcagcg                                        30

<210> SEQ ID NO 119
<211> LENGTH: 25
<212> TYPE: DNA
<213> ORGANISM: Homo sapiens

<400> SEQUENCE: 119
gatgccctcc atgaaggctg ggtag                                             25

<210> SEQ ID NO 120
<211> LENGTH: 83
<212> TYPE: DNA
<213> ORGANISM: Homo sapiens

<400> SEQUENCE: 120 gcagggctc cagataatcg ggcagggatg gcggccgagg cttcagagct ggcggcagcc        60
cgggtcccca agcgcgatga ggt                                               83

<210> SEQ ID NO 121
<211> LENGTH: 24
<212> TYPE: DNA
<213> ORGANISM: Homo sapiens

<400> SEQUENCE: 121
cccagctctg cacggagcct gttc                                              24

<210> SEQ ID NO 122
<211> LENGTH: 24
<212> TYPE: DNA
<213> ORGANISM: Homo sapiens

<400> SEQUENCE: 122
gggaaagtga ctcctgtttt ctgt                                              24
```

<210> SEQ ID NO 123
<211> LENGTH: 82
<212> TYPE: DNA
<213> ORGANISM: Homo sapiens

<400> SEQUENCE: 123
cctggcccgc atggcgagac acagtgccaa caccagcatg catgcccgca acctggccat    60
tgtctgggca cccaacctgc ta    82

<210> SEQ ID NO 124
<211> LENGTH: 24
<212> TYPE: DNA
<213> ORGANISM: Homo sapiens

<400> SEQUENCE: 124
tcaagagctg gttcgagccc ctgg    24

<210> SEQ ID NO 125
<211> LENGTH: 24
<212> TYPE: DNA
<213> ORGANISM: Homo sapiens

<400> SEQUENCE: 125
gaacaccagg tccagttcac agac    24

<210> SEQ ID NO 126
<211> LENGTH: 63
<212> TYPE: DNA
<213> ORGANISM: Homo sapiens

<400> SEQUENCE: 126
gttttggtgg cgaggacgca caaagaggca tttatctccc tggacaggta ggcggtcatc    60
aat    63

<210> SEQ ID NO 127
<211> LENGTH: 50
<212> TYPE: DNA
<213> ORGANISM: Homo sapiens

<400> SEQUENCE: 127
tgcaggcagg caaacagccc cagcagcagt agcagcaggc ccttcagcag    50

<210> SEQ ID NO 128
<211> LENGTH: 24
<212> TYPE: DNA
<213> ORGANISM: Homo sapiens

<400> SEQUENCE: 128
ctgggtggca tcaatgtcca gcct    24

<210> SEQ ID NO 129
<211> LENGTH: 30
<212> TYPE: DNA
<213> ORGANISM: Homo sapiens

<400> SEQUENCE: 129
cgggagaagc gacgtctggg tgggcaggaa    30

<210> SEQ ID NO 130
<211> LENGTH: 24
<212> TYPE: DNA

```
<213> ORGANISM: Homo sapiens

<400> SEQUENCE: 130
tcccggcggg gatacctgcc caca                                              24

<210> SEQ ID NO 131
<211> LENGTH: 76
<212> TYPE: DNA
<213> ORGANISM: Homo sapiens

<400> SEQUENCE: 131
ggcccctaga ctcatctctt ggagcattct gtggtgcgat tgtctttgca ggacttcttc       60
gtgaagggat gtgatg                                                       76

<210> SEQ ID NO 132
<211> LENGTH: 24
<212> TYPE: DNA
<213> ORGANISM: Homo sapiens

<400> SEQUENCE: 132
tgccccgagg cctagcttgg ccag                                              24

<210> SEQ ID NO 133
<211> LENGTH: 49
<212> TYPE: DNA
<213> ORGANISM: Homo sapiens

<400> SEQUENCE: 133
caagccatcc tcccttcttg ttctcccaaa acgttgggat tacaggcat                   49

<210> SEQ ID NO 134
<211> LENGTH: 24
<212> TYPE: DNA
<213> ORGANISM: Homo sapiens

<400> SEQUENCE: 134
tggcactgtg gctctgggga gctg                                              24

<210> SEQ ID NO 135
<211> LENGTH: 115
<212> TYPE: DNA
<213> ORGANISM: Homo sapiens

<400> SEQUENCE: 135
agggctgtgt atccatgttc atgctgatga caatttacat cggctccatg tcgcagtagt       60
aatttgcaca tatcgagttt tcctttatat gctgcatgca ttagaggagt cattc           115

<210> SEQ ID NO 136
<211> LENGTH: 24
<212> TYPE: DNA
<213> ORGANISM: Homo sapiens

<400> SEQUENCE: 136
acatatctta cccaagcctg cact                                              24

<210> SEQ ID NO 137
<211> LENGTH: 24
<212> TYPE: DNA
<213> ORGANISM: Homo sapiens

<400> SEQUENCE: 137
ccatggccca aagaccctcc tccc                                              24
```

<210> SEQ ID NO 138
<211> LENGTH: 24
<212> TYPE: DNA
<213> ORGANISM: Homo sapiens

<400> SEQUENCE: 138
tgatggcata aacaccccccc caac                                       24

<210> SEQ ID NO 139
<211> LENGTH: 24
<212> TYPE: DNA
<213> ORGANISM: Homo sapiens

<400> SEQUENCE: 139
caaagcagtc aaggagccac cacc                                        24

<210> SEQ ID NO 140
<211> LENGTH: 176
<212> TYPE: DNA
<213> ORGANISM: Homo sapiens

<400> SEQUENCE: 140
accttgtgcg acatactgct gtaatgaact tgaggagaca attctgggat atgataaact    60
ctcactgagg tctgcttcct gcagttcatg acatgctgct gactcaagag atgttacagc   120
agggctggcc caggcatggg tttcctgcct ttccgctggt ggtgatatgc tagact        176

<210> SEQ ID NO 141
<211> LENGTH: 30
<212> TYPE: DNA
<213> ORGANISM: Homo sapiens

<400> SEQUENCE: 141
gctttccctc ctctgccctc atccctctag                                  30

<210> SEQ ID NO 142
<211> LENGTH: 24
<212> TYPE: DNA
<213> ORGANISM: Homo sapiens

<400> SEQUENCE: 142
cgagccagca ccactgaacc cacc                                        24

<210> SEQ ID NO 143
<211> LENGTH: 34
<212> TYPE: DNA
<213> ORGANISM: Homo sapiens

<400> SEQUENCE: 143
gcttttctcc ctaactcagg cccctgtctc caac                             34

<210> SEQ ID NO 144
<211> LENGTH: 24
<212> TYPE: DNA
<213> ORGANISM: Homo sapiens

<400> SEQUENCE: 144
ggacaaaaag cgagacccgc ttct                                        24

<210> SEQ ID NO 145
<211> LENGTH: 94
<212> TYPE: DNA

```
<213> ORGANISM: Homo sapiens

<400> SEQUENCE: 145
tggcggcctt cagcaagtac ttgacggcgc gaaactcctc gctggctggt gccgcgttcc      60
tgctgctctg cctgctccac aagcggcgcc gcgc                                 94

<210> SEQ ID NO 146
<211> LENGTH: 380
<212> TYPE: DNA
<213> ORGANISM: Homo sapiens

<400> SEQUENCE: 146
gctggtttat cctccgcact tacttggtac tcgatctcca gcgaggcctt caggggcatg      60
ggctggtaga agcactcctt ctggccggcg ggaagggtaa aggtgaagtc gctatcgagg     120
gaaggtgtga agccggccgc cccaggcagc agcaccggag gcagagcggc cagaaggagc     180
acggggaagg gcagccagat cttgtcgccc atccctgctg gggcgatccc gggctgaaag     240
aggcgtcagg tactgttgtc tccgctccgc gtttcctctc tggactcctc gtggttgaca     300
gggaaatctg gagtctgaag aaactccagg tggcggccgc ggcggcggcg aacactccct     360
ccgaaagaga agcgcagttc                                                380

<210> SEQ ID NO 147
<211> LENGTH: 34
<212> TYPE: DNA
<213> ORGANISM: Homo sapiens

<400> SEQUENCE: 147
ccactatgcc gcaggccgcc ctacccacct tcag                                 34

<210> SEQ ID NO 148
<211> LENGTH: 24
<212> TYPE: DNA
<213> ORGANISM: Homo sapiens

<400> SEQUENCE: 148
tgagctgggg gcctaattcc tgac                                            24

<210> SEQ ID NO 149
<211> LENGTH: 29
<212> TYPE: DNA
<213> ORGANISM: Homo sapiens

<400> SEQUENCE: 149
atgatggaca cccgcgtgca agatgctgt                                       29

<210> SEQ ID NO 150
<211> LENGTH: 93
<212> TYPE: DNA
<213> ORGANISM: Homo sapiens

<400> SEQUENCE: 150
gccaggactc caggtctagg gcaggggtcc aggagcagag gccatcaggg cctacagtcc      60
ctcgtacctt gctaccctga ccggtgtccc agg                                  93

<210> SEQ ID NO 151
<211> LENGTH: 24
<212> TYPE: DNA
<213> ORGANISM: Homo sapiens

<400> SEQUENCE: 151
```

```
tggcccggca cgtgttccta acgg                                              24

<210> SEQ ID NO 152
<211> LENGTH: 24
<212> TYPE: DNA
<213> ORGANISM: Homo sapiens

<400> SEQUENCE: 152
acccggagtc tgcagagcgc gccg                                              24

<210> SEQ ID NO 153
<211> LENGTH: 24
<212> TYPE: DNA
<213> ORGANISM: Homo sapiens

<400> SEQUENCE: 153 tgcggggcg gggtctcgcg tcat                                               24

<210> SEQ ID NO 154
<211> LENGTH: 49
<212> TYPE: DNA
<213> ORGANISM: Homo sapiens

<400> SEQUENCE: 154
catctgtgcg tggcgactcc aagagagcac ccgactccag atggcgaca                   49

<210> SEQ ID NO 155
<211> LENGTH: 94
<212> TYPE: DNA
<213> ORGANISM: Homo sapiens

<400> SEQUENCE: 155
cggcggtacg aggcgcgcgc tcggggtccc ggtcgcgagg aggaggagga tgtggcgcgc       60 ggagggaaa tggctgccga aaacaagccg gaag                                    94

<210> SEQ ID NO 156
<211> LENGTH: 46
<212> TYPE: DNA
<213> ORGANISM: Homo sapiens

<400> SEQUENCE: 156
caaggacagc caaaaggccc gggcagcctt ctgacgcagc caggaa                      46

<210> SEQ ID NO 157
<211> LENGTH: 24
<212> TYPE: DNA
<213> ORGANISM: Homo sapiens

<400> SEQUENCE: 157
gctggacggt ggagcccgag aggg                                              24

<210> SEQ ID NO 158
<211> LENGTH: 26
<212> TYPE: DNA
<213> ORGANISM: Homo sapiens

<400> SEQUENCE: 158
actagtaaat ctctccgggc tctggg                                            26

<210> SEQ ID NO 159
<211> LENGTH: 145
<212> TYPE: DNA
```

<213> ORGANISM: Homo sapiens

<400> SEQUENCE: 159

```
cggatcaaca tgccccaaaa ggaggaggcc cgggagcgaa gcgggtcagt tcccctttgc     60
cctgccctat ccaggccaca cagatcgaag cggcccggct ccttcctcct ccccggggc    120
gtgactaagg tcacgaatcc ggccc                                         145
```

<210> SEQ ID NO 160
<211> LENGTH: 29
<212> TYPE: DNA
<213> ORGANISM: Homo sapiens

<400> SEQUENCE: 160

```
gtggagaggc ctggcagaac gaagaggat                                      29
```

<210> SEQ ID NO 161
<211> LENGTH: 32
<212> TYPE: DNA
<213> ORGANISM: Homo sapiens

<400> SEQUENCE: 161

```
gttatggctg actcacggcc ttcgactcca gc                                  32
```

<210> SEQ ID NO 162
<211> LENGTH: 79
<212> TYPE: DNA
<213> ORGANISM: Homo sapiens

<400> SEQUENCE: 162

```
aggagccaga cgtgtggagt cccagcagag gccaacctgt gtctcttcat ctccgtgaga    60
aaggtgcccc cgaagtgaa                                                 79
```

<210> SEQ ID NO 163
<211> LENGTH: 24
<212> TYPE: DNA
<213> ORGANISM: Homo sapiens

<400> SEQUENCE: 163

```
ggggaaagtg ctaaagccgc tgag                                           24
```

<210> SEQ ID NO 164
<211> LENGTH: 29
<212> TYPE: DNA
<213> ORGANISM: Homo sapiens

<400> SEQUENCE: 164

```
cgagtcctcg ttctcgctgc tgtagcagc                                      29
```

<210> SEQ ID NO 165
<211> LENGTH: 319
<212> TYPE: DNA
<213> ORGANISM: Homo sapiens

<400> SEQUENCE: 165

```
gacctccgct atgacccgaa ctggaagagt aagaaggagg aagggcagct gctgtctgtg     60
gaagcgttgc cggagtccac ggacagctct ttagaaaatc tgcctttggc tcccctctac   120
ccttcccagg agacgtcaat ggaactctcc gggggaaaag gcgagcagaa agagagtcca   180
cagagtgcag cttctttact tggtagtgaa tttttaagcc caaactatga gcatggtgcc   240
cgtcgcagca agccgttttc agagctgagc gacagtgacc tggaggagaa gtcgagcagc   300
```
ctttctccgt acgtgaaga 319

<210> SEQ ID NO 166
<211> LENGTH: 168
<212> TYPE: DNA
<213> ORGANISM: Homo sapiens

<400> SEQUENCE: 166
acgcgggcct cagtgaggtc tgtcctcatg gccagctgtt cccgcgcata cacgtctggg    60
tagtgggtct tctggaagac cttctccagc tcctccagct ggtagctggt gaaggtggtc   120
cggttccgcc gcttcttgcc cttgttgctc tctgagtcgg ccttctcc                168

<210> SEQ ID NO 167
<211> LENGTH: 25
<212> TYPE: DNA
<213> ORGANISM: Homo sapiens

<400> SEQUENCE: 167
atggggatgg ccgtgttcat gaaaa    25

<210> SEQ ID NO 168
<211> LENGTH: 25
<212> TYPE: DNA
<213> ORGANISM: Homo sapiens

<400> SEQUENCE: 168
ccttccgcag ggcgaggttg tcttt    25

<210> SEQ ID NO 169
<211> LENGTH: 24
<212> TYPE: DNA
<213> ORGANISM: Homo sapiens

<400> SEQUENCE: 169
tgcagtcggg cactcactgg agag    24

<210> SEQ ID NO 170
<211> LENGTH: 30
<212> TYPE: DNA
<213> ORGANISM: Homo sapiens

<400> SEQUENCE: 170
tgggcgaccc ggatctcctg gaagtgttgg    30

<210> SEQ ID NO 171
<211> LENGTH: 26
<212> TYPE: DNA
<213> ORGANISM: Homo sapiens

<400> SEQUENCE: 171
tggccggcaa cgtgaagaag agctct    26

<210> SEQ ID NO 172
<211> LENGTH: 24
<212> TYPE: DNA
<213> ORGANISM: Homo sapiens

<400> SEQUENCE: 172
accccagccc ccttcggagg agca    24

<210> SEQ ID NO 173

```
<211> LENGTH: 28
<212> TYPE: DNA
<213> ORGANISM: Homo sapiens

<400> SEQUENCE: 173
ttctgccctt gcgagggttc ctcctcac                                          28

<210> SEQ ID NO 174
<211> LENGTH: 189
<212> TYPE: DNA
<213> ORGANISM: Homo sapiens

<400> SEQUENCE: 174
agggactcgg tcccccttgc cgtgctcccc tccctcctcg tctgccaagc ctcgcctcct       60
accacaccac accaggccac cccagctgca agtgccttcc ttggagcaga gaggcagcct      120
cgtcctcctg tccctctctc tcccagccac catcgttcat ctgctccggg cagaactgtg      180
tggcccctg                                                              189

<210> SEQ ID NO 175
<211> LENGTH: 24
<212> TYPE: DNA
<213> ORGANISM: Homo sapiens

<400> SEQUENCE: 175
tgtaccggct cacgctgcgc acaa                                              24

<210> SEQ ID NO 176
<211> LENGTH: 106
<212> TYPE: DNA
<213> ORGANISM: Homo sapiens

<400> SEQUENCE: 176
gcttcagcac catgccgctc aggtcggccg tgctctcctg cgacgggttg aagatgcgga       60
cgaacttctc ccggcagctc acagccacga tcttcaggcc tgtcgg                    106

<210> SEQ ID NO 177
<211> LENGTH: 30
<212> TYPE: DNA
<213> ORGANISM: Homo sapiens

<400> SEQUENCE: 177 tagggcctg gagggtgcag ggtcattaat                                         30

<210> SEQ ID NO 178
<211> LENGTH: 32
<212> TYPE: DNA
<213> ORGANISM: Homo sapiens

<400> SEQUENCE: 178
tcggcccctc tgtcgtacca ggagcccag ac                                      32

<210> SEQ ID NO 179
<211> LENGTH: 25
<212> TYPE: DNA
<213> ORGANISM: Homo sapiens

<400> SEQUENCE: 179 aaaaggggg aaatgcatct cagtt                                              25

<210> SEQ ID NO 180
<211> LENGTH: 73
```

```
<212> TYPE: DNA
<213> ORGANISM: Homo sapiens

<400> SEQUENCE: 180
agactgggac ggaagtccct cagtccccca ggagcctcct tcatggaccc ggggatccca    60
agaggggctg cct                                                       73

<210> SEQ ID NO 181
<211> LENGTH: 25
<212> TYPE: DNA
<213> ORGANISM: Homo sapiens

<400> SEQUENCE: 181
gaaggcccgg aggagaacaa gatcc                                          25

<210> SEQ ID NO 182
<211> LENGTH: 43
<212> TYPE: DNA
<213> ORGANISM: Homo sapiens

<400> SEQUENCE: 182
tgtatgacga ctcctacgtg cccgggtttg aggactcgga ggc                      43

<210> SEQ ID NO 183
<211> LENGTH: 35
<212> TYPE: DNA
<213> ORGANISM: Homo sapiens

<400> SEQUENCE: 183
aaacatcatt tgtcgaccgt cctttcactg ccatg                               35

<210> SEQ ID NO 184
<211> LENGTH: 28
<212> TYPE: DNA
<213> ORGANISM: Homo sapiens

<400> SEQUENCE: 184
cagctgtcag ggtttatcct ggcccgtt                                       28

<210> SEQ ID NO 185
<211> LENGTH: 25
<212> TYPE: DNA
<213> ORGANISM: Homo sapiens

<400> SEQUENCE: 185
cagcgaggac tccagcgtat ccgcc                                          25

<210> SEQ ID NO 186
<211> LENGTH: 33
<212> TYPE: DNA
<213> ORGANISM: Homo sapiens

<400> SEQUENCE: 186
ggcgagagcc atacggccac ctggggcccg cag                                 33

<210> SEQ ID NO 187
<211> LENGTH: 24
<212> TYPE: DNA
<213> ORGANISM: Homo sapiens

<400> SEQUENCE: 187
cttctcgtct cttccgaagc tctt                                           24
```

```
<210> SEQ ID NO 188
<211> LENGTH: 26
<212> TYPE: DNA
<213> ORGANISM: Homo sapiens

<400> SEQUENCE: 188
ttgcgtgagg tactcgggtc cgtccc                                          26

<210> SEQ ID NO 189
<211> LENGTH: 101
<212> TYPE: DNA
<213> ORGANISM: Homo sapiens

<400> SEQUENCE: 189
tgccggcccg cgaatgagta ctttgccaag aagctgcggg acgccgtggt tgatggcacc    60
ccctgctacc aggtccgagc cagccgggac ctctgcatca a                       101

<210> SEQ ID NO 190
<211> LENGTH: 57
<212> TYPE: DNA
<213> ORGANISM: Homo sapiens

<400> SEQUENCE: 190
tggggctacc aacctgcctg cctgcaagga tggctccgag ccgtggccct atgtggt       57

<210> SEQ ID NO 191
<211> LENGTH: 216
<212> TYPE: DNA
<213> ORGANISM: Homo sapiens

<400> SEQUENCE: 191
gctgacacct ctcaagggcc cggaggcggc ccaccccaa gccaaagcca aaggctctaa    60
gagtccatct gctggcagga aaggctccca gctgagtcct cagccccaga agaaaggcct  120
ccctagtcct cagggcaccc ggaagagtgc tccaagttcc aaggccaccc ctcaggcctc  180
agagccagtc accactcagt tgttgggaca gcctcc                             216

<210> SEQ ID NO 192
<211> LENGTH: 42
<212> TYPE: DNA
<213> ORGANISM: Homo sapiens

<400> SEQUENCE: 192 tcctgaccttt ccagctcctc cttgtcttcc ttcatatccc ac                      42

<210> SEQ ID NO 193
<211> LENGTH: 32
<212> TYPE: DNA
<213> ORGANISM: Homo sapiens

<400> SEQUENCE: 193
ctacaactga gacccggagg agactagacc cc                                   32

<210> SEQ ID NO 194
<211> LENGTH: 24
<212> TYPE: DNA
<213> ORGANISM: Homo sapiens

<400> SEQUENCE: 194
tgcggcaggc ccgagtgagg ccat                                            24
```

```
<210> SEQ ID NO 195
<211> LENGTH: 120
<212> TYPE: DNA
<213> ORGANISM: Homo sapiens

<400> SEQUENCE: 195
agtgctgtcc gctgacggtg tgctcagagc cgtgcgggtc attcgggttc ccccagtgca      60
ggtgcagctg cgtggcactg tagcgagact ggaggccctg gatgtgcatg tccgagggca     120

<210> SEQ ID NO 196
<211> LENGTH: 24
<212> TYPE: DNA
<213> ORGANISM: Homo sapiens

<400> SEQUENCE: 196
tgggagcact gtggttctgc ctca                                             24

<210> SEQ ID NO 197
<211> LENGTH: 30
<212> TYPE: DNA
<213> ORGANISM: Homo sapiens

<400> SEQUENCE: 197
ctcaaaaacg acatacccag gcaggagaag                                       30

<210> SEQ ID NO 198
<211> LENGTH: 92
<212> TYPE: DNA
<213> ORGANISM: Homo sapiens

<400> SEQUENCE: 198
aggcagctcg aaggcggcct tgcagagctg gtgagaagca cagcagccgc tcattctcag      60
ccagcagctt caaggtccct ttgtccaggt tg                                    92

<210> SEQ ID NO 199
<211> LENGTH: 196
<212> TYPE: DNA
<213> ORGANISM: Homo sapiens

<400> SEQUENCE: 199
gtcctgcgcc tcacacctgc tgtgcctctc gacctttggc tgcctcctct cgtgggccgg      60
cttctcgggg ccaggccctg ctgggcccca gacttgccag acctgtcttc tccgggctct     120
gggagccctg ctcctctctg tggctcaggg caagtctgta cttccagctc agcctggtga     180
ttgctccacc ccaggg                                                    196

<210> SEQ ID NO 200
<211> LENGTH: 24
<212> TYPE: DNA
<213> ORGANISM: Homo sapiens

<400> SEQUENCE: 200
gtggtgacaa aggagtagcc acgc                                             24

<210> SEQ ID NO 201
<211> LENGTH: 27
<212> TYPE: DNA
<213> ORGANISM: Homo sapiens

<400> SEQUENCE: 201
tccttgctac gagccctgtc tcccagg                                          27
```

<210> SEQ ID NO 202
<211> LENGTH: 186
<212> TYPE: DNA
<213> ORGANISM: Homo sapiens

<400> SEQUENCE: 202

```
gtcatcgacc gctgtaacta tgtgcgagtt ggcaccaccc gggtgccact gacggggccg      60
gtgaaggaaa agatcatggc ggtgatcaag gagtggggca ctggccggga caccctgcgc     120
tgcttggccc tggccacccg ggacaccccc ccgaagcgag aggaaatggt cctggatgac     180
tctgcc                                                                186
```

<210> SEQ ID NO 203
<211> LENGTH: 34
<212> TYPE: DNA
<213> ORGANISM: Homo sapiens

<400> SEQUENCE: 203

```
gggaccccag gagactcaag cctctgaagc ctcc                                  34
```

<210> SEQ ID NO 204
<211> LENGTH: 25
<212> TYPE: DNA
<213> ORGANISM: Homo sapiens

<400> SEQUENCE: 204

```
cagaggtatt gggagggcac agggg                                            25
```

<210> SEQ ID NO 205
<211> LENGTH: 171
<212> TYPE: DNA
<213> ORGANISM: Homo sapiens

<400> SEQUENCE: 205

```
aataggtgct tgtcgtccac cggaggaacc ctgtcctgct cgtcgtcctc atcaaactca      60
tactcgtcct tgacgggggc cgtggccttc tgtggctctg ggttcttggc cttgtgcttg     120
aggccttttt cgaactcgga gtccgtgttg ttgccgtcga ctgaactgga a              171
```

<210> SEQ ID NO 206
<211> LENGTH: 32
<212> TYPE: DNA
<213> ORGANISM: Homo sapiens

<400> SEQUENCE: 206

```
ccatcaagaa ggaggaaaag gtgctgccta ag                                    32
```

<210> SEQ ID NO 207
<211> LENGTH: 27
<212> TYPE: DNA
<213> ORGANISM: Homo sapiens

<400> SEQUENCE: 207

```
ggagcaacgg ttgagggtcg tgtcctc                                          27
```

<210> SEQ ID NO 208
<211> LENGTH: 24
<212> TYPE: DNA
<213> ORGANISM: Homo sapiens

<400> SEQUENCE: 208

```
gagaaaggct cctagaggct actg                                             24
```

```
<210> SEQ ID NO 209
<211> LENGTH: 58
<212> TYPE: DNA
<213> ORGANISM: Homo sapiens

<400> SEQUENCE: 209
cctcccaggt gaggtcggcc accagcccca tggagtcgta gccgctgctc accagctg      58

<210> SEQ ID NO 210
<211> LENGTH: 135
<212> TYPE: DNA
<213> ORGANISM: Homo sapiens

<400> SEQUENCE: 210
gccagacatc ctgcgacctg tctccttcct cccggggaag ctgcagggcc ccagctccgc    60
cgggggcccc tccttccctg gcgggcaggg ccaggcccgg ctccgtgcct ttcccattgc   120
gtttgggcaa ggtac                                                    135

<210> SEQ ID NO 211
<211> LENGTH: 77
<212> TYPE: DNA
<213> ORGANISM: Homo sapiens

<400> SEQUENCE: 211
caggtgcaca gaggcgtgtt ggccggtgca ggtgaagata cacatggtga caaagtggca    60
aacctggtcc cgagcct                                                   77

<210> SEQ ID NO 212
<211> LENGTH: 152
<212> TYPE: DNA
<213> ORGANISM: Homo sapiens

<400> SEQUENCE: 212
cagggtctcg atgaggcggg catagccctg ggcagcagcc aggtgcagaa ggctcatgcc    60
ccggaagggg cttccatggg ccagacgttc aggacccttc caggtggagc gtgggatcat   120
gctttctacc aagaccacta cccgtgcttc ga                                 152

<210> SEQ ID NO 213
<211> LENGTH: 30
<212> TYPE: DNA
<213> ORGANISM: Homo sapiens

<400> SEQUENCE: 213
cctctggtgg tcaattagcg gctgcacgct                                     30

<210> SEQ ID NO 214
<211> LENGTH: 24
<212> TYPE: DNA
<213> ORGANISM: Homo sapiens

<400> SEQUENCE: 214
tcctcactca ccgggataga taga                                           24

<210> SEQ ID NO 215
<211> LENGTH: 24
<212> TYPE: DNA
<213> ORGANISM: Homo sapiens

<400> SEQUENCE: 215
```
ttccggtacc ggtcctccga tctg           24

<210> SEQ ID NO 216
<211> LENGTH: 24
<212> TYPE: DNA
<213> ORGANISM: Homo sapiens

<400> SEQUENCE: 216
agtgagggtg gtccgcactc cgat           24

<210> SEQ ID NO 217
<211> LENGTH: 104
<212> TYPE: DNA
<213> ORGANISM: Homo sapiens

<400> SEQUENCE: 217
ctcgatgcca tggtcggggt tgcagctgaa ggcgatggtg atggcgtaac gggtgcccca      60
gtggaccttc tccacgcggt gtaggttctc ggaccccgag gtga                     104

<210> SEQ ID NO 218
<211> LENGTH: 28
<212> TYPE: DNA
<213> ORGANISM: Homo sapiens

<400> SEQUENCE: 218
ctccagattg ggcctgtccc caaagctc        28

<210> SEQ ID NO 219
<211> LENGTH: 38
<212> TYPE: DNA
<213> ORGANISM: Homo sapiens

<400> SEQUENCE: 219
gcctgcatct tgacgggcct cctgtcggct gctggagg       38

<210> SEQ ID NO 220
<211> LENGTH: 29
<212> TYPE: DNA
<213> ORGANISM: Homo sapiens

<400> SEQUENCE: 220
tctggggatg agtcggaggt gggcaggca      29

<210> SEQ ID NO 221
<211> LENGTH: 28
<212> TYPE: DNA
<213> ORGANISM: Homo sapiens

<400> SEQUENCE: 221
cccagcagcc ttggaccttc acctggtg        28

<210> SEQ ID NO 222
<211> LENGTH: 24
<212> TYPE: DNA
<213> ORGANISM: Homo sapiens

<400> SEQUENCE: 222
gacaaggtgc cttggccttt tcct           24

<210> SEQ ID NO 223
<211> LENGTH: 29
<212> TYPE: DNA
<213> ORGANISM: Homo sapiens

```
<400> SEQUENCE: 223
ggcttggagt tgccggtggt tctccttca                                29

<210> SEQ ID NO 224
<211> LENGTH: 31
<212> TYPE: DNA
<213> ORGANISM: Homo sapiens

<400> SEQUENCE: 224
tggatcccag agacggtgaa gtagggatc t                              31

<210> SEQ ID NO 225
<211> LENGTH: 56
<212> TYPE: DNA
<213> ORGANISM: Homo sapiens

<400> SEQUENCE: 225
ggccagggtg aacactcccg gctccagccc cttctccacc atagtggggc tccctt   56

<210> SEQ ID NO 226
<211> LENGTH: 29
<212> TYPE: DNA
<213> ORGANISM: Homo sapiens

<400> SEQUENCE: 226
gaaagggaga aagtacagaa gacagatga                                29

<210> SEQ ID NO 227
<211> LENGTH: 94
<212> TYPE: DNA
<213> ORGANISM: Homo sapiens

<400> SEQUENCE: 227
gagaagccct ggtggttgat ctgatgttcc gagccggctc cgtcgcgagc tccaaacagc   60
agccgcagtt cactgagtcg gtggctgtaa agga                          94

<210> SEQ ID NO 228
<211> LENGTH: 175
<212> TYPE: DNA
<213> ORGANISM: Homo sapiens

<400> SEQUENCE: 228
ccttgcggaa caccttgccg atcttcttaa atgtccccac gggcttagg gcttccacga   60 ggacgtccaa atccacatct ttgcagacat cggggacgct ccaaagaatg aggcagtcgg  120
gggacggcag gaagccccag gggaaccagc ccccacgtg gcttttctcg agagt        175

<210> SEQ ID NO 229
<211> LENGTH: 24
<212> TYPE: DNA
<213> ORGANISM: Homo sapiens

<400> SEQUENCE: 229
gaccaggtgc caggccttgc gcgg                                     24

<210> SEQ ID NO 230
<211> LENGTH: 43
<212> TYPE: DNA
<213> ORGANISM: Homo sapiens

<400> SEQUENCE: 230
```
cagcagagat ggatccccgg cctggagggg agctggcagc agg     43

<210> SEQ ID NO 231
<211> LENGTH: 26
<212> TYPE: DNA
<213> ORGANISM: Homo sapiens

<400> SEQUENCE: 231
cagttctgta actttctccc agagag     26

<210> SEQ ID NO 232
<211> LENGTH: 51
<212> TYPE: DNA
<213> ORGANISM: Homo sapiens

<400> SEQUENCE: 232
cttctgcggg ggtgccctga tccatgcccg cttcgtgatg accgcggcca g     51

<210> SEQ ID NO 233
<211> LENGTH: 30
<212> TYPE: DNA
<213> ORGANISM: Homo sapiens

<400> SEQUENCE: 233
agaggaaaga ctgaaggcca ggagggagag     30

<210> SEQ ID NO 234
<211> LENGTH: 29
<212> TYPE: DNA
<213> ORGANISM: Homo sapiens

<400> SEQUENCE: 234
cggtccatgg cctcccgggc ctgggccat     29

<210> SEQ ID NO 235
<211> LENGTH: 26
<212> TYPE: DNA
<213> ORGANISM: Homo sapiens

<400> SEQUENCE: 235
accctgaaac cctctacgcc tgggag     26

<210> SEQ ID NO 236
<211> LENGTH: 30
<212> TYPE: DNA
<213> ORGANISM: Homo sapiens

<400> SEQUENCE: 236
gggggacagc ctcctggaga ccagctgcgg     30

<210> SEQ ID NO 237
<211> LENGTH: 137
<212> TYPE: DNA
<213> ORGANISM: Homo sapiens

<400> SEQUENCE: 237
cgagcgcccg gtggcgcccg aggacgcgtg tcgtacgggg ggtggcgcgt cgtaggcccc     60
ggccatggcc tcctcgccgc cccgctgcc cgggccatcg gcctcgtcgt agtcggagcc    120
ccggtagtag ccatggt     137

<210> SEQ ID NO 238
<211> LENGTH: 27

```
<212> TYPE: DNA
<213> ORGANISM: Homo sapiens

<400> SEQUENCE: 238
cgcaggaccc cgacatgagc cttgaag                                          27

<210> SEQ ID NO 239
<211> LENGTH: 44
<212> TYPE: DNA
<213> ORGANISM: Homo sapiens

<400> SEQUENCE: 239 agcagcccccg taacctccac ctggtctccc gccaacccac ggag                      44

<210> SEQ ID NO 240
<211> LENGTH: 115
<212> TYPE: DNA
<213> ORGANISM: Homo sapiens

<400> SEQUENCE: 240
tgtacctgcc ggcgtcgtag tcgtccaggc tctgctggat caggtcctcc tccatgagca      60
ccgcctcgcc ctcgccctcg ccctcaccgt ccccgtcgcc gtcgccctct gtcgg          115

<210> SEQ ID NO 241
<211> LENGTH: 34
<212> TYPE: DNA
<213> ORGANISM: Homo sapiens

<400> SEQUENCE: 241
ccagggaccg agcctgagaa agacccgggg ccgc                                  34

<210> SEQ ID NO 242
<211> LENGTH: 33
<212> TYPE: DNA
<213> ORGANISM: Homo sapiens

<400> SEQUENCE: 242
acgcggaccc ggtgcacgac cccacctggc gct                                   33

<210> SEQ ID NO 243
<211> LENGTH: 24
<212> TYPE: DNA
<213> ORGANISM: Homo sapiens

<400> SEQUENCE: 243
acagcccccg taaggctcct gttc                                             24

<210> SEQ ID NO 244
<211> LENGTH: 24
<212> TYPE: DNA
<213> ORGANISM: Homo sapiens

<400> SEQUENCE: 244
cctggatcct cttgttccgc tcct                                             24

<210> SEQ ID NO 245
<211> LENGTH: 28
<212> TYPE: DNA
<213> ORGANISM: Homo sapiens

<400> SEQUENCE: 245
ccggagccag aggacccgta gctgctag                                         28
```

```
<210> SEQ ID NO 246
<211> LENGTH: 61
<212> TYPE: DNA
<213> ORGANISM: Homo sapiens

<400> SEQUENCE: 246
gggaaaacta cagttcccga catgccctgc cacgggtgcg cctgcgtacc ggagctactg      60
c                                                                    61

<210> SEQ ID NO 247
<211> LENGTH: 97
<212> TYPE: DNA
<213> ORGANISM: Homo sapiens

<400> SEQUENCE: 247
tggcgcctca cgacccgggt agtcttacga ccctggtgcc ctgggctgcc gccctgctcc      60
tcgctctggg cgtggaaagg gctctggcgc tacccga                              97

<210> SEQ ID NO 248
<211> LENGTH: 53
<212> TYPE: DNA
<213> ORGANISM: Homo sapiens

<400> SEQUENCE: 248
ttgagctgca gctcgtctgt gtcagtggcc gtgtagtcgt gctgggcctg tac             53

<210> SEQ ID NO 249
<211> LENGTH: 27
<212> TYPE: DNA
<213> ORGANISM: Homo sapiens

<400> SEQUENCE: 249
cgatctcggc ggctcactac aacctct                                         27

<210> SEQ ID NO 250
<211> LENGTH: 82
<212> TYPE: DNA
<213> ORGANISM: Homo sapiens

<400> SEQUENCE: 250
ctcactctgt cacccaggct ggagtgcact ggtgcgatct tggctcactg caacctccaa      60
ctcccaagtt caagcggttc tc                                              82

<210> SEQ ID NO 251
<211> LENGTH: 31
<212> TYPE: DNA
<213> ORGANISM: Homo sapiens

<400> SEQUENCE: 251
ccctcaagac accgctggct gctggacacc c                                    31

<210> SEQ ID NO 252
<211> LENGTH: 31
<212> TYPE: DNA
<213> ORGANISM: Homo sapiens

<400> SEQUENCE: 252
gccggcgcct acgcccacac ggtgaaccgc a                                    31

<210> SEQ ID NO 253
<211> LENGTH: 25
```

```
<212> TYPE: DNA
<213> ORGANISM: Homo sapiens

<400> SEQUENCE: 253 gaagggccc ggaacacctg ctctc                                            25

<210> SEQ ID NO 254
<211> LENGTH: 25
<212> TYPE: DNA
<213> ORGANISM: Homo sapiens

<400> SEQUENCE: 254
gctcatcctc ggagtcgtag cccac                                           25

<210> SEQ ID NO 255
<211> LENGTH: 24
<212> TYPE: DNA
<213> ORGANISM: Homo sapiens

<400> SEQUENCE: 255
tggacgaaga gacccacgca ggcg                                            24

<210> SEQ ID NO 256
<211> LENGTH: 24
<212> TYPE: DNA
<213> ORGANISM: Homo sapiens

<400> SEQUENCE: 256
acaggtgcga tcccccagtg gagg                                            24

<210> SEQ ID NO 257
<211> LENGTH: 132
<212> TYPE: DNA
<213> ORGANISM: Homo sapiens

<400> SEQUENCE: 257
ctgctcagcg cagccagtcg cggaggcggg gaggctgcgc ggtcagaggc gcctggagcg     60
agcgaatcct ggcccaccgc ctgcccaacc gcgtgacctt gattgagtta atgaacttca   120
cgcctcagcg tc                                                       132

<210> SEQ ID NO 258
<211> LENGTH: 33
<212> TYPE: DNA
<213> ORGANISM: Homo sapiens

<400> SEQUENCE: 258
gttatgccaa aggctcgtcg cagctgctgc tcc                                  33

<210> SEQ ID NO 259
<211> LENGTH: 26
<212> TYPE: DNA
<213> ORGANISM: Homo sapiens

<400> SEQUENCE: 259
gccgaggcgt tagcccttc ttgcac                                           26

<210> SEQ ID NO 260
<211> LENGTH: 73
<212> TYPE: DNA
<213> ORGANISM: Homo sapiens

<400> SEQUENCE: 260
```

```
cctctctttg ctcctggtgg ctgctgtggt ttggaagatc aaacaaagtt gttgggcctc    60
cagacgtaga gag                                                       73

<210> SEQ ID NO 261
<211> LENGTH: 27
<212> TYPE: DNA
<213> ORGANISM: Homo sapiens

<400> SEQUENCE: 261
gagtgggccg ctggtccggg cacagtg                                        27

<210> SEQ ID NO 262
<211> LENGTH: 25
<212> TYPE: DNA
<213> ORGANISM: Homo sapiens

<400> SEQUENCE: 262
tgtgaagaca gcgggtgtga ggcgg                                          25

<210> SEQ ID NO 263
<211> LENGTH: 25
<212> TYPE: DNA
<213> ORGANISM: Homo sapiens

<400> SEQUENCE: 263
tggtcctgag aaagggtgc cagcg                                           25

<210> SEQ ID NO 264
<211> LENGTH: 25
<212> TYPE: DNA
<213> ORGANISM: Homo sapiens

<400> SEQUENCE: 264
tgtcgaaggc gggcgtctgg gccat                                          25

<210> SEQ ID NO 265
<211> LENGTH: 89
<212> TYPE: DNA
<213> ORGANISM: Homo sapiens

<400> SEQUENCE: 265
gtccggggca actacaccga aggccgagcg gcggcttcac ggtaccggcc gggcaccgcc    60
ggaggggccc aagccggagc tgggagagc                                      89

<210> SEQ ID NO 266
<211> LENGTH: 27
<212> TYPE: DNA
<213> ORGANISM: Homo sapiens

<400> SEQUENCE: 266
gacttctctg tgccggagtc gtctcat                                        27

<210> SEQ ID NO 267
<211> LENGTH: 24
<212> TYPE: DNA
<213> ORGANISM: Homo sapiens

<400> SEQUENCE: 267
gcaccccgcg cagcggctga gccg                                           24

<210> SEQ ID NO 268
<211> LENGTH: 24
```

```
<212> TYPE: DNA
<213> ORGANISM: Homo sapiens

<400> SEQUENCE: 268
cctgaagtac cctgcacccc aata                                          24

<210> SEQ ID NO 269
<211> LENGTH: 25
<212> TYPE: DNA
<213> ORGANISM: Homo sapiens

<400> SEQUENCE: 269
ttgcaggcca ggcagtgcca ggagt                                         25

<210> SEQ ID NO 270
<211> LENGTH: 358
<212> TYPE: DNA
<213> ORGANISM: Homo sapiens

<400> SEQUENCE: 270
ggctgcgggc gcatcagcgc agccacagca gcggggctc caccagcccg ggctgcaccc    60
accacgactc catggacccc tcggacgagg agggccgcgg tggcgcgggc ggcggggcg    120 cgggcagcga gcactcggag accctcagca gcctctcgct cacctccctc ttctgcccgc    180
cgcccccgcc gccagccccc ggcctcacgc ccgccaggaa gttcagcagc accagcagcc    240
tggccgcccc cggccgcccc cacgccgccg ccctggccca cggcctggcc cggagcccct    300
cgtgggccgc ggaccgcagc aaggaccccc ccggccgggc accgctgccc atgggcct     358

<210> SEQ ID NO 271
<211> LENGTH: 242
<212> TYPE: DNA
<213> ORGANISM: Homo sapiens

<400> SEQUENCE: 271
ggtgccggga tcaacaaatg aaattgtgac gggaagtcct ggcccttggc ccaacctcct    60
gctgtccccg gtctgagggc ccaagcccg cgtctccgcc ttgccgtcca gcctgtcctt     120
ggtgtggggt gcttggaagt gtgagcaccc tctctggctc tttgccggcc caagggtcg     180 ttgcggcggc ccccgggccc agtcatcagc cctcttttcc ggtgccggaa ctatcgtact     240
gg                                                                   242

<210> SEQ ID NO 272
<211> LENGTH: 30
<212> TYPE: DNA
<213> ORGANISM: Homo sapiens

<400> SEQUENCE: 272
attgtgaagc aaggcccgag gccttgactg                                     30

<210> SEQ ID NO 273
<211> LENGTH: 25
<212> TYPE: DNA
<213> ORGANISM: Homo sapiens

<400> SEQUENCE: 273
aggagaagaa gacgccggca gccga                                          25

<210> SEQ ID NO 274
<211> LENGTH: 24
<212> TYPE: DNA
```

```
<213> ORGANISM: Homo sapiens

<400> SEQUENCE: 274
tgaccacaaa aggacctgga gaca                                           24

<210> SEQ ID NO 275
<211> LENGTH: 24
<212> TYPE: DNA
<213> ORGANISM: Homo sapiens

<400> SEQUENCE: 275
tggtgaatcg aaagacgggg aagt                                           24

<210> SEQ ID NO 276
<211> LENGTH: 51
<212> TYPE: DNA
<213> ORGANISM: Homo sapiens

<400> SEQUENCE: 276
ggagacggcg gctgttccag aggagggagt cgtcataacc ggctactgcc g             51

<210> SEQ ID NO 277
<211> LENGTH: 24
<212> TYPE: DNA
<213> ORGANISM: Homo sapiens

<400> SEQUENCE: 277
attaaggggt tcctctacag cttt                                           24

<210> SEQ ID NO 278
<211> LENGTH: 26
<212> TYPE: DNA
<213> ORGANISM: Homo sapiens

<400> SEQUENCE: 278
tgagggagaa attgcaagca gcgagg                                         26

<210> SEQ ID NO 279
<211> LENGTH: 33
<212> TYPE: DNA
<213> ORGANISM: Homo sapiens

<400> SEQUENCE: 279
aggtcacctt tgtcgccctt ctcacctttg gct                                 33

<210> SEQ ID NO 280
<211> LENGTH: 24
<212> TYPE: DNA
<213> ORGANISM: Homo sapiens

<400> SEQUENCE: 280
cccgtgcctg gtccaggttt tctc                                           24

<210> SEQ ID NO 281
<211> LENGTH: 101
<212> TYPE: DNA
<213> ORGANISM: Homo sapiens

<400> SEQUENCE: 281
cactccagcc tggggaacag agcaagactc cgtctcaaaa aaaaaaaaa aaaaaaaga      60 aaagaaatcc ctcctaattt ccttcttttt aatctctaca g                       101
```

```
<210> SEQ ID NO 282
<211> LENGTH: 38
<212> TYPE: DNA
<213> ORGANISM: Homo sapiens

<400> SEQUENCE: 282
gtctttgagc cccagagtag cctttcggat tccctcgt                              38

<210> SEQ ID NO 283
<211> LENGTH: 26
<212> TYPE: DNA
<213> ORGANISM: Homo sapiens

<400> SEQUENCE: 283
ctggagaaga aagcacggac aggcag                                           26

<210> SEQ ID NO 284
<211> LENGTH: 66
<212> TYPE: DNA
<213> ORGANISM: Homo sapiens

<400> SEQUENCE: 284
tgaagagctg gcagtagaag ataaacaggc tggggaagaa gagaaagtgc tcaaggagaa      60
ggagca                                                                 66

<210> SEQ ID NO 285
<211> LENGTH: 24
<212> TYPE: DNA
<213> ORGANISM: Homo sapiens

<400> SEQUENCE: 285
aattgagttt agtgccggcc ccca                                             24

<210> SEQ ID NO 286
<211> LENGTH: 36
<212> TYPE: DNA
<213> ORGANISM: Homo sapiens

<400> SEQUENCE: 286
gcctttcccc gaagaactca ctcggcaagc cgtcag                                36

<210> SEQ ID NO 287
<211> LENGTH: 49
<212> TYPE: DNA
<213> ORGANISM: Homo sapiens

<400> SEQUENCE: 287
cgaaagggcg aggagttgga ggaggagtgg acgcctacgg agaaagtca                  49

<210> SEQ ID NO 288
<211> LENGTH: 24
<212> TYPE: DNA
<213> ORGANISM: Homo sapiens

<400> SEQUENCE: 288
tgttggcgaa gaatgctgtc tgcc                                             24

<210> SEQ ID NO 289
<211> LENGTH: 24
<212> TYPE: DNA
<213> ORGANISM: Homo sapiens

<400> SEQUENCE: 289
```

```
ccctggaaga agggacgtca gagg                                              24
```

\<210> SEQ ID NO 290
\<211> LENGTH: 24
\<212> TYPE: DNA
\<213> ORGANISM: Homo sapiens

\<400> SEQUENCE: 290

```
tccagcttgg gaacaggcta cttc                                              24
```

\<210> SEQ ID NO 291
\<211> LENGTH: 88
\<212> TYPE: DNA
\<213> ORGANISM: Homo sapiens

\<400> SEQUENCE: 291

```
cagtggcgaa ccacgtgccg gtaggaggtg gccaggtagt cgaagtagtt gatgttgagt        60
ttccgggcga tgtaacggcc caagtatt                                          88
```

\<210> SEQ ID NO 292
\<211> LENGTH: 30
\<212> TYPE: DNA
\<213> ORGANISM: Homo sapiens

\<400> SEQUENCE: 292

```
tttccagcgc ccggaatcct tccactgtct                                        30
```

\<210> SEQ ID NO 293
\<211> LENGTH: 25
\<212> TYPE: DNA
\<213> ORGANISM: Homo sapiens

\<400> SEQUENCE: 293

```
gtcaccacct ccccttgtcg cctag                                             25
```

\<210> SEQ ID NO 294
\<211> LENGTH: 105
\<212> TYPE: DNA
\<213> ORGANISM: Homo sapiens

\<400> SEQUENCE: 294

```
tccagggtga ggctccgttc tccccatgag actgggggtt cctggtttgc atccctcgct        60
tctcatcatc ctgggggttc cagtaactgg gggttcagga acagg                       105
```

\<210> SEQ ID NO 295
\<211> LENGTH: 24
\<212> TYPE: DNA
\<213> ORGANISM: Homo sapiens

\<400> SEQUENCE: 295

```
ttctcctcgt ggtggccttc tctg                                              24
```

\<210> SEQ ID NO 296
\<211> LENGTH: 24
\<212> TYPE: DNA
\<213> ORGANISM: Homo sapiens

\<400> SEQUENCE: 296

```
gctcctgtcc ccaggttttc ccca                                              24
```

\<210> SEQ ID NO 297
\<211> LENGTH: 30

```
<212> TYPE: DNA
<213> ORGANISM: Homo sapiens

<400> SEQUENCE: 297
ggcaaagccg ggagaaactg ctgagacgag                                    30

<210> SEQ ID NO 298
<211> LENGTH: 32
<212> TYPE: DNA
<213> ORGANISM: Homo sapiens

<400> SEQUENCE: 298
aacttgagca ggtccctttc gcccatgggc gt                                 32

<210> SEQ ID NO 299
<211> LENGTH: 30
<212> TYPE: DNA
<213> ORGANISM: Homo sapiens

<400> SEQUENCE: 299
tgccggccgt ggtcgtgctg ttggcctctt                                    30

<210> SEQ ID NO 300
<211> LENGTH: 27
<212> TYPE: DNA
<213> ORGANISM: Homo sapiens

<400> SEQUENCE: 300
tgagtggaac cgtgtgaaag agccggg                                       27

<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 301
gctttgggtc caggaatgg                                                19

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 302
gttgtccaca gtcagcaatg gt                                            22

<210> SEQ ID NO 303
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
agaccagcaa gaagat                                                   16

<210> SEQ ID NO 304
<211> LENGTH: 20
```

```
-continued

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 304
ccatggatct ccaggtgggt                                                    20

<210> SEQ ID NO 305
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 305
ccagtggggc tgctgttatc tg                                                 22

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 306
actcaaactg tgggggcact                                                    20

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 307
ctctagaggg aagcgctttc tg                                                 22
```